US010758545B2

(12) United States Patent
Ichida et al.

(10) Patent No.: US 10,758,545 B2
(45) Date of Patent: Sep. 1, 2020

(54) METHODS TO TREAT NEUROLOGICAL DISEASES

(71) Applicant: UNIVERSITY OF SOUTHERN CALIFORNIA, Los Angeles, CA (US)

(72) Inventors: Justin Ichida, Los Angeles, CA (US); Shaoyu Lin, Monterey Park, CA (US); Yichen Li, Oxford (GB); Yingxiao Shi, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/579,546

(22) PCT Filed: Jun. 24, 2016

(86) PCT No.: PCT/US2016/039425
§ 371 (c)(1),
(2) Date: Dec. 4, 2017

(87) PCT Pub. No.: WO2016/210372
PCT Pub. Date: Dec. 29, 2016

(65) Prior Publication Data
US 2018/0161335 A1 Jun. 14, 2018

Related U.S. Application Data

(60) Provisional application No. 62/184,732, filed on Jun. 25, 2015.

(51) Int. Cl.
A61K 31/5377 (2006.01)
A61P 25/28 (2006.01)
A61K 45/06 (2006.01)
A61K 31/27 (2006.01)

(52) U.S. Cl.
CPC .......... A61K 31/5377 (2013.01); A61K 31/27 (2013.01); A61K 45/06 (2013.01); A61P 25/28 (2018.01)

(58) Field of Classification Search
CPC .... A61K 31/5377; A61K 31/27; A61K 45/06; A61P 25/28
See application file for complete search history.

(56) References Cited

FOREIGN PATENT DOCUMENTS

WO 2014/114303 A1 7/2014

OTHER PUBLICATIONS

Juopperi, Tarja A., et. al., "Modeling neurological diseases using patient-derived induced pluripotent stem cells", Future Neurology, May 2011, vol. 6, No. 3, pp. 1-17 (published in final form as pp. 363-373).
McCartney, Amber Joyce,"The Dynamic Neuron: Cellular Mechanisms Maintaining Neural Activity and the Consequences of Phosphatidylinositol 3,5-bisphosphate Biosynthesis on Synapse Function", A dissertation submitted in partial fulfillment of the requirements for the degree of Doctor of Philosophy (Neuroscience) in the University of Michigan 2014, pp. 1-248.
Min, Sang H., et. al., "Loss of PIKfyve in platelets causes a lysosomal disease leading to inflammation and thrombosis in mice", Published in final edited form as: Nat Commun., vol. 5, No. 4691, pp. 1-28, Available in PMC Sep. 2, 2015.
Rentzos, Michael, et. al., "Interleukin-12 is reduced in cerebrospinal fluid of patients with Alzheimer's disease and frontotemporal dementia", Journal of the Neurological Sciences, vol. 249, No. 2, Available online Jul. 14, 2006, pp. 110-114.
Wada, Yumiko, et. al., "Apilimod Inhibits the Production of IL-12 and IL-23 and Reduces Dendritic Cell Infiltration in Psoriasis", PLoS One, Apr. 6, 2012, vol. 7, Issue 4, e35069, pp. 1-10.
Zolov, Sergey N., et. al., "In vivo, Pikfyve generates PI(3,5)P2, which serves as both a signaling lipid and the major precursor for PI5P", Proceedings of the National Academy of Sciences, Oct. 9???? 23, 2012, vol. 109, No. 43, pp. 17472-17477.
Thomas, Shane, International Search Report and Written Opinion, PCT/US2016/039425, United States Patent and Trademark Office, dated Dec. 9, 2016.
Wittmann-Regis, Agnes, International Preliminary Report on Patentability and Written Opinion, PCT/US2016/039425, The International Bureau of WIPO, dated Jan. 4, 2018.

Primary Examiner — Barbara P Badio
(74) Attorney, Agent, or Firm — Gavrilovich, Dodd & Lindsey LLP

(57) ABSTRACT

Disclosed is a method of treating a subject who has a neurological disease. The neurological disease may be associated with altered C9ORF72 protein activity. In one aspect, the method includes a step of administering an effective dose of a pharmaceutical composition to a subject in need thereof, thereby rescuing the defects associated with altered C9ORF72 protein activity. Also described are methods for identifying a compound for inhibiting motor neuron degeneration.

8 Claims, 82 Drawing Sheets
Specification includes a Sequence Listing.

CTRL2 C9ORF72+/-

WT      5'TGTGTGTTGATAGATTAACACATATAATCCGGAAAGG
Allele 1 5'TGTGTGTTGATAGATTAACACATATAATCCGGAAAGG
Allele 2 5'TGTGTGTTGATAGATTAACACATATAATCC-GAAAGG

CTRL2 C9ORF72-/-

WT      5'TGTTGATAGATTAACACATATAATCCGGAAAGG
Allele 1 5'TGTTGATAGATTAACACATATAATCC-GAAAGG
Allele 2 5'TGTTGATAGATTAACACATATAATCCTATGTGTTGAAA Nonsense-mediated decay of C9ORF72 mRNA Mouse

*Control 4 and C9-ALS4 were not used in this study

+ Neurotrophic Factors anti-C9ORF72
western blot
HEK cell extract

SEQUENCE LISTING

```
<160> NUMBER OF SEQ ID NOS: 20

<210> SEQ ID NO 1
<211> LENGTH: 41
<212> TYPE: DNA
<213> ORGANISM: Artificial Sequence
<220> FEATURE:
<223> OTHER INFORMATION: RP-PCT primer, Forward
<220> FEATURE:
<221> NAME/KEY: 5'clip
<222> LOCATION: (1)..(1)
<223> OTHER INFORMATION: 6FAM
```

```
<400> SEQUENCE: 1
tgtaaaacga cggccagtca aggagggaaa caaccgcagc c                    41

<210> SEQ ID NO 2
<211> LENGTH: 18
<212> TYPE: DNA
<213> ORGANISM: Artificial Sequence
<220> FEATURE:
<223> OTHER INFORMATION: RP-PCT primer, Reverse-1
<220> FEATURE:
<221> NAME/KEY: 5'clip
<222> LOCATION: (1)..(1)

<400> SEQUENCE: 2
caggaaacag ctatgacc                                              18

<210> SEQ ID NO 3
<211> LENGTH: 54
<212> TYPE: DNA
<213> ORGANISM: Artificial Sequence
<220> FEATURE:
<223> OTHER INFORMATION: RP-PCT primer, Reverse-2
<220> FEATURE:
<221> NAME/KEY: 5'clip
<222> LOCATION: (1)..(1)

<400> SEQUENCE: 3
caggaaacag ctatgaccgg gcccgccccg accacgcccc ggccccggcc ccgg       54

<210> SEQ ID NO 4
<211> LENGTH: 18
<212> TYPE: DNA
<213> ORGANISM: Artificial Sequence
<220> FEATURE:
<223> OTHER INFORMATION: Primer for generating Southern probe, Forward
<220> FEATURE:
<221> NAME/KEY: 5'clip
<222> LOCATION: (1)..(1)

<400> SEQUENCE: 4
agaacaggac aagttgcc                                              18

<210> SEQ ID NO 5
<211> LENGTH: 19
<212> TYPE: DNA
<213> ORGANISM: Artificial Sequence
<220> FEATURE:
<223> OTHER INFORMATION: Primer for generating Southern probe, Reverse
<220> FEATURE:
<221> NAME/KEY: 5'clip
<222> LOCATION: (1)..(1)

<400> SEQUENCE: 5
aacacacacc tcctaaacc                                             19

<210> SEQ ID NO 6
<211> LENGTH: 23
<212> TYPE: DNA
<213> ORGANISM: Artificial Sequence
<220> FEATURE:
<223> OTHER INFORMATION: Genotyping primers for C9ORF72 exon 2, Forward
<220> FEATURE:
<221> NAME/KEY: 5'clip
<222> LOCATION: (1)..(1)

<400> SEQUENCE: 6
cccacacctg ctcttgctag acc                                        23
```

<210> SEQ ID NO 7
<211> LENGTH: 23
<212> TYPE: DNA
<213> ORGANISM: Artificial Sequence
<220> FEATURE:
<223> OTHER INFORMATION: Genotyping primers for C9ORF72 exon 2, Forward
<220> FEATURE:
<221> NAME/KEY: 5'clip
<222> LOCATION: (1)..(1)

<400> SEQUENCE: 7
cccacacctg ctcttgctag acc                                          23

<210> SEQ ID NO 8
<211> LENGTH: 23
<212> TYPE: DNA
<213> ORGANISM: Artificial Sequence
<220> FEATURE:
<223> OTHER INFORMATION: qRT-PCR primer for C9ORF72, transcriptional
      variants 1,3, Forward
<220> FEATURE:
<221> NAME/KEY: 5'clip
<222> LOCATION: (1)..(1)

<400> SEQUENCE: 8
gtaacctacg gtgtcccgct agg                                          23

<210> SEQ ID NO 9
<211> LENGTH: 23
<212> TYPE: DNA
<213> ORGANISM: Artificial Sequence
<220> FEATURE:
<223> OTHER INFORMATION: qRT-PCR primer for C9ORF72, transcriptional
      variants 1,3, Reverse
<220> FEATURE:
<221> NAME/KEY: 5'clip
<222> LOCATION: (1)..(1)

<400> SEQUENCE: 9
cccacacctg ctcttgctag acc                                          23

<210> SEQ ID NO 10
<211> LENGTH: 22
<212> TYPE: DNA
<213> ORGANISM: Artificial Sequence
<220> FEATURE:
<223> OTHER INFORMATION: qRT-PCR primer for C9ORF72, transcriptional
      variants 2, Forward
<220> FEATURE:
<221> NAME/KEY: 5'clip
<222> LOCATION: (1)..(1)

<400> SEQUENCE: 10
gtggcgagtg gatatctccg ga                                           22

<210> SEQ ID NO 11
<211> LENGTH: 23
<212> TYPE: DNA
<213> ORGANISM: Artificial Sequence
<220> FEATURE:
<223> OTHER INFORMATION: qRT-PCR primer for C9ORF72, transcriptional
      variants 2, Reverse
<220> FEATURE:
<221> NAME/KEY: 5'clip
<222> LOCATION: (1)..(1)

<400> SEQUENCE: 11
tggagcccaa atgtgcctta ctc                                          23

<210> SEQ ID NO 12
<211> LENGTH: 20
<212> TYPE: DNA
<213> ORGANISM: Artificial Sequence
<220> FEATURE:
<223> OTHER INFORMATION: qRT-PCR primer for GAPDH, Forward
<220> FEATURE:
<221> NAME/KEY: 5'clip
<222> LOCATION: (1)..(1)

<400> SEQUENCE: 12
cgagatccct ccaaaatcaa                                              20

<210> SEQ ID NO 13
<211> LENGTH: 20
<212> TYPE: DNA
<213> ORGANISM: Artificial Sequence
<220> FEATURE:
<223> OTHER INFORMATION: qRT-PCR primer for GAPDH, Reverse
<220> FEATURE:
<221> NAME/KEY: 5'clip
<222> LOCATION: (1)..(1)

<400> SEQUENCE: 13
gtcttctggg tggcagtgat                                              20

<210> SEQ ID NO 14
<211> LENGTH: 20
<212> TYPE: DNA
<213> ORGANISM: Artificial Sequence
<220> FEATURE:
<223> OTHER INFORMATION: qRT-PCR primer for NMDAR1, Forward
<220> FEATURE:
<221> NAME/KEY: 5'clip
<222> LOCATION: (1)..(1)

<400> SEQUENCE: 14
ccagcgtgtg gtttgagatg                                              20

<210> SEQ ID NO 15
<211> LENGTH: 20
<212> TYPE: DNA
<213> ORGANISM: Artificial Sequence
<220> FEATURE:
<223> OTHER INFORMATION: qRT-PCR primer for NMDAR1, Reverse
<220> FEATURE:
<221> NAME/KEY: 5'clip
<222> LOCATION: (1)..(1)

<400> SEQUENCE: 15
ttctctgcct tggactcacg                                              20

<210> SEQ ID NO 16
<211> LENGTH: 20
<212> TYPE: RNA
<213> ORGANISM: Artificial Sequence
<220> FEATURE:
<223> OTHER INFORMATION: sgRNA-1 targeting upstream of repeat expansion
<220> FEATURE:
<221> NAME/KEY: 5'clip
<222> LOCATION: (1)..(1)

<400> SEQUENCE: 16
guaaccuacg gugucccgcu                                              20

<210> SEQ ID NO 17
<211> LENGTH: 20

```
<212> TYPE: RNA
<213> ORGANISM: Artificial Sequence
<220> FEATURE:
<223> OTHER INFORMATION: sgRNA-2a targeting downstream of repeat
      expansion (+ strand)
<220> FEATURE:
<221> NAME/KEY: 5'clip
<222> LOCATION: (1)..(1)

<400> SEQUENCE: 17
gggguucggc ugccgggaag                                            20

<210> SEQ ID NO 18
<211> LENGTH: 20
<212> TYPE: DNA
<213> ORGANISM: Artificial Sequence
<220> FEATURE:
<223> OTHER INFORMATION: sgRNA-2b targeting downstream of repeat
      expansion (- strand)
<220> FEATURE:
<221> NAME/KEY: 5'clip
<222> LOCATION: (1)..(1)

<400> SEQUENCE: 18
accccaaaca gccacccgcc                                            20

<210> SEQ ID NO 19
<211> LENGTH: 20
<212> TYPE: RNA
<213> ORGANISM: Artificial Sequence
<220> FEATURE:
<223> OTHER INFORMATION: sgRNA-3 targeting C9ORF72 exon 2
<220> FEATURE:
<221> NAME/KEY: 5'clip
<222> LOCATION: (1)..(1)

<400> SEQUENCE: 19
uuaacacaua uaauccggaa                                            20

<210> SEQ ID NO 20
<211> LENGTH: 20
<212> TYPE: RNA
<213> ORGANISM: Artificial Sequence
<220> FEATURE:
<223> OTHER INFORMATION: sgRNA-4 targeting C9ORF72 exon 2
<220> FEATURE:
<221> NAME/KEY: 5'clip
<222> LOCATION: (1)..(1)

<400> SEQUENCE: 20
caccacucuc ugcauuucga                                            20
```

METHODS TO TREAT NEUROLOGICAL DISEASES

CROSS REFERENCE TO RELATED APPLICATION(S)

This application is a U.S. National Stage Application filed under 35 U.S.C. § 371 and claims priority to International Application No. PCT/US2016/039425, filed Jun. 24, 2016, which application claims priority to U.S. Provisional Application No. 62/184,732, filed on Jun. 25, 2015, which are incorporated herein by reference in their entirety.

STATEMENT OF GOVERNMENT INTEREST

This invention was made with government support under grant number R00NS077435, awarded by the National Institute of Neurological Disorders and Stroke (NIH), and under grant number W81XWH-15-1-0187, awarded by the U.S. Department of Defence (DOD). The government has certain rights in the invention.

TECHNICAL FIELD

The present disclosure is directed to methods to prevent and/or treat neurological diseases. Compositions useful in the herein described methods include PIKFYVE kinase inhibitors, potassium channel activators, glutamate receptor inhibitors, and endosomal and lysosomal trafficking modulators.

INCORPORATION BY REFERENCE OF SEQUENCE LISTING

Accompanying this filing is a Sequence Listing entitled "Sequence_ST25.txt", created on Dec. 4, 2017 and having 5,617 bytes of data, machine formatted on IBM-PC, MS-Windows operating system. The sequence listing is hereby incorporated herein by reference in its entirety for all purposes.

BACKGROUND

Many neurological diseases are progressive and may result in a wide range of symptoms such as weakness in the extremities, slurring of speech, vision abnormalities, difficulty breathing, difficulty swallowing, dementia, impaired balance, loss of memory, unsteady gait, muscle twitching, depression, anxiety, and mood swings. Some of these diseases are inherited, but the etiology of many cases is unknown. Indeed, the basis for many of these diseases may be due to environmental, toxic, or viral factors, as well as genetic predisposition, or a combination thereof. A GGGGCC repeat expansion ($(GGGGCC)_n$) in C9ORF72 is a cause of neurological diseases, including amyotrophic lateral sclerosis (ALS) and frontotemporal dementia (FTD), accounting for about 10% of each worldwide. There is no cure for many neurological diseases and treatment options are limited, thus there is a need in the art for methods of treating the diseases.

SUMMARY

In one embodiment, the present invention provides a method for treating a subject with a neurological disease, which includes the step of administering an effective dose of a PIKFYVE kinase inhibitor. In further embodiments, the present method includes treatment with a PIKFYVE kinase inhibitor that is selected from the group consisting of apilimod and PIKFYVE inhibitor YM201636. In certain embodiments, the present method includes treating amyotrophic lateral sclerosis. In certain embodiments, the present method includes treating frontotemporal dementia. In certain embodiments, the method includes treating neurological disease that is associated with aberrant endosomal trafficking. In certain embodiments, the method includes treating neurological disease that is associated with aberrant lysosomal trafficking. In further embodiments, the present method includes treating a subject who has a $(GGGGCC)_n$ repeat expansion in the C9ORF72 gene. In further embodiments, the subject is haploinsufficient for C9ORF72. In further embodiments the present method includes treating patients who have a 50% or greater reduction in C9ORF72 protein activity. In further embodiments, the present method includes a C9ORF72 gene product that comprises a dipeptide repeat resulting from the $(GGGGCC)_n$ expansion. In further embodiments, the present method includes a gain-of-function or loss of function mutation resulting from the $(GGGGCC)_n$ expansion. In further embodiments, the neurological disease is associated with neuronal hyperexcitability.

In another embodiment, the present invention includes treating a subject having neurological disease, characterized by neuronal hyperexcitability, which includes the step of administering to the subject an effective dose of a potassium channel activator. In further embodiments, present the method includes treatment wherein the potassium channel activator is retigabine. In certain embodiments, the present method includes treating amyotrophic lateral sclerosis. In certain embodiments, the present method includes treating frontotemporal dementia. In certain embodiments, the method includes treating neurological disease that is associated with aberrant endosomal trafficking. In certain embodiments, the method includes treating neurological disease that is associated with aberrant lysosomal trafficking. In further embodiments, the present method includes treating a subject who has a $(GGGGCC)_n$ repeat expansion in the C9ORF72 gene. In further embodiments, the subject is haploinsufficient for C9ORF72. In further embodiments the present method includes treating patients who have a 50% or greater reduction in C9ORF72 protein activity. In further embodiments, the present method includes a C9ORF72 gene product that comprises a dipeptide repeat resulting from the $(GGGGCC)_n$ expansion. In further embodiments, the present method includes a gain-of-function or loss of function mutation resulting from the $(GGGGCC)_n$ expansion.

In another embodiment, the present method includes treatment wherein the pharmaceutical composition includes an effective dose of an inhibitor of glutamate receptors. In further embodiments, the present method includes the glutamate receptors NMDA, AMPA, and kainite. In further embodiments, the inhibitor of glutamate receptors is selected from the group consisting of AP5, CNQX, and NBQX. In certain embodiments, the present method includes treating amyotrophic lateral sclerosis. In certain embodiments, the present method includes treating frontotemporal dementia. In certain embodiments, the method includes treating neurological disease that is associated with aberrant endosomal trafficking. In certain embodiments, the method includes treating neurological disease that is associated with aberrant lysosomal trafficking. In further embodiments, the present method includes treating a subject who has a $(GGGGCC)_n$ repeat expansion in the C9ORF72 gene. In further embodiments, the subject is haploinsufficient for C9ORF72. In further embodiments the present method includes treating patients who have a 50% or greater reduction in C9ORF72 protein activity. In further embodiments, the present method includes a C9ORF72 gene product that comprises a dipeptide repeat resulting from the $(GGGGCC)_n$ expansion. In further embodiments, the present method includes a gain-of-function or loss of function mutation resulting from the $(GGGGCC)_n$ expansion.

In another embodiment, the present method includes identifying a compound for inhibiting motor neuron degeneration, the method comprising: a. reprogramming a cell into a pluripotent stem cell, wherein the cell is from a subject having a neurological disease; b. converting the pluripotent stem cell into a motor neuron cell; c. contacting the motor neuron cell with a candidate compound; d. determining whether the motor neuron cell degenerates; wherein if the motor neuron cell does not degenerate, the candidate compound is an inhibitor of motor neuron degeneration. In certain embodiments, the cell from a subject having a neurological disease is a lymphocyte. In further embodiments, the neurological disease is selected from the group consisting of amyloid lateral sclerosis, frontal temporal dementia, Alzheimer's, Parkinson's disease, multiple sclerosis, peripheral myopathy, Rasmussen's encephalitis, attention deficit hyperactivity disorder, autism, central pain syndromes, anxiety, and/or depression. In further embodiments, the cell from the subject having the neurological disease comprises a $(GGGGCC)_n$ hexanucleotide expansion in C9ORF72. In further embodiments, the number of GGGGCC repeats is at least 30. In certain embodiments, step (d) is performed via imaging analysis.

Figure 1A:
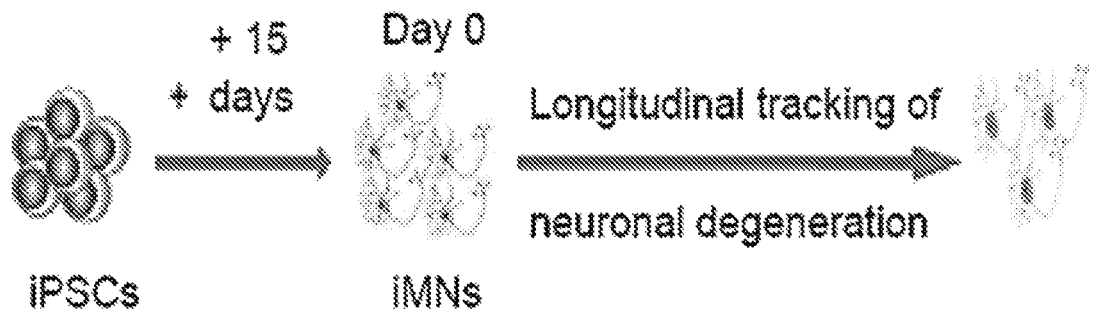
FIG. 1 shows that C9ORF72 patient iMNs undergo rapid neurodegeneration that can be rescued by C9ORF72 expression. a, The schematic shows the production of Hb9::RFP+ iMNs and subsequent survival tracking by time-lapse microscopy. b-d, The graphs show the survival of control and C9-ALS iMNs with neurotrophic factors (b) or in excess glutamate (shown in aggregate (c) or for each patient line (d)). e, The image shows iMNs at day 22 in excess glutamate. f-g, The graphs show the survival of control and C9-ALS iMNs in excess glutamate with glutamate receptor antagonists (f) or without neurotrophic factors (g). h, The graph shows survival of iMNs and induced dopaminergic (iDA) neurons in excess glutamate. Each trace includes neurons from at least 2 donors with the specified genotype; see full detail in Example 1. Scale bar: 100 μm (e). All survival experiments were analyzed by log-rank. *–p<0.05, –p<0.01, *–p<0.001. iMN survival experiments in (b-g) were performed in a Nikon Biostation and experiments in (h) were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.

Other aspects of the invention will become apparent by consideration of the detailed description and accompanying drawings.

DETAILED DESCRIPTION

Disclosed herein are methods for treating neurological diseases, such as amyotrophic lateral sclerosis and frontotemporal dementia. An intronic GGGGCC repeat expansion in C9ORF72 is the most common cause of amyotrophic lateral sclerosis (ALS) and frontotemporal dementia (FTD), but its pathogenic mechanism remains unclear. The repeat expansion reduces C9ORF72 expression and C9ORF72-associated activities, triggering neurodegeneration through two mechanisms. First, glutamate receptors accumulate on motor neurons (MNs) and spinal motor neurons in vivo, leading to glutamate-induced excitotoxicity due to neuronal hyperexcitability. Second, clearance of dipeptide repeat proteins generated from the expansion is impaired, enhancing their neurotoxicity. Thus, cooperativity between gain- and loss-of-function mechanisms leads to neurodegeneration.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," "may" and variants thereof, as used herein, are intended to be open-ended transitional phrases, terms, or words that do not preclude the possibility of additional acts or structures. The singular forms "a," "and"

and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

"Inhibit" as used herein refers to the ability to substantially antagonize, prohibit, prevent, restrain, slow, disrupt, alter, eliminate, stop, or reverse the progression or severity of the activity of a particular agent (e.g., infectious agent) or disease.

A "therapeutically effective amount," or "effective dosage" or "effective amount" as used interchangeably herein unless otherwise defined, means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of the estrogen receptor. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the drug may be administered at various times during the course of treatment of the subject. The times of administration and dosages used will depend on several factors, such as the goal of treatment (e.g., treating v. preventing), condition of the subject, etc. and can be readily determined by one skilled in the art.

As used herein, the term "treat" or "treating" a subject, such as a subject having a motor neuron disease, refers to administering a composition described herein to the subject, such that at least one symptom of a neurological disease is healed, alleviated, relieved, altered, remedied, reduced, ameliorated, or improved. Treating includes administering an amount effective to alleviate, relieve, alter, remedy, reduce, ameliorate, and/or improve one or more symptoms associated with motor neuron disease. The treatment may inhibit deterioration or worsening of a symptom associated with motor neuron disease. For example, treatment may alleviate or reduce pain associated with motor neuron disease.

"Haploinsufficiency" or "haploinsufficient" as used herein may refer to when a diploid organism has only a single functional copy of a gene (with the other copy inactivated or suppressed by mutation (e.g. expansion, deletion, substitution, etc.)) and the single functional copy does not produce enough of a gene product (typically a protein) to bring about a wild-type condition, leading to an abnormal or diseased state.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. METHODS OF TREATING NEUROLOGICAL DISEASES

The herein described methods of treatment may comprise administering to a subject in need thereof a composition comprising an effective amount of a compound that treats neurological diseases. The compound may decrease or inhibit neurodegeneration. The compound may decrease neuronal hyperexcitability. The compound may rescue, or compensate for, defects associated with a $(GGGGCC)_n$ repeat expansion in the C9ORF72 gene. For example, the compound may rescue any defect associated with haploinsufficiency of C9ORF72. The compound may increase C9ORF72 protein expression or increase C9ORF72 protein activity. The compound may increase C9ORF72 protein expression and increase C9ORF72 protein activity. The compound may rescue defects associated with altered C9ORF72 expression or C9ORF72 protein activity. "Altered" as used in this context may refer to an expression of the C9ORF72 gene or activity of the C9ORF72 protein that is different from the expression of the C9ORF72 gene or activity of C9ORF72 protein in a wild-type or disease free motor neuron. The compound may rescue defects associated with altered C9ORF72 expression and C9ORF72 protein activity. The compound may rescue defects associated with haploinsufficient RAB5, which may be associated with low levels of C9ORF72 protein expression and/or activity. The compound may be a kinase inhibitor, a potassium channel activator, a glutamate receptor inhibitor, or an endosomal and lysosomal trafficking modulator, for example. The compound may be a compound disclosed herein.

A 50% reduction in C9ORF72 activity, due to the presence of the $(GGGGCC)_n$ expansion, increases neurotransmission through the glutamate receptors NMDA, AMPA, and kainite. In addition, glutamate receptors accumulate on neurons. The increased neurotransmission and accumulation of glutamate receptors leads to glutamate-induced excitotoxicity due to the neuronal hyperexcitability. Inhibiting glutamate receptors would treat the neuronal hyperexcitability. Clearance of dipeptide repeat proteins generated from the expansion is impaired, enhancing their neurotoxicity. C9ORF72 promotes early endosomal trafficking through activation of RAB5, which requires phosphatidylinositol 3-phosphase (PI3P). PIKFYVE converts PI3P to phosphatidylinositol (3,5)-bisphosphate $(PI(3,5)P_2)$. Inhibiting PIKFYVE would compensate for altered RAB5 levels by increasing PI3P levels to enable early endosomal maturation, which would ultimately lead to the clearance of dipeptide repeat proteins. Neurons also use endosomal trafficking to regulate sodium and potassium ion channel localization. Inhibiting PIKFYVE may also treat neuronal hyperexcitability.

The compositions may be useful for treating neurological diseases in a subject related to altered C9ORF72 protein activity. Treatment of neurological diseases may be effected by rescuing defects associated with altered C9ORF72 protein activity in a subject, by administering a composition of the disclosure, either alone or in combination with another active agent as part of a therapeutic regimen to a subject in need thereof.

a. Composition

The composition may rescue defects associated with altered C9ORF72 protein activity. The composition may modulate endosomal trafficking or lysosomal biogenesis. The composition may inhibit kinase activity. The composition may inhibit PIKFYVE kinase. The PIKFYVE kinase inhibitor may be apilimod. The PIKFYVE kinase inhibitor may be YM201636. The PIKFYVE kinase inhibitor may be a combination of apilimod and YM201636.

In some embodiments, the composition may treat neuronal hyperexcitability. The composition may activate potassium channels. The composition may be retigabine. Additional examples would be a halogenated and/or fluorinated derivative of retigabine, mecleofenamic acid, diclofenac, and BMS-204352.

In other embodiments, the composition may be an inhibitor of glutamate receptors. The composition may inhibit glutamate receptor NMDA. The composition may inhibit glutamate receptor AMPA. The composition may inhibit kainite receptors. The inhibitor of glutamate receptors may be AP5. The inhibitor of glutamate receptors may be CNQX. The inhibitor of glutamate receptors may be NBQX. The inhibitor of glutamate receptors may be a combination of at least two inhibitors, selected from the group consisting of AP5, CNQX, and NBQX.

In some embodiments the composition may rescue defects associated with altered C9ORF72 protein activity and treat neuronal hyperexcitability.

b. Neurological Disease

A neurological disease is any disease that causes electrical, biochemical, or structural abnormalities in the brain, spine, or neurons. For example, a neurological disease may be a neurodegenerative disease. The neurodegenerative disease may result in motor neuron degeneration, for example. The neurological disease may be amyloid lateral sclerosis, Huntington's disease, Alzheimer's disease, or frontotemporal dementia, for example. Further examples of neurological diseases include, but are not limited to Parkinson's disease, multiple sclerosis, peripheral myopathy, Rasmussen's encephalitis, attention deficit hyperactivity disorder, autism, central pain syndromes, anxiety, and/or depression, for example.

The neurological disease may be associated with aberrant endosomal trafficking. For example, endosomal pathways and endosomes are necessary components for the recycling or breakdown of membrane-bound proteins, trafficking of golgi-associated proteins, and the extracellular release of proteins in exosomes. These processes aid neurotransmission and drive a balance between recycling and degradation of synaptic vesicles or neurotransmitter receptors, for example.

The neurological disease may be associated with aberrant lysosome degradation. Alterations in the lysosome degradation may be present in the neurological disease, such as a neurodegenerative disease. Cathepsin imbalance during aging and age-related diseases may provoke deleterious effects on CNS neurons and lysosomes may be sites for the unfolding and partial degradation of membrane proteins or their precursors that subsequently become expelled from a cell, or are released from dead cells and accumulate as pathological entities.

A health care professional may diagnose a subject as having a disease associated with motor neuron degeneration by the assessment of one or more symptoms of motor neuron degeneration. To diagnose a neurological disease, a physical exam may be followed by a thorough neurological exam. The neurological exam may assess motor and sensory skills, nerve function, hearing and speech, vision, coordination and balance, mental status, and changes in mood or behavior. Non-limiting symptoms of a disease associated with a neurological disease may be weakness in the arms, legs, feet, or ankles; slurring of speech; difficulty lifting the front part of the foot and toes; hand weakness or clumsiness; muscle paralysis; rigid muscles; involuntary jerking or writing movements (chorea); involuntary, sustained contracture of muscles (dystonia); bradykinesia; loss of automatic movements; impaired posture and balance; lack of flexibility; tingling parts in the body; electric shock sensations that occur with movement of the head; twitching in arm, shoulders, and tongue; difficulty swallowing; difficulty breathing; difficulty chewing; partial or complete loss of vision; double vision; slow or abnormal eye movements; tremor; unsteady gait; fatigue; loss of memory; dizziness; difficulty thinking or concentrating; difficulty reading or writing; misinterpretation of spatial relationships; disorientation; depression; anxiety; difficulty making decisions and judgments; loss of impulse control; difficulty in planning and performing familiar tasks; aggressiveness; irritability; social withdrawal; mood swings; dementia; change in sleeping habits; wandering; change in appetite.

Tests may be performed to rule diseases and disorders that may have symptoms similar to those of neurological diseases, measure muscle involvement, assess neuron degeneration. Non limiting examples of tests are electromyography (EMG); nerve conduction velocity study; laboratory tests of blood, urine, or other substances; magnetic resonance imaging (MRI); magnetic resonance spectroscopy; muscle or nerve biopsy; transcranial magnetic stimulation; genetic screening; x-rays; fluoroscopy; angiography; computed tomography (CT); positron emission tomography; cerebrospinal fluid analysis; intrathecal contrast-enhanced CT scan; electroencephalography; electronystagmography; evoked response; polysomnogram; thermography; and ultrasound. A health care professional may also assess the patient's family history of diseases associated with motor neuron degeneration and make a diagnosis in part based on a familial history of neurological diseases. A healthcare professional may diagnose a disease associated with neurological disease in a subject after the presentation of one or more symptoms.

1. NEURODEGENERATIVE DISEASE

Neurodegenerative diseases result in the progressive destruction of neurons that affects neuronal signaling. For example, a neurodegeneration may be amyotrophic lateral sclerosis, Alzheimer's disease, Huntington's disease, Friedreich's ataxia, Lewy body disease, Parkinson's disease, spinal muscle atrophy, primary lateral sclerosis, progressive muscle atrophy, progressive bulbar palsy, and pseudobulbar palsy.

(i) Motor Neuron Degeneration

Diseases associated with motor neuron degeneration may be a condition that results in the progressive destruction of motor neurons that interferes with neuronal signaling to the muscles, leading to muscle weakness and wasting. In healthy individuals, upper motor neurons transmit signals from the brain to lower motor neurons in the brain stem and spinal cord, which then transmit the signal to the muscles to result in voluntary muscle activity. The destruction of upper and lower motor neurons affects activity such as breathing, talking, swallowing, and walking, and overtime these functions can be lost. Examples of motor neuron diseases include, but are not limited to, amyotrophic lateral sclerosis, primary lateral sclerosis, progressive muscle atrophy, progressive bulbar palsy, and pseudobulbar palsy. The etiology of disease associated with motor neuron degeneration has not been fully elucidated and has been attributed to genetic factors and sporadic cases.

2. NEURONAL HYPEREXCITABILITY

Neuronal hyperexcitability may occur when receptors for the excitatory neurotransmitter glutamate (glutamate receptors) such as the NMDA receptor and AMPA receptor are over-activated by excess glutamate or by other compounds or neurotransmitters acting on the glutamate receptors. Excitotoxicity may result from neuronal hyperexcitability. Excitotoxicity is the pathological process by which nerve cells are damaged or killed by excessive stimulation. The excessive stimulation allows high levels of calcium ions ($Ca^{2+}$) to enter the cell. $Ca^{2+}$ influx into cells activates a number of enzymes, including phospholipases, endonucleases, and proteases such as calpain. These enzymes can damage cell structures such as components of the cytoskeleton, membrane, and DNA.

Neuronal hyperexcitability may be involved in spinal cord injury, stroke, traumatic brain injury, hearing loss (through noise overexposure or ototoxicity), epilepsy, painful neuropathies, attention deficit hyperactivity disorder, autism, central pain syndromes, neurodegenerative diseases, multiple sclerosis, Alzheimer's disease, amyotrophic lateral sclerosis (ALS), Parkinson's disease, frontotemporal dementia, schizophrenia, Rasmussen's encephalitis, Huntington's disease, alcoholism or alcohol withdrawal and especially over-rapid benzodiazepine withdrawal, and also Huntington's disease. Other common conditions that cause excessive glutamate concentrations around neurons are hypoglycemia. Blood sugars are the primary glutamate removal method from inter-synaptic spaces at the NMDA and AMPA receptor site.

c. PIKFYVE

PIKFYVE, also known in the art as phosphatidylinositol-3-phosphate 5-kinase type III or PIPKIII, is a FYVE finger-containing phosphoinositide kinase encoded by the PIKFYVE gene. PIKFYVE is a highly evolutionarily conserved lipid kinase and also has protein kinase activity, which regulates endomembrane homeostasis and plays a role in the biogenesis of endosome carrier vesicles from early endosomes. PIKFYVE-mediated conversion of PI3P to PI(3,5)P$_2$ blocks recruitment of the protein EEA1. The recruitment is blocked, because PIP3 is needed to form a platform with RAB5 that enables anchoring of EEA1 to early endosomes. EEA1 then drives fusion with endocytic and other endosomal vesicles. Mutations in PIKFYVE are known to lead to Francois-Neetens corneal fleck dystrophy. Disruption of both Pikfyve alleles is embryonic lethal in mice at the pre-implantation state of the embryo. A link between type 2 diabetes and PIKFYVE is inferred by the observations that PIKFYVE perturbation inhibits insulin-regulated glucose uptake.

d. PIKFYVE Kinase Inhibitor

The PIKFYVE kinase inhibitor may inhibit or suppress the kinase activity of PIKFYVE. The PIKFYVE kinase inhibitor may be any PIKFYVE kinase inhibitor such as, for example, Apilimod or YM201636 (6-Amino-N-(3-(4-(4-morpholinyl)pyrido[3'2':4,5]furo[3,2-d]pyrimidin-2-yl)phenyl)-3-pyridinecarboxamide).

e. Glutamate Receptors

Glutamate receptors are synaptic receptors located primarily on the membranes of neuronal cells. Glutamate is abundant in the human body, but particularly in the nervous system and especially prominent in the human brain where it is the body's most prominent neurotransmitter, the brain's main excitatory neurotransmitter, and also the precursor for GABA, the brain's main inhibitory neurotransmitter. Glutamate receptors are responsible for the glutamate-mediated postsynaptic excitation of neural cells, and are important for neural communication, memory formation, learning, and regulation. Glutamate receptors can be divided into two groups according to the mechanism by which their activation gives rise to a postsynaptic current. Ionotropic glutamate receptors (iGluRs) form the ion channel pore that activates when glutamate binds to the receptor. Metabotropic glutamate receptors (mGluRs) indirectly activate ion channels on the plasma membrane through a signaling cascade that involves G proteins. Ionotropic receptors tend to be quicker in relaying information, but metabotropic ones are associated with a more prolonged stimulus. This is due to the usage of many different messengers to carry out the signal, but since there is a cascade, just one activation of a G-protein can lead to multiple activations. Glutamate receptors are usually not specifically geared towards glutamate exclusively as the ligand and sometimes even requires another agonist. Examples of glutamate receptors include, but are not limited to, NMDA, AMPA, and kainite receptors.

f. Glutamate Receptor Inhibitor

Glutamate receptor inhibitors are a type of compound that may prevent the transfer of electrical signals between neurons in the brain and in the spinal cord by preventing the passage of glutamate. Examples of glutamate receptor inhibitors include, but are not limited to, AP5 ((2R)-amino-5-phosphonovaleric acid; (2R)-amino-5-phosphonopentanoate), CNQX (6-cyano-7-nitroquinoxaline-2,3-dione), and NBQX (2,3-dihydroxy-6-nitro-7-sulfamoyl-benzo[f]quinoxaline-2,3-dione).

g. Potassium Channel

Potassium channels function to conduct potassium ions down their electrochemical gradient, doing so both rapidly (up to the diffusion rate of K+ ions in bulk water) and selectively (excluding, most notably, sodium despite the sub-angstrom difference in ionic radius). Biologically, these channels act to set or reset the resting potential in many cells. In excitable cells, such as neurons, the delayed counter-flow of potassium ions shapes the action potential. Potassium channels have a tetrameric structure in which four identical protein subunits associate to form a fourfold symmetric (C4) complex arranged around a central ion conducting pore (i.e., a homotetramer). Alternatively four related but not identical protein subunits may associate to form heterotetrameric complexes with pseudo C4 symmetry. All potassium channel subunits have a distinctive pore-loop structure that lines the top of the pore and is responsible for potassium selective permeability.

h. Potassium Channel Activator

Potassium channel activators are a type of compound that facilitates ion transmission through potassium channels. An example of a potassium channel activator includes, but is not limited to, retigabine (also may be known as ezogabine and D-23129), a halogenated and/or fluorinated derivative of retigabine, meclofenamic acid, and diclofenac.

i. C9ORF72

The C9ORF72 gene, which may also be known as chromosome 9 open reading frame 72, FTDALS1, ALSFTD, and FTDALS, is located on the short (p) arm of chromosome 9 at position 21.2. C9ORF72 is a 481 amino acid protein with a molecular mass of 54328 Da, which may undergo post-translational modifications of ubiquitination and phosphorylation. The expression levels of C9ORF72 may be highest in the central nervous system and the protein localizes in the cytoplasm of neurons as well as in presynaptic terminals. C9ORF72 plays a role in endosomal and lysosomal trafficking regulation and has been shown to interact with RAB proteins that are involved in autophagy and endocytic transport. C9ORF72 activates RAB5, a GTPase that mediates early endosomal trafficking. Mutations in C9ORF72 have been associated with ALS and FTD. The GGGGCC repeat expansion $((GGGGCC)_n)$ in C9ORF72 may be present in subjects suffering from a neurological disease. For example, $(GGGGCC)_n$ hexanucleotide expansion is the most common cause of amyotrophic lateral sclerosis (ALS) and frontotemporal dementia (FTD), accounting for about 10% of each worldwide. The $(GGGGCC)_n$ hexanucleotide expansion may be located between exons 1a and 1b of C9ORF72. The $(GGGGCC)_n$ hexanucleotide expansion may be present in a neurological disease, wherein n is greater than 25, wherein n is greater than 30, wherein n is greater than 35, wherein n is greater than 40, wherein n is greater than 45, wherein n is greater than 50, wherein n is greater than 55, wherein n is greater than 60, wherein n is greater than 65, or wherein n is greater than 70, for example. n may be between 25 and 100, between 29 and 95, between 30 and 90, between 35 and 85, between 40 and 80, between 45 and 75, between 50 and 70, between 55 and 65, or between 55 and 60, for example.

3. MODES OF ADMINISTRATION

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. The following formulations and methods are merely exemplary and are in no way limiting. The pharmaceutical composition optionally may be sterile.

Formulations suitable for oral administration may comprise (a) liquid solutions, such as an effective amount of the active ingredient (i.e., PIKFYVE inhibitor, potassium channel activator, glutamate receptor inhibitor, endosomal and lysosomal trafficking modulator, or the metabolite thereof) dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms may comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which may contain anti-oxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. The formulations may be presented in unit-dose or multi-dose sealed containers, such as ampules and vials, and may be stored in a freeze-dried (lyophilized) condition requiring only the addition of the sterile liquid excipient, for example, water, for injections, immediately prior to use. Extemporaneous injection solutions and suspensions may be prepared from sterile powders, granules, and tablets of the kind previously described.

Formulations suitable for topical administration of PIKFYVE inhibitor, potassium channel activator, glutamate receptor inhibitor, endosomal and lysosomal trafficking modulator, or metabolite thereof, may include liquids, ointments, creams, gels, pastes, powders, transdermal patches, microneedles, and sprays. The active component may be admixed under sterile conditions with a physiologically acceptable carrier and any preservatives, buffers, propellants, or absorption enhancers as may be required.

Additionally, PIKFYVE inhibitor, potassium channel activator, glutamate receptor inhibitor, or metabolite thereof, may be formulated into suppositories by mixing with a variety of bases such as emulsifying bases or water-soluble bases.

a. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present disclosure. The above combinations include combinations of a compound of the present disclosure not only with one other active compound, but also with two or more other active compounds. For example, the compound of the disclosure may be combined with a variety of drugs to treat neurological diseases.

The disclosed compounds can be combined with the following, but are not limited, anticholinergic drugs, anticonvulsants, antidepressants, benzodiazepines, decongestants, muscle relaxants, pain medications, and/or stimulants.

Additional types of therapy and treatment include, but are not limited to digital communication devices, feeding tubes, mechanical ventilation, nutritional support, deep brain stimulation, occupational therapy, physical therapy, and/or speech therapy.

4. PHARMACEUTICAL COMPOSITIONS

The disclosed composition(s) may be incorporated into a pharmaceutical composition suitable for administration to a subject (such as a patient, which may be a human or non-human). The pharmaceutical compositions may comprise a carrier (e.g., a pharmaceutically acceptable carrier). Any suitable carrier can be used within the context of the invention, and such carriers are well known in the art. The choice of carrier will be determined, in part, by the particular use of the composition (e.g., administration to an animal) and the particular method used to administer the composition. Accordingly, there is a wide variety of suitable formulations of the composition of the present invention.

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of the present disclosure, may be about 0.1 mg/kg to about 1000 mg/kg, about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg. A skilled practitioner, such as a physician, e.g., a neurologist can readily determine optimal dosage levels. The compound may be administered once per day, twice per day, once per week, or at a timing prescribed by a skilled artisan. The skilled artisan will appreciate that certain factors influence dosage and timing required to effectively treat a patient, including but not limited to the severity of the disease, previous treatments, the general health of the patient, the age of the patient, and other diseases present.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

The compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active compound and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which may be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants may be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration may have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds may be topically administered. Topical compositions that may be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound, and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

5. SCREENING METHODS

Disclosed herein are methods for identifying compounds capable of treating a neurological disease. The identified compounds may be capable of compensating for defective C9ORF72 protein activity. In certain aspects, screening for such compounds may be accomplished by contacting a motor neuron cell from a subject with a neurological disease with a test compound and determining whether the motor neuron cell degenerates. If the motor neuron cell does not degenerate, the test compound is a candidate compound that may be capable of reducing or inhibiting motor neuron degeneration. The motor neuron cell may be derived from a pluripotent stem cell. The pluripotent stem cell may have been reprogrammed from a cell from the subject. The cell from the subject may be a somatic cell, for example. The somatic cell may be a fibroblast, a lymphocyte, or a keratinocyte, for example. The assessment of whether a motor neuron cell degenerates or not may be based on a comparison to a control. In some embodiments, the control level may be a predetermined or reference value, which is employed as a benchmark against which to assess the measured and/or visual result. The predetermined or reference value may be a level in a sample (e.g. motor neuron cell) from a subject not suffering from a neurological disease or from a sample from a subject suffering from a neurological disease but wherein the motor neuron cell is not contacted with the test compound. The predetermined or reference value may be a level in a sample from a subject suffering from a neurological disease. In any of these screening methods, the cell from the subject having the neurological disease may comprise the $(GGGGCC)_n$ hexanucleotide expansion in C9ORF72.

The level of activity of a motor neuron may also be determined by measuring the action potential of the motor neuron. Action potentials can be measured by patch clamp recording, for example. The motor neuron may be analyzed visually (e.g. image analysis).

In vivo testing of candidate compounds may be conducted by means known to one of ordinary skill in the art. For example, the candidate compound(s) may be administered to a mammal, such as a mouse or a rabbit. The mammal may be administered, by any route deemed appropriate, a dose of a candidate compound. Conventional methods and criteria can then be used to monitor animals for signs of reduction or improvement of motor neuron activity. If needed, the results obtained in the presence of the candidate compounds can be compared with results in control animals that are not treated with the candidate compound. Dosing studies may be performed in, or in conjunction with, the herein described methods for identifying compounds capable of treating a neurological disease and/or any follow-on testing of candidate compounds in vivo. One of skill in the art of medicine may determine the appropriate dosage of a pharmaceutical compound. The dosage may be determined by monitoring the subject for signs of disease inhibition or amelioration. The dosage may be increased or decreased to obtain the desired frequency of treatment. The toxicity and efficacy of a pharmaceutical compound may be determined by standard pharmaceutical procedures in cell cultures or experimental animals, e.g. determining the lethal dose to 50% of the population (LD50) and the dose therapeutically effective in 50% of the population (ED50). The dose ratio of LD50/ED50 is the therapeutic index and, indicating the ratio between the toxic and therapeutic effects. A compound with a high therapeutic index is preferred for administration to a subject. A delivery system may be designed to help prevent toxic side effects, by delivering the compound to specific targets, e.g., delivered specifically to motor neurons. The optimal dose of the compound may be determined based on results of clinical electrophysiology or electromyography to analyze excitability in peripheral nerves, for example. One of skill in the art would know how to adjust the dose in response to the amelioration of neuronal hyperexcitability or the increase in hyperexcitability, for example.

The dosage for use in humans may be determined by evaluating data obtained from animal studies and cell culture assays. The preferred dosage will have little or no toxicity and include the ED50. The dosage may vary depending on the dosage form and route of administration. For any compound used in the methods described herein, the dosage may be estimated initially in cell culture. A dose may be formulated in animal models to determine the a circulating plasma concentration range that that includes the concentration of the test compound which achieves a half maximal inhibition of symptoms (LD50) as determined in cell culture. Such information obtained from cell cultures and animal models may be used to more accurately determine useful doses in humans. Levels of the compound in plasma may be determined by, for example, high performance liquid chromatography.

The present invention has multiple aspects, illustrated by the following non-limiting examples.

6. EXAMPLES

Example 1

Materials and Methods iPSC reprogramming experiments were performed using human lymphocytes from healthy subjects and ALS patients that were obtained from the NINDS Biorepository at the Coriell Institute for Medical Research and reprogrammed into iPSCs as previously described using episomal vectors (Okita et al. *Nat Methods* 8: 409-412 (2011)). Briefly, mammalian expression vectors containing Oct4, Sox2, Klf4, L-Myc, Lin28, and a p53 shRNA were introduced into the lymphocytes using the Adult Dermal Fibroblast NUCLEOFECTOR™ Kit and NUCLEOFECTOR™ 2b Device (Lonza) according to the manufacturer's protocol. The cells were then cultured on mouse feeders until iPSC colonies appeared. The colonies were then expanded and maintained on Matrigel (BD) in mTeSR1 medium (Stem Cell Technologies).

Repeat Primed PCR (RP-PCR) was performed to provide a quantitative measure of $(GGGGCC)_n$ hexanucleotide expansion in C9ORF72, 100 ng of genomic DNA was amplified by touchdown PCR using primers shown in Table 1, in a 28-μl PCR reaction consisting of 0.2 mM each of 7-deaza-2-deoxyguanine triphosphate (deaza-dGTP) (NEB), dATP, dCTP and dTTP, 7% DMSO, 1× Q-Solution, 1× Taq PCR buffer (Roche), 0.9 mM $MgCl_2$, 0.7 μM reverse primer (four GGGGCC repeats with an anchor tail), 1.4 μM 6FAM-fluorescently labeled forward primer, and 1.4 μM anchor primer corresponding to the anchor tail of reverse primer (Table 1). During the PCR, the annealing temperature was gradually decreased from 70° C. and 56° C. in 2° C. increments with a 3 min extension time for each cycle. The PCR products were purified using the QiaQuick PCR purification kit (Qiagen) and analyzed using an ABI3730 DNA ANALYZER AND PEAK SCANNER™ Software v1.0 (Life Technologies).

TABLE 1

Primers, probes and single guide RNAs (sgRNAs) used in this study.

| | | |
|---|---|---|
| RP-PCR primer, Forward | 5'-6FAM-TGTAAAACGACGGCCAGTCAAGGAGGGAAACAACCGCAGCC | SEQ ID NO: 1 |
| RP-PCR primer, Reverse-1 | 5'-CAGGAAACAGCTATGACC | SEQ ID NO: 2 |
| RP-PCR primer, Reverse-2 | 5'-CAGGAAACAGCTATGACCGGGCCCGCCCCGACCACGCCCCGGCCCCGGCCCCGG | SEQ ID NO: 3 |
| Primer for generating Southern probe, Forward | 5'-AGAACAGGACAAGTTGCC | SEQ ID NO: 4 |
| Primer for generating Southern probe, Reverse | 5'-AACACACACCTCCTAAACC | SEQ ID NO: 5 |
| Genotyping primers for C9ORF72 exon 2, Forward | 5'-CCCACACCTGCTCTTGCTAGACC | SEQ ID NO: 6 |
| Genotyping primers for C9ORF72 exon 2, Forward | 5'-CCCACACCTGCTCTTGCTAGACC | SEQ ID NO: 7 |

TABLE 1-continued

Primers, probes and single guide RNAs (sgRNAs) used in this study.

| Description | Sequence | SEQ ID NO |
|---|---|---|
| qRT-PCR primer for C9ORF72, transcriptional variants 1,3, Forward | 5'-GTAACCTACGGTGTCCCGCTAGG | SEQ ID NO: 8 |
| qRT-PCR primer for C9ORF72, transcriptional variants 1,3, Reverse | 5'-CCCACACCTGCTCTTGCTAGACC | SEQ ID NO: 9 |
| qRT-PCR primer for C9ORF72, transcriptional variants 2, Forward | 5'-GTGGCGAGTGGATATCTCCGGA | SEQ ID NO: 10 |
| qRT-PCR primer for C9ORF72, transcriptional variants 2, Reverse | 5'-TGGAGCCCAAATGTGCCTTACTC | SEQ ID NO: 11 |
| qRT-PCR primer for GAPDH, Forward | 5'-CGAGATCCCTCCAAAATCAA | SEQ ID NO: 12 |
| qRT-PCR primer for GAPDH, Reverse | 5'-GTCTTCTGGGTGGCAGTGAT | SEQ ID NO: 13 |
| qRT-PCR primer for NMDAR1, Forward | 5'-CCAGCGTGTGGTTTGAGATG | SEQ ID NO: 14 |
| qRT-PCR primer for NMDAR1, Reverse | 5'-TTCTCTGCCTTGGACTCACG | SEQ ID NO: 15 |
| sgRNA-1 targeting upstream of repeat expansion | 5'-GUAACCUACGGUGUCCCGCU | SEQ ID NO: 16 |
| sgRNA-2a targeting downstream of repeat expansion (+ strand) | 5'-GGGGUUCGGCUGCCGGGAAG | SEQ ID NO: 17 |
| sgRNA-2b targeting downstream of repeat expansion (- strand) | 5'-ACCCCAAACAGCCACCCGCC | SEQ ID NO: 18 |
| sgRNA-3 targeting C9ORF72 exon 2 | 5'-UUAACACAUAUAAUCCGGAA | SEQ ID NO: 19 |
| sgRNA-4 targeting C9ORF72 exon 2 | 5'-CACCACUCUCUGCAUUUCGA | SEQ ID NO: 20 |

C9ORF72 Southern Blotting was performed using a 241-bp digoxigenin (DIG)-labeled probe was generated from 100 ng control genomic DNA (gDNA) by PCR reaction using Q5® High-Fidelity DNA Polymerase (NEB) with primers shown in Table 1. Genomic DNA was harvested from control and patient iPSCs using cell lysis buffer (100 mM Tris-HCl pH 8.0, 50 mM EDTA, 1% w/v sodium dodecyl sulfate (SDS)) at 55° C. overnight and performing phenol:chloroform extraction. A total of 25 µg of gDNA was digested with XbaI at 37° C. overnight, run on a 0.8% agarose gel, then transferred to a positive charged nylon membrane (Roche) using suction by vacuum and UV-cross-linked at 120 mJ. The membrane was pre-hybridized in 25 ml DIG EasyHyb solution (Roche) for 3 hrs at 47° C. then hybridized at 47° C. overnight in a shaking incubator, followed by two 5-min washes each in 2× Standard Sodium Citrate (SSC) and in 0.1% SDS at room temperature, and two 15-min washes in 0.1×SSC and in 0.1% SDS at 68° C. Detection of the hybridized probe DNA was carried out as described in DIG System User's Guide. CDP-STAR® Chemilumnescent Substrate (Sigma-Aldrich) was used for detection and the signal was developed on X-ray film (Genesee Scientific) after 20 to 40 min.

To perform molecular cloning and viral production, complementary DNAs (cDNAs) for the iMN factors (Ngn2, Lhx3, Isl1, NeuroD1, Ascl1, Myt1l, and Brn2) and iDA neuron factors (Ascl1, Brn2, Myt1l, Lmx1a, and Foxa2), were purchased from Addgene. cDNA for C9ORF72 was purchased from Thermo Scientific. Each cDNA was cloned into the pMXs retroviral expression vector using Gateway cloning technology (Invitrogen). The Hb9::RFP lentiviral vector was also purchased from Addgene (ID: 37081). Viruses were produced as follows. HEK293 cells were transfected at 80-90% confluency with viral vectors containing genes of interest and viral packaging plasmids (PIK-MLV-gp and pHDM for retrovirus; pPAX2 and VSVG for lentivirus) using polyethylenimine (PEI)(Sigma-Aldrich). The medium was changed 24 h after transfection. Viruses were harvested at 48 h and 72 hrs after transfection. Viral supernatants were filtered with 0.45 µM filters, incubated with Lenti-X concentrator (Clontech) for 24 hrs at 4° C., and centrifuged at 1,500×g at 4° C. for 45 min. The pellets were resuspended in 300 µl DMEM+10% FBS and stored at −80° C.

To perform the conversion of iPSCs into induced motor neurons and dopaminergic neurons, the reprogramming was performed in 96-well plates (8×10$^3$ cells/well) or 13 mm plastic coverslips (3.2×10$^4$ cells/coverslip) that were sequentially coated with gelatin (0.1%, 1 hour) and laminin (2-4 hrs) at room temperature. To enable efficient expression of the transgenic reprogramming factors, iPSCs were cultured in fibroblast medium (DMEM+10% FBS) for at least 48 hrs and either used directly for retroviral transduction or passaged before transduction for each experiment. 7 iMN factors or 5 iDA factors were added in 100-200 µl fibroblast medium per 96-well well with 5 µg/ml polybrene. For iMNs, cultures were transduced with lentivirus encoding the Hb9::RFP reporter 48 hrs after transduction with transcription factor-encoding retroviruses. On day 5, primary mouse cortical glial cells from P1 ICR pups (male and female) were added to the transduced cultures in glia medium containing MEM (Life Technologies), 10% donor equine serum (HyClone), 20% glucose (Sigma-Aldrich), and 1% penicillin/streptomycin. On day 6, cultures were switched to N3 medium containing DMEM/F12 (Life Technologies), 2% FBS, 1% penicillin/streptomycin, N2 and B27 supplements (Life Technologies), 7.5 µM RepSox (Selleck), and 10 ng/ml each of GDNF, BDNF, and CNTF (R&D). The iMN and iDA neuron cultures were maintained in N3 medium, changed every other day, unless otherwise noted.

To perform immunocytochemistry, iMNs were fixed in 4% paraformaldehyde (PFA) for 1 h at 4° C., permeabilized with 0.5% PBS-T overnight at 4° C., blocked with 10% FBS in 0.1% PBS-T at room temperature for 2 h, and incubated with primary antibodies at 4° C. overnight. Cells were then washed with 0.1% PBS-T and incubated with ALEXA FLUOR® secondary antibodies (Life Technologies) in blocking buffer for 2 hrs at room temperature. To visualize nuclei, cells were stained with DAPI (Life Technologies) then mounted on slides with VECTASHIELD® (Vector Labs). Images were acquired on a LSM 780 confocal microscope (Zeiss). The following primary antibodies were used: mouse anti-HB9 (Developmental Studies Hybridoma Bank); mouse anti-TUJ1 (EMD Millipore); rabbit anti-VACHT (Sigma); rabbit anti-C9ORF72 (Sigma-Aldrich); mouse anti-EEA1 (BD Biosciences); mouse anti-RAB5 (BD Biosciences); mouse anti-RAB7 (GeneTex); mouse anti-LAMP1 (Abcam); rabbit anti-GluR1 (EMD Millipore); mouse anti-GluR1 (Santa Cruz); rabbit anti-NR1 (EMD Millipore); mouse anti-NR1 (EMD Millipore); chicken anti-GFP (GeneTex). For detection of surface-bound glutamate receptors, iMNs were directly blocked without permeabilization and incubated with an antibody recognizing the extracellular domain of NR1 or GLUR1 at 4° C. overnight. In order to detect internalized glutamate receptors, permeabilization was performed with 0.5% PBS-T before incubation with primary antibodies. To analyze both surface and total receptor in the same sample, surface staining was performed first, followed by washing with 0.1% PBS-T, permeabilization, and incubation with the second primary antibody for receptor staining. To detect levels of internalized glutamate receptors and measure their co-localization with RAB7, neurons were first treated with 50 µM NMDA for 20 min before fixation to enhance NMDA receptor endocytosis.

To perform whole cell patch clamp electrophysiology, whole cell membrane potential and current recordings in voltage- and current-clamp configurations were made using an EPC9 patch clamp amplifier controlled with PatchMaster software (HEKA Electronics). Voltage- and current-clamp data was acquired at 50 kHz and 20 kHz, respectively, with a 2.9 kHz low-pass Bessel filter, while spontaneous action potential recordings were acquired at 1 kHz sampling frequency. For experiments, culture media was exchanged with warm extracellular solution consisting of (in mM): 140 NaCl, 2.8 KCl, 10 HEPES, 1 MgCl$_2$, 2 CaCl$_2$, and 10 glucose, with pH adjusted to 7.3 and osmolarity adjusted to 305 mOsm. Glass patch pipettes were pulled on a Narishige PC-10 puller and polished to 5-7 MΩ resistance. Pipettes were also coated with Sylgard 184 (Dow Corning) to reduce pipette capacitance. The pipette solution consisted of (in mM): 130 K-gluconate, 2 KCl, 1CaCl$_2$, 4 MgATP, 0.3 GTP, 8 phosphocreatine, 10 HEPES, 11 EGTA, adjusted to pH 7.25 and 290 mOsm. Pipettes were sealed to cells in GΩ-resistance whole cell configuration, with access resistances typically between 10-20 MΩ, and leakage currents less than 50 pA. Capacitance transients were compensated automatically through software control. For voltage clamp, cells were held at −70 mV. For Current-voltage traces, a P/4 algorithm was used to subtract leakage currents from the traces. Measurements were taken at room temperature (approximately 20-25° C.). Data was analyzed and plotted in Igor Pro 6 (WaveMetrics) using Patcher's Power Tools plug-in and custom programmed routines. Current density was obtained by dividing the measured ion channel current by the cell capacitance. For control iMNs, 10/10 tested fired action potentials. For C9-ALS iMNs, 9/10 tested fired action potentials.

To perform multielectrode array recordings, local field potentials (LFPs) were recorded from iPSC-derived motor neurons on days 17-21 in culture in 6-well multielectrode chips (9 electrodes and 1 ground per well) using a Multi-Channel Systems MEA-2100 multielectrode array (MEA) amplifier (ALA Scientific) with built-in heating elements set to 37° C. Cells were allowed to acclimate for 5 minutes after chips were placed into the MEA amplifier, and after glutamate addition (10 µM final concentration). For 1 µM apilimod treatments, chips were incubated for 35 min in a humidified incubator in the presence of the particular drug, then returned to the MEA amplifier and acclimated for 5 min before beginning recordings. For each condition, recordings (5 min baseline, 10 min glutamate and/or drug, 40 kHz sampling rate) were filtered between 1-500 Hz, and average LFP frequency per well was determined using the accompanying MC Rack software.

Figure 8A:
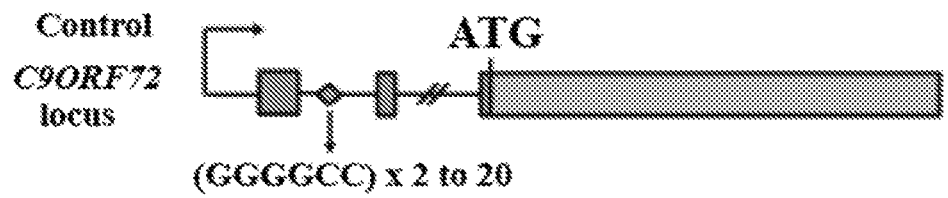
FIG. 8 shows the generation of functional motor neurons from controls and C9ORF72 patients. a, The schematic shows the C9ORF72 locus in healthy controls and C9ORF72-ALS (C9-ALS) patients. b, The schematic shows the conversion of patient iPSCs into iMNs. iPSC, induced pluripotent stem cell; iMN, induced motor neuron. c-d, The images show through immunocytochemistry that iMNs express the Hb9::RFP reporter (red, c, d), TUJ1 (yellow, c, d), HB9 (green, c) and vesicular acetylcholine transporter (VACHT) (green, d). Nuclei (blue) are labeled with Hoechst. Scale bars: 10 μm. e, The graph shows the number of control and C9-ALS iMNs generated per 0.5 mm2 of culture dish area (mean of 2 biological replicates±s.d., n>23 cells per replicate). f, The graph shows the representative quantification of iMN generation (CTRL1), showing the amount of HB9+ cells as a proportion of HB9::RFP+ cells, or of DAPI-staining nuclei, or of MAP2+ cells (mean of 3 biological replicates±s.d., n>20 cells per replicate). g-i, The graphs show sample patch clamp recordings showing that iMNs possess functional sodium and potassium channels (g) and fire action potentials spontaneously (h) or in response to a current injection (i). j, The graph shows channel rhodopsin-transduced iMNs actuate contractions of primary chick embryonic muscle (top) in response to light (bottom).
Figure 8A:
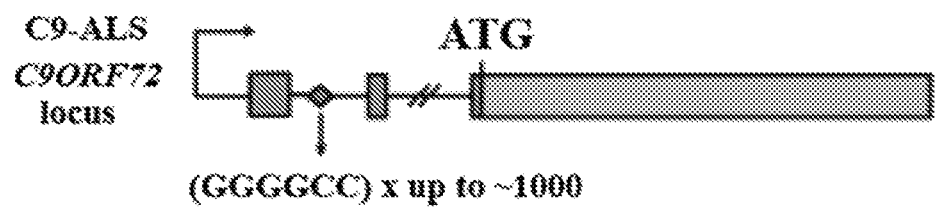
Figure 8B:
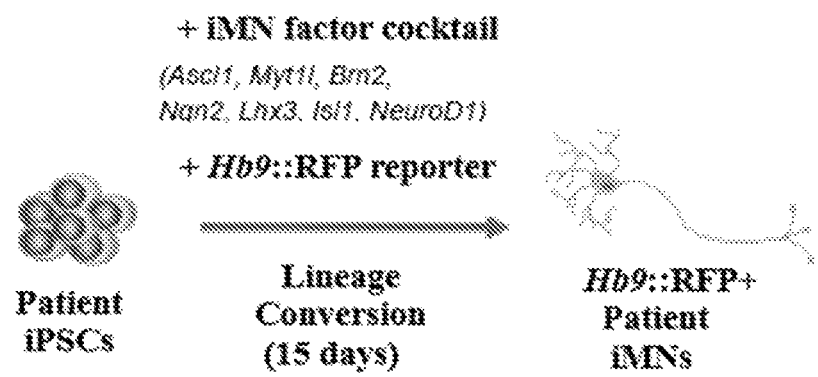
Figure 8C:
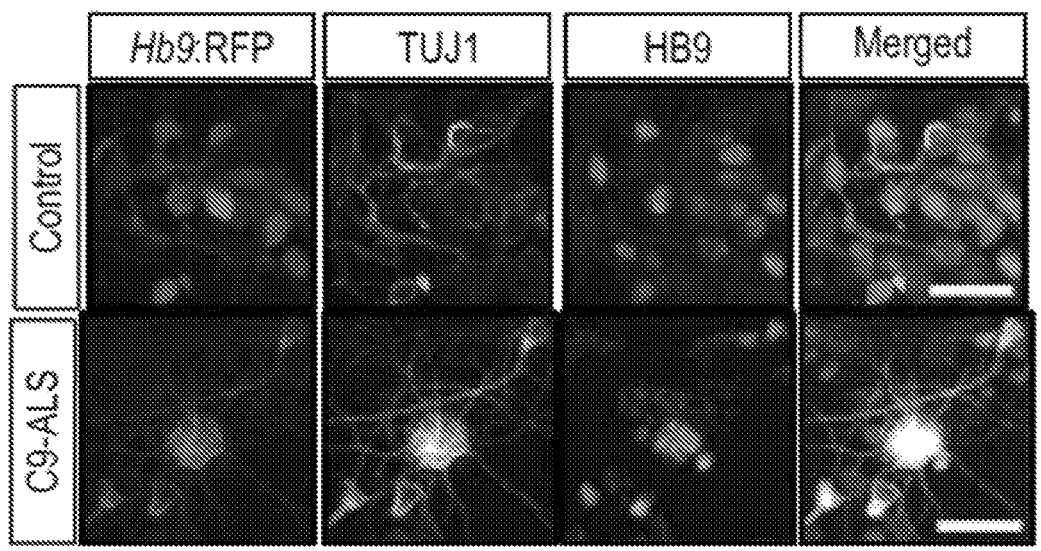
Figure 8D:
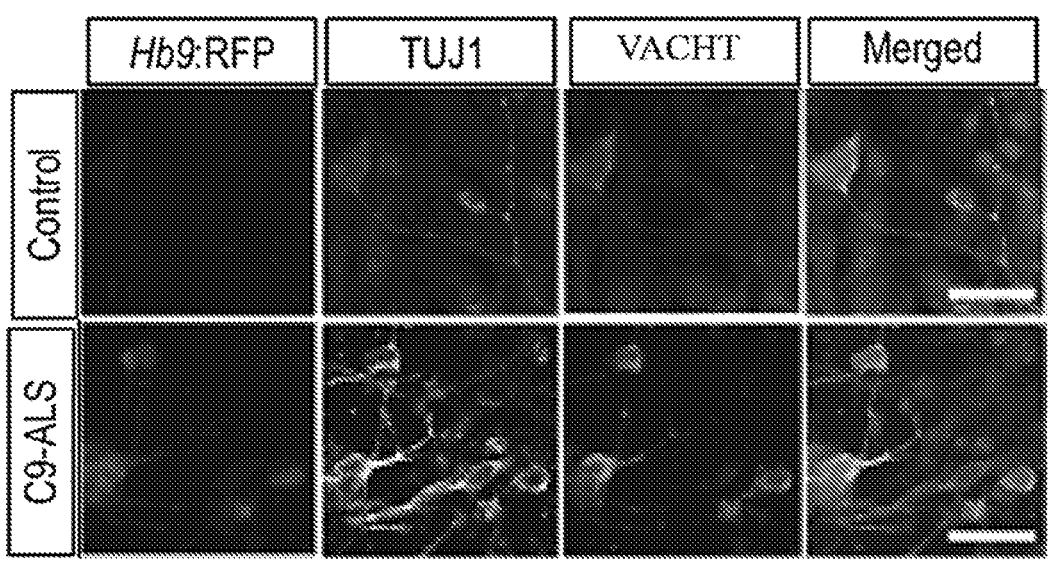

To perform neuromuscular junction assays, primary chick myoblasts were dissected from D11 chick embryos and plated onto plastic dishes pre-coated with 0.1% gelatin. After 3 days of culture in muscle medium containing F10 (Life Technologies), 10% horse serum, 5% chicken serum (Life Technologies), 0.145 mg/ml CaCl$_2$ (Sigma), and 2% Penicillin/Streptomycin, myoblasts were trypsinized and replated onto iMNs which were at days 15-18 post-transduction. The co-culture was maintained in neuronal medium containing DMEM/F12, 2% B27, 1% GlutaMax, and 1% Penicillin/Streptomycin, supplemented with 10 ng/ml BDNF, GDNF, and CNTF for 7 days in order to allow neuromuscular junctions to form. Light-stimulated contraction shown in FIG. 8*j* are representative of contraction observed in 2 biological replicates, with 5 contractile sites per replicate.

To perform induced neuron survival assays, Hb9::RFP$^+$ iMNs appeared between days 13-16 after retroviral transduction and RepSox was removed at day 17, then the survival assay was initiated. For the glutamate treatment conditions, 10 μM glutamate was added to the culture medium on day 17 and removed after 12 hrs. Cells were then maintained in N3 medium with neurotrophic factors without RepSox. For the glutamate treatment conditions with glutamate receptor antagonists, cultures were co-treated with 10 μM MK801 and CNQX, and 2 μM Nimodipine during the 12 hr glutamate treatment. The antagonists were maintained for the remainder of the experiment. For the neurotrophic factor withdrawal condition, BDNF, GDNF, and CNTF were removed from the culture medium starting at day 17. Longitudinal tracking was performed by imaging neuronal cultures in a Nikon Biostation CT or Molecular Devices ImageExpress once every 24 hrs starting at day 17. Tracking of neuronal survival was performed using SVcell 2.0 (DRVision Technologies). Neurons were scored as dead when their soma was no longer detectable by RFP fluorescence. All neuron survival assays were performed at least twice, with one of the trials being used for the quantification shown. All trials quantified were representative of other trials of the same experiment. In each condition in the Kaplan-Meier plots, traces for each genotype represent a composite of the number of donors and iMNs per donor as listed in Table 2

TABLE 2

Numbers of iMNs counted for each line for survival experiments.

Figure 1B:
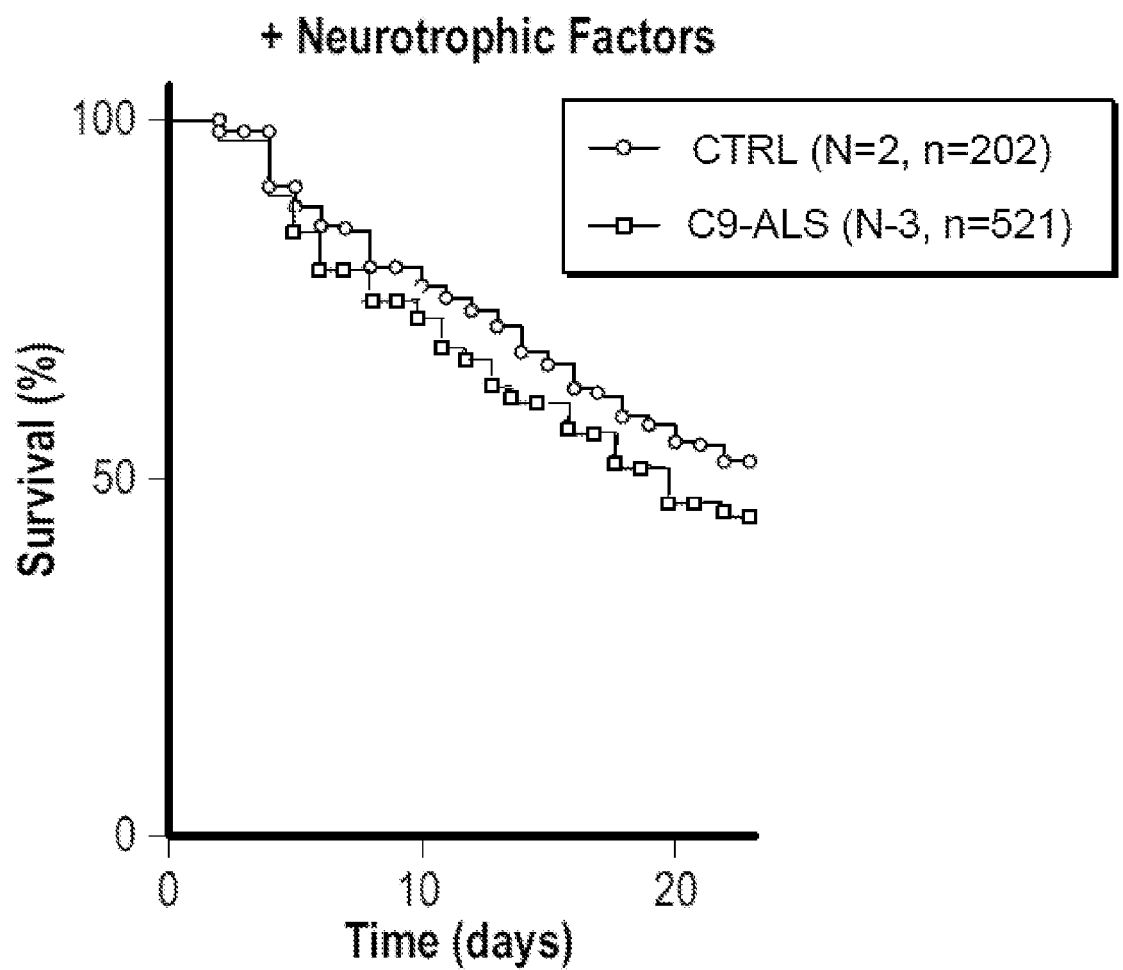
Figure 1C:
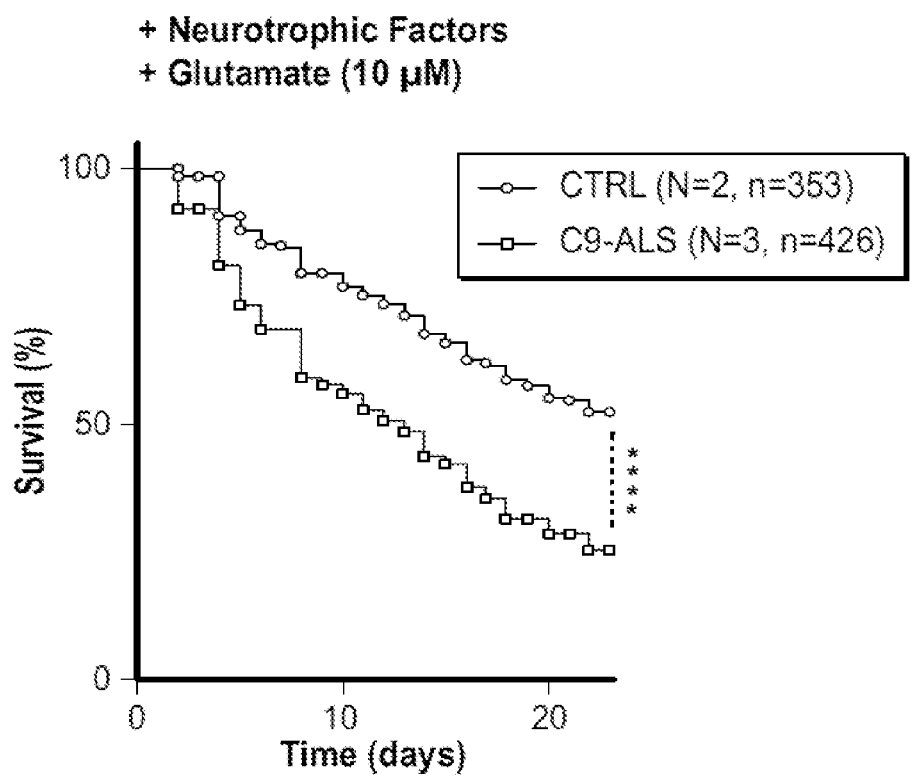
Figure 1D:
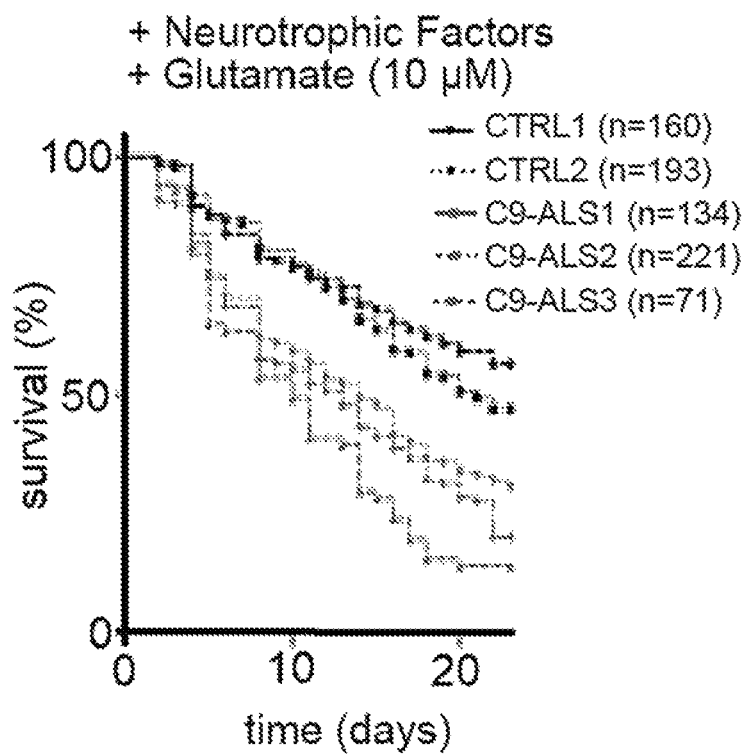
Figure 1E:
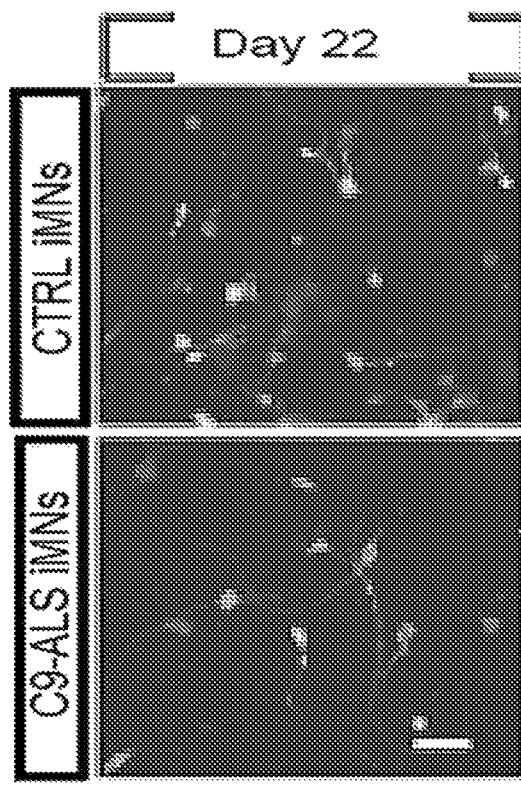
Figure 1F:
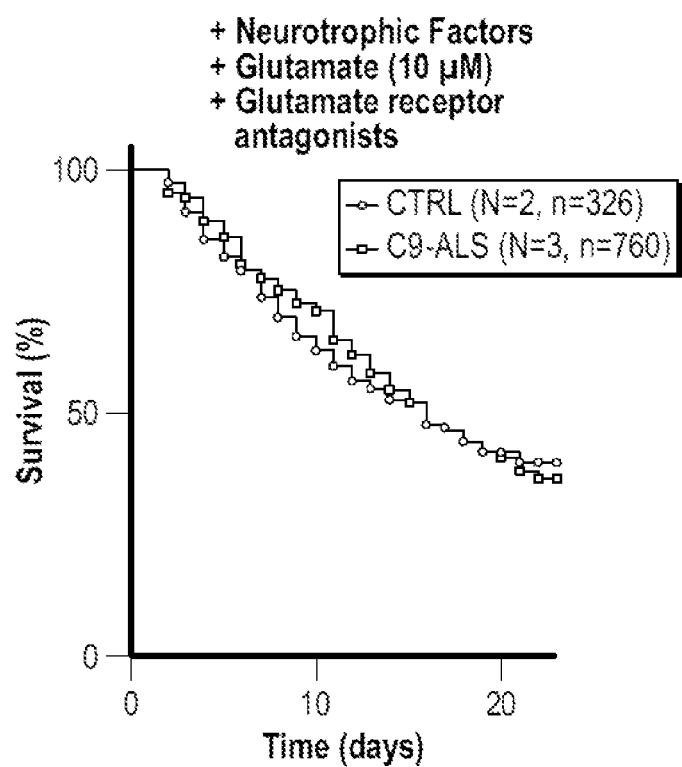
Figure 1G:
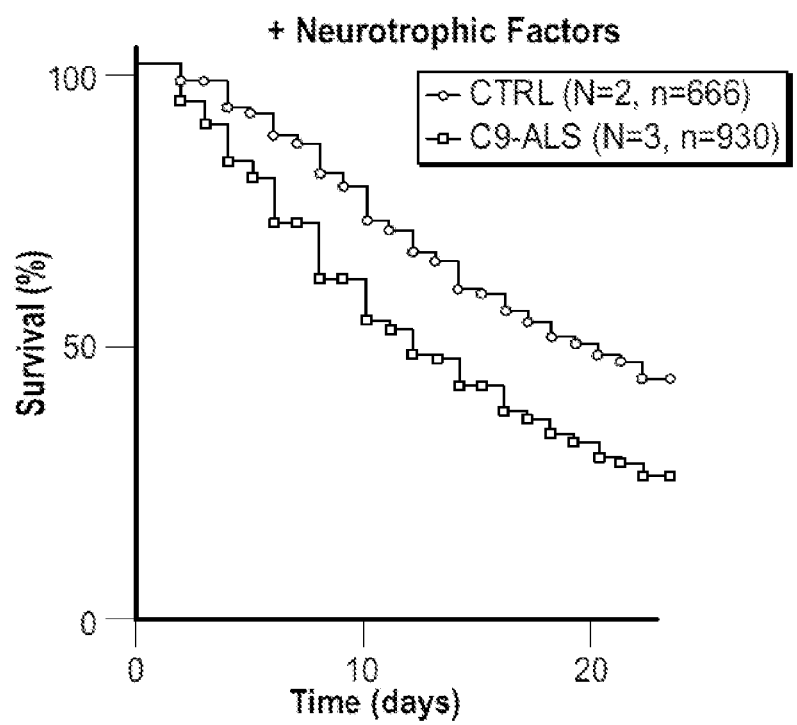
Figure 1H:
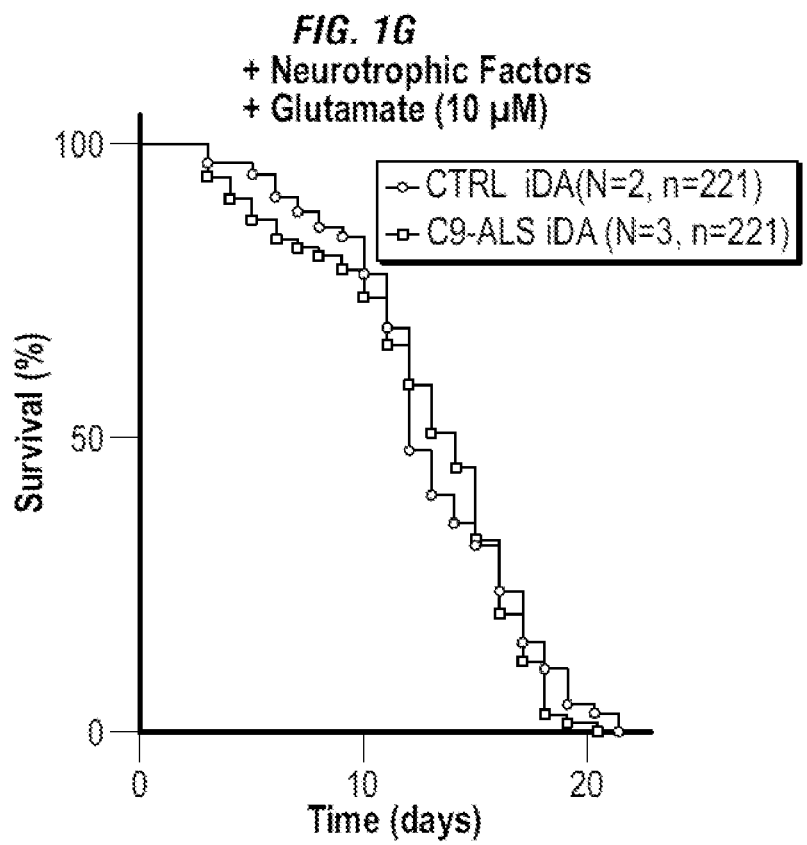
Figure 2A:
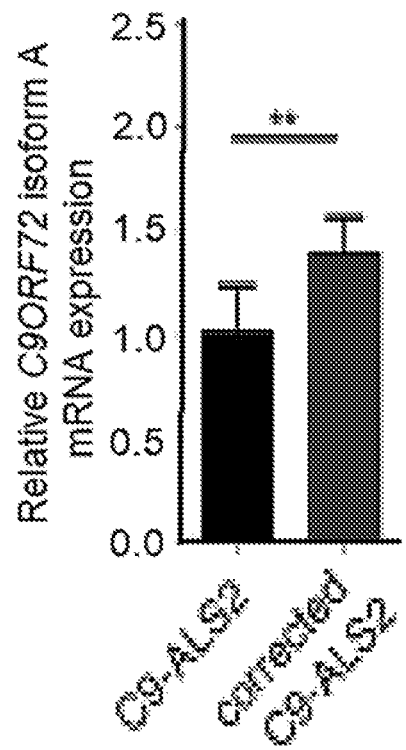
FIG. 2 shows that C9ORF72 protein levels determine iMN survival. a-b, The graph and image shows the levels of C9ORF72 variant 2 mRNA transcripts (a) and that C9ORF72 protein (isoform A) (b) are reduced in patient (C9-ALS2) iMNs relative to its isogenic control (values are mean±s.d., two-tailed t-test). c-e, The graphs show that the introduction of C9ORF72 (C9 isoform A or B) into C9-ALS iMNs (c), but not control (e) or SOD1-ALS iMNs (d), prolongs motor neuron survival in excess glutamate. Each trace includes iMNs from 2-3 donors with the specified genotype (except SOD1-ALS (d)); see full details in Example 1. f-g, The schematics show the strategy for knocking out C9ORF72 from control iPSCs using CRISPR/Cas9 (0 and sequencing of the mutant lines (g). h, The graph shows the C9ORF72 mRNA expression in control (CTRL2) iMNs and the isogenic heterozygous (C9$^{+/-}$) and homozygous (C9$^{-/-}$) CRISPR mutant iMNs (3 biological replicates, mean±s.e.m., two-tailed t-test). i, The image shows the C9ORF72 protein expression in CTRL2 iMNs and the isogenic C9ORF72$^{-/-}$ iMNs. j, The graph shows the survival of control (CTRL2) iMNs, the isogenic heterozygous (C9$^{+/-}$) and homozygous (C9$^{-/-}$) iMNs and C9-ALS iMNs in excess glutamate. All survival experiments were analyzed by log-rank. *–p<0.05, –p<0.01, *–p<0.001. iMN survival experiments in (c and e) were performed in a Nikon Biostation, and (d and j) were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.
Figure 2B:
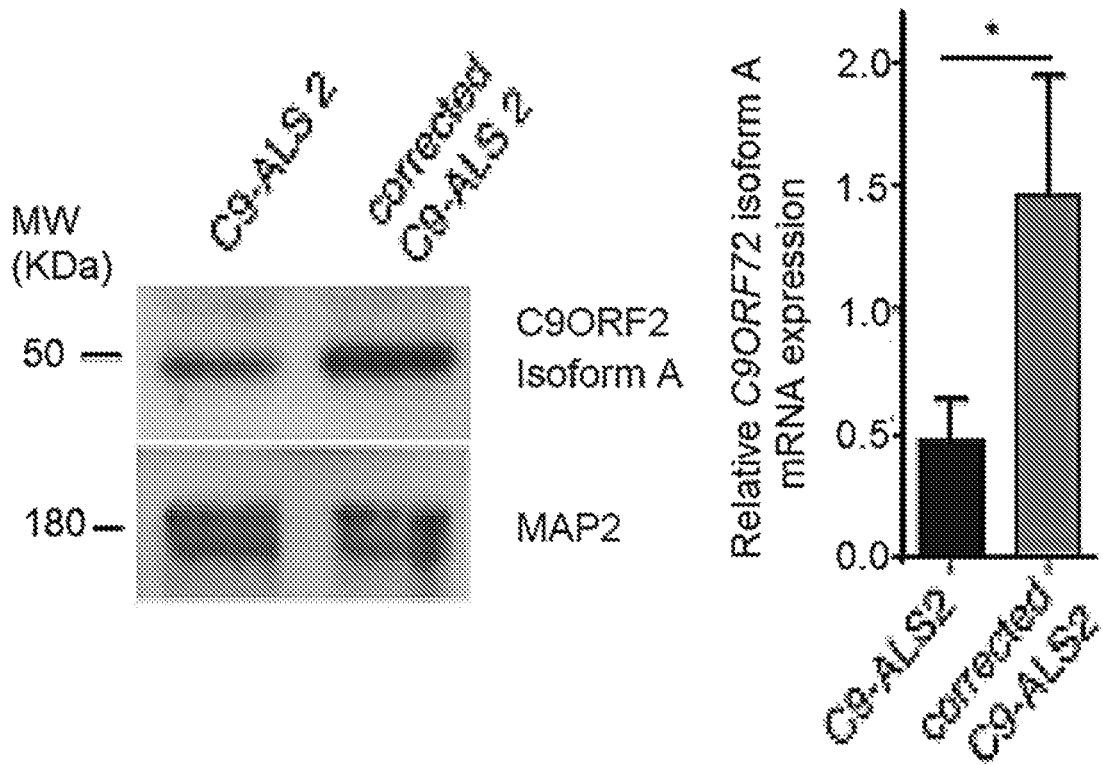
Figure 2C:
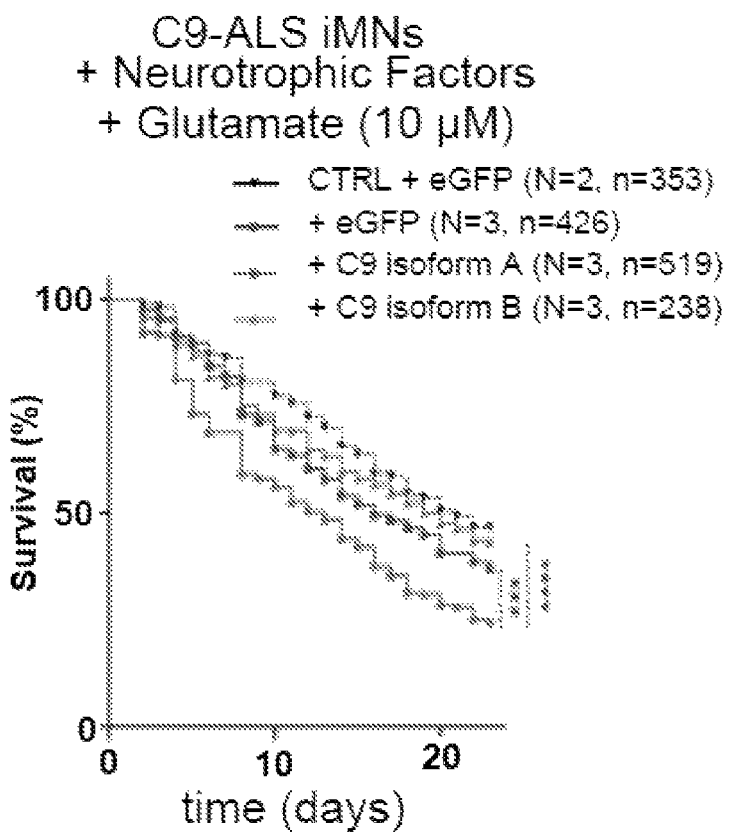
Figure 2D:
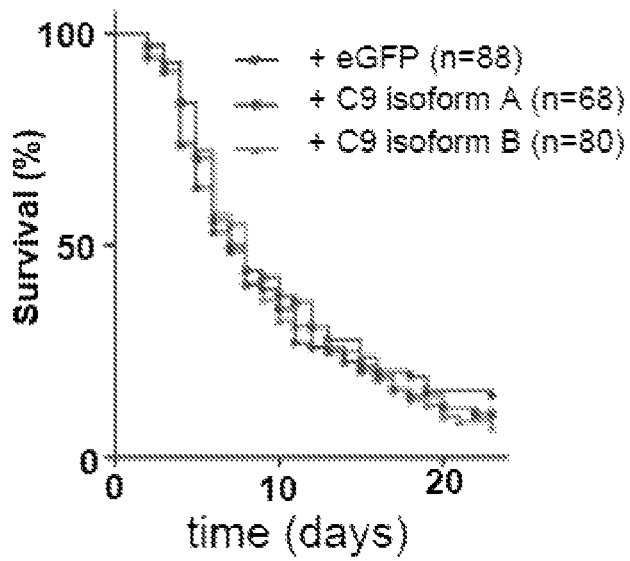
Figure 2E:
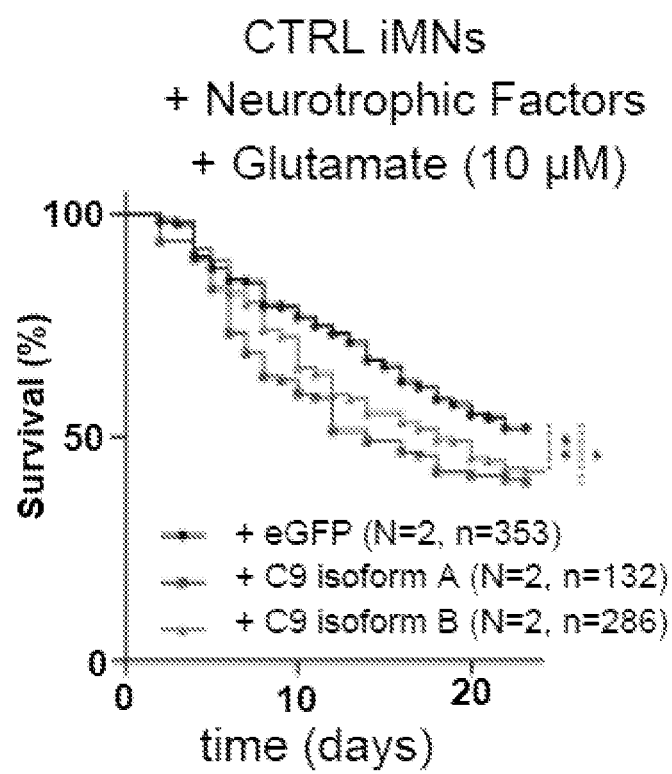
Figure 2F:
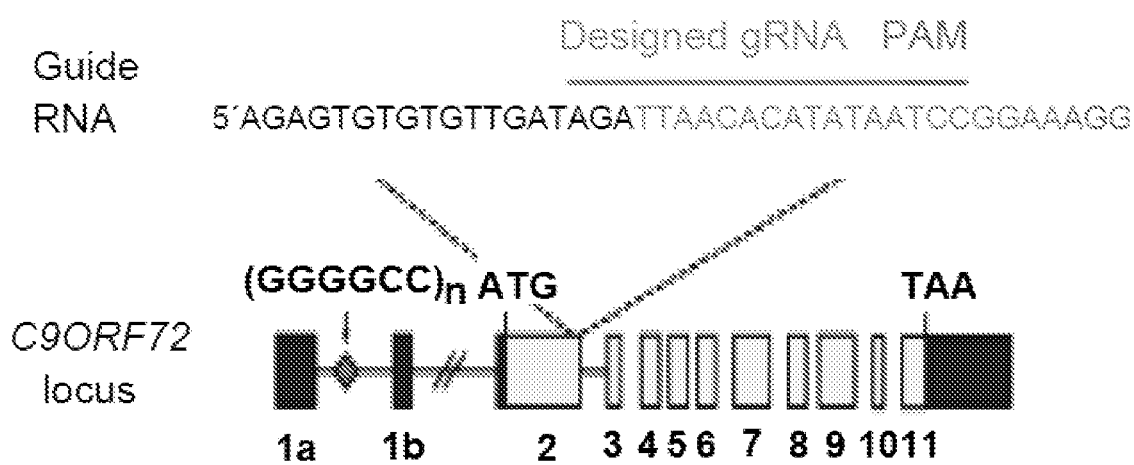
Figures 2G, 2H:
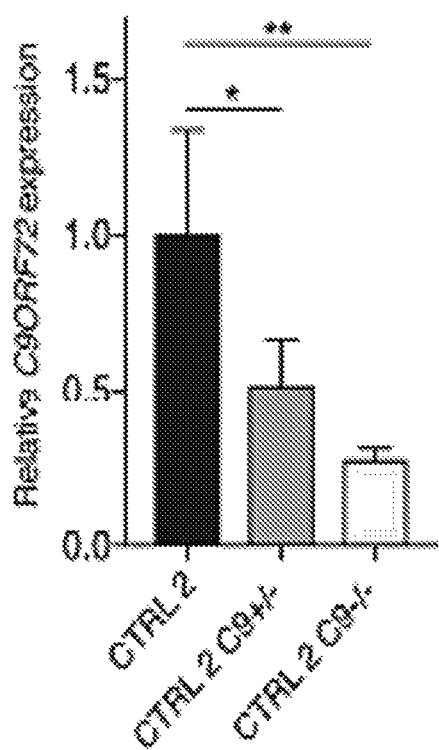
Figure 2I:
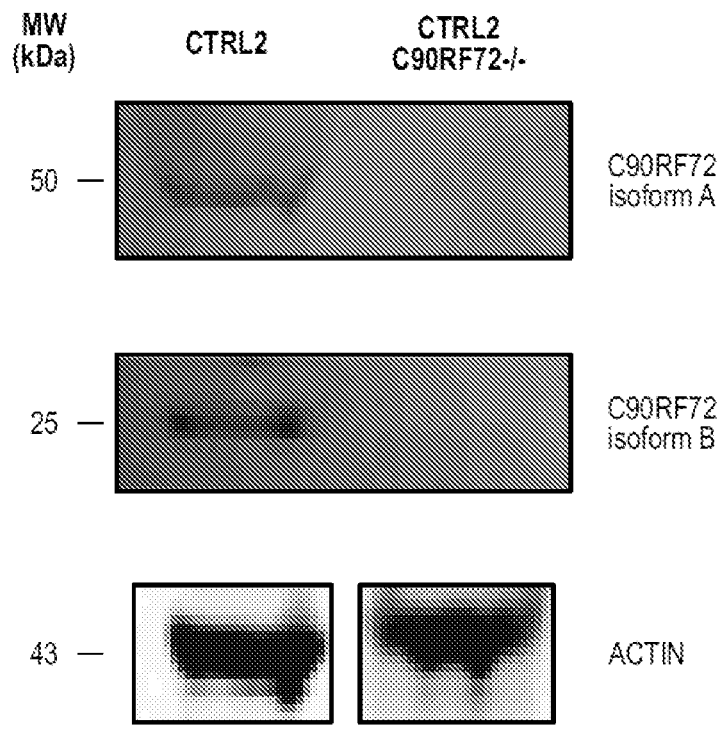
Figure 2J:
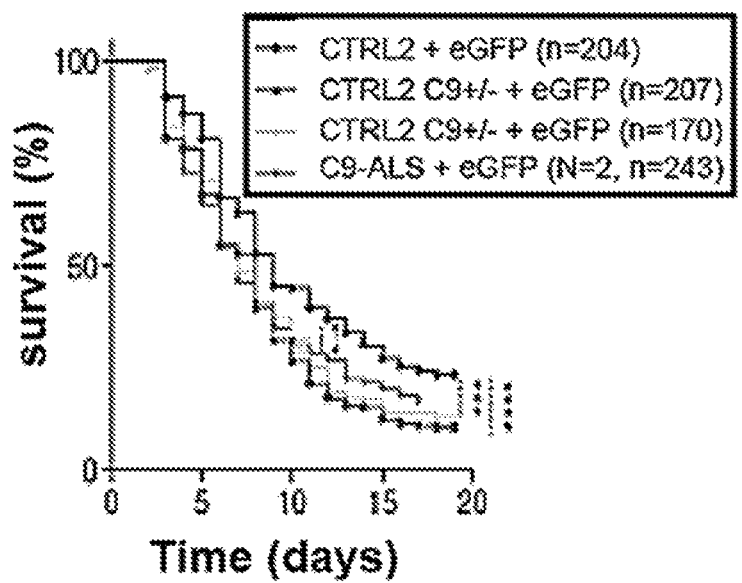

| FIGS. | Line | Cell Number |
|---|---|---|
| FIG. 1b | CTRL1 (12133) | 34 |
| | CTRL2 (3231) | 168 |
| | C9-ALS1 (6769) | 215 |
| | C9-ALS2 (10689) | 199 |
| | C9-ALS3 (12099) | 107 |
| FIG. 1c | CTRL1 | 160 |
| | CTRL2 | 193 |
| | C9-ALS1 | 134 |
| | C9-ALS2 | 221 |
| | C9-ALS3 | 71 |
| FIG. 1f | CTRL1 | 182 |
| | CTRL2 | 144 |
| | C9-ALS1 | 378 |
| | C9-ALS2 | 319 |
| | C9-ALS3 | 63 |
| FIG. 1g | CTRL1 | 409 |
| | CTRL2 | 257 |
| | C9-ALS1 | 463 |
| | C9-ALS2 | 365 |
| | C9-ALS3 | 102 |
| FIG. 1h | CTRL1 | 112 |
| | CTRL2 | 109 |
| | C9-ALS1 | 110 |
| | C9-ALS2 | 111 |
| FIG. 2c | CTRL1+eGFP | 160 |
| | CTRL2+eGFP | 193 |
| | C9-ALS1+eGFP | 134 |
| | C9-ALS1+isoA | 92 |
| | C9-ALS1+isoB | 184 |
| | C9-ALS2+eGFP | 221 |
| | C9-ALS2+isoA | 109 |
| | C9-ALS2+isoB | 306 |
| | C9-ALS3+eGFP | 71 |
| | C9-ALS3+isoA | 37 |
| | C9-ALS3+isoB | 29 |
| FIG. 2d | SOD1-ALS+eGFP | 88 |
| | SOD1-ALS+isoA | 68 |
| | SOD1-ALS+isoB | 80 |
| FIG. 2e | CTRL1+eGFP | 160 |
| | CTRL1+isoA | 71 |
| | CTRL1+isoB | 223 |
| | CTRL2+eGFP | 193 |
| | CTRL2+isoA | 61 |
| | CTRL2+isoB | 63 |
| FIG. 2j | CTRL2+eGFP | 204 |
| | CTRL2 C9+/−+eGFP | 207 |
| | CTRL2 C9 −/−+eGFP | 170 |

TABLE 2-continued

Numbers of iMNs counted for each line for survival experiments.

Figure 3A:
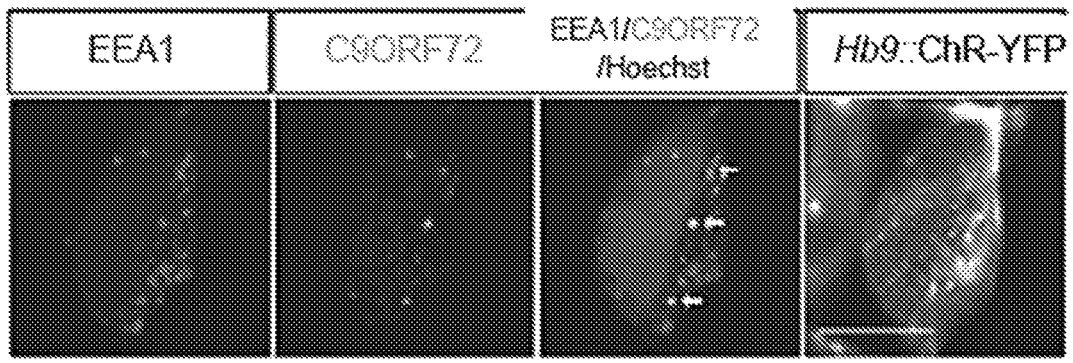
FIG. 3 shows that C9ORF72 induces guanine exchange on RAB5 and ARF3. a, The confocal images show control iMNs showing colocalization (arrows) of C9ORF72 (green) with EEA1 (red). Scale bar: 10 μm. b, The graph shows the percent of C9ORF72+ vesicles containing EEA1, RAB5, RAB7 or LAMP1 in control (CTRL1) and C9-ALS1 iMNs (mean of 2 biological replicates±s.d., n>9 cells per replicate). c, The schematic and graph show in vitro guanine exchange assay using BODIPY® FL GDP. d-e, The graphs show fluorescence intensity changes of BODIPY® FL GDP bound to purified RAB5A (d)(traces are mean of 3 biological replicates) and the summary of C9ORF72 guanine exchange activity toward various small GTPases (e)(mean of 3 biological replicates±s.e.m). Dashed line in (e) represents an arbitrary threshold (mean value of all GTPases+1 standard deviation). * Denote GTPases that did not exhibit decreases in GDP binding with EDTA treatment. f, The graph shows the survival of control iMNs in excess glutamate with overexpression of constitutively active RAB5 (RAB5-CA). g-i, The graphs show the survival of C9-ALS3 iMNs with overexpression of RAB5-CA (g), wild-type RAB5 (h), or constitutively active RAB7 (RAB7-CA)(i). j-k, Confocal images of isogenic CTRL2 iMNs overexpressing RFP-RAB5 (green)(j), and quantification of RFP-RAB5+ punctae (k)(mean of 2 biological replicates±s.d., n>18 cells per replicate). Scale bars: 10 μm (j). l, Size of EEA1+ vesicles in CTRL2 iMNs overexpressing eGFP or C9ORF72 isoform B (mean of 2 biological replicates±s.d., n>18 cells per replicate). m, The image shows the electron micrograph of EEA1+ vesicles in isogenic iPSC-derived fibroblasts. Scale bars: 50 nm. n, The image shows the representative electron micrographs of electron-dense spherical perinuclear structures in isogenic iPSC-derived fibroblasts. Scale bar: 500 nm. o, LAMP1 staining in isogenic iMNs. Scale bars: 10 μm. p, The graph shows fluorescence intensity of LAMP1+ punctae in control iMNs (white bars), C9-ALS iMNs (black bars) and CTRL2 C9ORF72$^{+/-}$ iMNs (grey bar) (mean±s.e.m of 2 biological replicates, n>16 cells per replicate). q-r, The graphs show the number of LAMP1+ punctae in isogenic iMNs of CTRL2 background (q) and C9-ALS2 background (r) overexpressing eGFP or C9ORF72 isoform B (mean±s.e.m of 2 biological replicates, n>29 cells per replicate). s, The image shows the lamp1 immunoreactivity in control and C9-KO mouse spinal neurons. Scale bar: 5 μm t, The graph shows the number of Lamp1+ punctae in Chat+ mouse spinal neurons (median±interquartile range, Mann-Whitney test). *-p<0.05, -p<0.01, *-<0.001, ****-p<0.0001. iMN survival experiments in (f-i) were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.
Figure 3B:
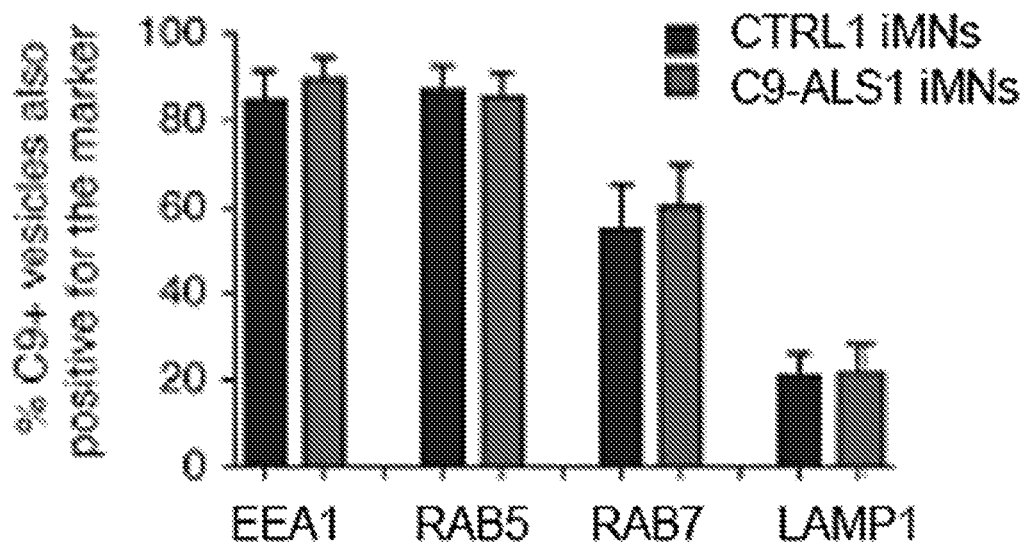
Figure 3C:
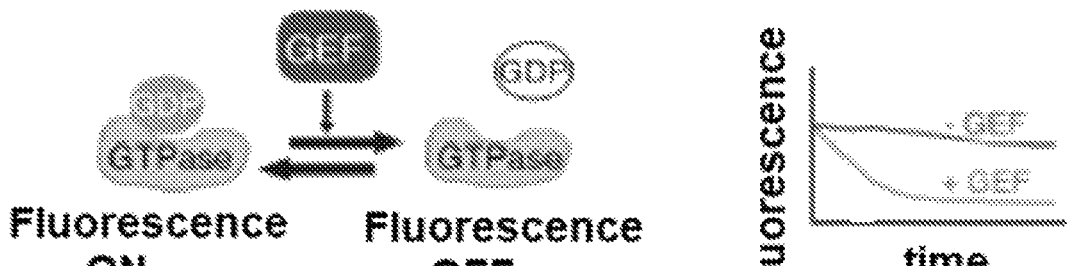
Figure 3D:
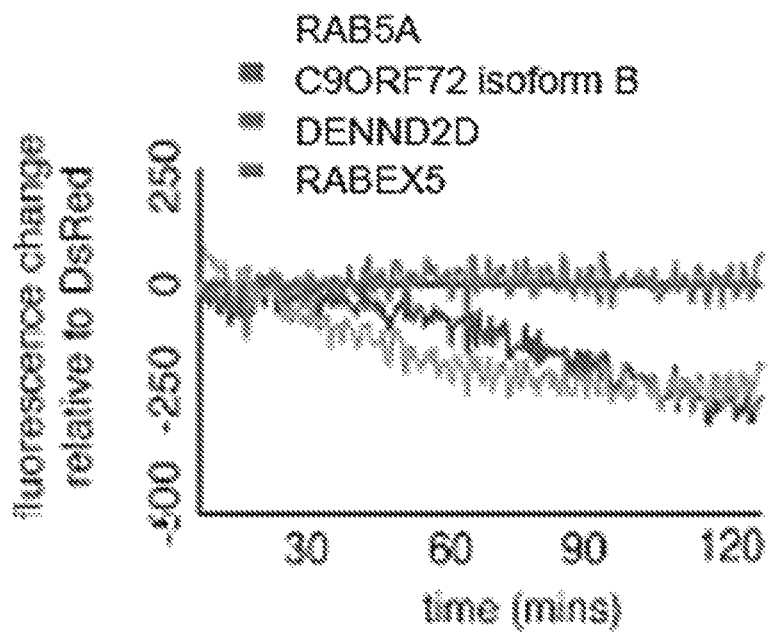
Figure 3E:
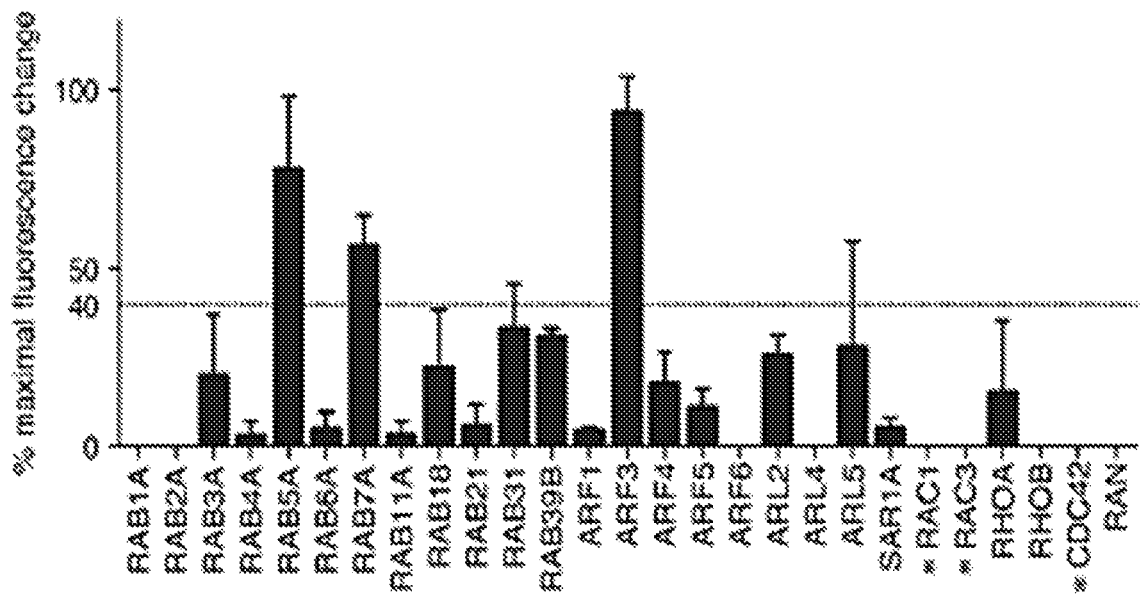
Figure 3F:
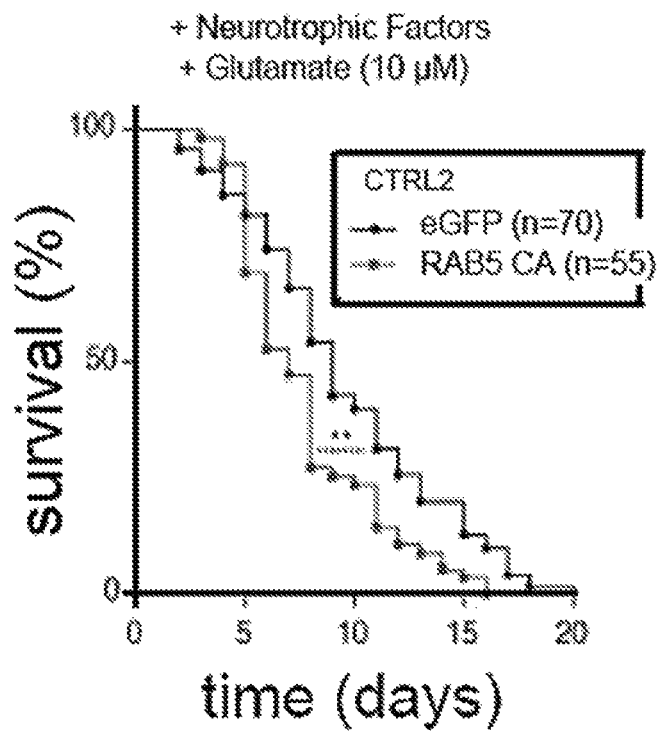
Figure 3G:
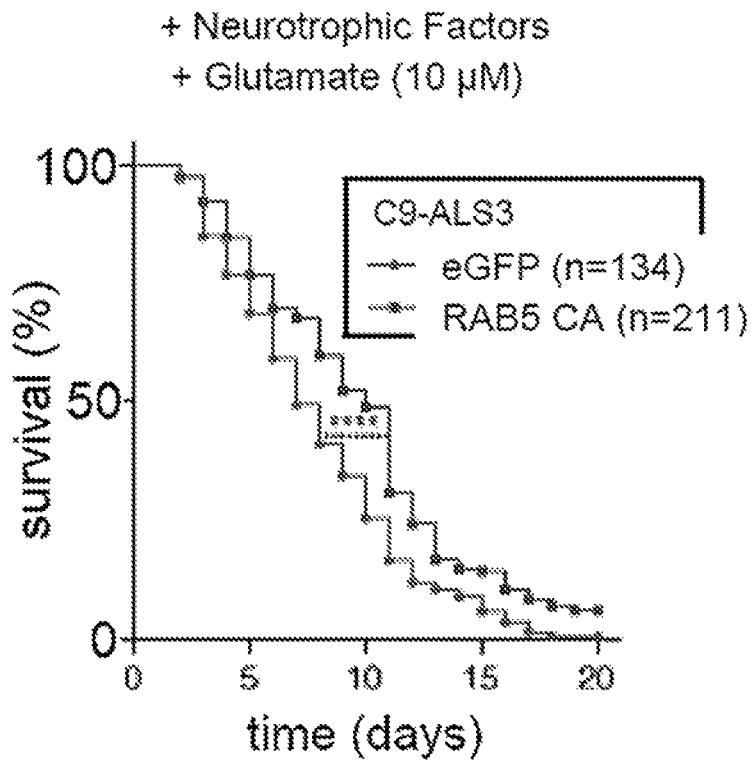
Figure 3H:
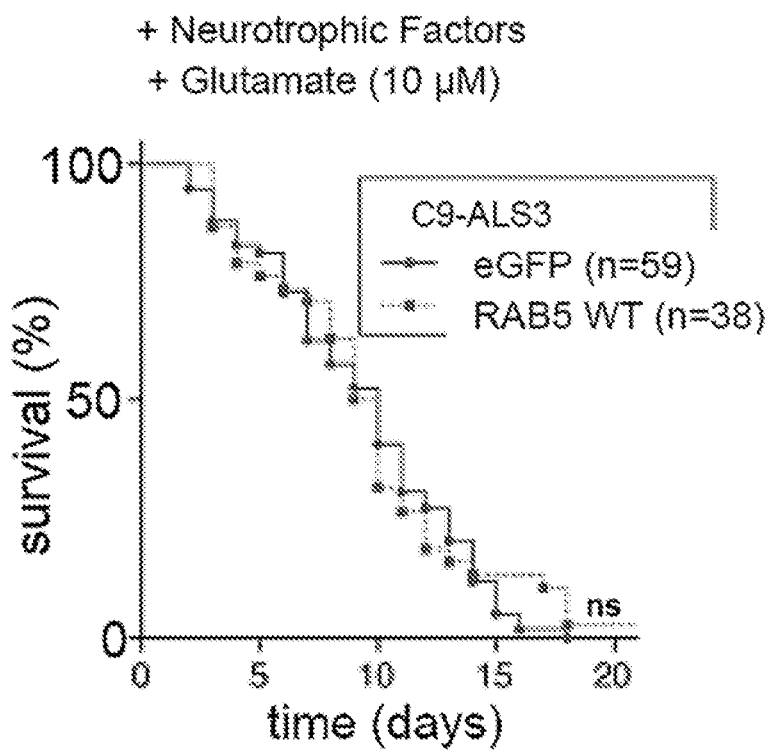
Figure 3I:
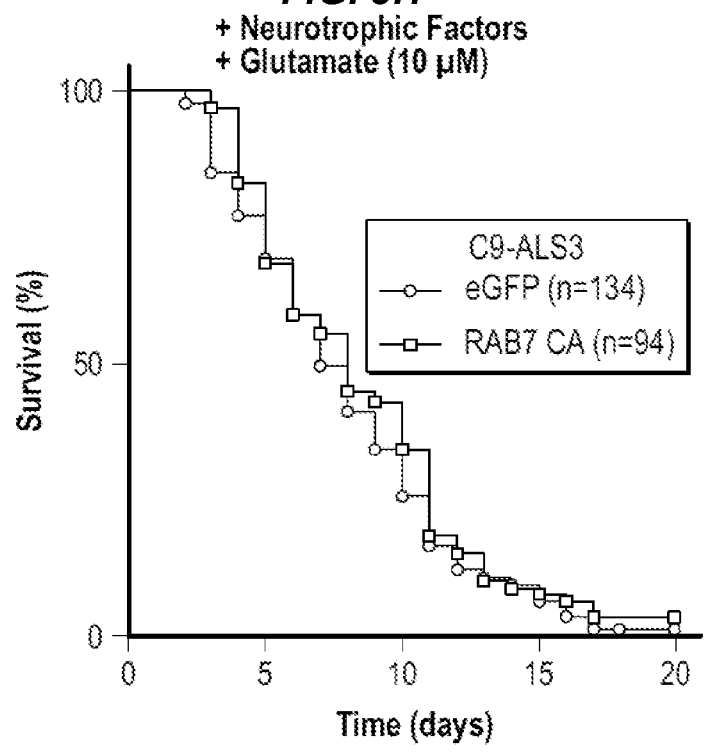
Figure 3J:
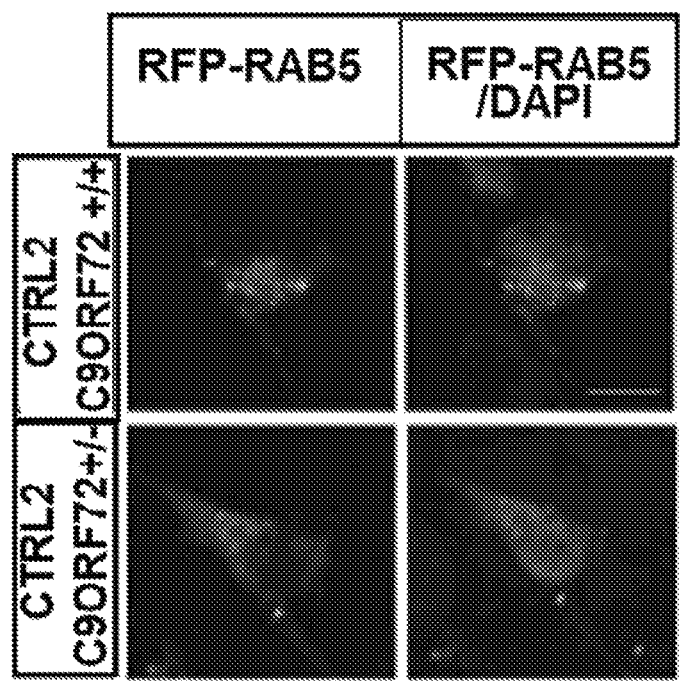
Figure 3K:
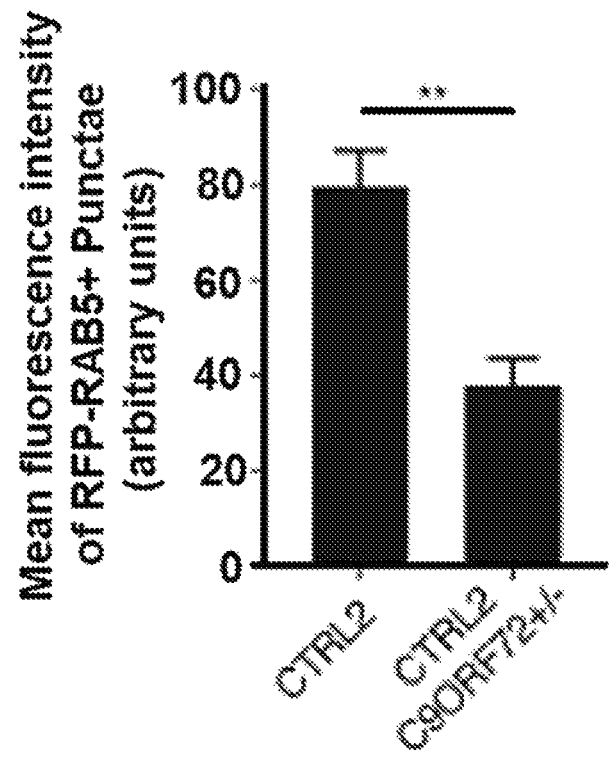
Figure 3L:
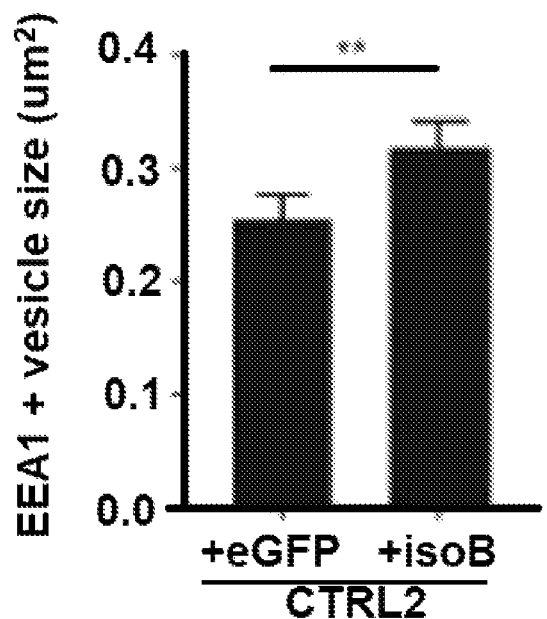
Figure 3M:
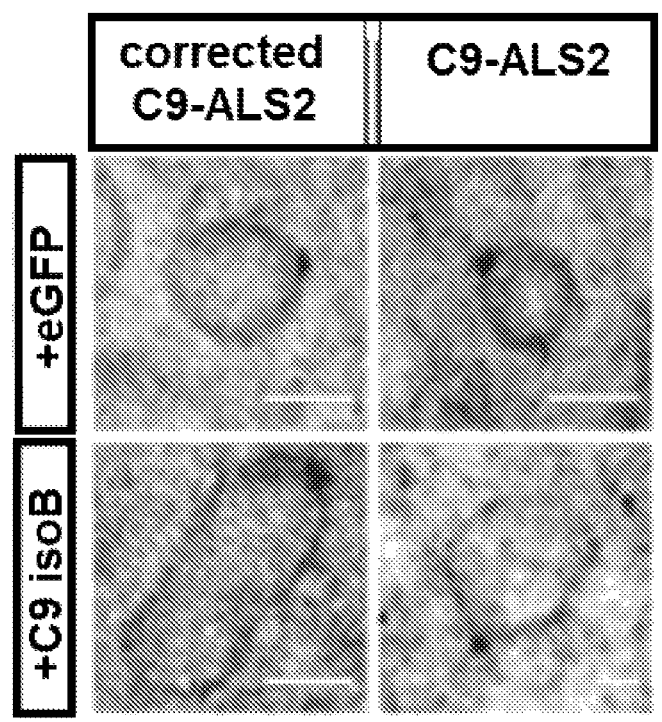
Figure 3N:
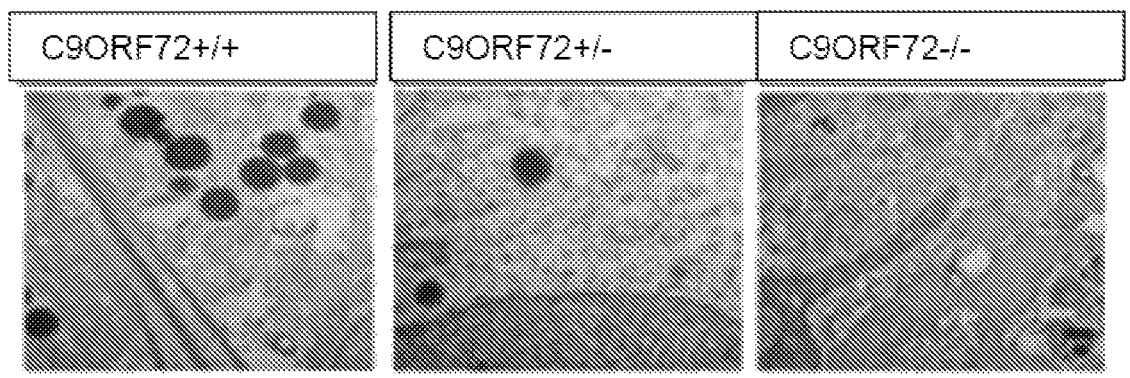
Figure 3O:
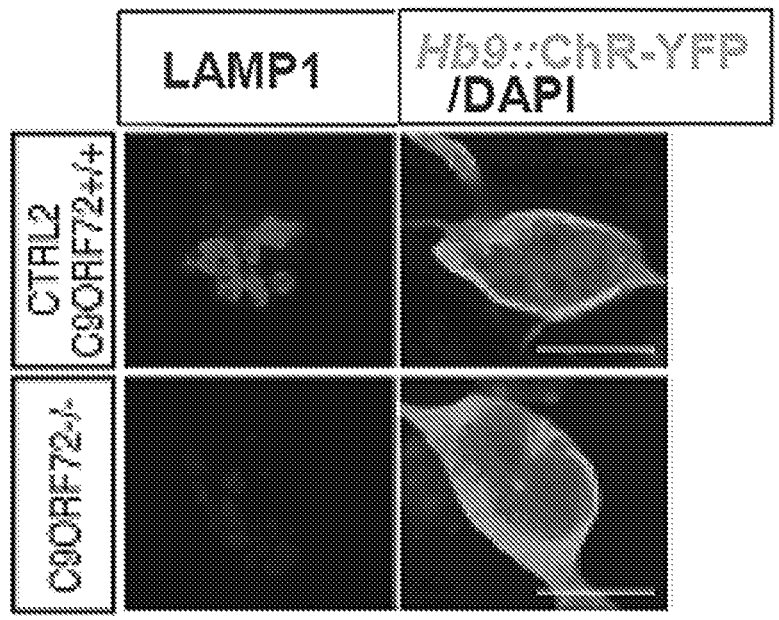
Figure 3P:
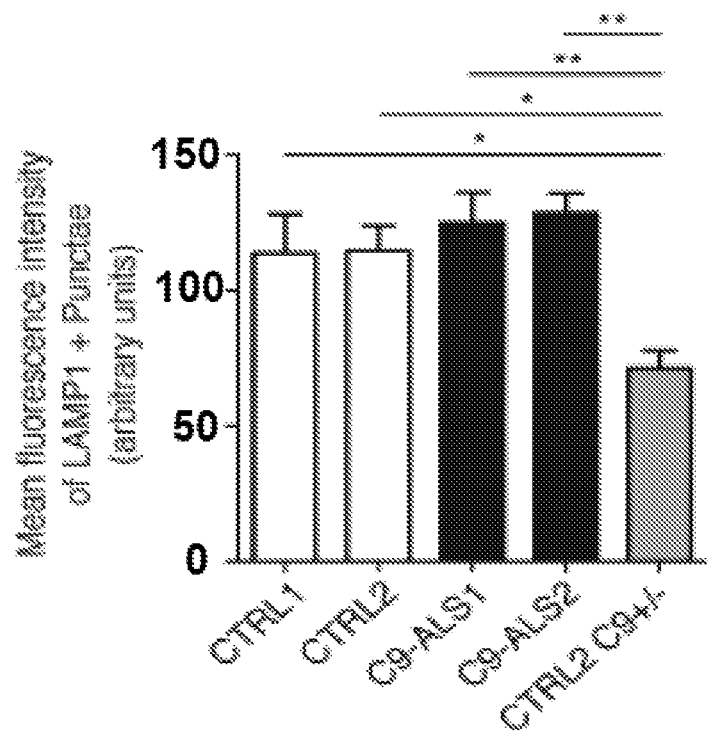
Figure 3Q:
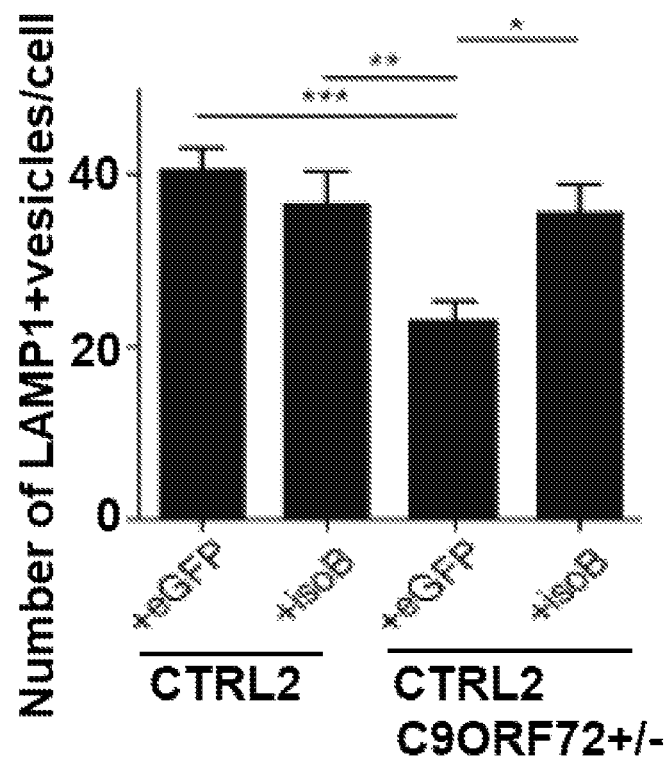
Figure 3R:
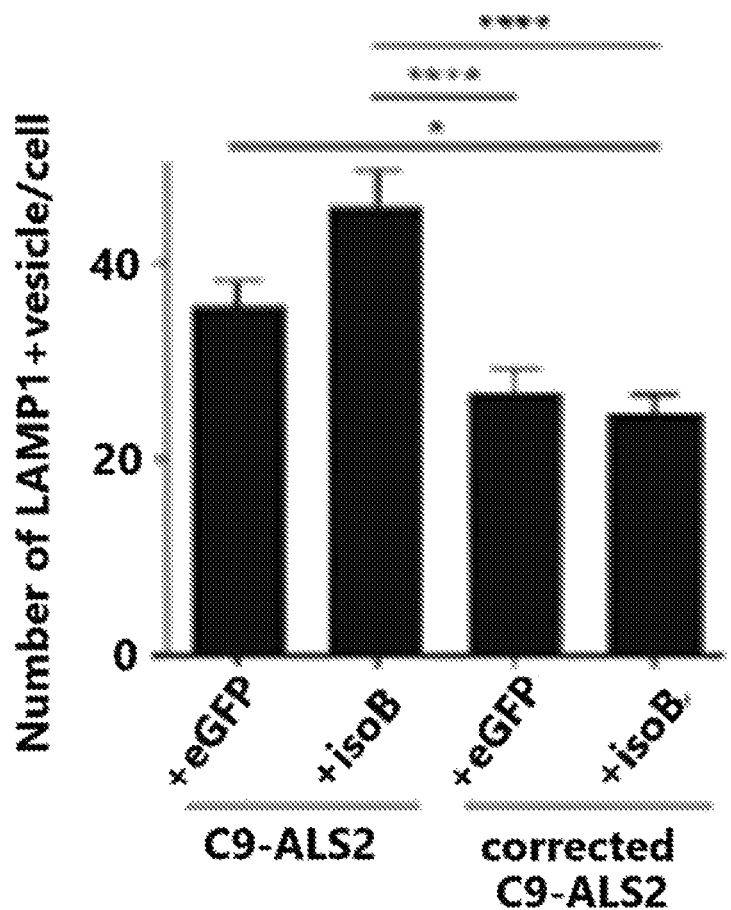
Figure 3S:
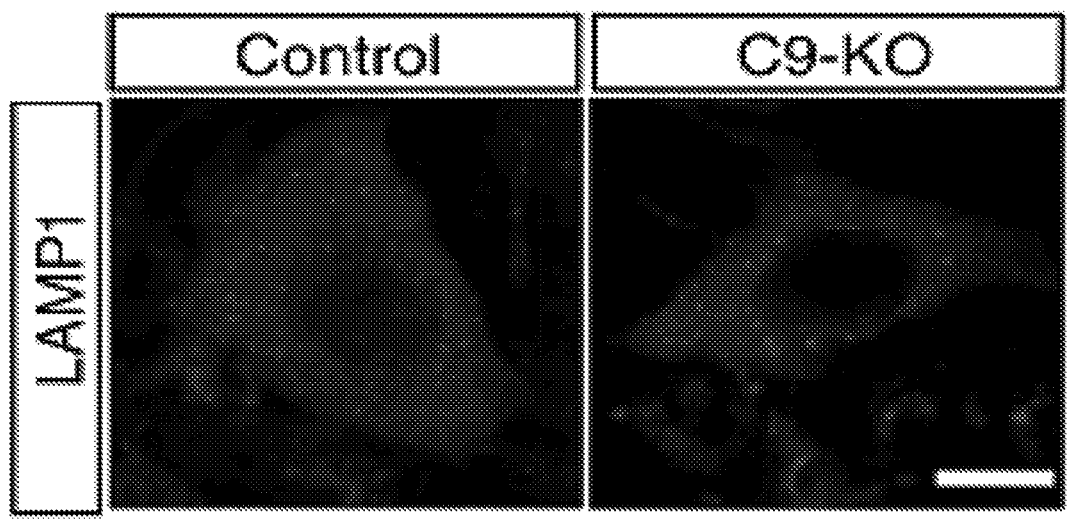
Figure 3T:
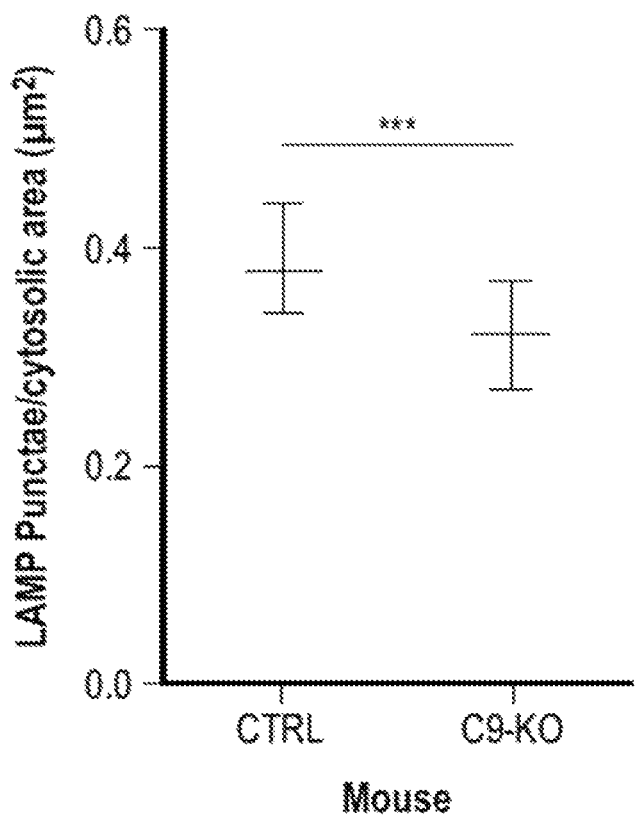
Figure 4A:
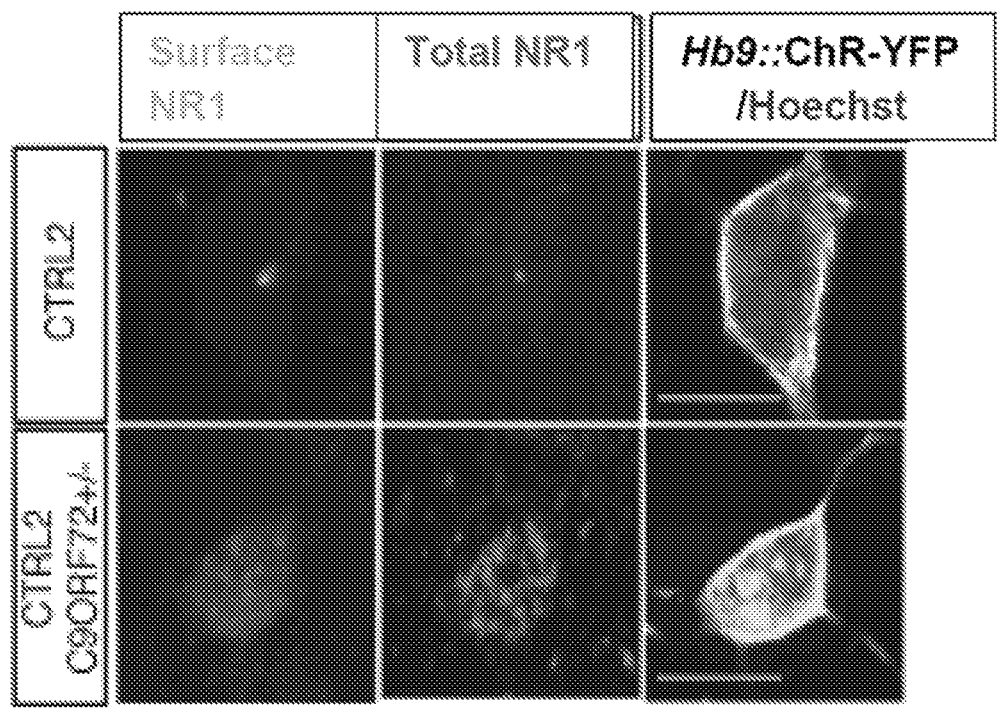
FIG. 4 shows that patient and C9ORF72-deficient neurons have increased glutamate receptor levels. a, The image shows immunofluorescence expression of total (red) and surface-localized (green) NR1 in iMNs. Immunostaining of surface-localized NR1 was performed without permeabilization using an antibody specific to the extracellular domain of NR1. Nuclei are marked with Hoechst. Scale bars: 10 μm. b-d, The graphs show the quantification of NR1 immunoreactivity in isogenic iMNs (CTRL2 wild-type and CRISPR mutant (b); C9-ALS2 and corrected C9-ALS2 (c)) and in control and C9-ALS iMNs in aggregate (d) (median±interquartile range, Mann-Whitney test). e, The graph shows the average $Ca^{2+}$ flux in the presence of glutamate per minute (mean of 3 biological replicates±s.e.m., n=25 cells per replicate). f, The graph shows the survival of C9-ALS iMNs in excess glutamate, treated with vehicle or the potassium channel agonist retigabine g-h, The image and graph show NR1 immunoreactivity in Chat+ spinal neurons of Nestin-Cre C9orf72$^{loxP/loxP}$ mice (g)(scale bar, 10 μm) and quantification (h) (median±interquartile range. Mann-Whitney test). i-j, The graphs show the quantification of NR1 (i) and GLUR6/7 (j) immunoreactivity in post mortem human spinal cord neurons (mean±s. d, two-tailed t-test and ANOVA with a Bonferroni posthoc analysis, respectively). *-p<0.05, -p<0.01, *-p<0.001, ****-p<0.0001. iMN survival experiments in (0 were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.
Figure 4B:
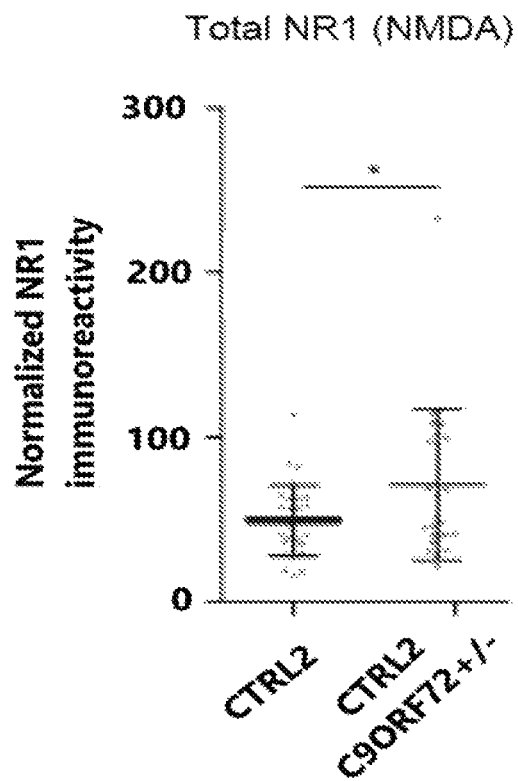
Figure 4C:
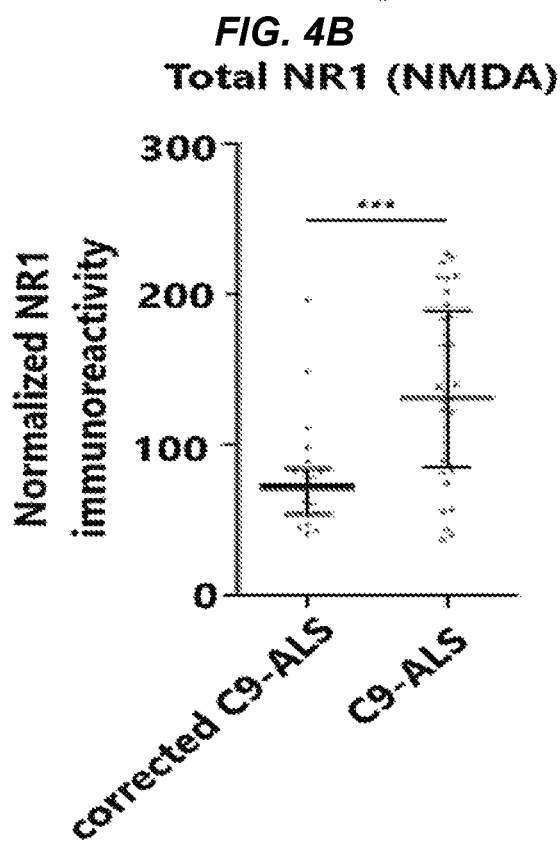
Figure 4D:
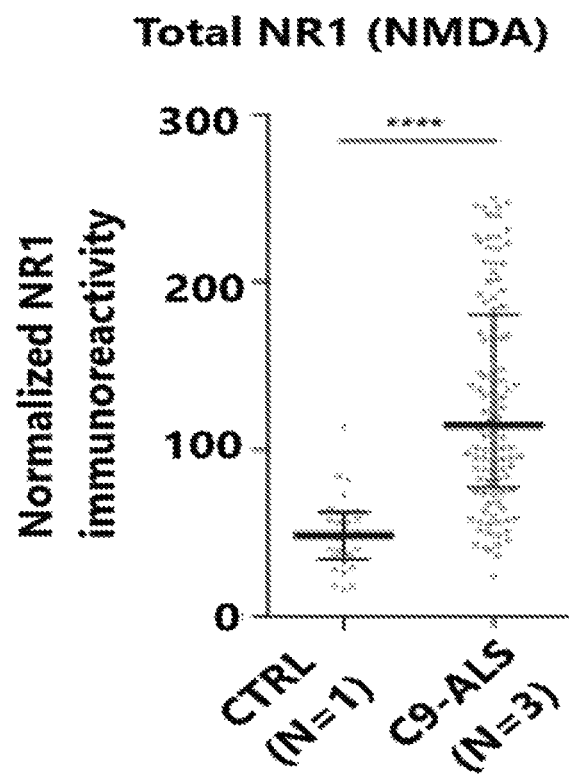
Figure 4E:
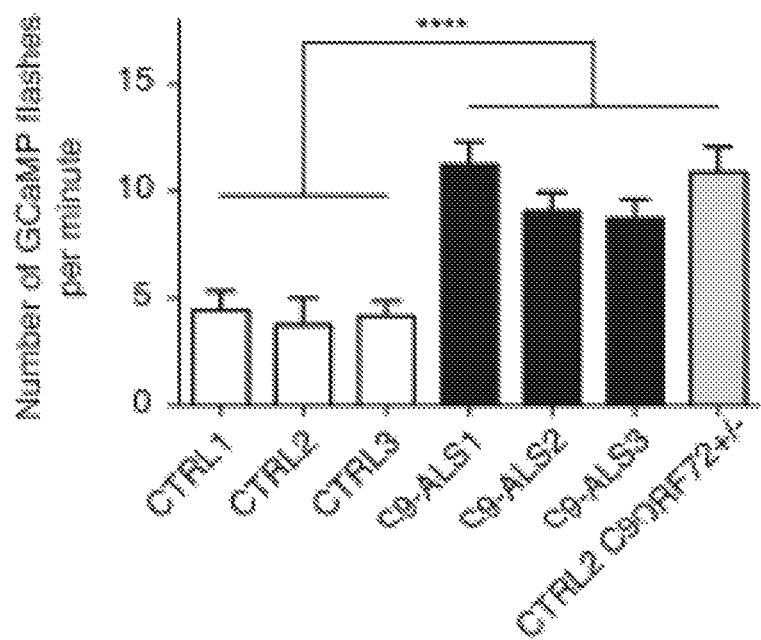
Figure 4F:
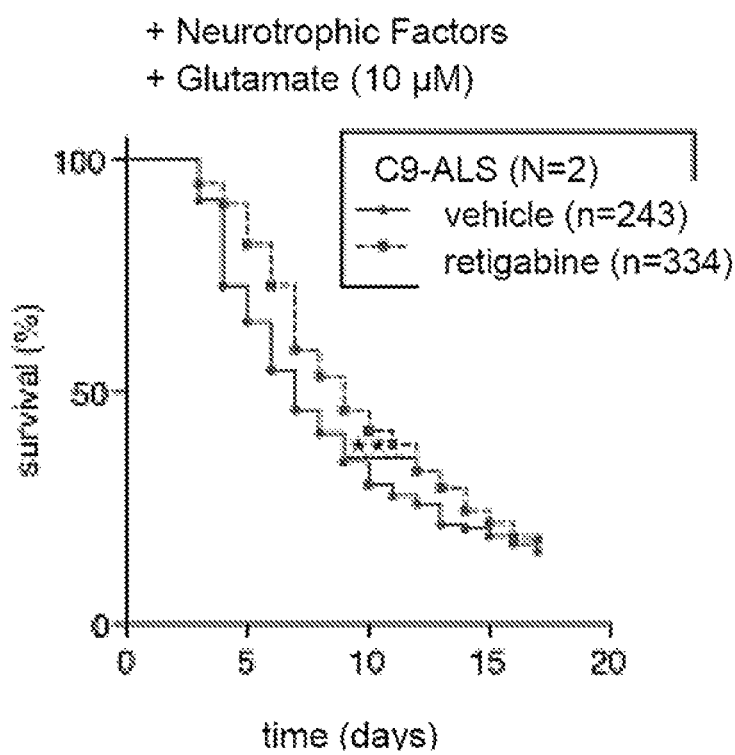
Figure 4G:
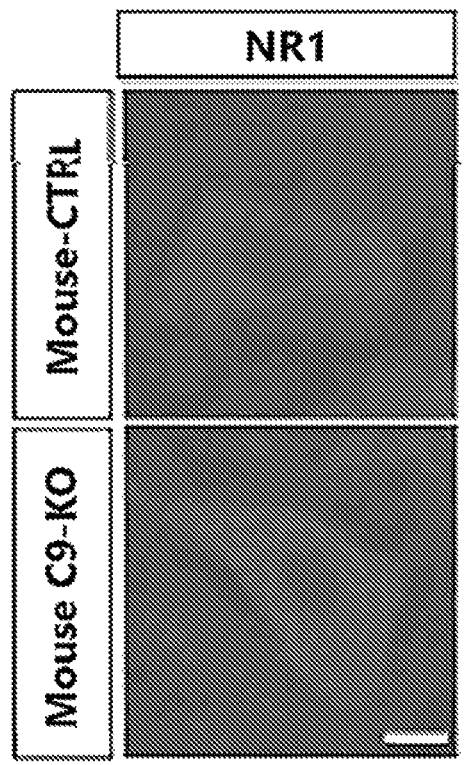
Figure 4H:
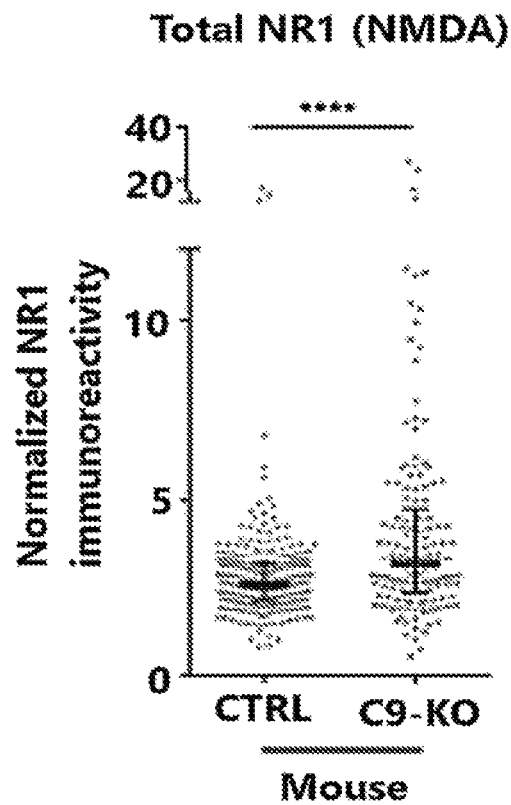
Figure 4I:
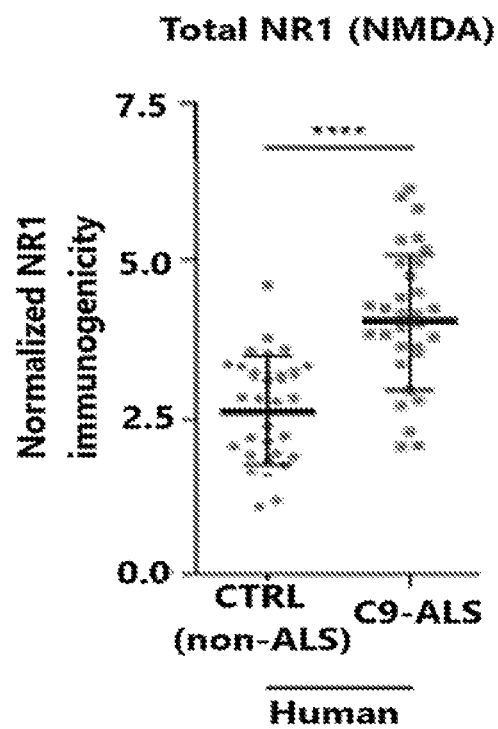
Figure 4J:
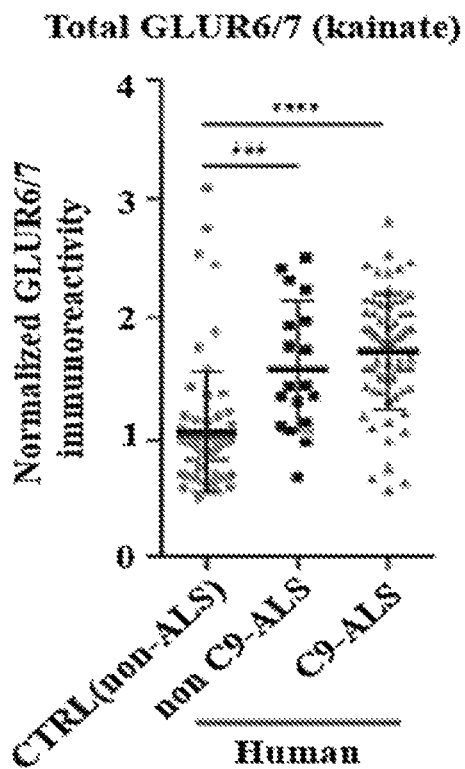
Figure 5A:
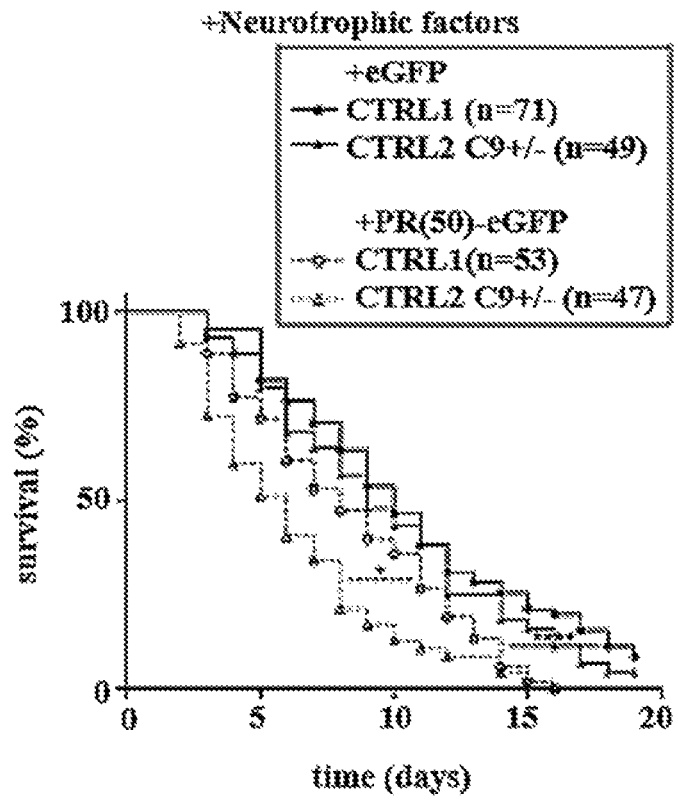
FIG. 5 shows that the C9ORF72 levels determine dipeptide repeat turnover. a-b, The graphs show the survival of control and CRISPR-mutant iMNs in excess glutamate with overexpression of eGFP or PR(50)-eGFP (a) or GR(50)-eGFP (b). c-d, The graphs show the survival of control and C9-ALS iMNs in excess glutamate with overexpression of eGFP or PR(50)-eGFP (c) or GR(50)-eGFP (d). e-f, The image and graph show PR(50)-Dendra2-expressing CTRL2 or C9($^{-/-}$) fibroblasts before and after Dendra2 photoconversion (e)(scale bar: 15 μm), and the relative decay in Dendra2 fluorescence after 12 hrs with overexpression of eGFP or C9ORF72 isoform B-T2A-eGFP (f)(mean+s.e.m of 3 biological replicates, ANOVA with Bonferroni correction for multiple testing). g-h, The image and graph show PR(50)-Dendra2-expressing CTRL2 iMNs before and after photoconversion (g)(scale bar: 10 μm), and the decay in Dendra2 fluorescence in isogenic iMNs after 12 hrs (h) (mean+s.e.m of 3 biological replicates, two-tailed t-test). All survival experiments were analyzed by log-rank. *-p<0.05, -p<0.01, *-p<0.001. iMN survival experiments in (a-d) were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.
Figure 5B:
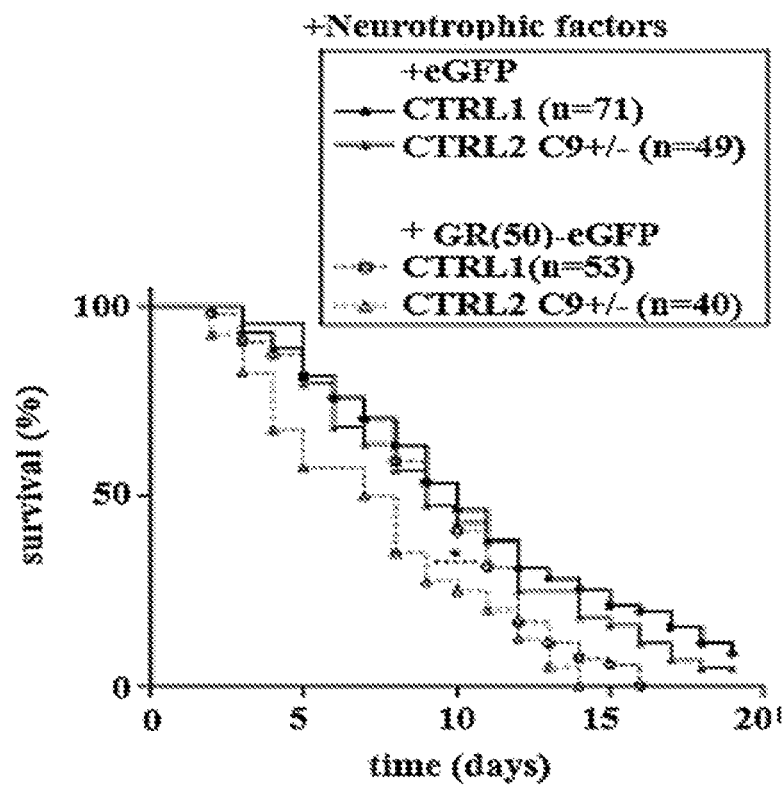

| FIGS. | Line | Cell Number |
|---|---|---|
| | C9-ALS1+eGFP | 211 |
| | C9-ALS3+eGFP | 32 |
| FIG. 3b | CTRL1-EEA1 | 14 |
| | CTRL1-RAB5 | 12 |
| | CTRL1-RAB7 | 14 |
| | CTRL1-LAMP1 | 12 |
| | C9-ALS1-EEA1 | 11 |
| | C9-ALS1-RAB5 | 9 |
| | C9-ALS1-RAB7 | 10 |
| | C9-ALS1-LAMP1 | 9 |
| FIG. 3f | CTRL2+eGFP | 70 |
| | CTRL2+RAB5CA | 55 |
| FIG. 3g | C9-ALS3+eGFP | 134 |
| | C9-ALS3+RAB5CA | 211 |
| FIG. 3h | C9-ALS3+eGFP | 59 |
| | C9-ALS3+RAB5WT | 38 |
| FIG. 3i | C9-ALS3+eGFP | 134 |
| | C9-ALS3+RAB7 CA | 94 |
| FIG. 3k | CTRL2+RFP-RAB5 | 18 |
| | CTRL2C9+/−-RFP-RAB5 | 16 |
| FIG. 3l | CTRL2+eGFP | 20 |
| | CTRL2+isoB | 18 |
| FIG. 3p | CTRL1 | 15 |
| | CTRL2 | 14 |
| | C9-ALS1 | 14 |
| | C9-ALS2 | 13 |
| | CTRL2 C9+/− | 14 |
| FIG. 3q | CTRL2+eGFP | 27 |
| | CTRL2+isoB | 25 |
| | CTRL2 C9+/− +eGFP | 28 |
| | CTRL2 C9+/− +isoB | 16 |
| FIG. 3r | C9-ALS2+eGFP | 33 |
| | C9-ALS2+isoB | 32 |
| | Corrected C9-ALS2 +eGFP | 29 |
| | Corrected C9-ALS2 +isoB | 33 |
| FIG. 3s | Mouse-CTRL | 56 |
| | Mouse-C9-KO | 59 |
| FIG. 4b | CTRL2 | 30 |
| | CTRL2 C9+/− | 25 |
| FIG. 4c | Corrected C9-ALS2 | 22 |
| | C9-ALS2 | 33 |
| FIG. 4d | CTRL1 | 30 |
| | C9-ALS1 | 26 |
| | C9-ALS2 | 33 |
| | C9-ALS3 | 49 |
| FIG. 4e | CTRL1 | 28 |
| | CTRL2 | 10 |
| | CTRL3 | 9 |
| | C9-ALS1 | 26 |
| | C9-ALS2 | 20 |
| | C9-ALS3 | 24 |
| | CTRL2 C9+/− | 15 |
| FIG. 4f | C9-ALS1+DMSO | 211 |
| | C9-ALS1+Retigabine | 313 |
| | C9-ALS3+DMSO | 32 |
| | C9-ALS3+Retigabine | 21 |
| FIG. 4h | Mouse CTRL | 297 |
| | Mouse C9-KO | 146 |
| FIG. 4i | Human CTRL (non-ALS) | 29 |
| | Human C9-ALS | 32 |
| FIG. 4k | Human CTRL (non-ALS) | 63 |
| | Human non-C9-ALS | 18 |
| | Human C9-ALS | 66 |
| FIG. 5a | CTRL1+eGFP | 71 |
| | CTRL1+PR | 53 |
| | CTRL2 C9+/− +eGFP | 49 |
| | CTRL2 C9+/− +PR | 47 |
| | CTRL2 C9−/− +eGFP | 44 |
| | CTRL2 C9−/− +PR | 44 |
| FIG. 5b | CTRL1+eGFP | 71 |
| | CTRL1+GR | 54 |
| | CTRL2 C9+/− +eGFP | 49 |
| | CTRL2 C9+/− +GR | 40 |
| | CTRL2 C9−/− +eGFP | 44 |
| | CTRL2 C9−/− +GR | 44 |

TABLE 2-continued

Numbers of iMNs counted for each line for survival experiments.

Figure 5C:
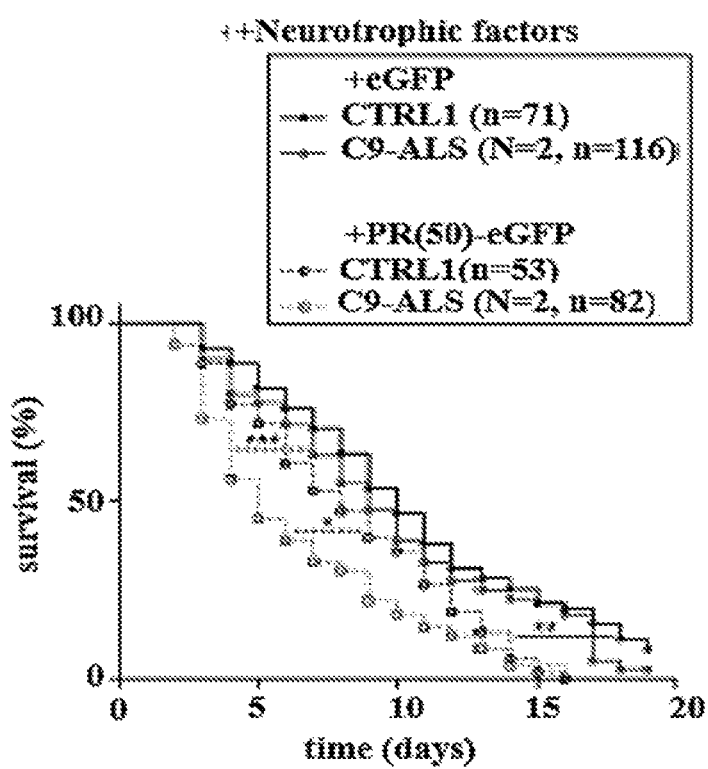
Figure 5D:
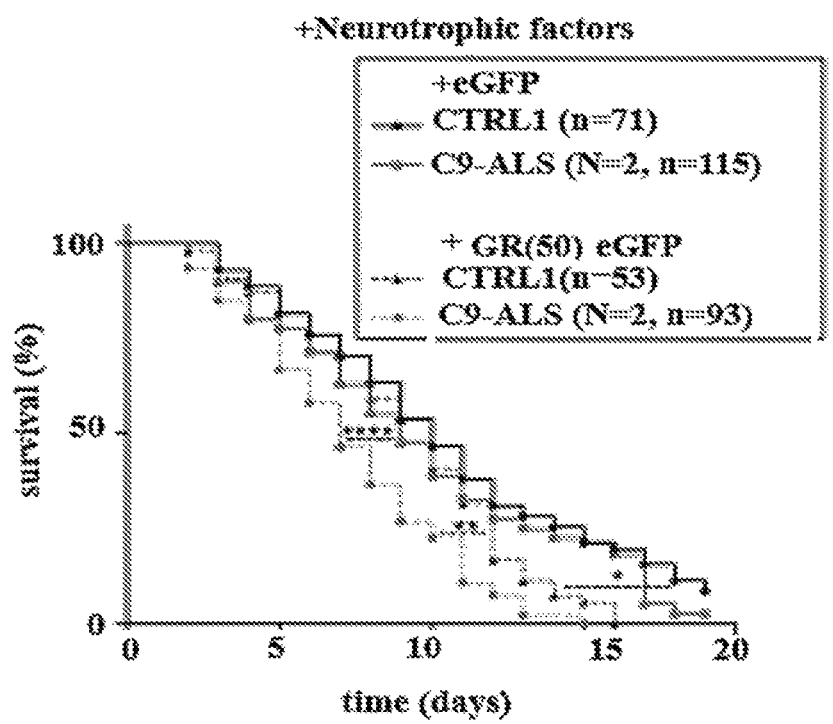
Figure 5E:
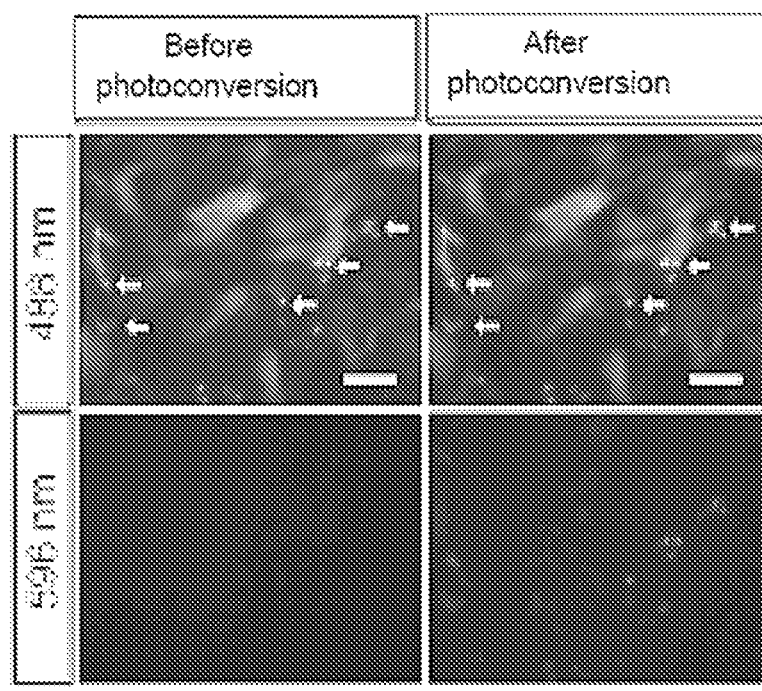
Figure 5F:
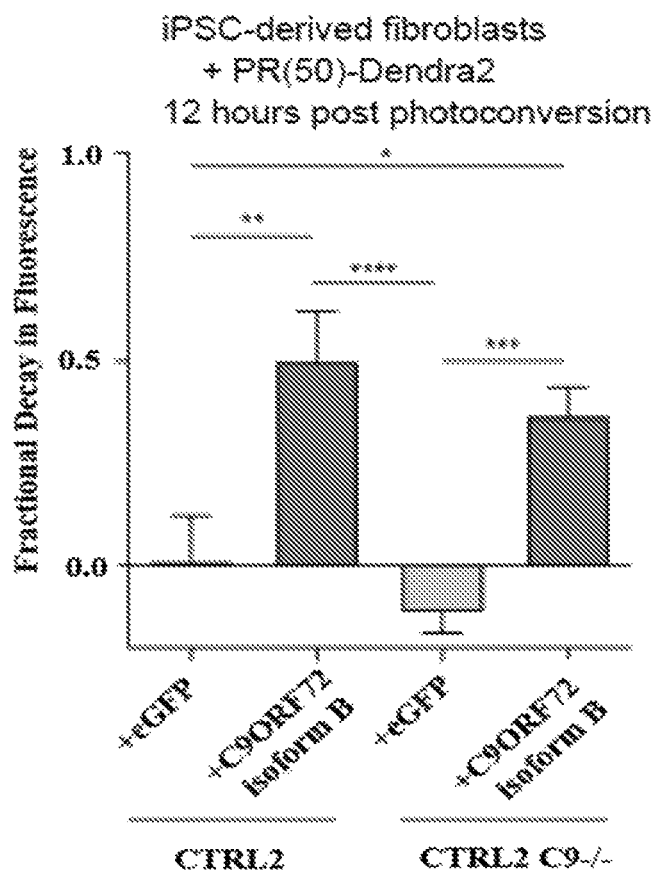
Figure 5G:
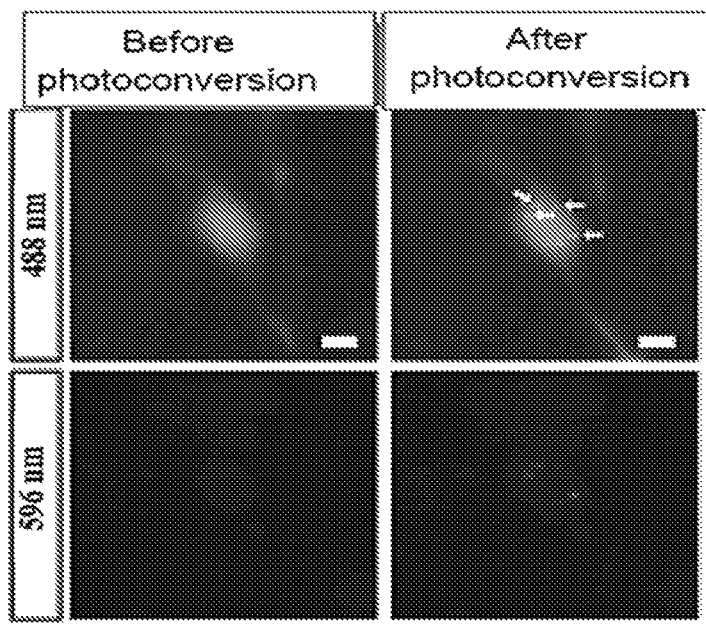
Figure 5H:
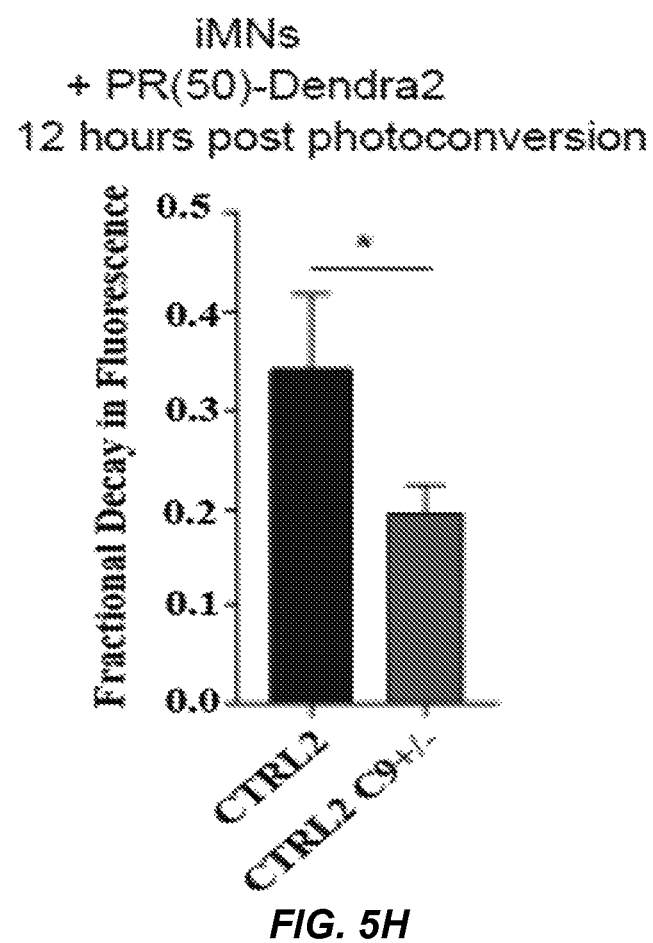
Figure 6A:
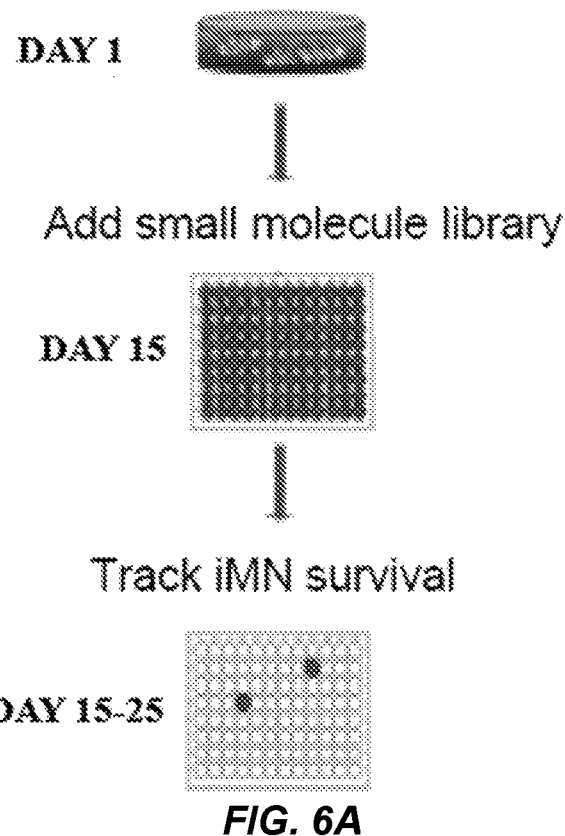
FIG. 6 shows that PIKFYVE inhibitors rescue C9-ALS iMN survival. a, The schematic shows the phenotypic screening for small molecules that enhance the survival of C9-ALS iMNs. b, The schematic shows the chemical structure of the PIKFYVE inhibitor YM201636 and apilimod. c, The image shows live cell images of iMNs at day 7 of treatment with DMSO or YM201636 (scale bar: 10 μm). d-f, The graphs show the survival effect of apilimod and YM201636 on C9-ALS1 (d), CTRL1 (e) C9-ALS2 (f) iMNs in excess glutamate. g, The schematic shows key players in early endosomal fusion. h-i, The graphs show the effect of YM201636 on NR1 and GLUR1 staining intensity in C9-ALS motor neurons (h)(median±interquartile range, Mann-Whitney test), and on their on local field potentials (LFP) as measured by micro-electrode array (i)(mean+s.e.m of 2 biological replicates, two-tailed t-test). j, The schematic shows the model for the mechanisms that cooperate to cause neurodegeneration in C9ORF72 ALS/FTD. Proteins in red are known to be mutated in ALS or FTD. All survival experiments were analyzed by log-rank. *-p<0.05, -p<0.01, *-p<0.001, ****-p<0.0001. iMN survival experiments in (c-f) were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.
Figure 6B:
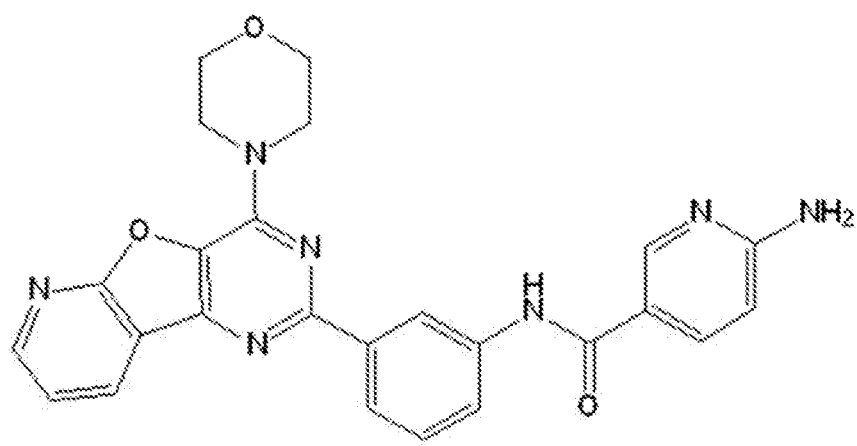
Figure 6C:
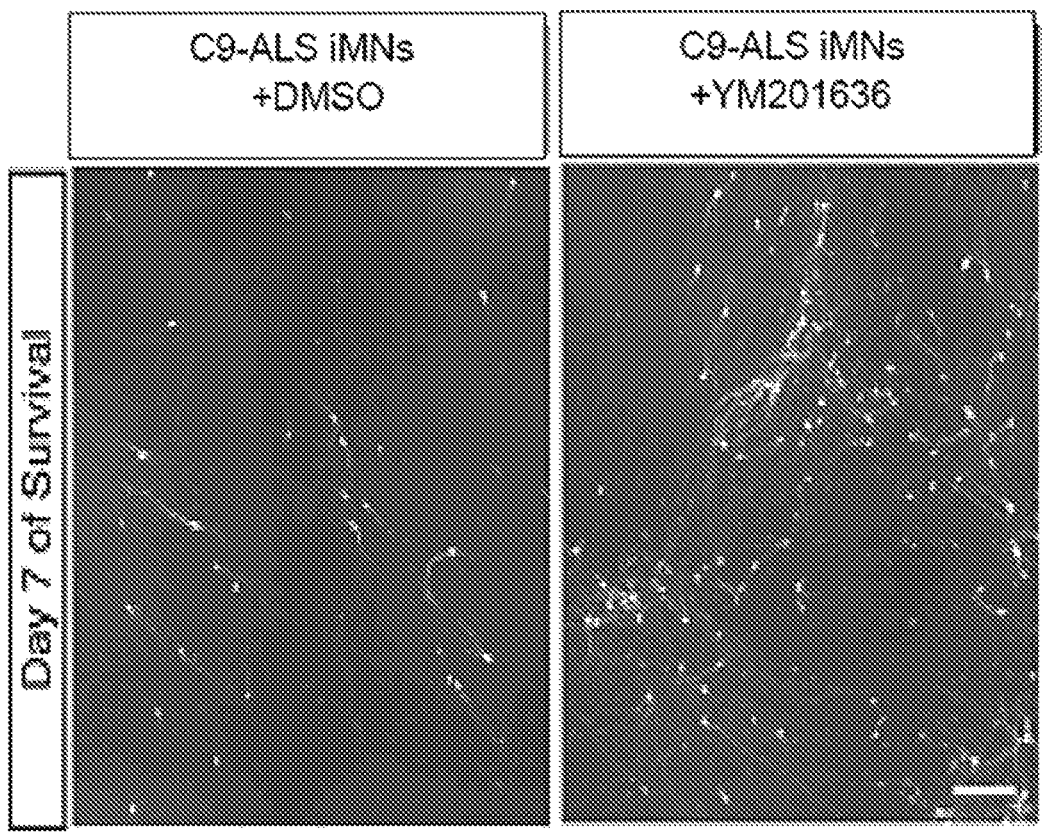
Figure 6D:
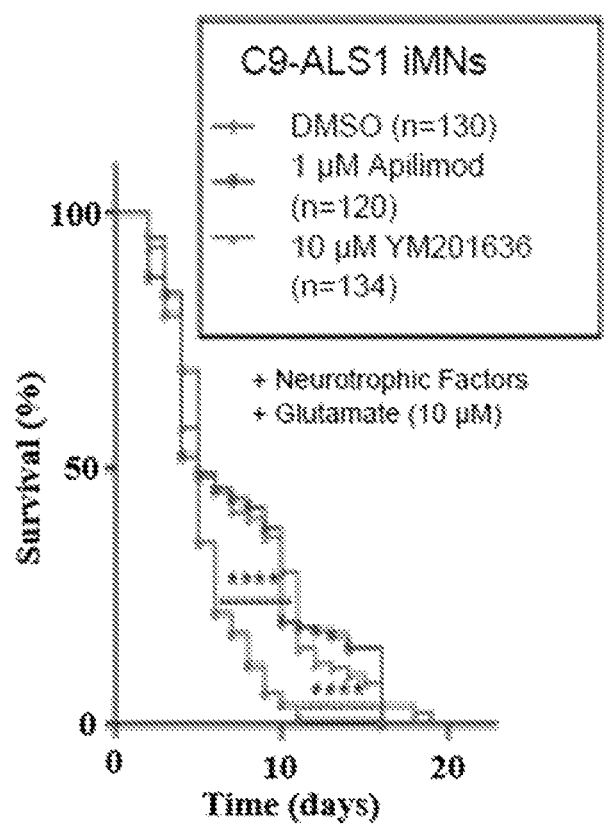
Figure 6E:
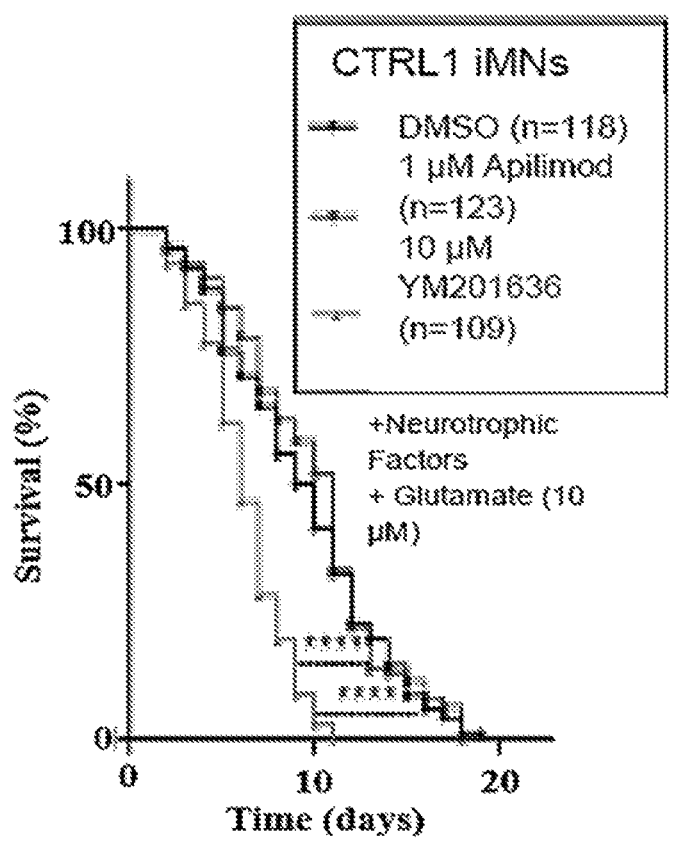
Figure 6F:
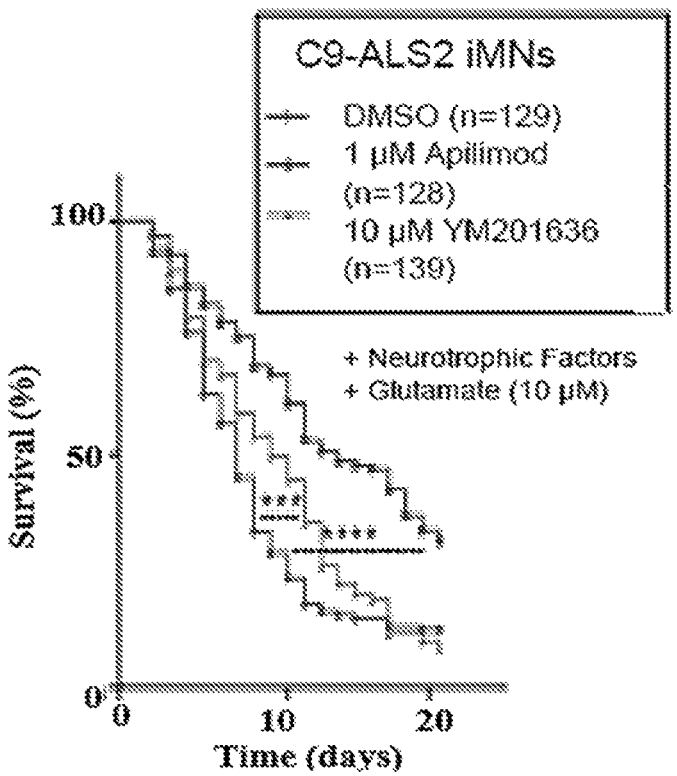
Figure 6G:
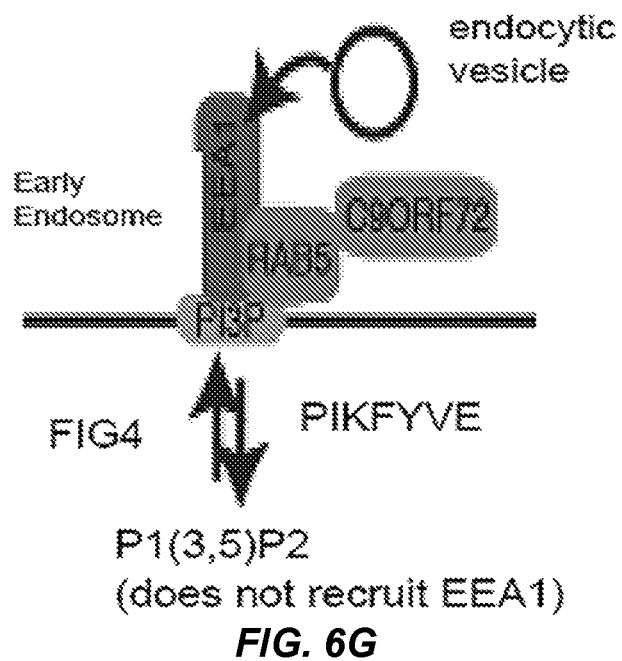
Figure 6H:
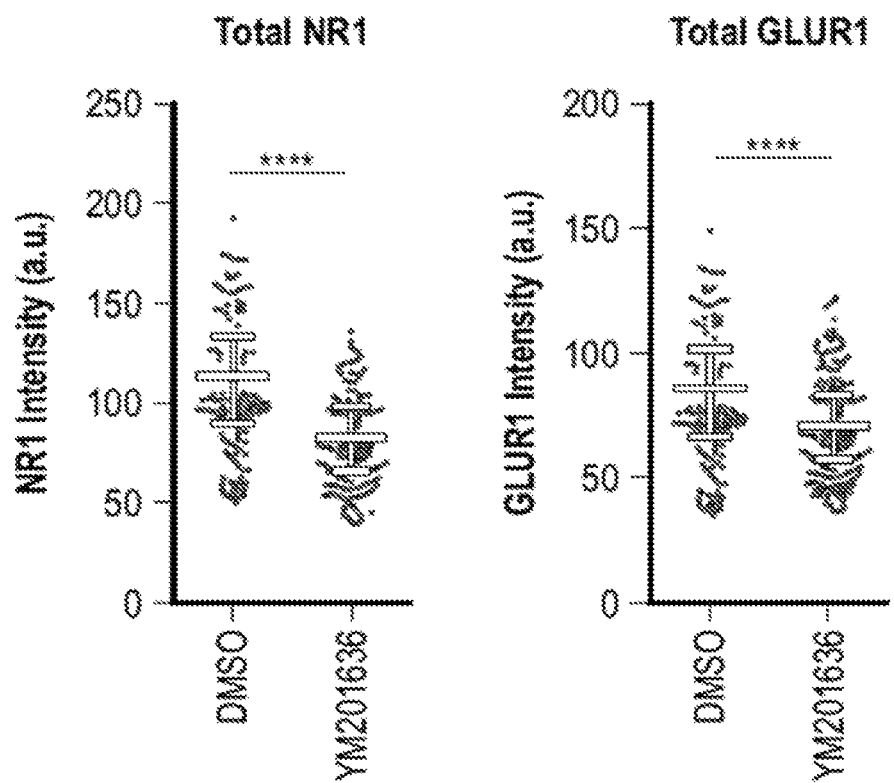
Figure 8E:
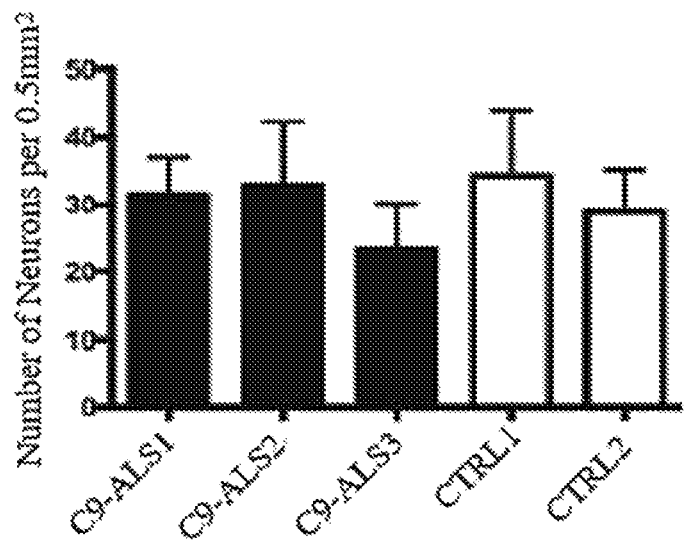
Figure 8F:
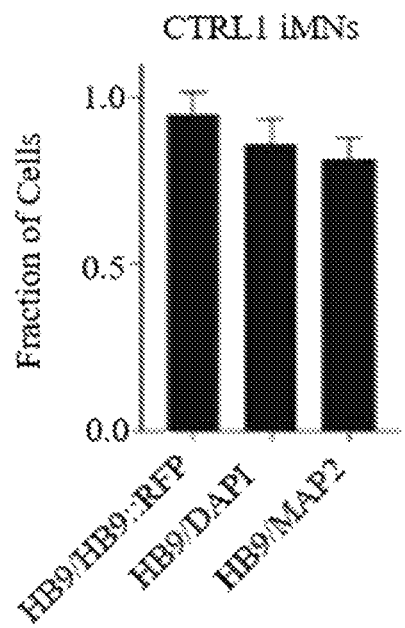
Figure 9A:
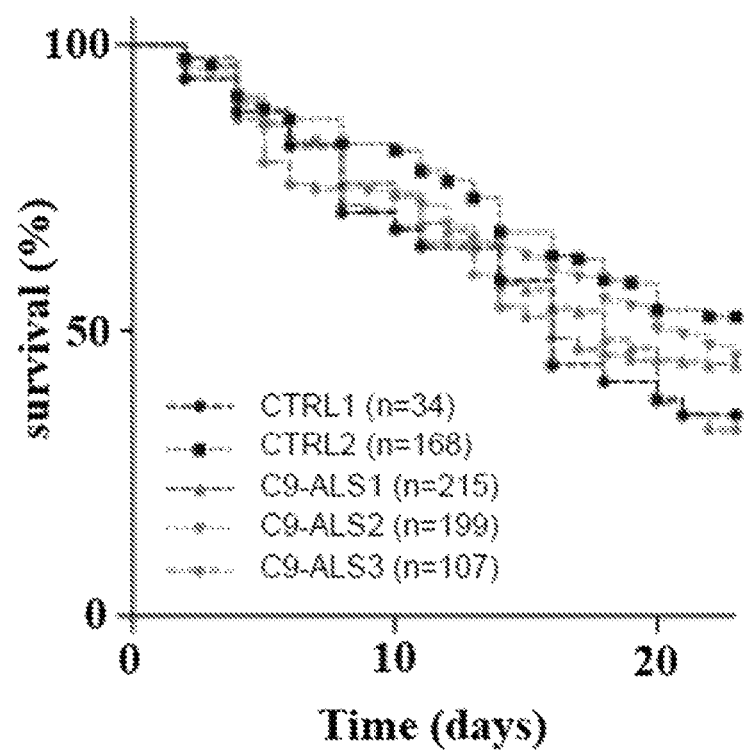
FIG. 9 shows that C9ORF72 iMNs display neurodegenerative phenotypes. a-e, The graphs show representative survival curves of control and C9-ALS iMNs with neurotrophic factors (a), in excess glutamate with glutamate receptor antagonists (30 (d), or without neurotrophic factors (e). iMNs from two independent clones of the same donor (CTRL1) gave consistent results in this assay (c). The survival experiment in excess glutamate was also performed in another independent device (Molecular Devices ImageExpress, MD)(b). f-h, The images show the generation of TH+ dopaminergic neurons from control and C9ORF72 patients. The induced neurons express the DA neuron marker tyrosine dehydroxylase (TH, green), as well as the neuronal marker TUJ1 (red) and DsRed (blue, co-infected with the iDA factors to mark transduced cells)(f). Scale bar: 10 μm. The graph shows the percentage of DsRed-labeled cells that express TH is comparable between control and C9-ALS genotypes (g) (mean of 3 biological replicates±s.e.m. n>32 cells per replicate, two-tailed t-test). *–$p<0.05$, –$p<0.01$, *–$p<0.001$. The graph shows the survival of induced TH+ (iDA) neurons in excess glutamate (h). i-k, The data show the correction of the C9ORF72 repeat expansion allele in iPSCs using CRISPR/Cas9. The image shows the strategy for removing the genomic C9ORF72 repeat expansion using CRISPR/Cas9 technology (i). The image shows the RP-PCR of the repeat region in the starting C9-ALS2 iPSCs and the corrected isogenic line after CRISPR/Cas9-mediated repeat removal (j). The images shows the southern blot, which depicts the loss of the high molecular weight band and appearance of a 1.2-kb band in the corrected C9-ALS2 iPSCs corresponding to the corrected allele with the introduction of a GGGGCCx2-PGK-Puror cassette (k). l, The graph shows the survival of C9-ALS2 (red) and corrected C9-ALS2 (blue) iMNs, as well as control (CTRL2) iMNs. m, The image shows the fluorescence in situ hybridization of control, C9-ALS1 and corrected C9-ALS1 iMNs using a probe for the G4C2 hexanucleotide repeat or a scrambled (Scrb) probe (green) (Scale bars: 10 μm). Nuclei (blue) are labeled with Hoechst. All iMN survival experiments were statistically analyzed using the log-rank test. *–$p<0.05$, –$p<0.01$, *–$p<0.001$. iMN survival experiments in (a, d, and e) were performed in a Nikon Biostation, and (b, c, h, and l) were performed in a Molecular Devices ImageExpress. For iMN survival experiments, if iMNs from more than one iPSC line were combined into one curve, "N" designates the number of iPSC lines (each line is from a different donor except in (c)). "n" indicates the total number of iMNs counted across all lines in each condition.
Figure 9B:
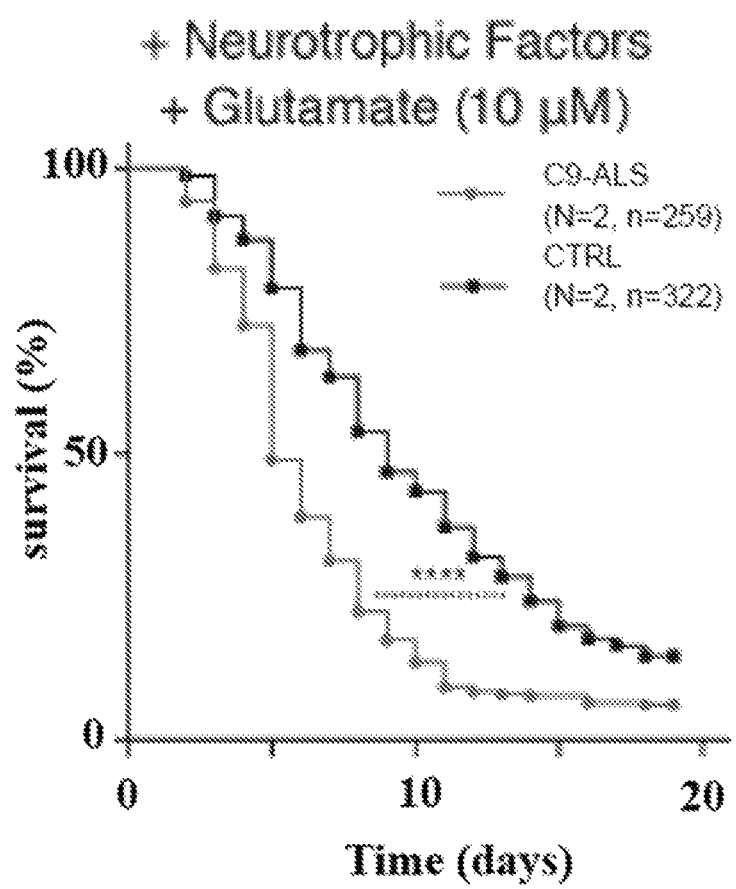
Figure 9C:
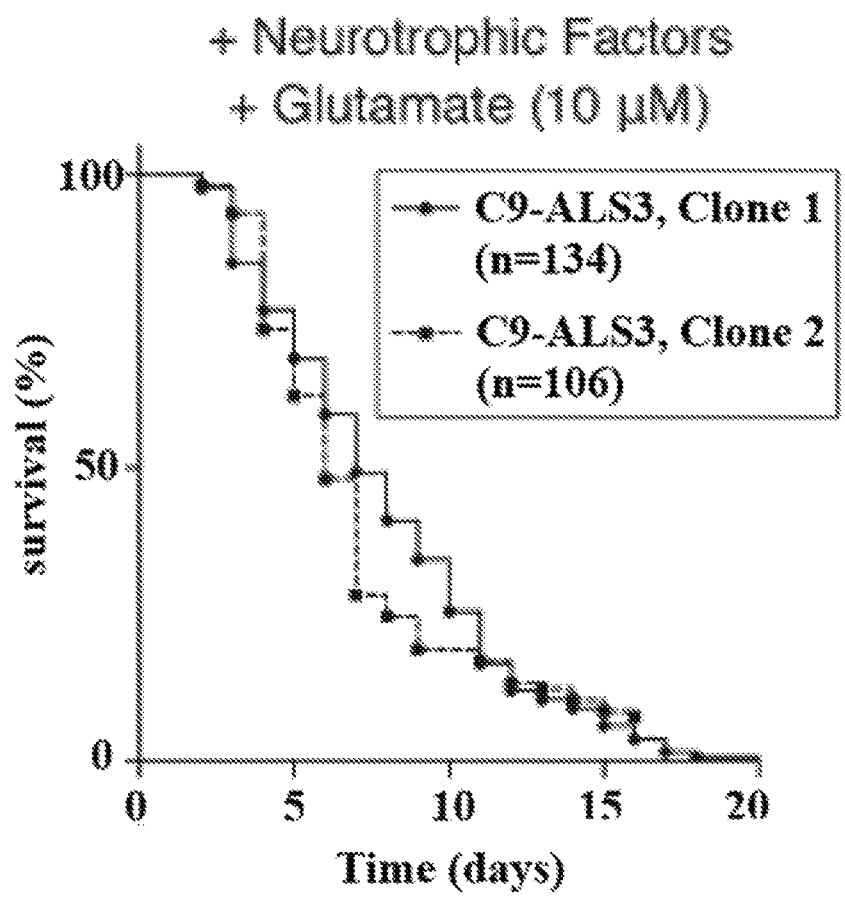
Figure 9D:
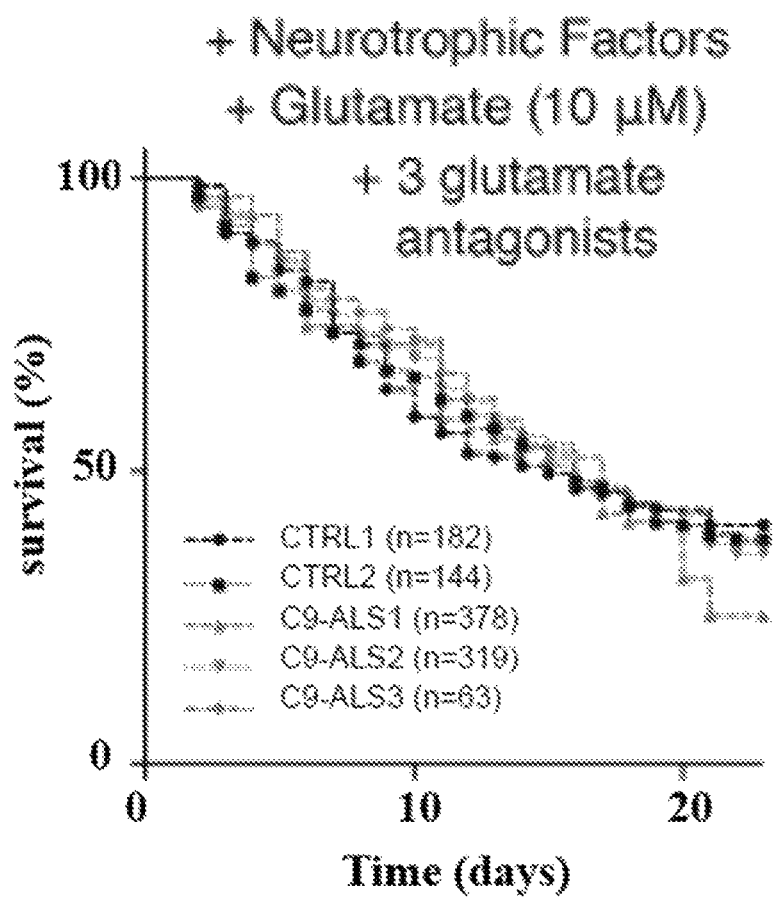
Figure 9E:
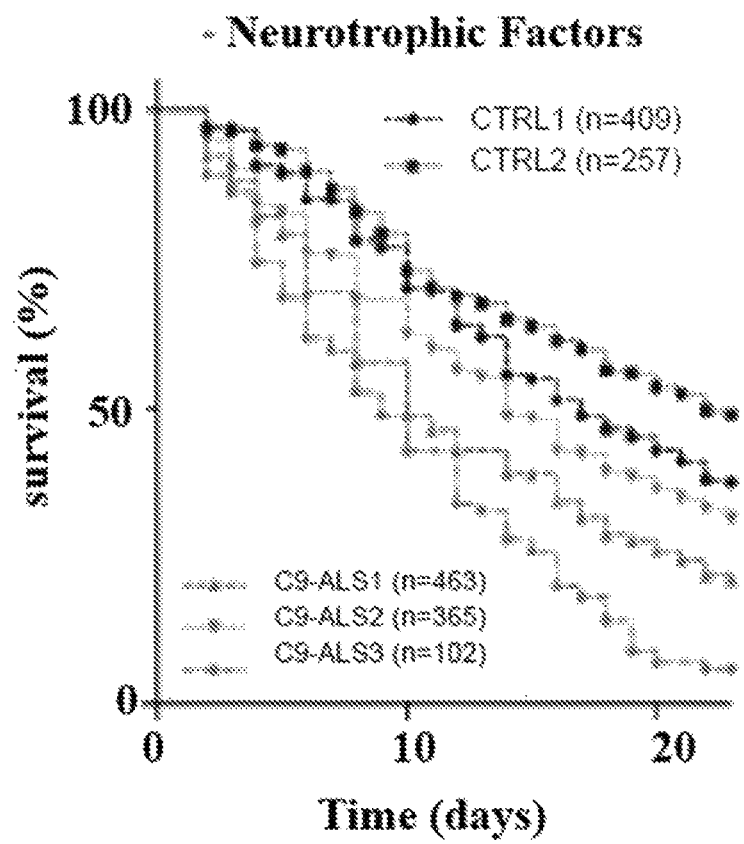
Figure 9F:
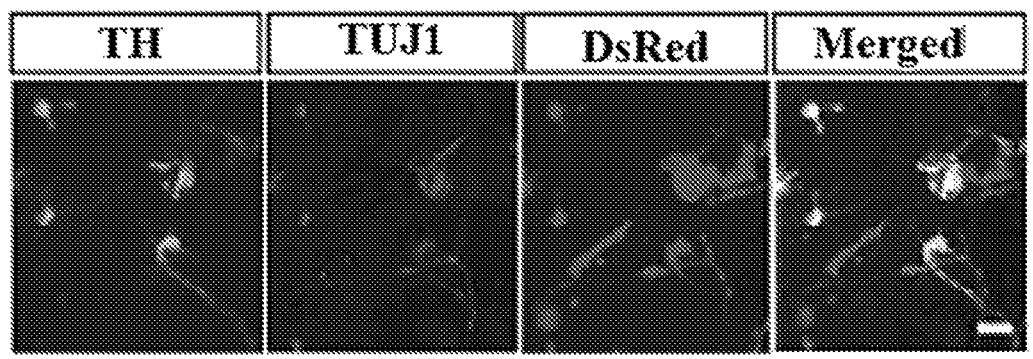
Figure 9G:
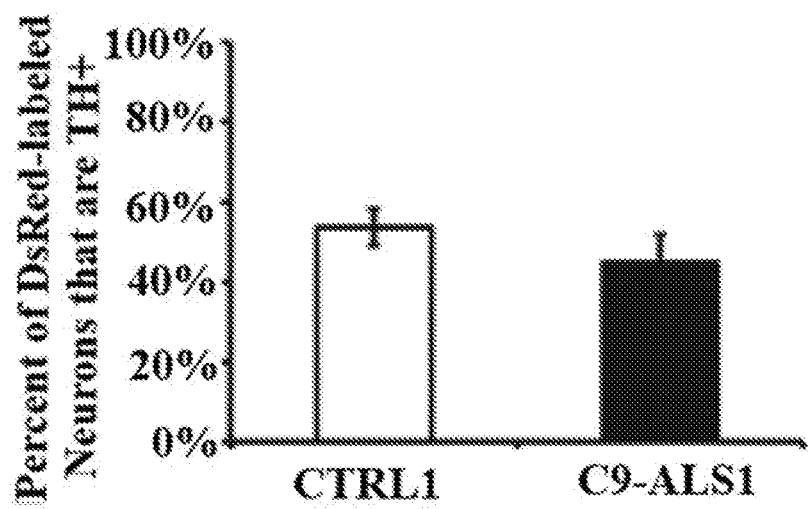
Figure 9H:
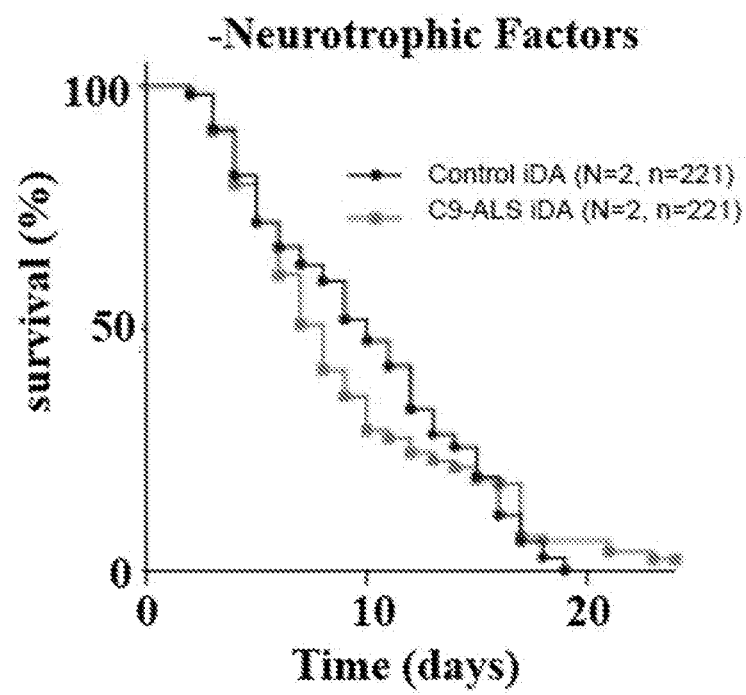
Figure 9I:
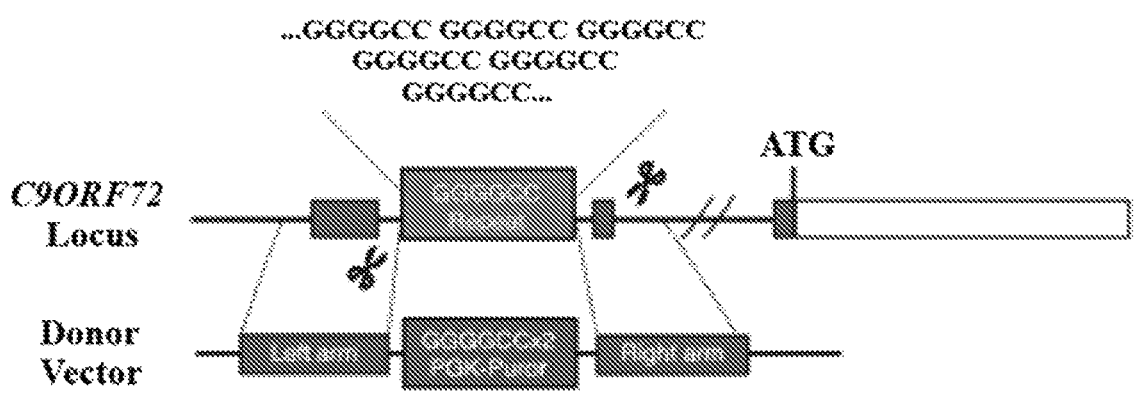
Figure 10A:
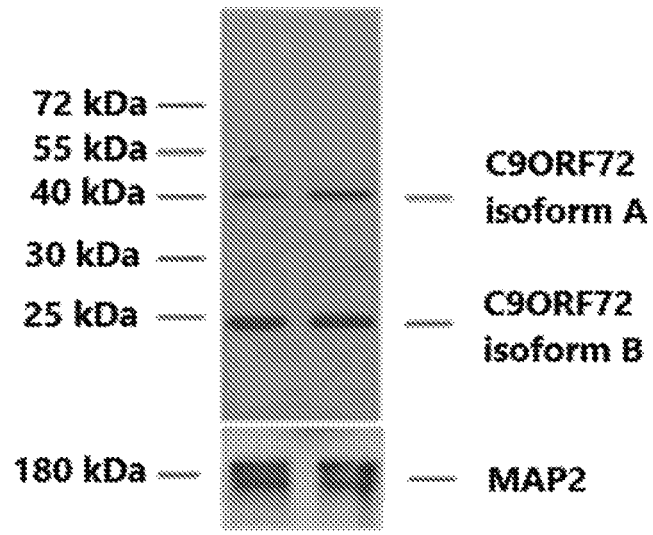
FIG. 10 shows the overexpression and deletion of C9ORF72 in iMNs. a, The image shows a western blot depicting C9ORF72 protein expression in patient and CRISPR-corrected iMNs. b, The graph shows the quantification of C9ORF72 isoform B protein levels in iMNs. c, The schematic shows the retroviral construct used in overexpression studies. d, The image shows the western blot depicting the expression of C9ORF72 isoform B in HEK cells transfected with the construct. DsRed-transfected cells are negative for C9ORF72 isoform B. e, The graph shows C9ORF72 mRNA expression levels (relative to GAPDH) in patient iMNs overexpressing eGFP or C9ORF72 (isoform A or B) (mean of 3 biological replicates±s.e.m.). f-g, The graphs show the RNA-sequencing (RNA-seq) analysis of iMNs of the starting control genotype (CTRL2) and isogenic C9ORF72 mutants C9$^{+/-}$, heterozygous; C9$^{-/-}$, homozygous) generated using CRISPR/Cas9. No significant changes in gene expression are observed in the top 10 genes predicted to have possible off-target sites for the sgRNAs used (f). Likewise, expression of most genes mediate upstream or downstream of C9ORF72 (10 genes in either direction) are not altered in the mutants (g). Values are the mean of 2 biological replicates±s.d. h-k, The graphs show the survival of iMNs in excess glutamate, either with C9ORF72 (isoform A or B) or eGFP overexpression. Expression of exogenous C9ORF72 does not enhance control iMN survival (h), but rescues the survival of C9-ALS2 iMNs (i), as well as CTRL2 iMNs with C9 mutations: CTRL2 C9ORF72$^{+/-}$ (j) and CTRL2 C9ORF72$^{-/-}$ (k). FPKM, fragments of kilobase of exon per million fragments mapped; n.s., not significant. iMN survival statistical analysis was performed using the log-rank test. All other statistical analysis was performed using a log-rank. *–$p<0.05$, –$p<0.01$, *–$p<0.001$, ****–$p<0.0001$. iMN survival experiments in (h and i) were performed in a Nikon Biostation, and (j and k) were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.
Figure 10B:
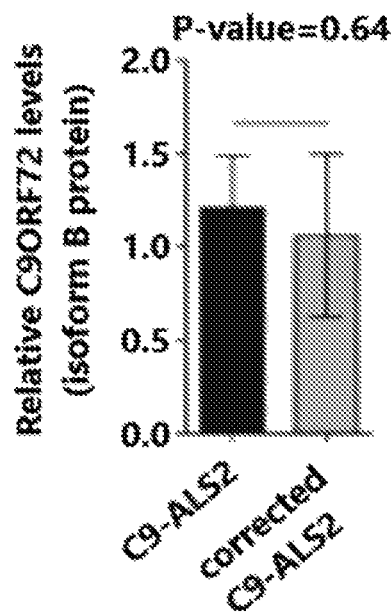
Figure 10C:
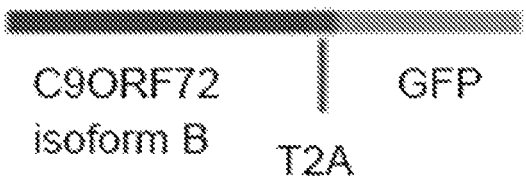
Figure 10D:
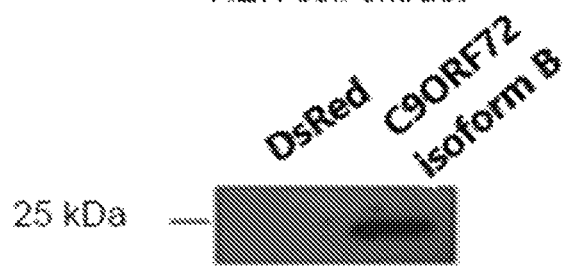
Figure 10E:
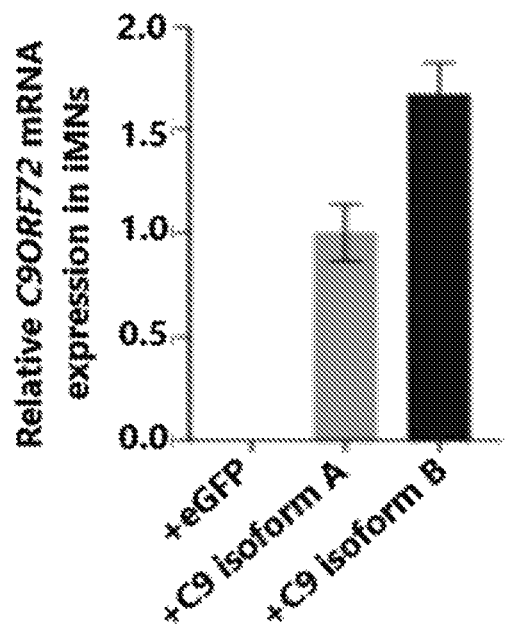
Figure 10F:
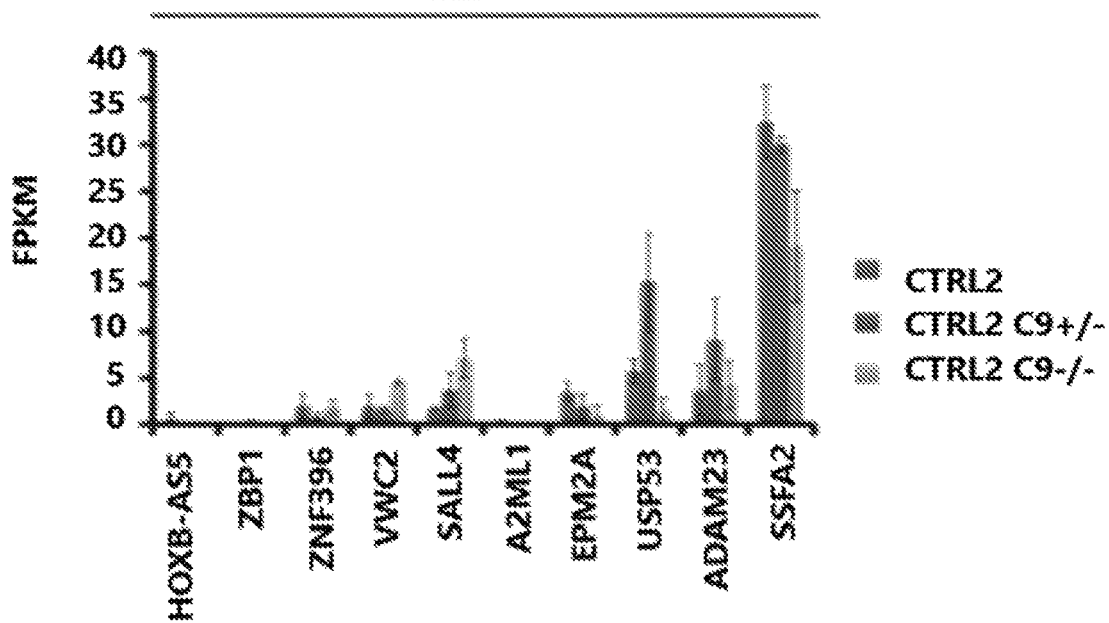
Figure 10G:
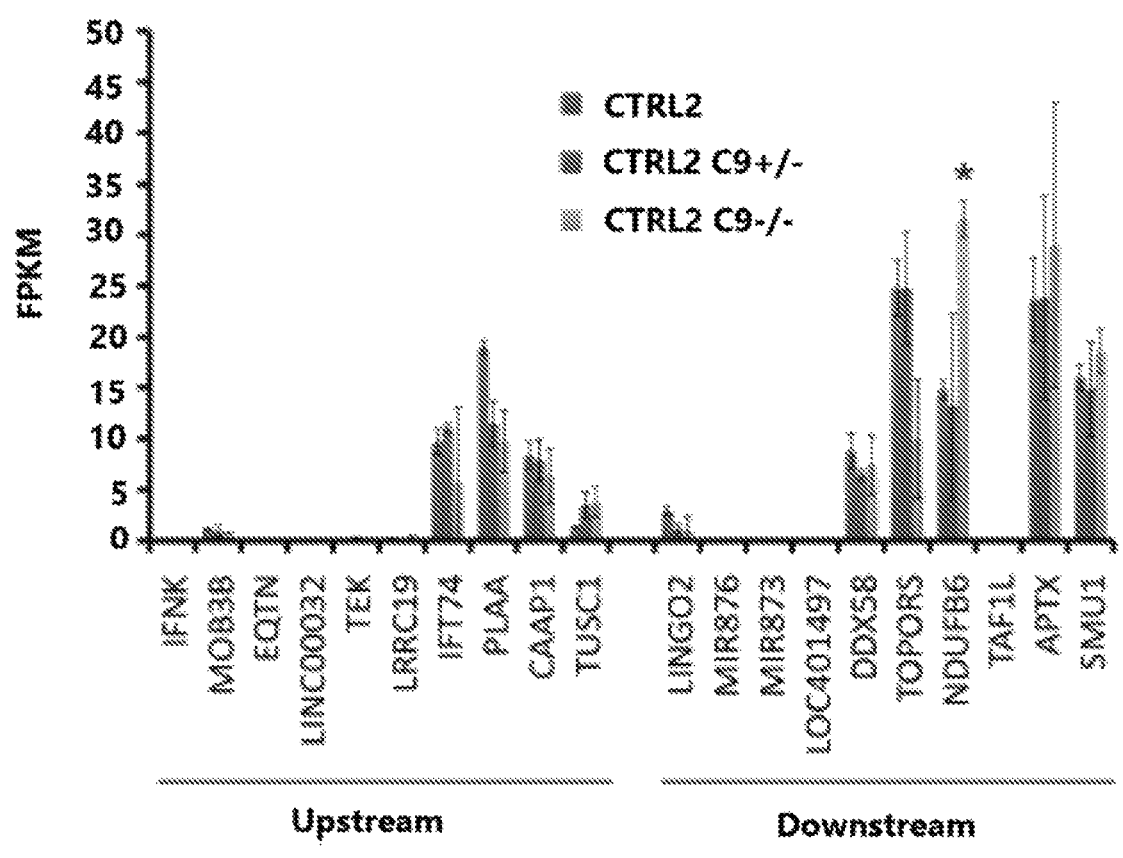
Figure 10H:
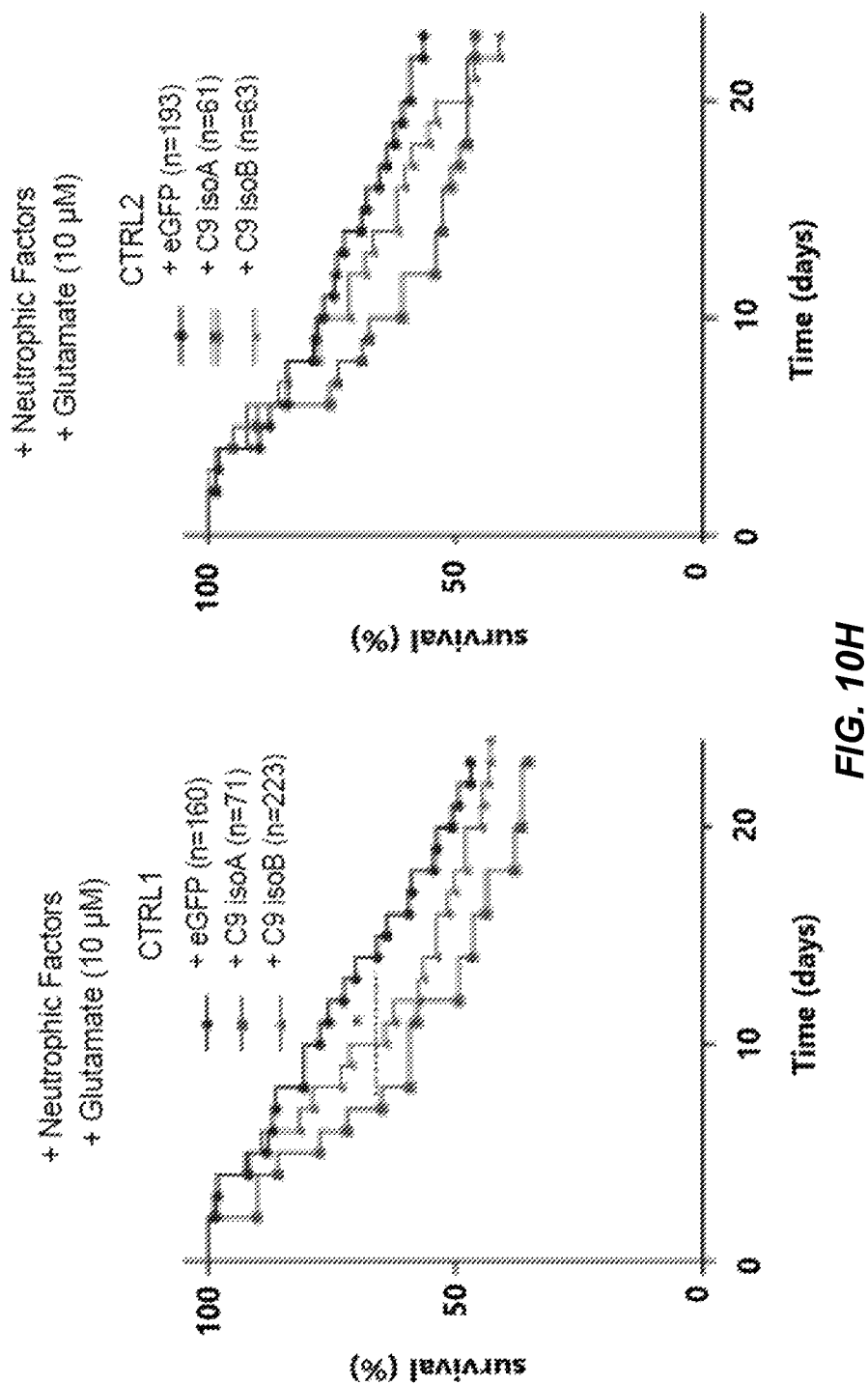
Figure 10I:
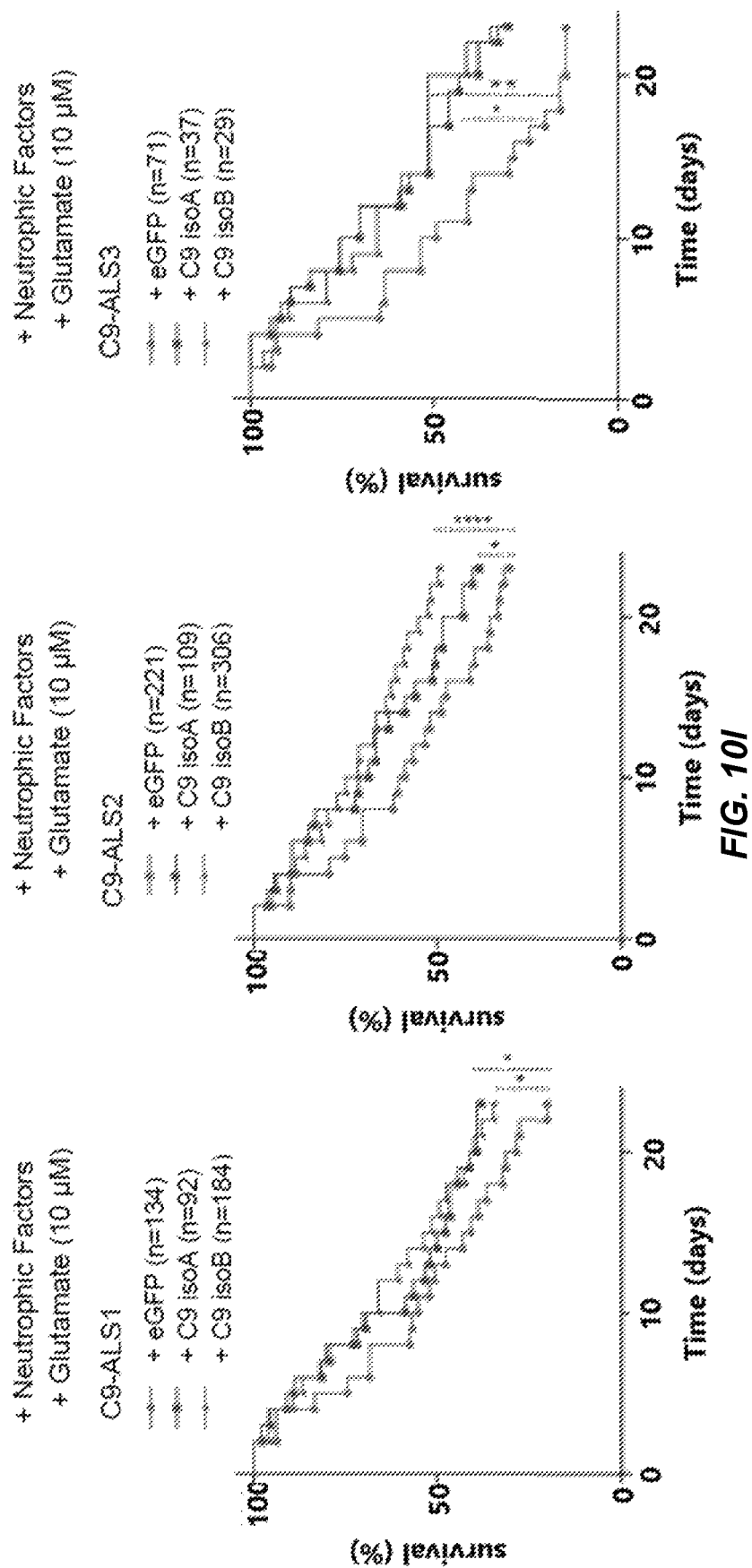
Figure 10J:
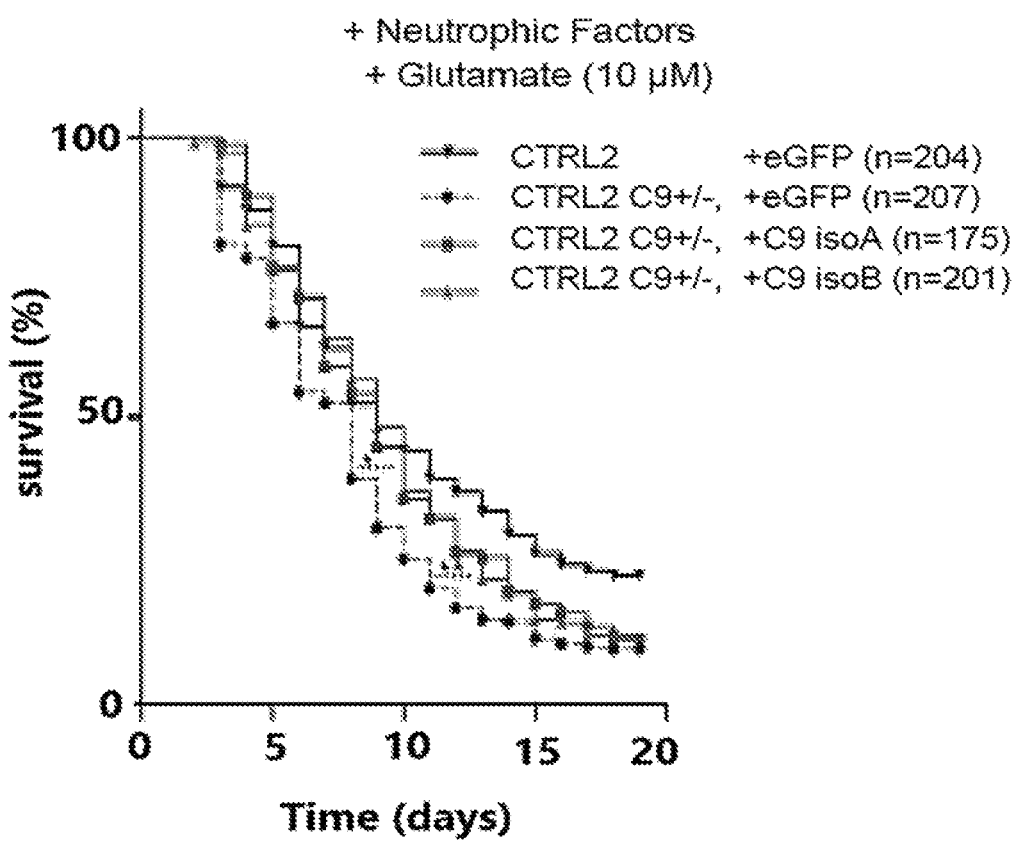
Figure 10K:
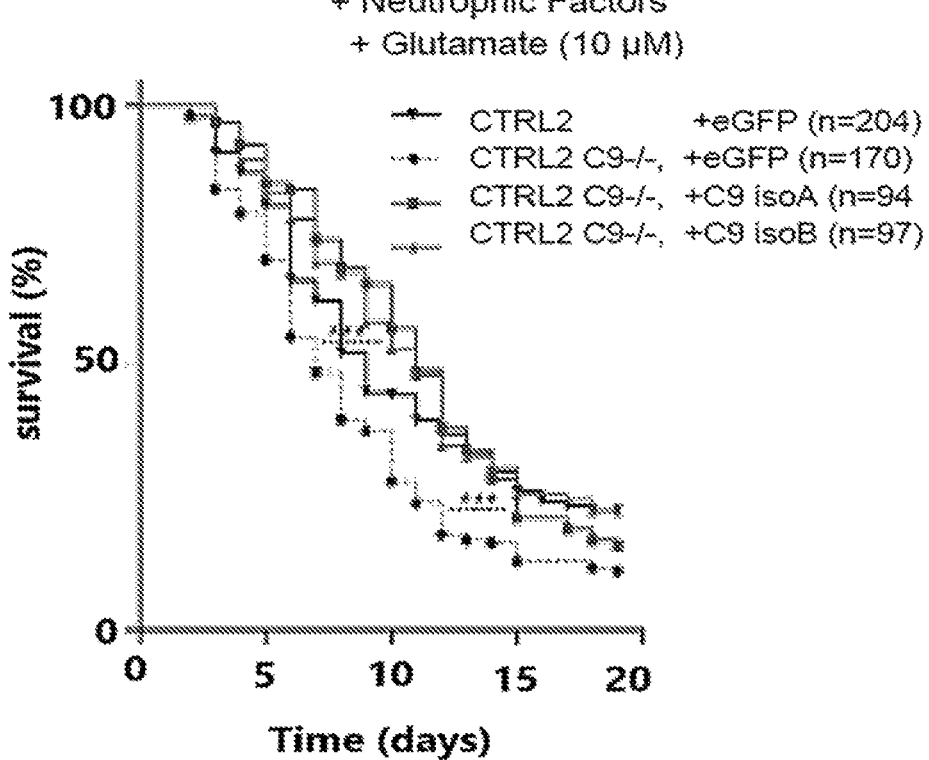
Figure 12A:
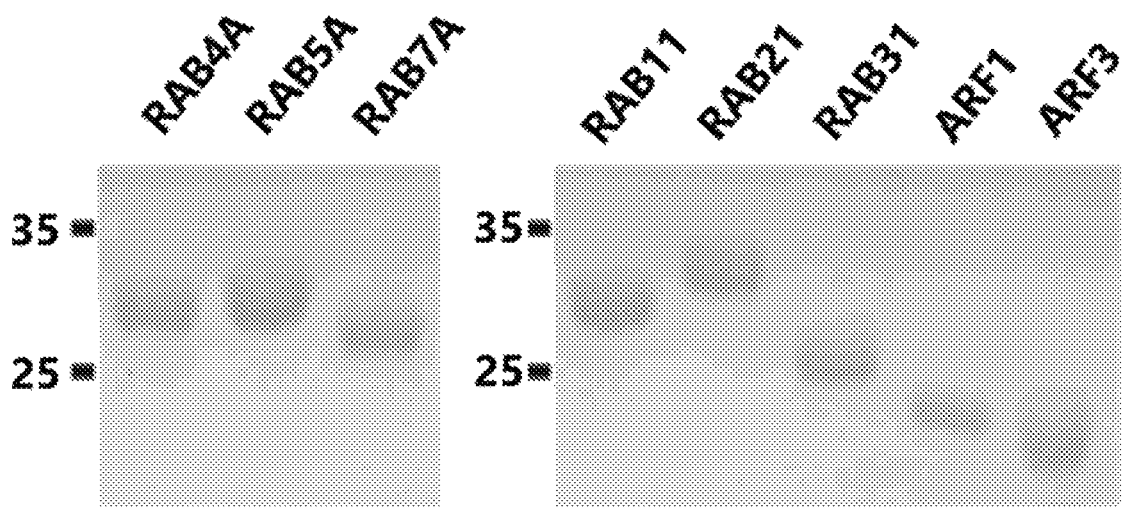
FIG. 12 shows that C9ORF72 stimulates guanine exchange on RAB5 and ARF3. a, The image shows polyacrylamide gel electrophoresis (PAGE) that depicts the successful purification of small GTPase proteins. b, The graph shows the summary of small GTPase expression in human iMNs (RNA seq data from this manuscript) and human iPSC-derived MNs (Kiskinis et al., *Cell Stem Cell*, 2014). Bar colors indicate the ability to purify each GTPase from *E. coli*. c, The graph shows an in vitro guanine exchange assay using BODIPY® FL GDP, showing fluorescence decrease of a panel of small GTPase-bound BODIPY® FL GDP upon EDTA treatment (normalized to DsRed-bound reference). d, The image shows western blots depicting the overexpression of HA-tagged C9ORF72 isoforms A and B in cell extracts used for the assay and a negative control GEF assay with no GTPase in order to test the effect of C9ORF72 on BODIPY® FL GDP fluorescence over time. e-f, The graphs show the fluorescence intensity change of small GTPase-bound BODIPY® FL GDP, treated with HA-tagged C9ORF72 isoform A (e) or RABEX5 (f)(mean of 3 biological replicates±s.d.). iMN survival experiments in (g) were performed in a Molecular Devices ImageExpress. For iMN survival experiments, if iMNs from more than one iPSC line were combined into one curve, "N" designates the number of iPSC lines (each line is from a different donor). "n" indicates the total number of iMNs counted across all lines in each condition.
Figure 12B:
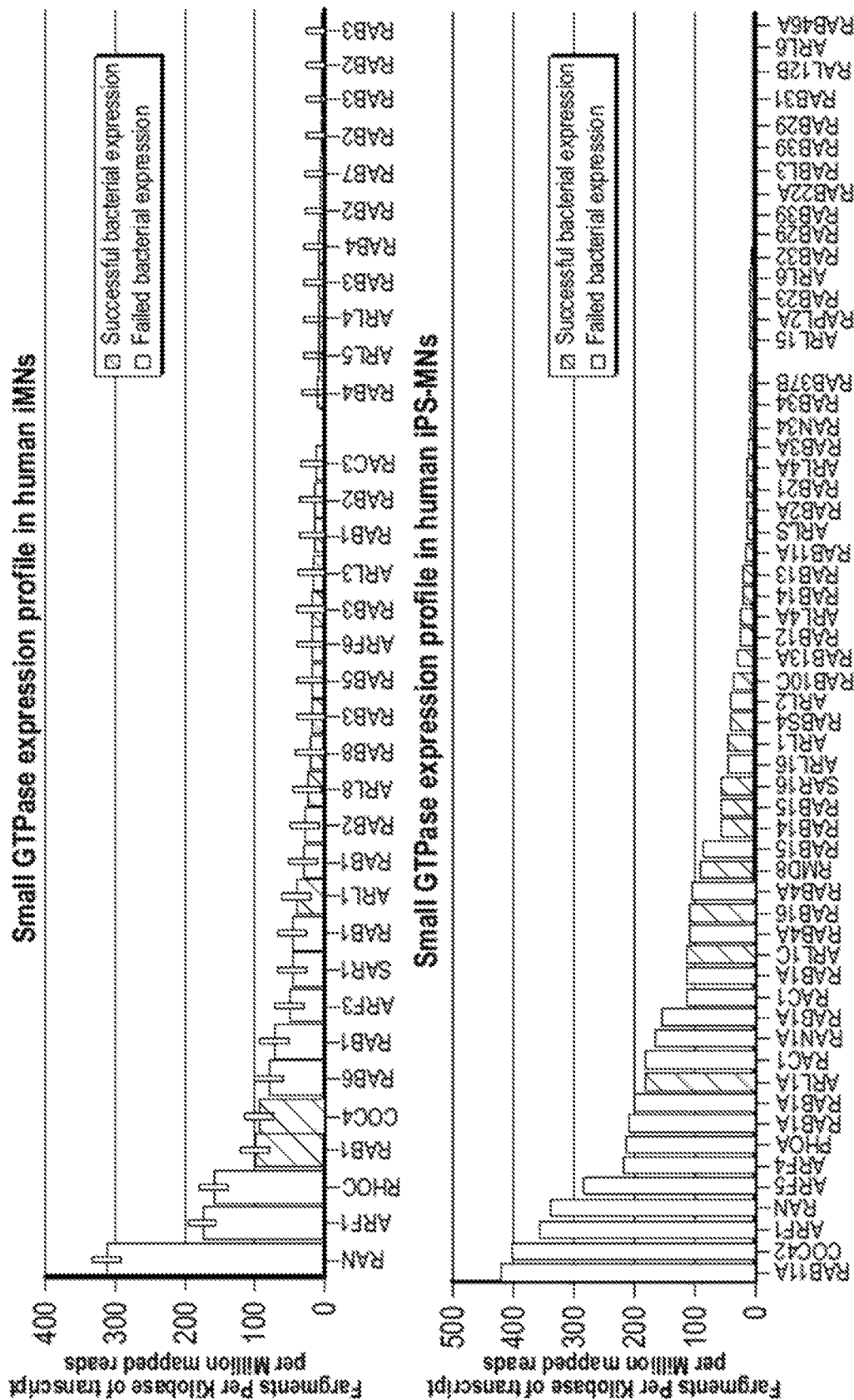
Figure 12C:
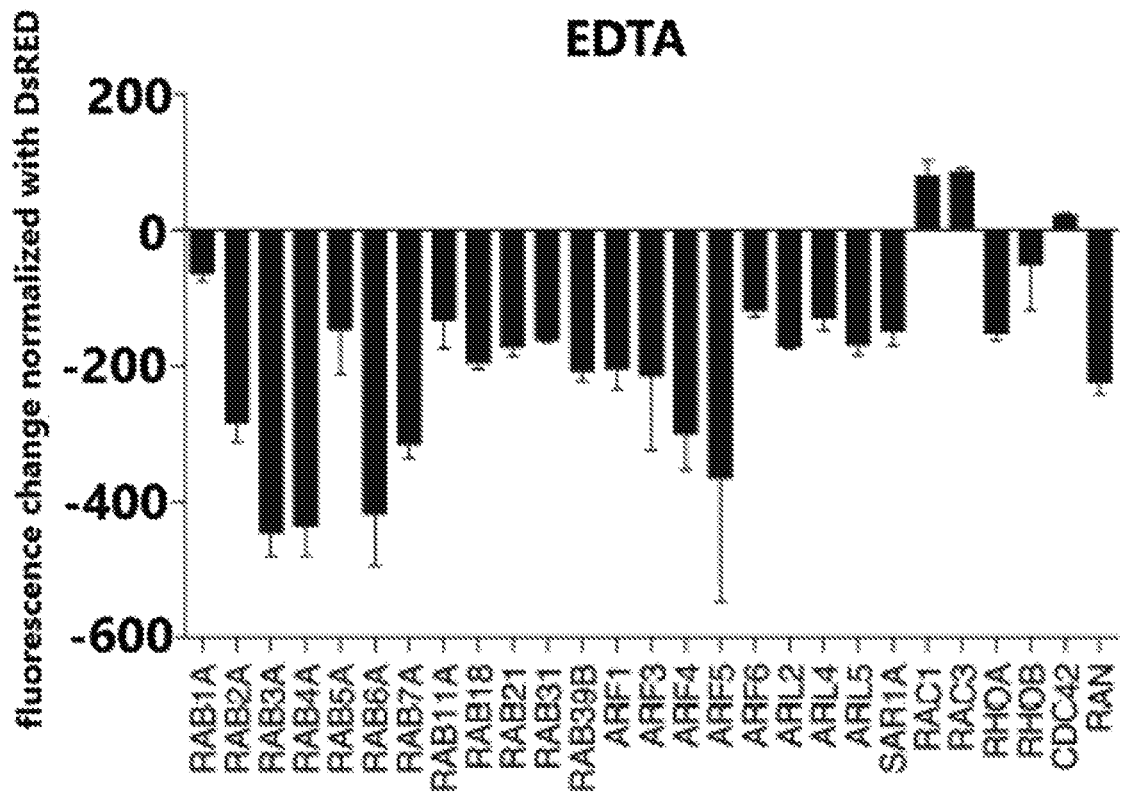
Figure 12D:
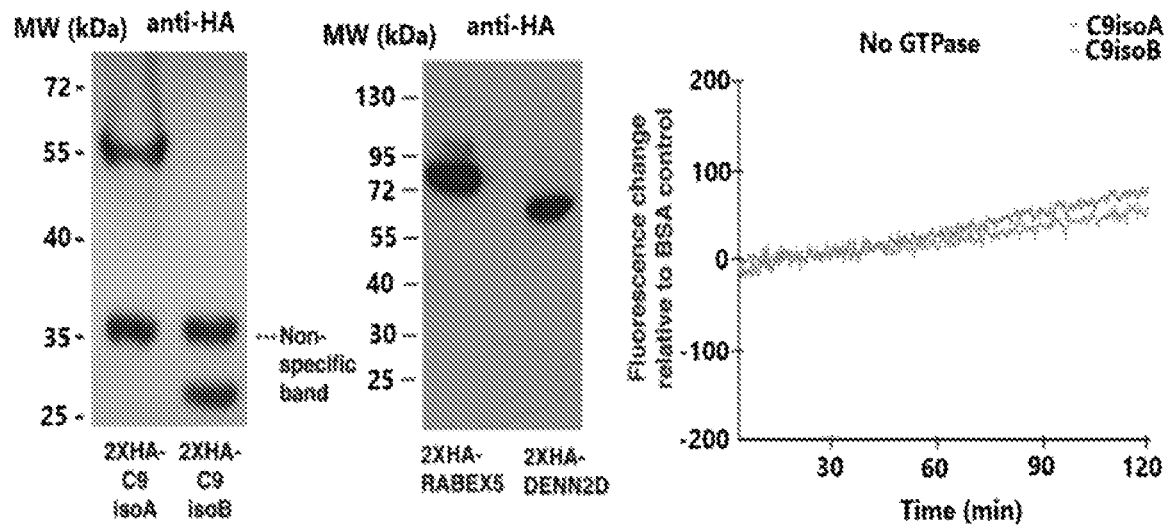
Figure 12E:
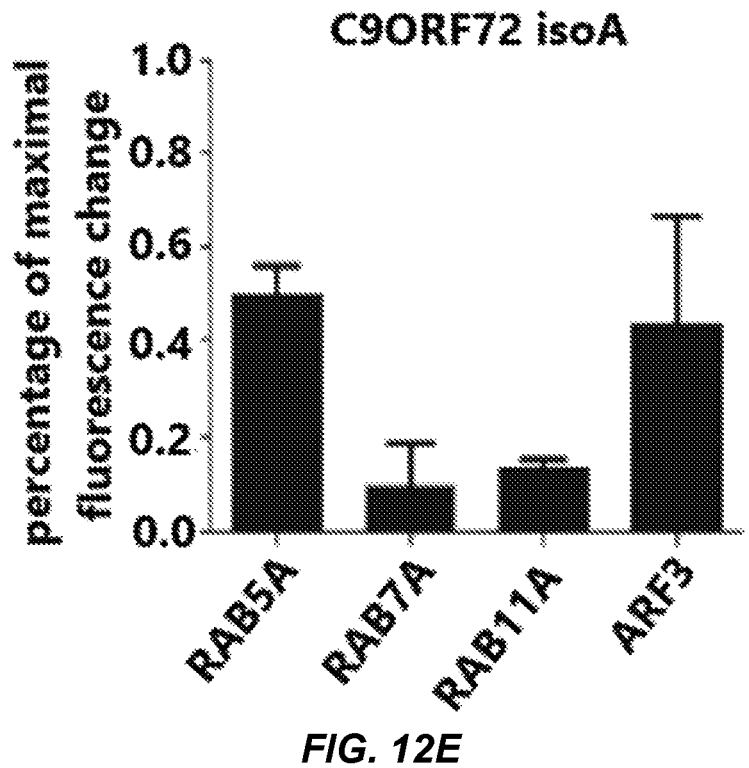
Figure 12F:
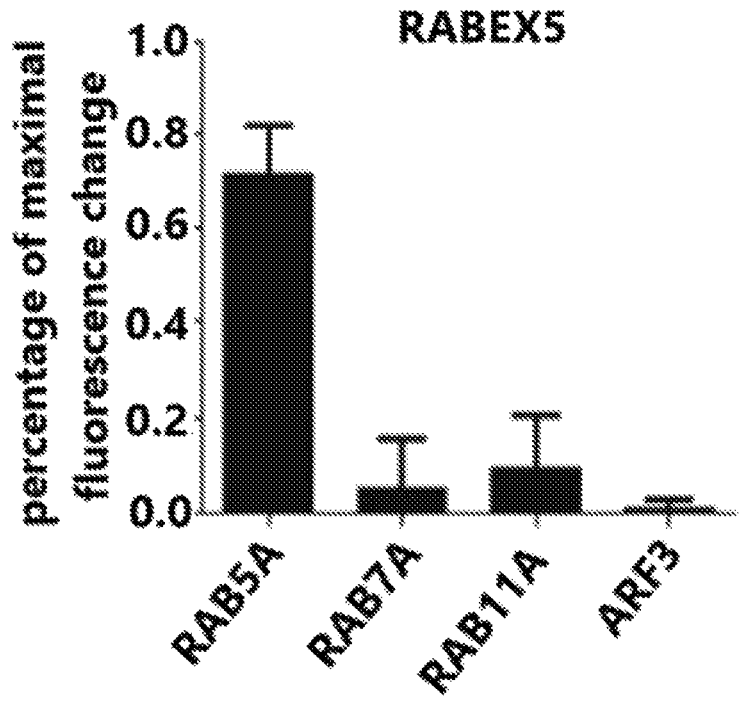
Figure 12G:
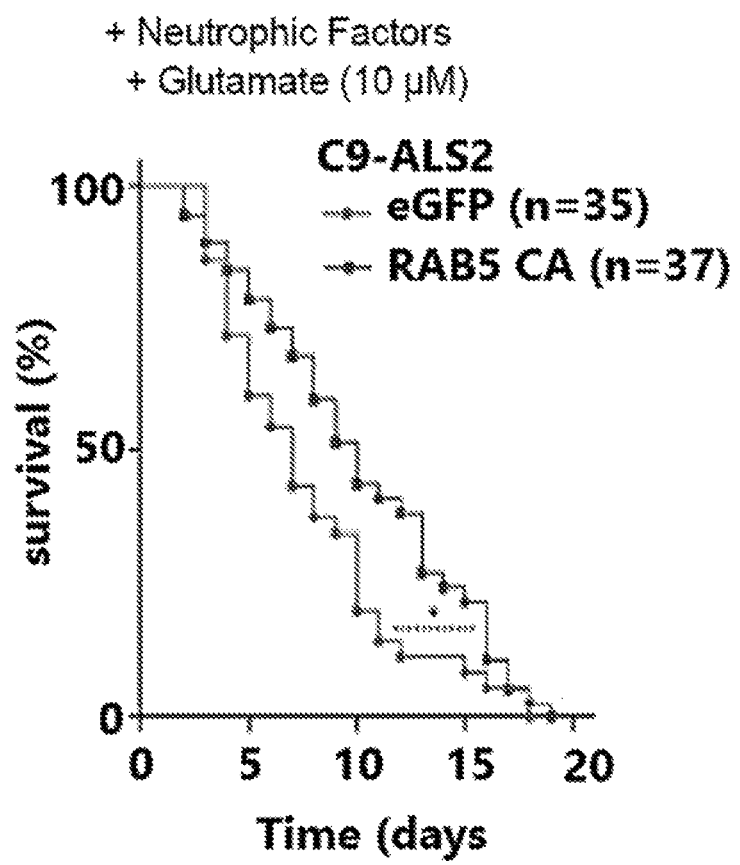
Figure 13A:
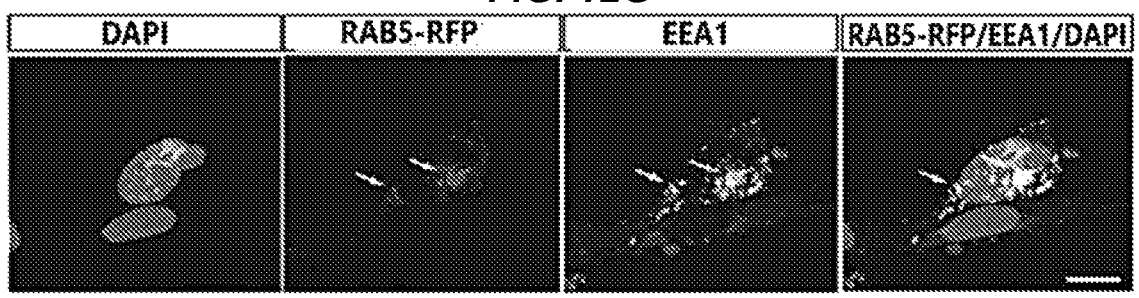
FIG. 13 shows that reduced C9ORF72 activity alters endosomal trafficking in human motor neuron. a-b, The confocal images show CTRL2 iMNs overexpressing RFP-RAB5 (red) stained for EEA1 (green), and the graph shows the quantification of fluorescence intensity of RFP-RAB5+ punctae in CTRL2 and CTRL2 C9$^{+/-}$ iMNs (b) (mean of 2 biological replicates±s.e.m.). c, Confocal imaging of iMNs overexpressing eGFP or C9ORF72 isoform B-T2A-eGFP shows the expression of EEA1 (red) and GFP (green). Scale bars: 10 μm (a); 5 μm (c).
Figure 13B:
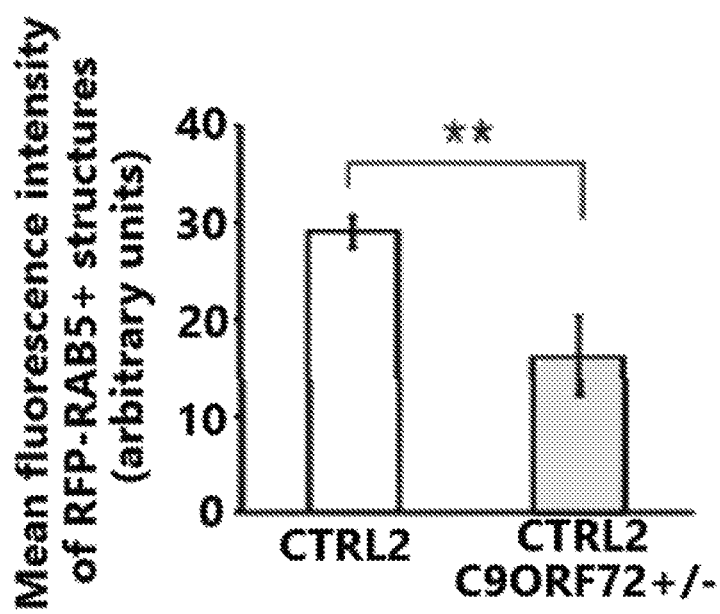
Figure 14A:
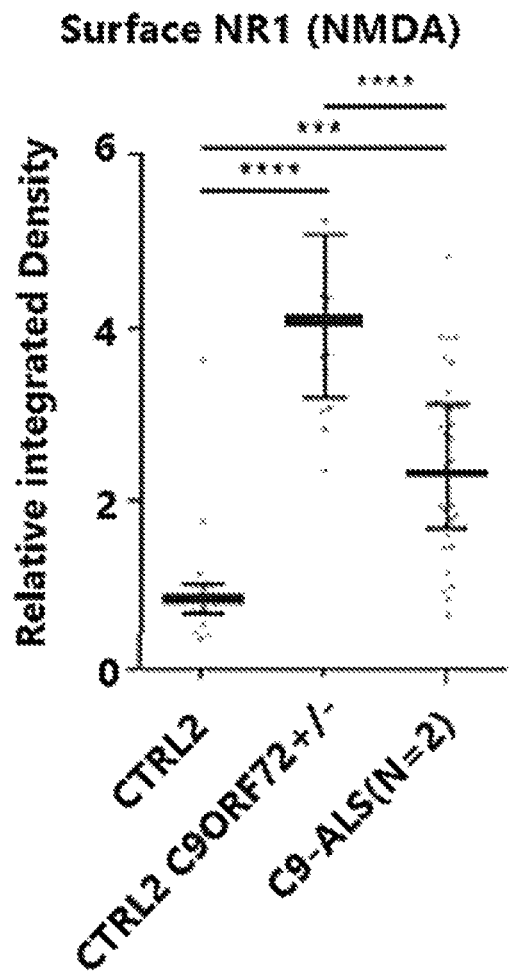
FIG. 14 shows that reduced C9ORF72 expression sensitizes iMNs to glutamate. a, The graph shows the quantification of surface NR1 protein expression in iMNs by immunostaining (mean of 2 biological replicates±s.d. n>10 cells per replicate). b, The diagram shows second C9ORF72$^{+/-}$ iPSC line generation using CRISPR/Cas9, and the sequence of the mutated C9ORF72 allele. c, The graph shows the quantification of total NR1 protein expression in iMNs by immunostaining (mean of 2 biological replicates±s.d. n>14 cells per replicate). d, The graphs shows immunostaining, which depicts the expression of total (turquoise) and surface-localized (red) GluR1 in C9ORF72 wild-type and heterozygous C9$^{+/-}$ Hb9::Channel Rhodopsin-YFP+ (green) iMNs. Scale bars: 10 μm. e-f, The graphs show the quantification of total and surface GluR1 protein expression in iMNs by immunofluorescence (mean of 2 biological replicates±s.d. n>10 cells per replicate). g, The graph shows the quantification of TRKB levels in iMNs by immunofluorescence (mean of 2 biological replicates±s.d. n>10 cells per replicate). h-i, The graphs show the qRT-PCR analysis of NR1 (h) and GluR1 (i) mRNA levels in C9ORF72 wild-type and heterozygous iMNs. Values are the mean of 3 biological replicates±s.e.m. j, The graph shows the distribution of mean fluorescence intensity of RAB11+ structures in C9-ALS2 iMNs and the wild-type isogenic control (corrected C9-ALS2) iMNs (mean of 2 biological replicates±s.d. n>10 cells per replicate). k, The graph shows the number of Fluo-4 flashes per two minutes in glutamate-treated C9-ALS2 as well as corrected C9-ALS2 iMNs, with or without treatment with glutamate receptor antagonists (3i)(mean of 3 biological replicates±s.e.m). l, The graph shows the GCaMP6 assay to look at the relative contributions of different glutamate receptors to the hyperexcitability phenotype of C9ORF72 mutant iMNs. C9ORF72$^{+/-}$ iMNs have heightened responses to NMDA, AMPA, and kainite, as well as to glutamate (Glu) that activates all three receptor types. This is still true when calcium influx from action potentials is blocked by TTX/TEA treatment (blue bars)(mean of 3 biological replicates±s.e.m., n=25 cells per replicate). m, The graphs show the sodium and potassium curves for control and C9ORF72$^{+/-}$ iMNs obtained by patch clamp electrophysiology. Curves are representative for each genotype (n=4 per genotype). Statistical analysis was performed using a two-tailed Student's t-test for pairwise comparisons, or one-way ANOVA for multiple comparisons. *-$p<0.05$, -$p<0.01$, *-$p<0.001$.
Figure 14B:
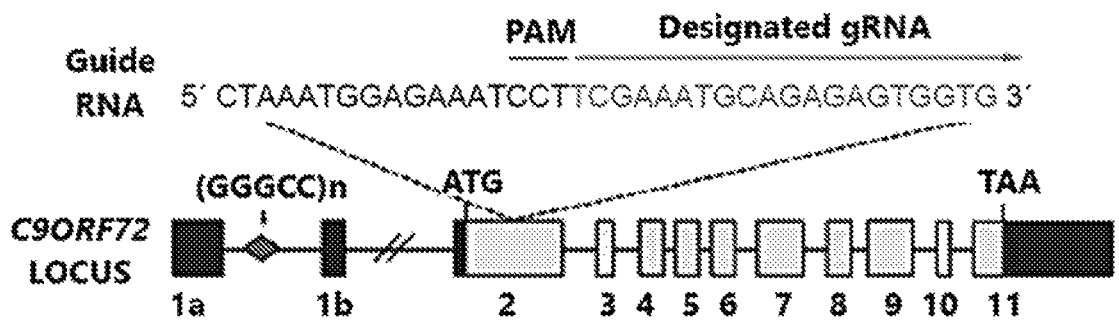
Figure 14C:
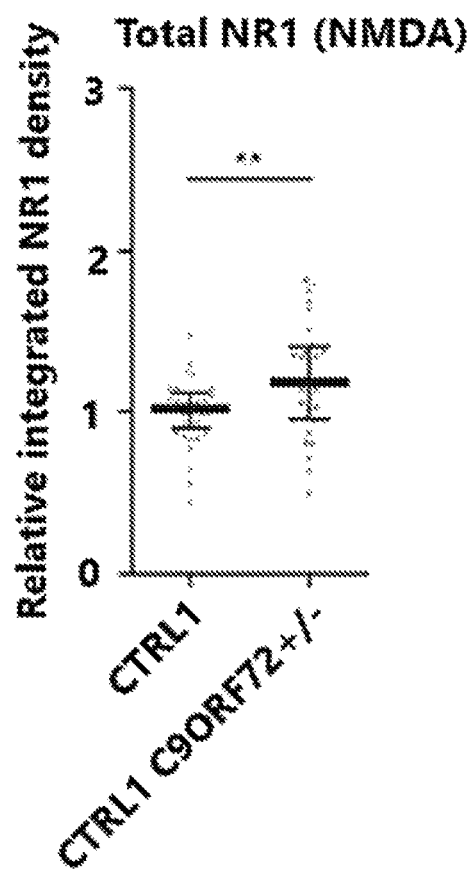
Figure 14D:
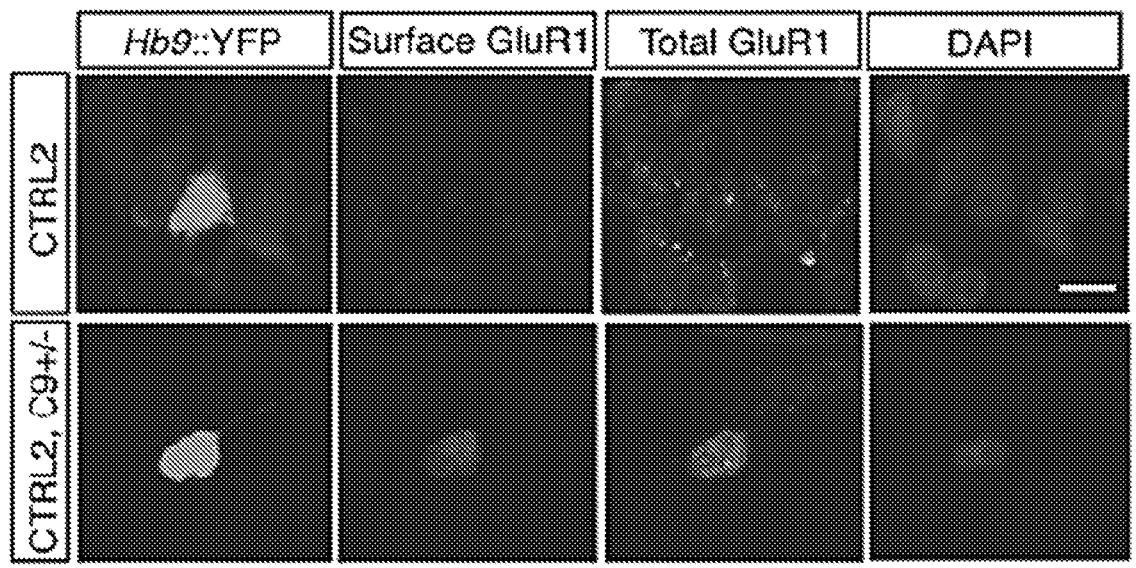
Figure 14E:
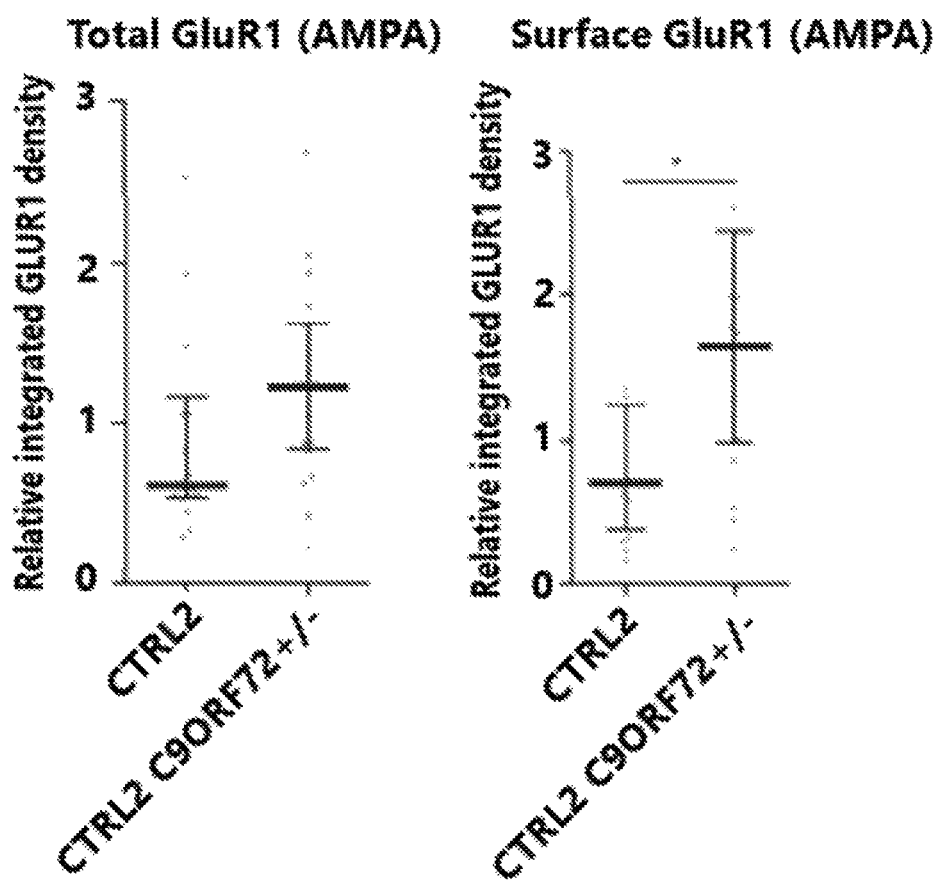
Figure 14F:
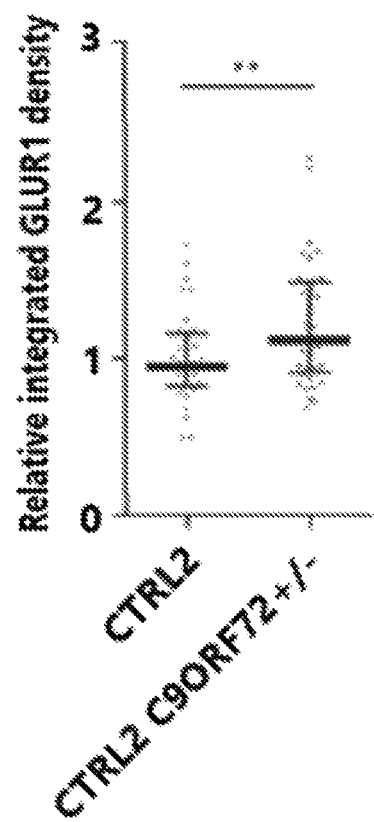
Figure 14G:
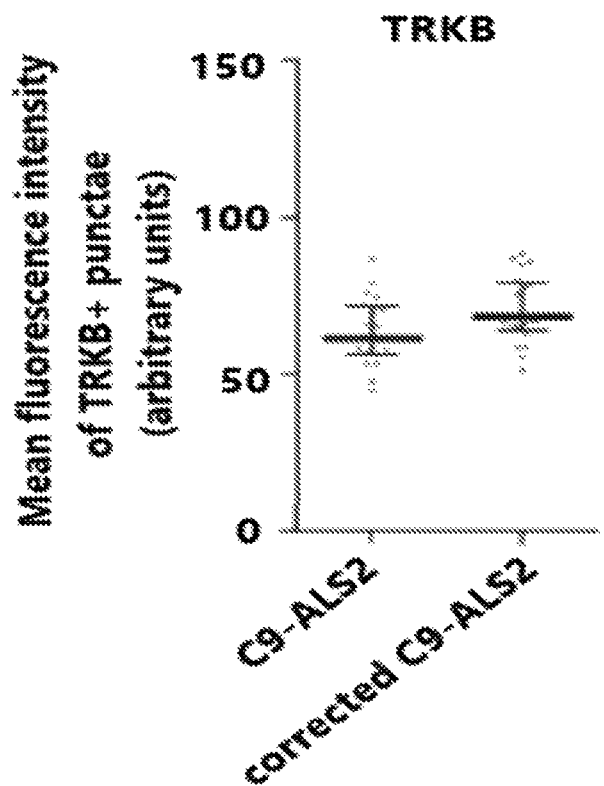
Figure 14H:
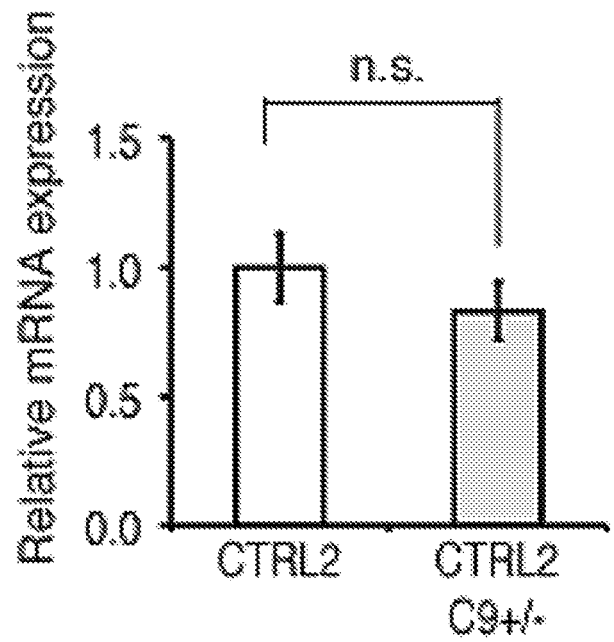
Figure 14I:
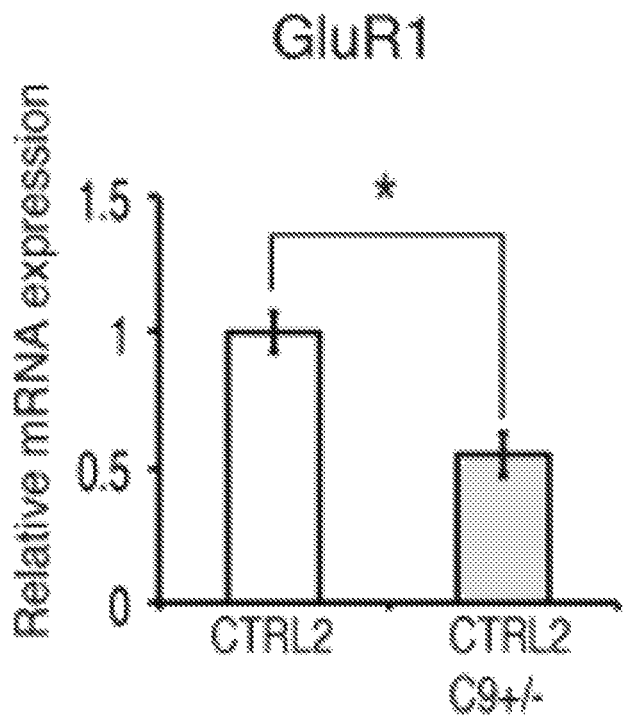
Figure 14J:
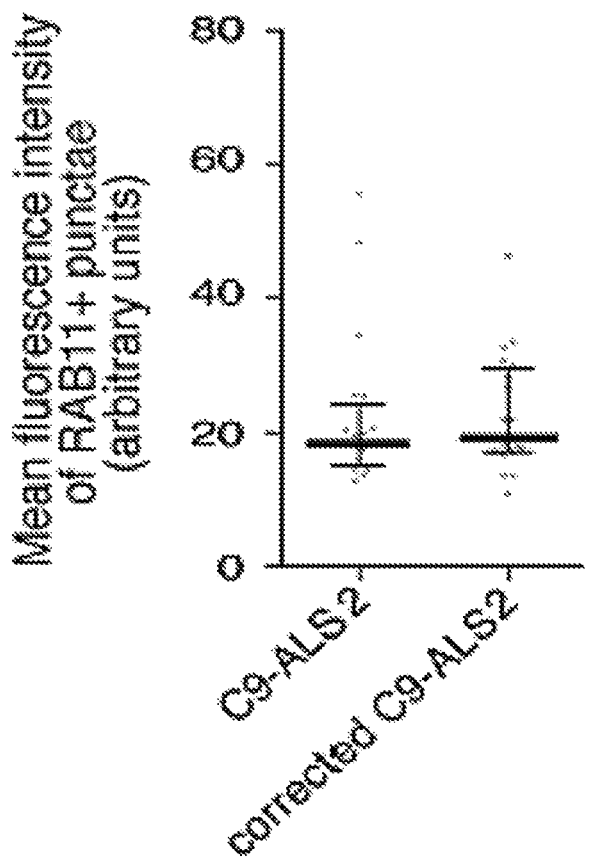
Figure 15A:
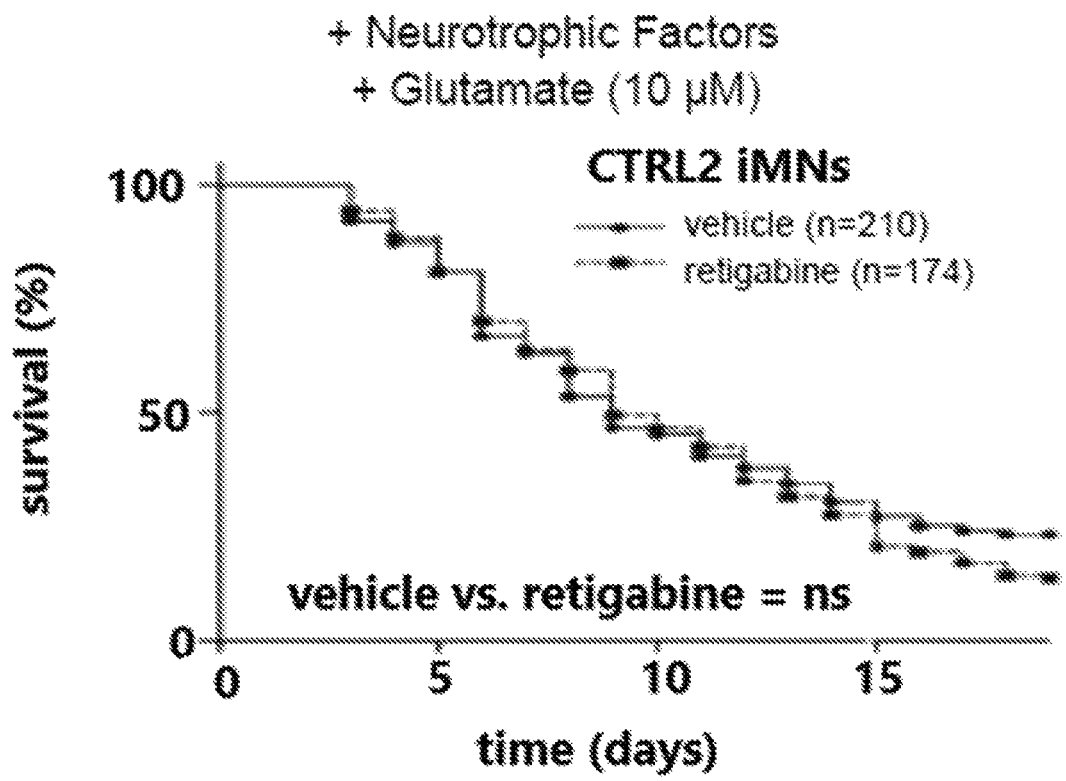
FIG. 15 shows that retigabine increases survival of C9ORF72$^{-/-}$ iMNs. a-c, The graphs show that the potassium channel agonist retigabine does not affect (a) control (CTRL2) or iMNs with heterozygous (b) mutations in C9ORF72, but enhances the survival of iMNs with homozygous (c) mutations in C9ORF72. iMN survival statistical analysis was performed using the log-rank test. *-$p<0.05$, -$p<0.01$, *-$p<0.001$. iMN survival experiments were performed in a Molecular Devices ImageExpress. For iMN survival experiments, "n" indicates the total number of iMNs counted.
Figure 15B:
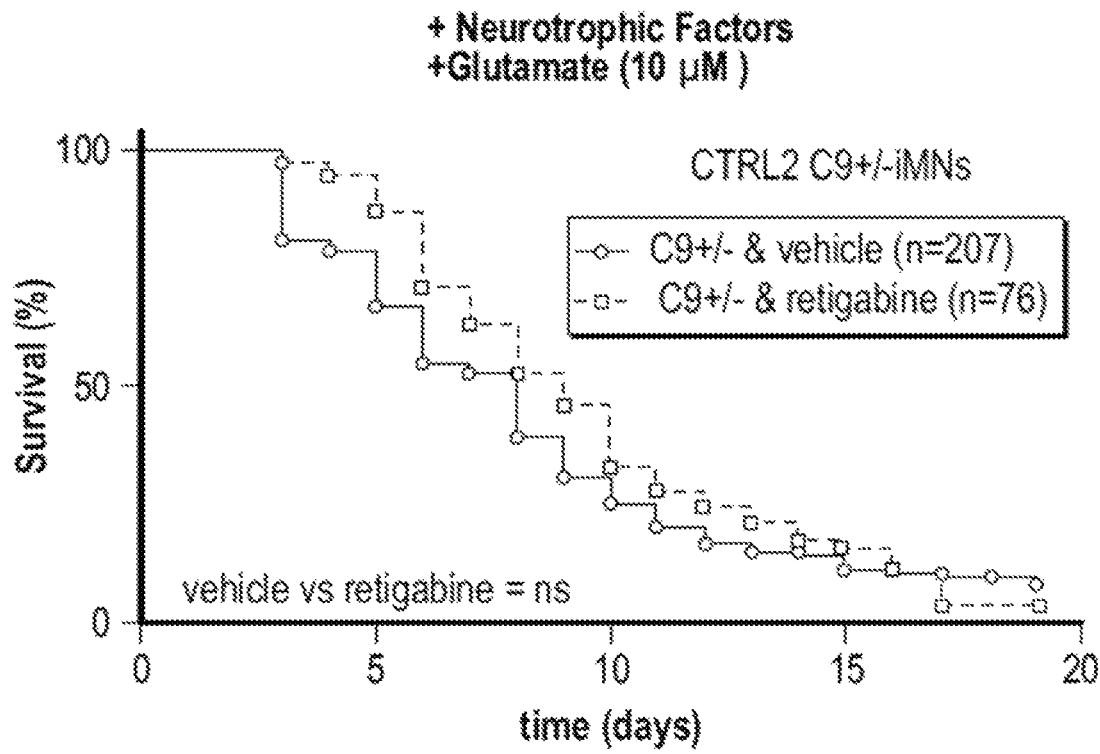
Figure 15C:
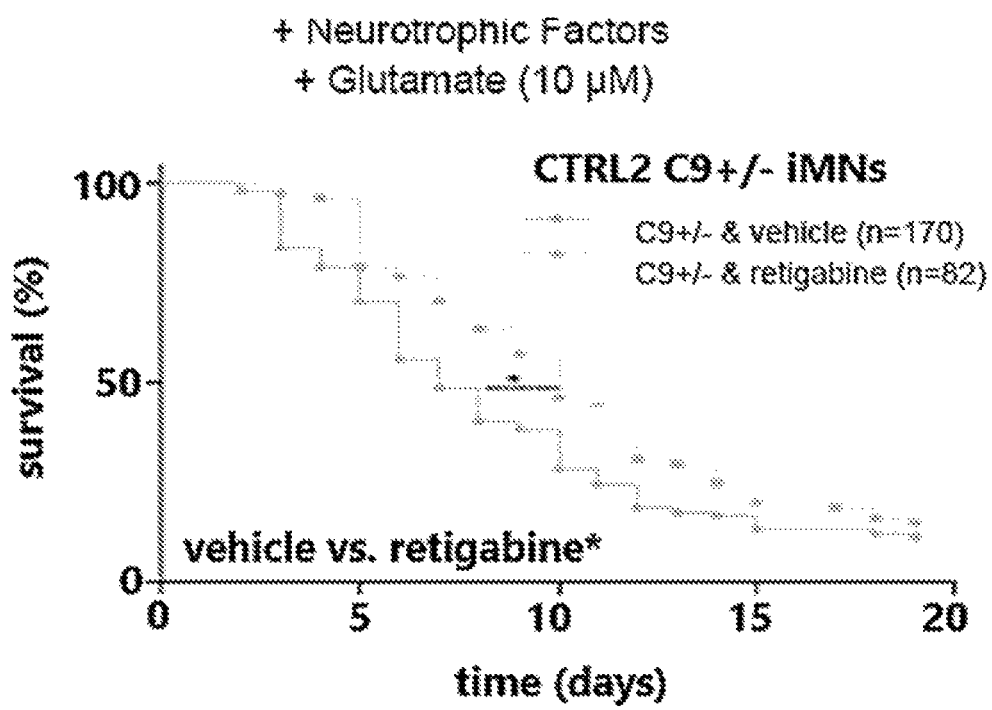
Figure 16A:
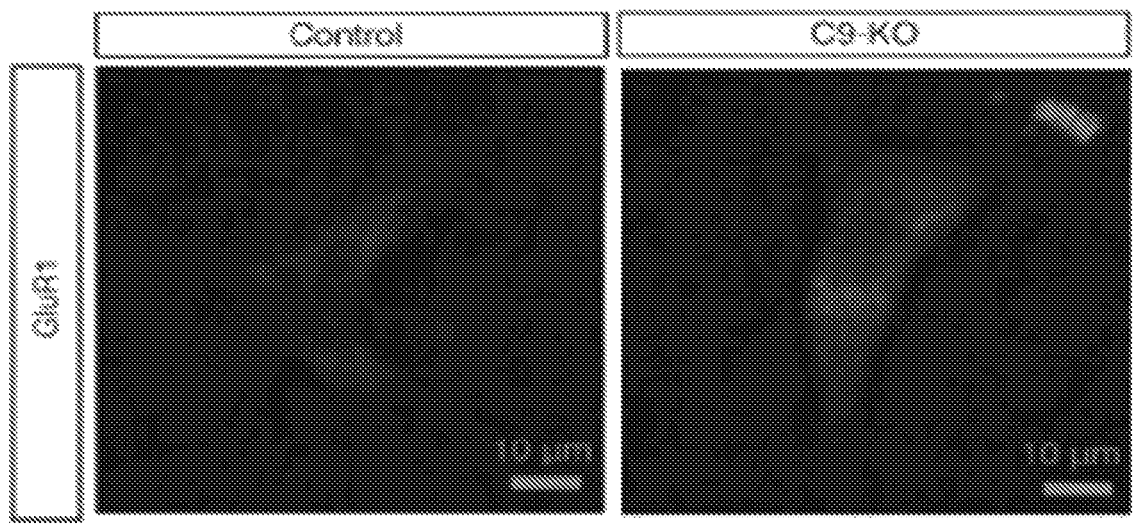
FIG. 16 shows that reduced C9ORF72 activity leads to increased glutamate receptor levels on motor neurons in vivo. a-d, The images show immunohistochemistry (a, c) and the graphs show quantification (b, d) of GluR1 (a, b) and GluR6/7 (c, d) in post-mortem lumbar sections of Nestin-Cre+/− C9orf72loxP/loxP. e, The images show representative immunohistochemistry of human post-mortem lumbar spinal cord, using CHAT and SMI-32 antibodies to identify spinal motor neurons. Scale bars: 4 μm. f, The images show representative NR1 immunohistochemistry of control and C9-ALS post-mortem lumbar spinal cord. Scale bars: 4 μm.
Figure 16B:
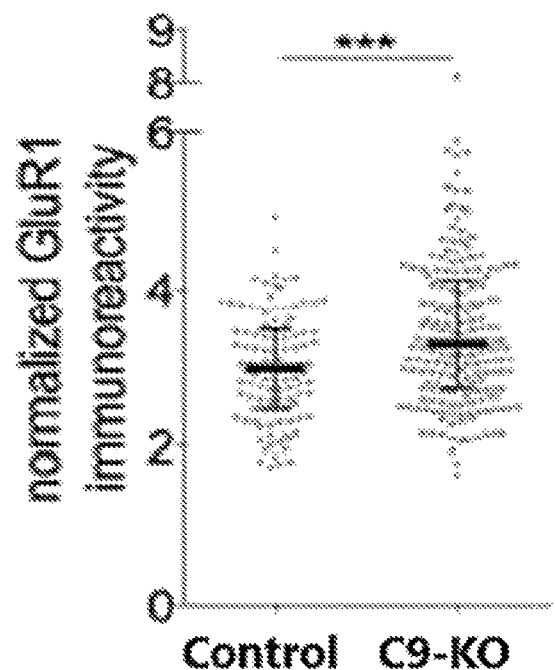
Figure 16C:
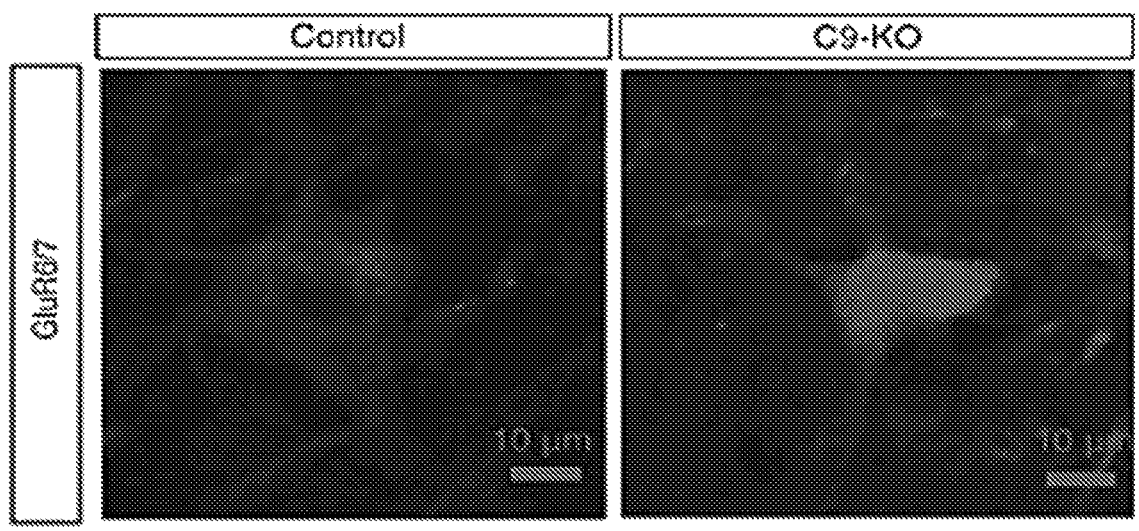
Figure 16D:
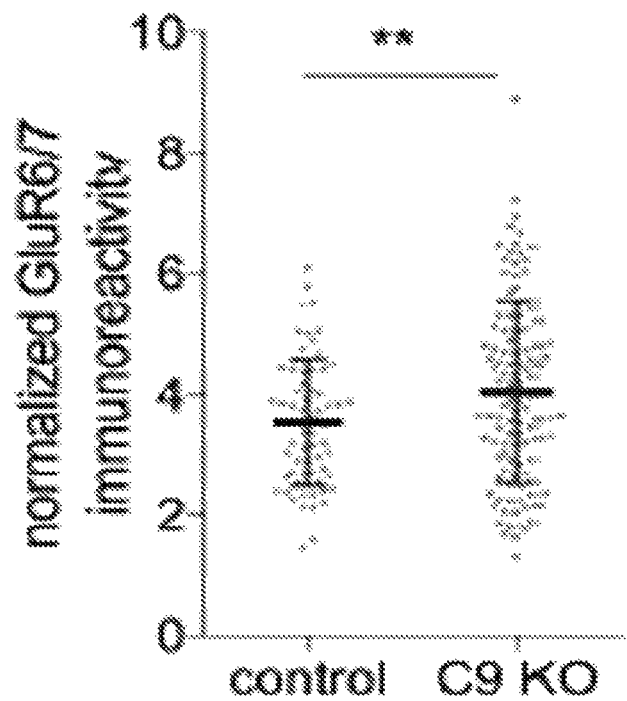

| FIGS. | Line | Cell Number |
|---|---|---|
| FIG. 5c | CTRL1+eGFP | 71 |
| | CTRL1+PR | 53 |
| | C9–ALS1+eGFP | 55 |
| | C9–ALS1+PR | 44 |
| | C9–ALS2+eGFP | 60 |
| | C9–ALS2+PR | 40 |
| FIG. 5d | CTRL1+eGFP | 71 |
| | CTRL1+GR | 54 |
| | C9–ALS1+eGFP | 55 |
| | C9–ALS1+GR | 48 |
| | C9–ALS2+eGFP | 60 |
| | C9–ALS2+GR | 45 |
| FIG. 5f | CTRL2 C9–/– Fibs+eGFP | 20 |
| | CTRL2 C9–/– Fibs+isoB | 20 |
| FIG. 5h | CTRL2 iMNs | 19 |
| | CTRL2 C9+/– iMNs | 25 |
| FIG. 6d | C9–ALS1+DMSO | 130 |
| | C9–ALS1-apilimod | 120 |
| | C9–ALS1-YM201636 | 134 |
| FIG. 6e | CTRL1+DMSO | 118 |
| | CTRL1-apilimod | 123 |
| | CTRL1-YM201636 | 109 |
| FIG. 6f | C9–ALS2+DMSO | 129 |
| | C9–ALS2-apilimod | 128 |
| | C9–ALS2-YM201636 | 139 |
| FIG. 6h | C9–ALS1 DMSO-NR1 | 34 |
| | C9–ALS2 DMSO-NR1 | 30 |
| | C9–ALS3 DMSO-NR1 | 37 |
| | C9–ALS1 YM201636-NR1 | 31 |
| | C9–ALS2 YM201636-NR1 | 28 |
| | C9–ALS3 YM201636-NR1 | 35 |
| | C9–ALS1 DMSO-GLUR1 | 35 |
| | C9–ALS2 DMSO-GLUR1 | 31 |
| | C9–ALS3 DMSO-GLUR1 | 35 |
| | C9–ALS1 YM201636-GLUR1 | 33 |
| | C9–ALS2 YM201636-GLUR1 | 35 |
| | C9–ALS3 YM201636-GLUR1 | 34 |
| FIG. 8e | CTRL1 | 206 |
| | CTRL2 | 173 |
| | CTRL3 | 61 |
| | C9–ALS1 | 188 |
| | C9–ALS2 | 197 |
| | C9–ALS3 | 140 |
| FIG. 8f | CTRL1 | 38 |
| FIG. 9a | CTRL1 | 34 |
| | CTRL2 | 168 |
| | C9–ALS1 | 215 |
| | C9–ALS2 | 199 |
| | C9–ALS3 | 107 |
| FIG. 9b | CTRL1 | 118 |
| | CTRL2 | 204 |
| | C9–ALS2 | 130 |
| | C9–ALS3 | 129 |
| FIG. 9c | CTRL1 Clone1 | 134 |
| | CTRL1 Clone2 | 106 |
| FIG. 9d | CTRL1 | 182 |
| | CTRL2 | 144 |
| | C9–ALS1 | 378 |
| | C9–ALS2 | 319 |
| | C9–ALS3 | 63 |
| FIG. 9e | CTRL1 | 409 |
| | CTRL2 | 257 |
| | C9–ALS1 | 463 |
| | C9–ALS2 | 365 |
| | C9–ALS3 | 102 |
| FIG. 9g | CTRL1 | 32 |
| | C9–ALS1 | 35 |
| FIG. 9h | CTRL1-iDA | 65 |
| | CTRL2-iDA | 49 |
| | C9–ALS2-iDA | 76 |
| | C9–ALS3-iDA | 52 |
| | CTRL1-iMN | 58 |
| | CTRL2-iMN | 52 |
| | C9–ALS2-iMN | 63 |
| | C9–ALS3-iMN | 46 |
| FIG. 9i | C9–ALS2 | 168 |
| | Corrected C9–ALS2 | 540 |
| FIG. 10h | CTRL1+eGFP | 160 |
| | CTRL1+IsoA | 71 |
| | CTRL1+IsoB | 223 |
| | CTRL2+eGFP | 193 |
| | CTRL2+isoA | 61 |
| | CTRL2+isoB | 63 |
| FIG. 10i | C9–ALS1+eGFP | 134 |
| | C9–ALS1+isoA | 92 |
| | C9–ALS1+isoB | 184 |
| | C9–ALS2+eGFP | 221 |
| | C9–ALS2+isoA | 109 |
| | C9–ALS2+isoB | 306 |
| | C9–ALS3+eGFP | 71 |
| | C9–ALS3+isoA | 37 |
| | C9–ALS3+isoB | 29 |
| | CTRL2 +eGFP | 204 |
| FIG. 10j | CTRL2 C9+/– +eGFP | 207 |
| | CTRL2 C9+/– +isoA | 175 |
| | CTRL2 C9+/– +isoB | 201 |
| FIG. 10k | CTRL2 +eGFP | 204 |
| | CTRL2 C9–/– +eGFP | 170 |
| | CTRL2 C9–/– +isoA | 94 |
| | CTRL2 C9–/– +isoB | 97 |
| FIG. 12g | C9–ALS2+eGFP | 35 |
| | C9–ALS2+RAB7 CA | 37 |
| FIG. 13b | CTRL2 RFP-RAB5 | 21 |
| | CTRL2 C9+/– RFP-RAB5 | 25 |
| FIG. 14a | CTRL2 | 18 |
| | CTRL2 C9+/– | 16 |
| | C9–ALS1 | 17 |
| | C9–ALS2 | 17 |
| FIG. 14c | CTRL1 | 37 |
| | CTRL1 C9+/– | 28 |
| FIG. 14e | CTRL2 Total GluR1 | 18 |
| | CTRL2 C9+/– Total GluR1 | 20 |
| | CTRL2 Surface GluR1 | 18 |
| | CTRL2 C9+/– Surface GluR1 | 20 |
| FIG. 14f | CTRL1 | 36 |
| | CTRL1 C9+/– | 38 |
| FIG. 14g | C9–ALS2 | 20 |
| | Corrected C9–ALS2 | 21 |
| FIG. 14j | C9–ALS2 | 20 |
| | Corrected C9–ALS2 | 20 |
| FIG. 14i | CTRL2+Glut | 23 |
| | CTRL2+Glut+TTX/TEA | 16 |
| | CTRL2+NMDA | 13 |
| | CTRL2+NMDA+TTX/TEA | 11 |
| | CTRL2+AMPA | 17 |
| | CTRL2+AMPA+TTX/TEA | 13 |
| | CTRL2+KAIN | 18 |
| | CTRL2+KAIN+TTX/TEA | 14 |
| | CTRL2 C9+/–+Glut | 38 |
| | CTRL2 C9+/–+Glut+TTX/TEA | 41 |
| | CTRL2 C9+/–+NMDA | 32 |
| | CTRL2 C9+/–+NMDA+TTX/TEA | 31 |
| | CTRL2-C9+/–+AMPA | 23 |
| | CTRL2-C9+/–+AMPA+TTX/TEA | 25 |
| | CTRL2-C9+/–+KAIN | 32 |
| | CTRL2-C9+/–+KAIN+TTX/TEA | 35 |
| FIG. 15a | CTRL2+DMSO | 210 |
| | CTRL2+Retigabine | 174 |
| FIG. 15b | CTRL2 C9+/– +DMSO | 207 |
| | CTRL2 C9+/– +Retigabine | 76 |
| FIG. 15c | CTRL2 C9–/– +DMSO | 170 |
| | CTRL2 C9–/– +Retigabine | 82 |
| FIG. 16b | Mouse-CTRL | 106 |
| | Mouse-C9-KO | 174 |
| FIG. 16d | Mouse-CTRL | 67 |
| | Mouse-C9-KO | 110 |

CRISPR/Cas9-mediated genome editing was performed in human iPSCs as previously described (Ran et al., *Nat Protoc*, 8: 2281-2308 (2013)). To generate isogenic control iPSCs by removing the repeat expansion, single guide RNAs (sgRNAs) targeting both side of the C9ORF72 intronic hexanucleotide repeat expansion were designed (Table 1, CRISPR DESIGN) and cloned into an empty gRNA cloning vector (Addgene ID: 31824). The donor plasmid for homologous recombination was generated by PCR-amplifying left and right homology arms (588 bp and 1149 bp, respectively) from control genomic DNA into the pUC19 vector with an added puroR cassette. $2\times10^6$ C9ORF72 ALS/FTD patient iPSCs were transfected with human codon-optimized Cas9 (Addgene ID: 31825), the appropriate gRNA constructs by nucleofection (Lonza) according to the manufacturer's protocol, and the homologous recombination donor vector. The cells were replated on wells pre-coated with Geltrex (Life Technologies) in mTeSR1 medium supplemented with 10 µm Y-27632 (Selleck). Y-27632 was removed on the next day followed by puromycin selection (7.5 ug/ml) for 48 h. On day 7 after transfection, the surviving colonies were manually picked and genotyped by sequencing the targeted genomic site (PCR primers shown in Table 1). Colonies showing removal of the repeat expansion were clonally purified by plating 1000 iPSCs on a 10-cm dish of irradiated MEF feeders in human ESC medium (DMEM/F12, 20% knockout serum replacement, 1% non-essential amino acids, 1% Glutamax, 1× penicillin/streptomycin (all Life Technologies), 0.1% beta mercaptoethanol (Sigma), and 10 ng/ml bFGF (Peprotech)) and re-picking of the resulting colonies. Normalization of C9ORF72 was verified by repeat-primed PCR and southern blotting. To generate loss-of-function alleles of C9ORF72, control iPSCs were transfected with a sgRNA targeting exon 2 of the C9ORF72 gene. Colonies were picked on day 7 after transfection and genotyped by PCR amplification and sequencing of exon 2. Colonies containing a frameshift mutation were clonally purified on MEF feeders and the resulting clones were re-sequenced to verify the loss-of-function mutation in C9ORF72.

To perform quantitative real time PCR (qRT-PCR), total RNA was extracted from sorted iMNs at day 21 post-transduction with Trizol RNA Extraction Kit (Life Technologies) and reverse transcribed with an Oligo dT primer using PROTOSCRIPT® II First Strand Synthesis Kit (NEB). RNA integrity was checked using the Experion system (Bio-Rad). Real-time PCR was performed with iTaq Universal SYBR Green Supermix (Bio-Rad) using primers shown in Table 1.

To perform Western Blotting, iMNs from healthy controls and ALS patients were collected on day 21 post-transduction in RIPA buffer (Sigma-Aldrich) with a protease inhibitor cocktail (Roche). Protein quantity was measured by the BCA assay (Pierce) and samples were run on a 10% SDS gel at 4° C. The gel was transferred onto an Immobilon membrane (Millipore). The membrane was blocked with 5% milk in 0.1% PBS-Tween 20 (PBS-T)(Sigma-Aldrich), incubated with primary antibodies overnight at 4° C., washed three times with 0.1% PBS-T, then incubated with horseradish peroxidase (HRP)-conjugated (Santa Cruz) or IRDYE® (LiCor) secondary antibodies. After three washes with 0.1% PBS-T, blots were visualized using an Amersham ECL Western Blotting Detection Kit (GE) and developed on X-ray film (Genesee) or using an Odyssey Imaging System (LiCor). The following primary antibodies were used: rabbit anti-C9ORF72 (GeneTex)(for isoform B), rabbit anti-C9ORF72 (Janice Roberston)(for isoform A), mouse anti-GAPDH (Santa Cruz).

To perform fluorescent in situ hybridization (FISH) for RNA foci detection, cells were grown on coverslips pre-coated with 0.1% gelatin and 0.01 mg/ml laminin and fixed with 4% PFA in PBS for 1 hrs at 4° C. The cells were then permeabilized with 0.2% Triton X-100 in diethyl pyrocarbonate (DEPC)-PBS (Thermo Fisher Scientific) at room temperature followed by three washes with DEPC-PBS. Prehybridization was performed by incubating the cells with hybridization buffer consisting of 50% formamide (IBI Scientific), DEPC-2×SSC (300 mM sodium chloride (Sigma-Aldrich), 30 mM sodium citrate at pH 7.0 (Sigma-Aldrich)), 10% dextran sulfate (Sigma-Aldrich), DEPC-50 mM sodium phosphate, pH 7.0 (Sigma-Aldrich) for 30 min at 66° C. The cells were then incubated with 40 nM $(GGGGCC)_4$ or scrambled probe in the dark for 3 hrs at 66° C., and washed once in DEPC-2×SSC/0.1% Tween 20 at room temperature and three times in DEPC-0.1×SSC at 65° C. After DAPI counterstaining, the coverslips were mounted with Shandon IMMU-MOUNT™ (Thermo Fisher Scientific). In FIG. 2k, the quantification represents three biological replicates with n=50 neurons per replicate. Error bars represent s.e.m.

To perform protein purification and in vitro guanine exchange assays, all RAB cDNAs were cloned into the pET28A vector with N-terminal 6× His-tags and expressed in BL21(DE3) cells (Life Technologies) at 18° C. for 12 to 14 h. Cells were pelleted, lysed on ice for 20 min in IMAC5 buffer (20 mM Tris-HCl, pH 8.0, 300 mM NaCl, 5 mM imidazole, 0.2% Triton X-100) supplemented with 0.5 mg/ml lysozyme (Sigma-Aldrich) and a protease inhibitor cocktail, then sonicated at 70% power four times for 30 sec with intervening rest periods of 30 s. After centrifugation at 15,000×g for 30 min, lysates were incubated with nickel-charged NTA-agarose (Qiagen) for 3 h, washed with 15 volumes of IMAC20 buffer (IMAC5 buffer with 20 mM imidazole), and eluted with 7.5 volumes MAC 200 buffer (IMAC5 buffer with 200 mM imidazole). Purified proteins were concentrated into Reaction buffer (10 mM NaCl, 50 mM Tris-HCl pH 8.0, 1 mM EDTA, 0.8 mM DTT, 0.005% Triton X-100) by dialysis. The guanine exchange assay was performed as follows: 40 µM purified RAB proteins were incubated with 50 µM BODIPY® FL GDP (Life Technologies) for 1 hr at room temperature in Reaction buffer and quenched with 10 mM $MgCl_2$. HEK cell lysates were prepared by transfecting HEK cells with pHAGE vectors containing 2× HA-tagged C9ORF72 isoform B, C9ORF72 isoform A, DENND2D, or RABEX5, or with a pMXs vector containing DsRed, then harvesting 48 hrs post-transfection in cell lysis buffer (10 mM NaCl, 50 mM Tris-HCl pH8.0, 12 mM $MgCl_2$, 0.8 mM DTT, 1% CA-630) supplemented with a protease inhibitor cocktail. After centrifugation at 15,000×g for 15 min at 4° C., the lysates were mixed with 2 µM preloaded RABs and 2 mM GDP, and the fluorescence intensity recorded using SpectroMAX M2 plate reader (Molecular Devices) every 30 sec over a 2 hr period.

To perform GCaMP6 calcium influx assays, GCaMP6 was cloned into the pMXs-Dest-WRE retroviral vector and transduced into reprogramming cultures concurrently with the motor neuron factors. To assess GCaMP6 activity, 1.5 µm glutamate was added to iMN cultures and cells were imaged continuously for 2 minutes at 24 frames per second. GFP flashes were scored manually using the video recording. At least 3 different fields of view from three independent cultures, totaling 50-100 iMNs, were scored per condition.

To perform calcium imaging, Fluo-4AM (Thermo Scientific) was diluted 1:4 in neuron medium and loaded into motor neuron cultures for 1 hour. The cultures were then treated with 20 µM cyclopiazonic acid for 30 minutes to deplete intracellular calcium before beginning the glutamate treatment assay. Cultures were treated with 1.5 µM glutamate with or without the 3 glutamate receptor antagonists (10 μM MK801 and CNQX, and 2 μM Nimodipine) and recorded using live imaging. Fluorescence flashes were scored manually by a scientist blinded to the identity of the samples.

To perform dipeptide repeat protein expression in iMNs and $PR_{50}$-Dendra2 turnover analysis, the effect of dipeptide repeat protein expression on iMN survival was measured, $PR_{50}$ and $GR_{50}$ were cloned into the pHAGE lentiviral vector as fusions with GFP to allow tracking of protein expression. iMN cultures were transduced with $PR_{50}$ and $GR_{50}$ lentiviruses at day 17 of reprogramming and longitudinal survival analysis was started the same day. 10 ng/ml of GDNF, BDNF, and CNTF was maintained throughout the experiment, and glutamate treatment was not performed. To measure $PR_{50}$ turnover, $PR_{50}$ was cloned into the pHAGE lentiviral vector as a fusion with Dendra2 (Addgene). iPSC-derived fibroblasts were generated according to Daley and colleagues (Park et al., Nature, 451: 141-146 (2008)). Briefly, when $C9ORF72^{-/-}$ iPSC cultures reached 80% confluence, the medium was switched from mTeSR1 (Stem Cell Technologies) to human fibroblast medium containing DMEM (Life Technologies), 10% fetal bovine serum (FBS) (Thermo Fisher Scientific), and 1% penicillin/streptomycin (Life Technologies). Cells were passaged 2 to 3 times using Accutase (Life Technologies) before use in experiments. iPSC-derived fibroblasts were transduced with either pMXs-eGFP or pMXs-C9ORF72 isoform B-T2A-eGFP retrovirus and treated with 10 μg/ml mitomycin C for 3 hrs to inhibit cell proliferation. The cells were then transduced with the $PR_{50}$-Dendra2 lentivirus and exposed to blue light for 1.5 sec using a lumencor LED light source to initiate photoconversion. The amount of decay (as a fraction of the starting level) of the red fluorescent punctae was monitored by longitudinal time lapse imaging in a Molecular Devices ImageExpress and analyzed using SVCell 2.0 (DRVision Technologies). Fluorescence was quantified at t=0 and 12 hrs after photoconversion Distinct photoconverted punctae were treated as discrete objects for analysis (n=20 each for +eGFP and +C9ORF72-T2A-eGFP). For each object, background fluorescence was subtracted and fluorescence was normalized according to object size. The fractional decay was statistically analyzed by two-tailed Student's t-test. **–p<0.01.

To perform iMN Dendra2 experiments, the procedure as described above was used except that $PR_{50}$-Dendra2 lentivirus was transduced into iMN cultures at day 14 of conversion.

To perform small molecule screen and PIKFYVE inhibitor assays, Hb9::RFP+C9ORF72 ALS/FTD iMNs were generated in 96-well plates. On Day 15 post transduction, neurotrophic factors and RepSox were withdrawn and the small molecule library was added (EMD Millipore kinase collection and Stemselect library, 3.3 μM final concentration) and added fresh every other day until the screen was terminated on Day 25 post-transduction. Identification of neuroprotective compounds was identified using SVcell 2.0 (DRVision Technologies).

To perform RNA sequencing, libraries were prepared from total RNA using Clontech SMARTer Stranded RNA-Seq kit, with Clontech RiboGone ribodepletion performed ahead of cDNA generation. Amounts of input RNA were estimated using the Bioanalyzer and libraries produced according to Clontech's protocol. Library generation and sequencing were performed at the Norris Cancer Center Sequencing Core at USC. All FASTQ files were analyzed using FastQC (version 0.10.1), trimmed using the FASTQ Toolkit (v 1.0), aligned to the GRCh37/hg19 reference genome using Tophat (version 2), and transcripts assembled and tested for differential expression using Cufflinks (version 2.1.1). Raw data is available for public download in the NCBI database under accession code PRJNA296854.

To perform the retinoic acid/purmorphamine protocol for iPSC-motor neuron differentiation, iPSC motor neurons were generated as described previously (Du et al., Nat Commun, 6: 6626 (2015)), except that the final concentrations of retinoic acid and purmorphamine were increased to 1 uM from day 18, and neurons were kept in embryoid body form until day 40 before replating onto laminin coated coverslips and further cultured for 1-2 weeks.

To perform electron microscopy, iMNs or iPSC-derived fibroblasts were fixed overnight at 4° C. in one-half Karnovsky's fixative (2% paraformaldehyde, 2.5% gluteraldehyde) in 0.1M cacodylate buffer, permeabilized with 0.5% PBS-T overnight at 4° C., blocked with 10% FBS in 0.1% PBS-T at room temperature for 2 h, and incubated with primary antibodies at 4° C. overnight. Cells were then washed with 0.1% PBS-T and incubated with gold conjugated secondary antibodies (TED PELLA) in blocking buffer for 2 hrs at room temperature. The samples were then washed 3 times with 0.1% PBS-T and post-fixed for 1 h in 1% osmium tetroxide. They were subsequently stained en bloc with 1% uranyl acetate, dehydrated in a graded series of ethanols, infiltrated with epon and polymerized overnight at 60° C. Samples were then mounted to the front of blank epon blocks, sectioned en face at 70 nm and placed on copper grids. Sections were examined and photographed using a JEOL JEM-2100 transmission electron microscope at 80 kV employing Gatan Micrograph software. EEA1+ vesicle size was quantified with ImageJ (v.1.49). The antibodies used are: mouse anti-EEA1 (BD Bioscience); goat anti-mouse immunogold conjugate IgG (H+L) 20 nm (TED PELLA). Lysosomes were recognized as electron dense spherical structures (Neiss, Histochemistry, 77: 63-77 (1983)).

To perform mouse staining and quantification, all animal use and care were in accordance with local institution guidelines of the University Medical Center Utrecht (Utrecht, the Netherlands) and approved by the Dierexperimenten Ethische Commissie Utrecht with the protocol number DEC 2013.I.09.069. Previously described Nestin-Cre$^{+/-}$ C9orf72$^{loxP/loxP}$ mice (Koppers et al., Ann Neurol, (2015)) and age-matched controls were transcardially perfused with phosphate buffered saline (PBS) and subsequently with 4% formaldehyde. Cryoprotection occurred in 30%. After snap freezing, tissue was sectioned by cryostat at 20 μm thickness and stained with the following primary antibodies: NMDAR1, GluR1, GluR2, GluR6/7 and Lamp1. Images were collected using a Zeiss LSM 780 confocal microscope.

To perform glutamate subunit intensity measurements with ImageJ, the mean cytosolic intensity was divided by a background measurement collected near to the measured neuron. The scientist performing the glutamate receptor subunit intensity and LAMP1 vesicle quantification was blinded to the genotypes of the samples.

To perform immunohistochemistry of human tissue, post mortem tissues were kindly provided by Neil Shneider (Columbia University) and were collected from the following individuals: Sample 1—age: 64, diagnosis: ALS, genotype: positive for C9ORF72 repeat expansion, Sample 2—age: 55, diagnosis: ALS, genotype: positive for C9ORF72 repeat expansion, Sample 3—age: 65, diagnosis: ALS, genotype: positive for C9ORF72 repeat expansion, Sample 4—age: 65, diagnosis: control, genotype: negative for C9ORF72 repeat expansion, Sample 5—age: 50, diagnosis: control, genotype: negative for C9ORF72 repeat expansion, Sample 6—age: 50, diagnosis: control, genotype: negative for C9ORF72 repeat expansion, Sample 7—age: 53, diagnosis: ALS, genotype: negative for C9ORF72 repeat expansion, Sample 8—age: 64, diagnosis: ALS, genotype: negative for C9ORF72 repeat expansion. All donors except donor 7 (sample 7) were female. For immunofluorescence, 10 µm sections were sliced from flash frozen lumbar spinal cord tissues. Sections were then air dried and fixed with ice cold acetone for 10 minutes, and blocked with 10% normal goat serum/1% BSA/0.3% Triton-X/PBS at room temperature for 1 hr followed by incubation with GluR6/7 antibody (1:100, Millipore) or NR1 antibody (1:200, BD Bioscience) in blocking buffer overnight at 4° C. Sections subsequently were blocked using avidin/biotin kit (Vector Lab), and washed with PBS. Then, sections were incubated with goat anti-rabbit IgG Biotin conjugate secondary antibody (1:750, Invitrogen) or with goat anti-mouse IgG Biotin conjugate secondary antibody (1:750, Invitrogen) for 1 hr at room temperature, washed and incubated with streptavidin-Alexa Fluor 488 conjugate (1:500, Invitrogen) in dark for 1 hr at room temperature. Sections were washed and blocked again in blocking buffer for 1 hr at room temperature. For neuronal marker staining, sections were incubated with Tu-20 antibody (1:1000, Abcam) or NeuN antibody (1:500, Abcam) at 37° C. for 1 hour. Sections were washed with PBS and incubated with goat anti-mouse Alexa Fluor 546 (1:500, Invitrogen) or goat anti-rabbit Alexa Fluor 546 (1:500, Invitrogen) for 1 hr at room temperature. Lipofuscin autofluorescence was quenched by immersing sections in autofluorescence eliminator reagent (Millipore) for 4 minutes following manufacture's instruction. Sections were then counterstained and mounted with Prolong Gold antifade mounting medium with DAPI (Invitrogen).

To perform statistical analysis, the statistical software package Prism Origin (GraphPad Software, La Jolla, USA) was used. Statistical analysis of iMN survival experiments was performed using the log-rank test to account for events that did not occur (i.e., iMNs that did not degenerate before the end of the experiment). If all iMNs degenerated in a given experiment, statistical significance was calculated using a two-tailed Student's t-test. For all other experiments, differences between two groups were analyzed using a two-tailed Student's t-test, unless the data was non-normally distributed for which Mann-Whitney testing was used. Differences between more than two groups were analyzed by ANOVA with Bonferroni correction for multiple testing. Significance was assumed at $p<0.05$. Error bars represent the standard deviation unless otherwise stated.

To perform all experiments, sample size was chosen using a power analysis based on pilot experiments that provided an estimate of effect size using a power/sample calculator available through The University of British Colombia. Mice used for immunohistochemical analysis were selected randomly from a set of genotyped animals (genotypes were known to investigators). Mouse and human tissue sections used for immunohistochemical analysis were selected randomly. For mouse tissues, sections were prepared using an approximately equal representation of all levels of the spinal cord, and of those, all were imaged and quantified. The sections were only not used if NeuN or Chat immunostaining failed. For iMN survival assays, assays were repeated at least twice, and one representative replicate was used to generate the Kaplan-Meier plot. iMN survival times were confirmed by manual longitudinal tracking by a scientist who was blinded to the identity of the genotype and condition of each sample. For quantification of glutamate receptor immunofluorescence, samples were quantified by a scientist who was blinded to the identity of the genotype of each sample.

The following antibodies were used in the experiments of Examples 1-7: mouse anti-HB9 (Developmental Studies Hybridoma Bank); 81.5C10. mouse anti-TUJ1 (EMD Millipore); AB9354. rabbit anti-VACHT (Sigma); SAB4200559. rabbit anti-C9ORF72 (Sigma-Aldrich); HPA023873. mouse anti-EEA1 (BD Biosciences); 610457. mouse antiRAB5 (BD Biosciences); 610281. mouse anti-RAB7 (GeneTex); GTX16196. mouse anti-LAMP1 (Abcam); ab25630. rabbit anti-GluR1 (EMD Millipore); pc246. mouse anti-GluR1 (Santa Cruz); sc13152. rabbit anti-NR1 (EMD Millipore); sc9058. mouse anti-NR1 (EMD Millipore); MAB363. chicken anti-GFP (GeneTex); GTX13970. rabbit anti-Glur6/7 (EMD Millipore); 04-921. Rabbit anti-C9ORF72 isoform A.

HEK 293T cells were used to produce retrovirus, lentivirus, and C9ORF72 protein. HEK cells were used for these purposes based on previous published studies using HEK cells in order to produce viral particles and mammalian proteins. HEK cells were obtained from American Type Culture Collection, catalog number CRL-11268. HEK cells were tested for mycoplasma before, during, and after the study and were negative.

Example 2

C9ORF72 Patient iMNs Recapitulate ALS Disease Processes

Figure 7A:
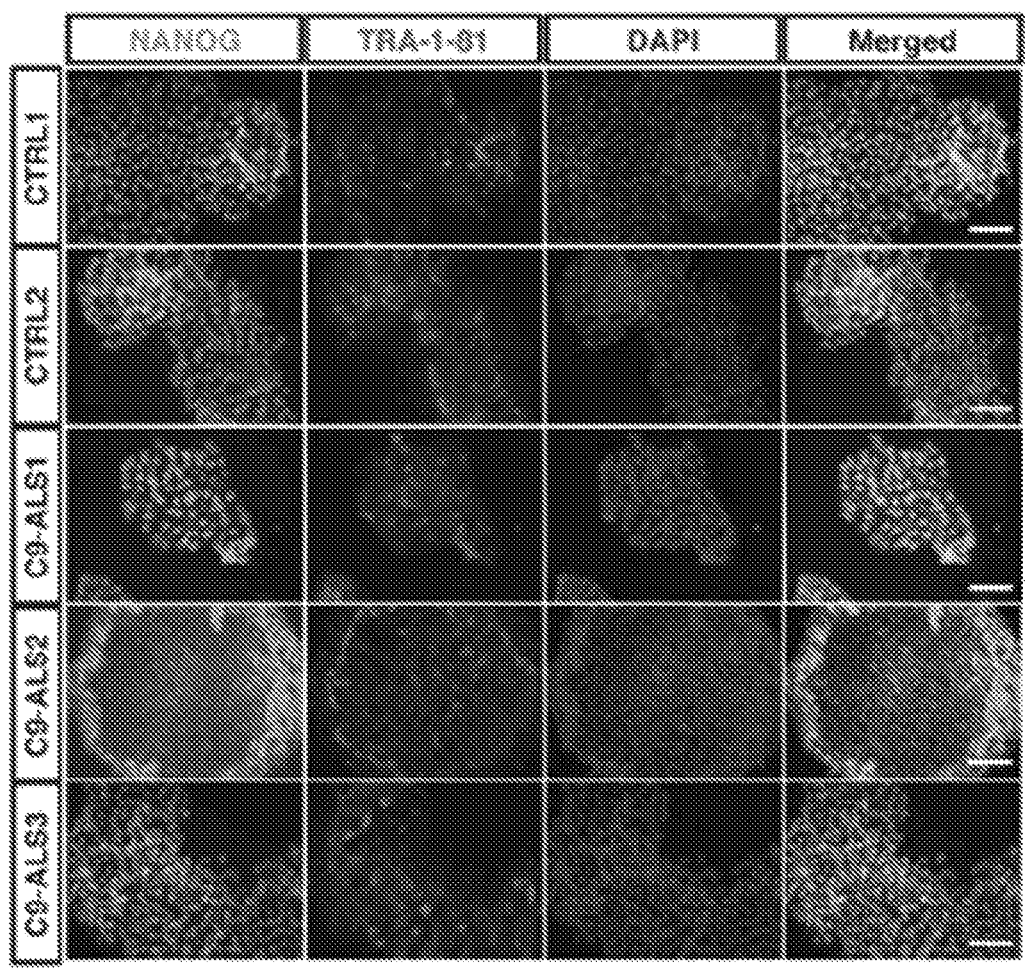
FIG. 7 shows the derivation of iPSCs from controls and C9ORF72 patients. a, The image shows that the control and C9-ALS patient iPSC lines express markers of pluripotency including NANOG (green) and TRA-1-81 (red). Nuclei (blue) are labeled with Hoechst. Scale bars: 200 μm. b, The image shows repeat-primed PCR (RP-PCR) to quantify the intronic repeats in C9ORF72 in control (CTRL) and C9-ALS patient iPSC lines. c, The image shows a southern blot to look at the C9ORF72 repeat region in control and patient iPSC lines. The wild-type allele gives a single 2.4-kb band, while the presence of an expanded allele gives an additional high molecular weight band (4-14 kb) in all four of the heterozygous patient lines (C9-ALS 1 through 4). *Note—Control 4 and C9-ALS 4 were not used in this study.
Figure 7B:
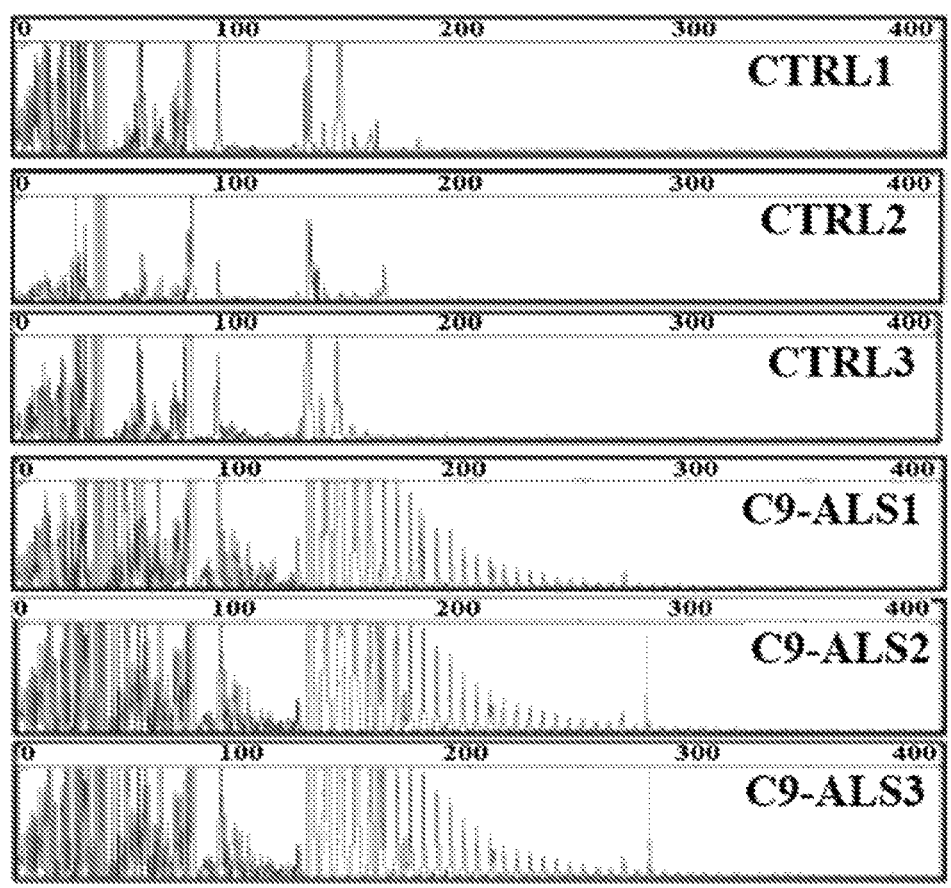
Figure 7C:
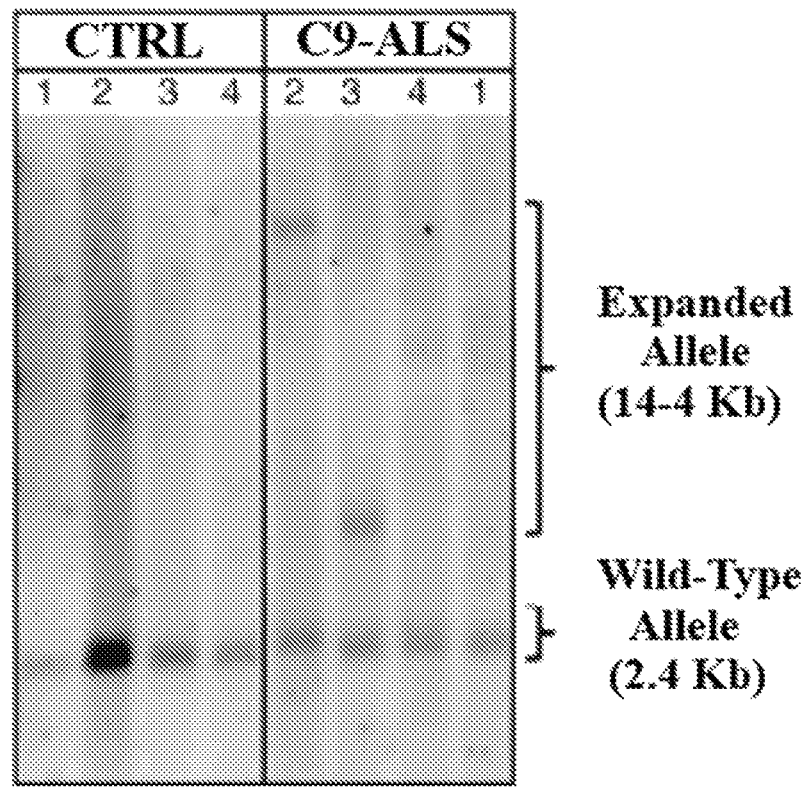
Figure 8G:
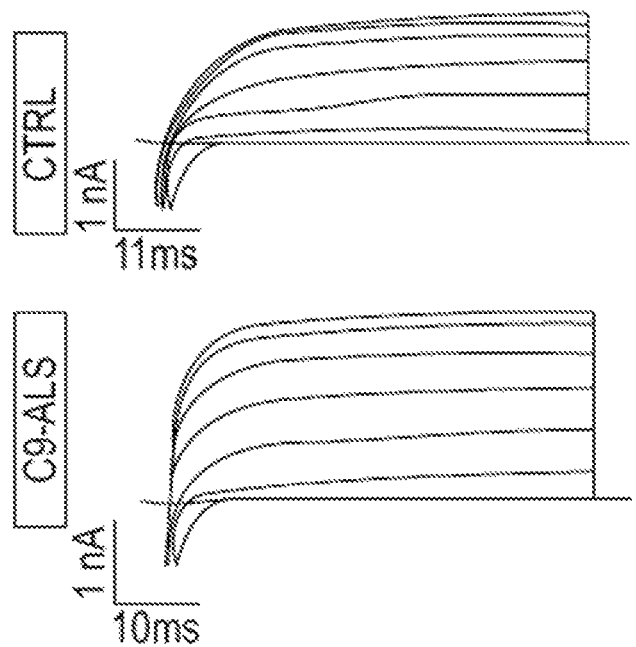
Figures 8H, 8I:
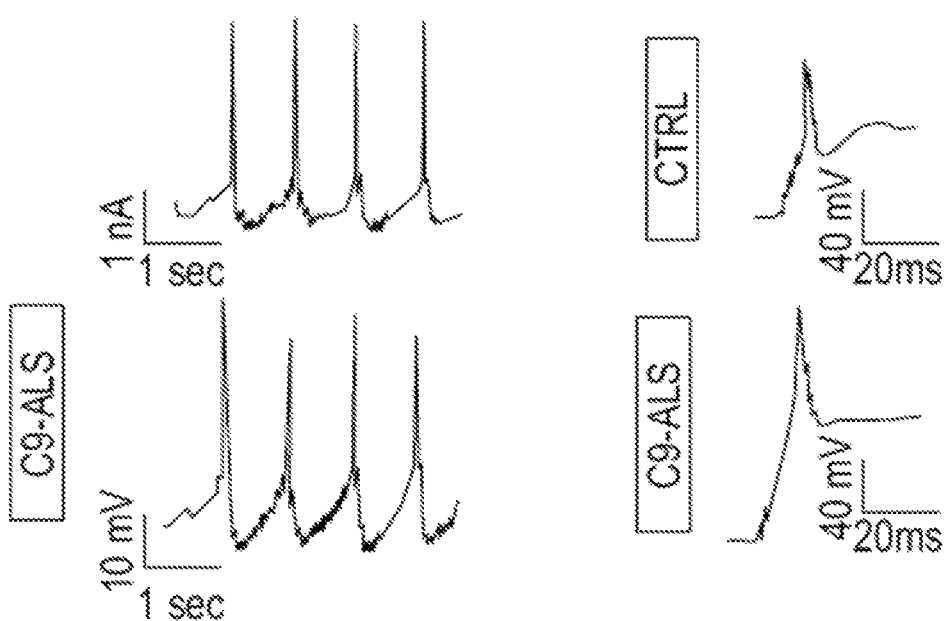
Figure 8J:
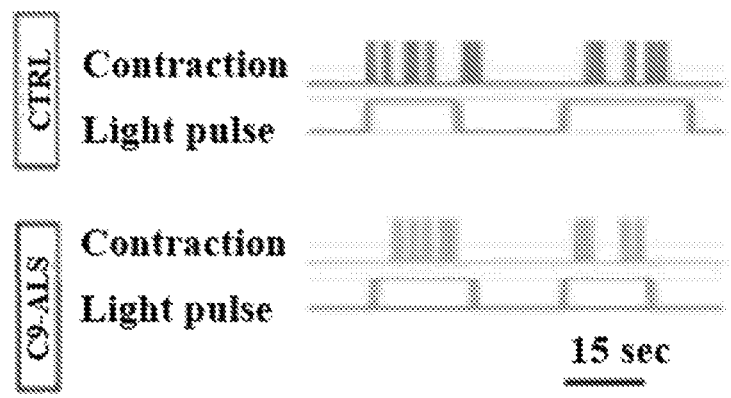

To study the pathogenic mechanism of the C9ORF72 repeat expansion in human motor neurons, the forced expression of the transcription factors Ngn2, Isl1, Lhx3, NeuroD1, Brn2, Ascl1, and Myt1l, was used to convert control and C9ORF72 ALS/FTD patient induced pluripotent stem cells (iPSCs) (FIG. 7 and Table 3) into iMNs (FIG. 8a-b) (Wen, et al., Neuron, 84: 1213-1225 (2014) and Son, et al., Cell Stem Cell, 9: 205-218 (2011)). iMNs were labeled with a lentiviral Hb9::RFP reporter that specifically labels spinal motor neurons (FIG. 8b-d) (Kiskinis, et al., Cell Stem Cell, 14: 781-795 (2014) and Marchetto, et al., Cell Stem Cell, 3: (2008)). Control and patient Hb9::RFP+ iMNs co-expressed motor neuron markers including TUJ1, HB9, and VACHT, were produced at similar rates amongst different iPSC lines, and possessed electrophysiological properties of motor neurons (FIG. 8c-i). Depolarizing voltage steps induced currents characteristic of sodium and potassium channels and iMNs fired single or repetitive action potentials (patient 90%, n=10; control 100%, n=10)(FIG. 8g-i). Previously, it was found that induced neurons generated without Ngn2, Isl1, and Lhx3, the key transcription factors that drive motor neuron specification in vivo, are not capable of forming neuromuscular junctions (Son, et al., Cell Stem Cell, 9: 205-218 (2011). When co-cultured with primary chick muscle, channel rhodopsin-expressing control and patient iMNs repeatedly induced myotube contraction upon depolarization with green light, indicating they formed neuromuscular junctions and actuated muscle contraction (FIG. 8j). Thus, control and C9ORF72 patient iMNs are functional motor neurons.

TABLE 3

Control and Patient sample information

| NINDS/ Coriell Code | Sample name | Mutation | Disease | Age of Onset | Age at sampling | Gender |
|---|---|---|---|---|---|---|
| ND12133 | control 1 | control | N/A | N/A | 43 | F |
| ND03231 | control 2 | control | N/A | N/A | 56 | M |
| ND01751 | control 3 | control | N/A | N/A | 78 | M |
| ND06769 | patient 1 | C9ORF72 | ALS/FTD | 45 | 46 | F |
| ND10689 | patient 2 | C9ORF72 | ALS/FTD | 49 | 51 | F |
| ND12099 | patient 3 | C9ORF72 | ALS/FTD | 48 | 49 | M |
| ND14587 | SOD1A4V | SOD1A4V | ALS | 46 | 46 | F |

It was previously shown that iMNs from C9ORF72 ALS/FTD patients produce dipeptide repeat proteins from the repeat expansion (Wen, et al., *Neuron*, 84: 1213-1225 (2014)). To determine if C9ORF72 iMNs recapitulate neurodegenerative ALS processes, their survival was examined. Previous studies have measured iPSC-derived neuron survival using cross-sectional analyses (Sareen, et al., *Sci Transl Med*, 5:208 (2013), Donnelly, et al., *Neuron*, 80: 415-428, (2013), Wen, et al., *Neuron*, 84: 1213-1225 (2014), Kiskinis, et al., *Cell Stem Cell*, 14: (2014)), but differences in survival and neurogenesis cannot be distinguished using this approach. To definitively measure survival, longitudinal tracking of Hb9::RFP+ iMNs was performed (FIG. 1a).

In basal neuronal medium supplemented with neurotrophic factors, control and C9ORF72 patient iMNs survived equally well (FIG. 9a and FIG. 1b). In vivo, however, ALS patients have elevated glutamate levels in their cerebrospinal fluid (Lin, et al., *Neuron*, 20: 589-602 (1998)). In C9ORF72 ALS patients, glutamate accumulation may be triggered by dipeptide repeat proteins because they induce aberrant splicing of excitatory amino acid transporter 2 (EAAT2) in human astrocytes, resulting in an EAAT2 isoform that cannot import glutamate from the extracellular environment (Kwon, et al., *Science*, (2014)). A 12 hr treatment of 10 µM glutamate initiated a robust degenerative response in patient, but not control, iMNs (FIG. 1c-e). This response was consistent between multiple patients and controls (FIG. 1c, d). In addition, though iMN survival varied between live imaging systems, the relative difference between control and C9-ALS patient iMNs was consistent (FIG. 1c—Nikon Biostation CT and FIG. 9b—Molecular Devices ImageExpress, Table 4). Moreover, iMNs from different iPSC lines derived from the same donor behaved similarly, suggesting genotypic differences accounted for these effects (FIG. 9c). Treatment with glutamate receptor antagonists during glutamate administration prevented patient iMN degeneration, confirming that glutamate signaling induced the neurodegeneration (Figure if and FIG. 9d). Alternatively, withdrawal of neurotrophic factors also caused rapid degeneration of patient iMNs even without glutamate treatment (FIG. 1g and FIG. 9e), revealing the presence of pathogenic processes in patient iMNs cultured with low glutamate. Thus, C9ORF72 patient iMNs degenerate more rapidly than control iMNs in response to excess glutamate or neurotrophin withdrawal.

To determine if patient iMN degeneration resulted from bona fide ALS disease processes, the survival of neurons with properties of dopaminergic neurons were measured, which are less vulnerable than motor neurons in ALS patients. Induced neuron cultures generated using FoxA2, Lmx1a, Brn2, Ascl1, and Mytl1 (Pfisterer, et al., *Proc Natl Acad Sci*, 108: 10343-10348 (2011)) expressed high levels of tyrosine hydroxylase, indicating they had established a key aspect of the dopamine synthesis pathway and were distinct from iMNs, which do not express this enzyme (Son, et al., Cell Stem Cell, 205-218 (2011)) (FIG. 9f, g). Unlike iMN cultures, tyrosine hydroxylase-enriched induced neuron cultures from C9ORF72 patients showed similar survival to controls in both glutamate treatment and neurotrophic factor withdrawal conditions (FIG. 1h, FIG. 9h), indicating that the in vitro neurodegenerative phenotype elicited by the C9ORF72 mutation is selective for motor neurons, consistent with its causal role in ALS pathogenesis.

Figure 9J:
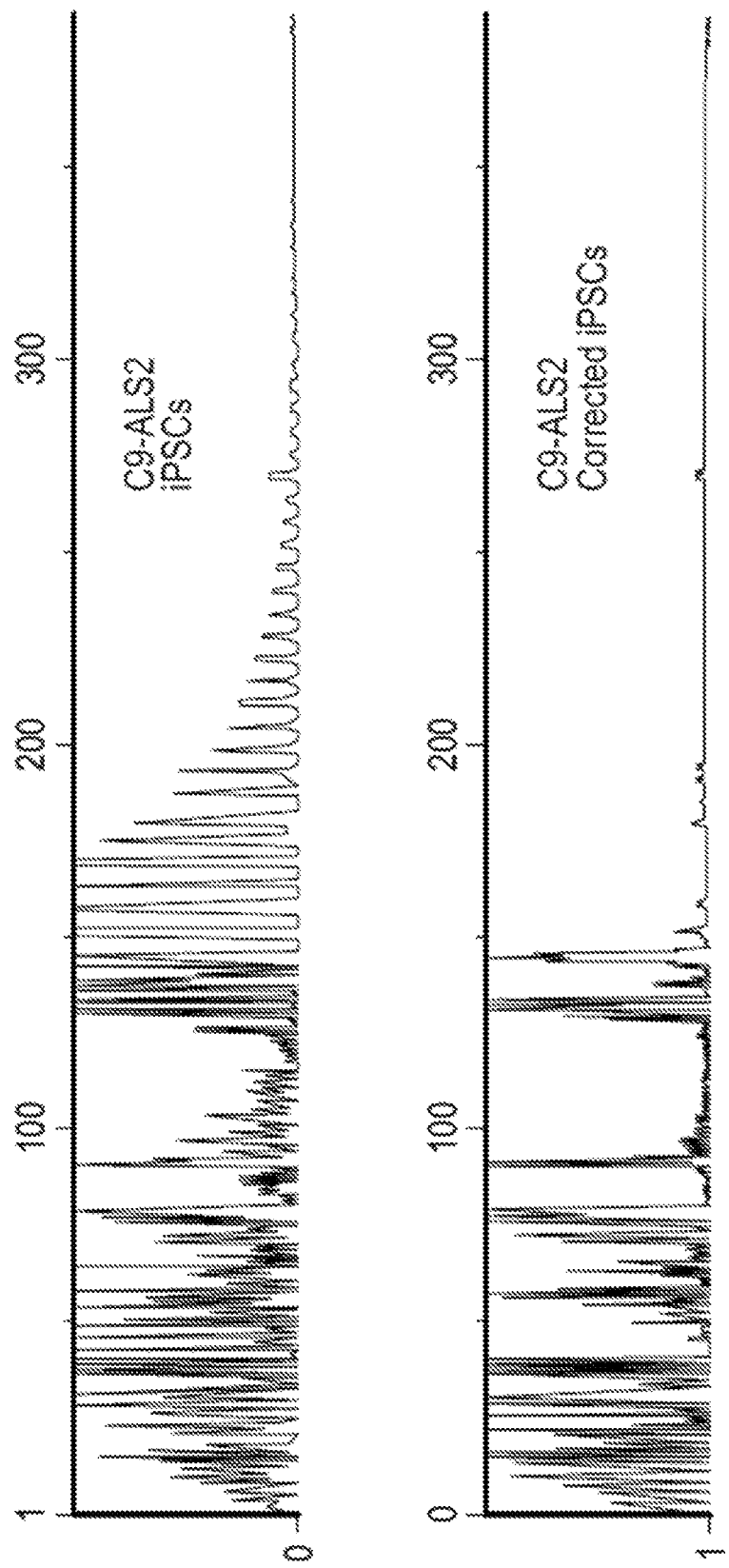
Figure 9K:
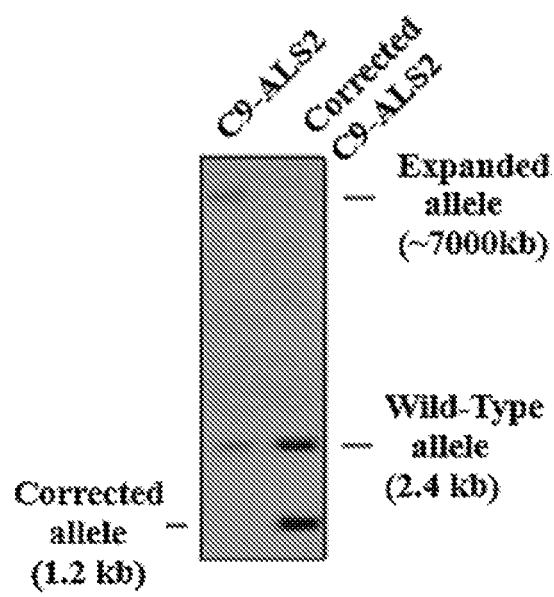
Figure 9L:
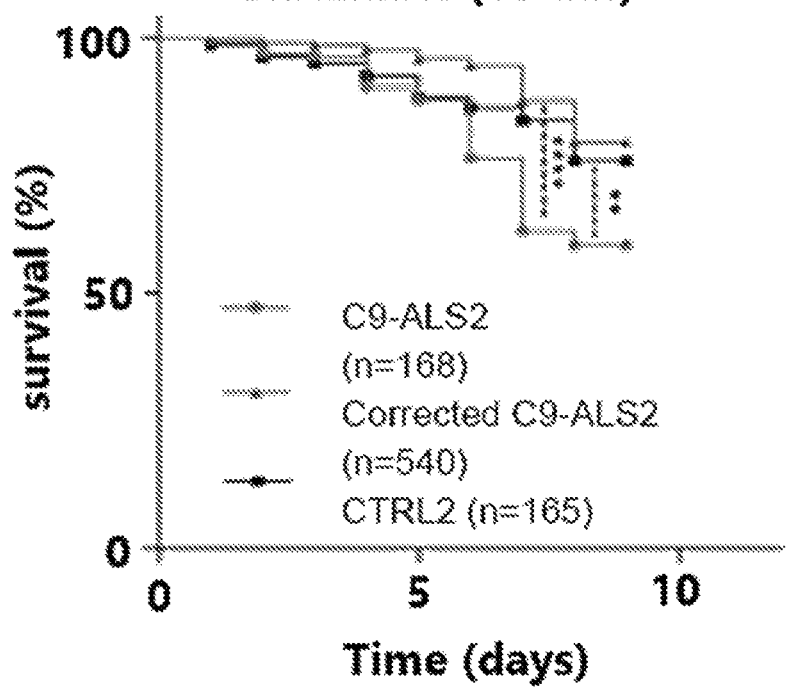

To eliminate the possibility that genetic variants outside the C9ORF72 locus caused patient iMN degeneration, CRISPR/Cas9-mediated genome editing was used to remove the repeat expansion from a patient iPSC line and replace it with the normal repeat (FIG. 9i-k). This fully rescued iMN survival (FIG. 9l), confirming that the repeat expansion causes the motor neuron degeneration in vitro.

Figure 9M:
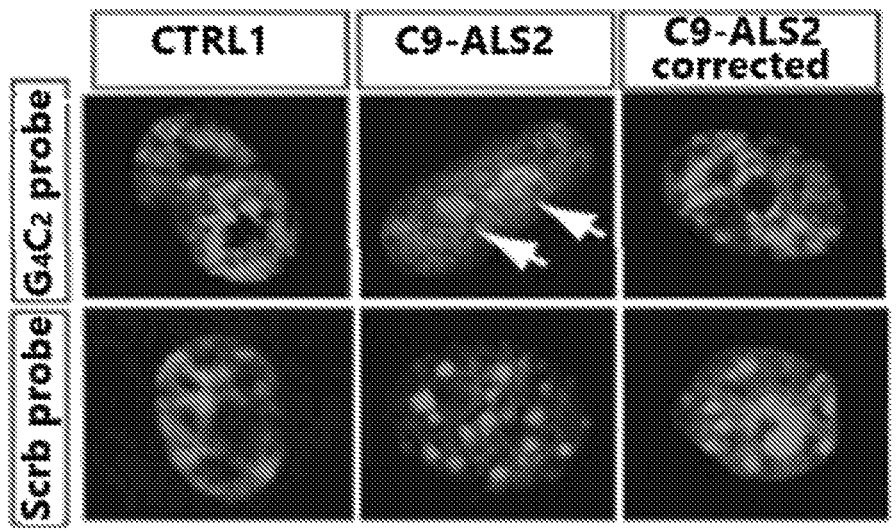

As further confirmation that patient iMNs recapitulate ALS disease processes, patient, but not control, iMNs exhibited prominent RNA foci nucleated by the repeat expansion (FIG. 9m). Therefore, patient-specific iMNs provide a relevant, human cell model of C9ORF72 ALS.

TABLE 4

Live imager used for each iMN survival experiment.

| Figure No | Machine Used for Live Imaging |
|---|---|
| 1b | BS (Nikon Biostation CT) |
| 1c | BS |
| 1d | BS |
| 1f | BS |
| 1g | BS |
| 1h | MD (Molecular Devices ImageExpress) |
| 2c | BS |
| 2d | MD |
| 2e | BS |
| 2j | MD |
| 3f | MD |
| 3g | MD |
| 3h | MD |
| 3i | MD |
| 4f | MD |
| 5a | MD |
| 5b | MD |
| 5c | MD |
| 5d | MD |
| 6d | MD |
| 6e | MD |
| 6f | MD |
| 9a | BS |
| 9b | MD |
| 9c | MD |
| 9d | BS |
| 9e | BS |
| 9h | MD |
| 9l | MD |
| 10h | BS |
| 10i | BS |
| 10j | MD |
| 10k | MD |
| 15a | MD |
| 15b | MD |
| 15c | MD |

Example 3

C9ORF72 is Haploinsufficient in ALS

Consistent with previous studies (DeJesus-Hernandez, et al., Neuron, 72: 245-256 (2011), Renton, et al., *Neuron*, 72: 257-268, (2011), Sareen, et al., *Sci Transl Med*, 5: (2013), Donnelly, et al., Neuron, 80: 415-428 (2013), and Lagier-Tourenne, et al., Proc Natl Acad Sci, 4530-4539 (2013)), patient iMNs expressed reduced levels of C9ORF72 mRNA and protein in comparison to iMNs in which the repeat expansion was removed using CRISPR/Cas9 editing (FIG. 2a, b and FIG. 10a, b). To determine if low C9ORF72 protein expression elicits iMN degeneration, C9ORF72 levels were restored in iMNs using a T2A-GFP-tagged retroviral cassette (FIG. 10c-e) and measured iMN survival in the glutamate treatment assay. Both C9ORF72 isoform A and isoform B fully rescued C9ORF72 patient iMN survival (FIG. 2c). This effect was specific for C9ORF72 iMNs, as forced expression of C9ORF72 did not rescue SOD1A4V iMN survival (FIG. 2d), nor did it improve the survival of control iMNs (FIG. 2e). Thus, restoring C9ORF72 protein levels specifically rescues C9ORF72 patient iMN survival, and isoform B is sufficient for this effect.

To confirm that reduced C9ORF72 protein levels causes neurodegeneration, CRISPR/Cas9-mediated genome editing was used to introduce a frameshift mutation into one or both alleles of C9ORF72 in control iPSCs (FIG. 2f, g). qPCR showed that targeting one allele reduced C9ORF72 transcript levels due to nonsense-mediated decay and transcript levels were more severely reduced in homozygous mutant cells (FIG. 2h). Frameshift mutations also eliminated C9ORF72 protein expression (FIG. 2i). Importantly, RNA sequencing of flow-purified Hb9::RFP+ iMNs showed that targeting C9ORF72 did not alter the expression of the top 10 genes with predicted off-target sites for the CRISPR guide RNA (FIG. 10f). In addition, expression of only 1 of the 20 genes nearest C9ORF72 on chromosome 9 was significantly altered in either the C9ORF72$^{+/-}$ and C9ORF72$^{-/-}$ iMNs, indicating that this approach specifically inactivated C9ORF72 (FIG. 10g).

Eliminating C9ORF72 protein expression from one or both alleles reduced iMN survival to levels comparable to patient iMNs (FIG. 2j), indicating that reduced C9ORF72 levels alone cause motor neuron degeneration in response to glutamate treatment. Exogenously restoring C9ORF72 expression in C9ORF72$^{+/-}$ and C9ORF72$^{-/-}$ iMNs rescued survival (FIG. 10j, k), verifying that depletion of C9ORF72 caused the observed neurodegeneration. These results indicate that the repeat expanded form of C9ORF72 is haploinsufficient in ALS. Tables 5 and 6 show the genomic locations of GGGGCCGGGGCCGGGGCC and GGGGC-CGGGGCCGGGGCCGGGGCC, respectively. This further indicates that gain of function mechanisms do not account for the full pathogenesis of the C9ORF72 repeat expansion, because if so, it would be expect that ALS/FTD patients would have expansions in these other genomic locations of GGGGCC repeats.

TABLE 5

Locations of GGGGCC x 3 in the human motor neuron transcriptome. Based on RNA Seq data from Ref. 7.

| Number | Ensembl Gene/ Transcript ID | Gene/ Transcript | Chromosome |
|---|---|---|---|
| 1 | ENSG00000175130.6 | MARCKSL1 | 1: 32333832-32336379 |
| 2 | ENSG00000198035.9 | AGAP9 | 1: 48189612:48237508 |
| 3 | ENSG00000036828.9 | CASR | 3: 122183683-122286503 |
| 4 | ENSG00000138685.8 | FGF2 | 4: 122826708-122898236 |
| 5 | ENST00000264498.3 | FGF2-001 | 4: 122826708-122898236 |
| 6 | ENST00000608478.1 | FGF2-002 | 4: 122826831-122895464 |
| 7 | ENST00000517260.1 | AC021205.1 | 4: 122827014-122827090 |
| 8 | ENSG00000138756.13 | BMP2K | 4: 78776342-78916372 |
| 9 | ENST00000389010.3 | BMP2K-002 | 4: 78776342-78879435 |

TABLE 5-continued

Locations of GGGGCC x 3 in the human motor neuron transcriptome. Based on RNA Seq data from Ref. 7.

| Number | Ensembl Gene/ Transcript ID | Gene/ Transcript | Chromosome |
|---|---|---|---|
| 10 | ENST00000502871.1 | BMP2K-001 | 4: 78776378-78879969 |
| 11 | ENST00000335016.5 | BMP2K-201 | 4: 78776378-78912185 |
| 12 | ENSG00000145214.9 | DGKQ | 4: 958885-986895 |
| 13 | ENST00000273814.3 | DGKQ-001 | 4: 958887-973556 |
| 14 | ENSG00000156427.7 | FGF18 | 5: 171419656-171457623 |
| 15 | ENSG00000096433.6 | ITPR3 | 6: 33620365-33696574 |
| 16 | ENST00000244496.5 | RRP36 | 6: 43021645-43034156 |
| 17 | ENSG00000013374.11 | NUB1 | 7: 151341699-151378449 |
| 18 | ENSG00000104490.13 | NCALD | 8: 101686543-102124907 |
| 19 | ENST00000517531.1 | NCALD-012 | 8: 101719315-102123950 |
| 20 | ENSG00000181790.6 | BAI1 | 8: 142449430-142545009 |
| 21 | ENSG00000158856.13 | DMTN | 8: 22048995-22082527 |
| 22 | ENST00000522148.1 | DMTN-012 | 8: 22048995-22069056 |
| 23 | ENSG00000029534.15 | ANK1 | 8: 41653220-41896762 |
| 24 | ENSG00000251349.3 | MSANTD3-TMEFF1 | 9: 100442271-100577636 |
| 25 | ENSG00000241697.3 | TMEFF1 | 9: 100473113-100577636 |
| 26 | ENSG00000130723.13 | PRRC2B | 9: 131394093-131500197 |
| 27 | ENSG00000160360.7 | GPSM1 | 9: 136327476-136359605 |
| 28 | ENSG00000148408.8 | CACNA1B | 9: 137877789-138124624 |
| 29 | ENSG00000147894.10 | C9orf72 | 9: 27546545-27573866 |
| 30 | ENSG00000107816.13 | LZTS2 | 10: 100996618-101007836 |
| 31 | ENST00000370220.1 | LZTS2 | 10: 100996618-101007836 |
| 32 | ENST00000454422.1 | LZTS2-006 | 10: 100999853-101003760 |
| 33 | ENSG00000242288.6 | RP11-464F9.1 | 10: 73674290-73730466 |
| 34 | ENSG00000183020.9 | AP2A2 | 11: 924894-1012245 |
| 35 | ENSG00000198176.8 | TFDP1 | 13: 113584721-113641470 |
| 36 | ENSG00000259993.1 | RP11-261B23.1 | 15: 30223017-30225564 |
| 37 | ENSG00000260211.2 | RP13-395E19.2 | 15: 32313126-32315654 |
| 38 | ENST00000348261.5 | CACNA1H-001 | 16: 1153241-1221768 |
| 39 | ENST00000358590.4 | CACNA1H-201 | 16: 1153241-1221771 |
| 40 | ENSG00000196557.6 | CACNA1H | 16: 1153241-1221771 |
| 41 | ENSG00000059145.14 | UNKL | 16: 1363205-1414751 |
| 42 | ENSG00000177548.8 | RABEP2 | 16: 28904421-28936526 |
| 43 | ENST00000358201.4 | RABEP2-001 | 16: 28904421-28925752 |
| 44 | ENST00000562590.1 | RABEP2-005 | 16: 28910287-28925684 |
| 45 | ENSG00000007384.11 | RHBDF1 | 16: 58059-76355 |
| 46 | ENSG00000225485.3 | ARHGAP23 (by BLAST) | 17: 38428418-38512392 |
| 47 | ENSG00000267131.1 | RP11-332H18.5 | 17: 61361668-61400243 |
| 48 | ENSG00000267280.1 | TBX2-AS1 | 17: 61393456-61411555 |
| 49 | ENSG00000007314.7 | SCN4A | 17: 63938554-63972918 |
| 50 | ENSG00000007237.14 | GAS7 | 17: 9910609-10198551 |
| 51 | ENSG00000172466.11 | ZNF24 | 18: 35332212-35345482 |
| 52 | ENST00000589539.1 | ZNF24-005 | 18: 35340345-35343932 |
| 53 | ENSG00000134046.7 | MBD2 | 18: 54151601-54224788 |
| 54 | ENST00000256429.3 | MBD2-001 | 18: 54151601-54224788 |
| 55 | ENST00000398398.2 | MBD2-005 | 18: 54202680-54224647 |
| 56 | ENST00000583046.1 | MBD2-002 | 18: 54202681-54224617 |
| 57 | ENSG00000101493.6 | ZNF516 | 18: 76358190-76495190 |

TABLE 5-continued

Locations of GGGGCC x 3 in the human motor neuron transcriptome. Based on RNA Seq data from Ref. 7.

| | Ensembl Gene/ Number Transcript ID | Gene/ Transcript | Chromosome |
|---|---|---|---|
| 58 | ENST00000353265.3 | PARD6G-001 | 18: 80157232-80247546 |
| 59 | ENSG00000178184.11 | PARD6G | 18: 80157232-80247546 |
| 60 | ENSG00000267662.1 | AC007796.1 | 19: 31348881-31417794 |
| 61 | ENSG0000104936.13 | DMPK | 19: 45769717-45782552 |
| 62 | ENSG00000196562.10 | SULF2 | 20: 47656348-47786616 |
| 63 | ENST00000359930.4 | SULF2-001 | 20: 47656912-47786586 |
| 64 | ENST00000463221.2 | SULF2-008 | 20: 47689548-47786054 |
| 65 | ENSG00000198355.4 | PIM3 | 22: 49960513-49964080 |
| 66 | ENST00000467480.1 | PIM3-002 | 22: 49960768-49961646 |
| 67 | ENST00000375135.3 | FGD1 | X: 54445454-54496166 |
| 68 | ENSG00000102302.7 | FGD1 | X: 54445454-54496166 |

TABLE 6

Locations of GGGGCC x 4 in the human motor neuron transcriptome. Based on RNA Seq data from Ref. 7.

| | Ensembl Gene/ Transcript ID | Gene/Transcript | Chromosome |
|---|---|---|---|
| 1 | ENSG00000235016.1 | SEMA3F-AS1 | 3: 50116022-50156085 |
| 2 | ENSG00000109794.9 | FAM149A | 4: 186104419-186172667 |
| 3 | ENSG00000169220.13 | RGS14 | 5: 177357837-177372601 |
| 4 | ENST00000509289.1 | RGS14-011 | 5: 177371066-177371582 |
| 5 | ENST00000244496.5 | RRP36-001 | 6: 43021645-43029597 |
| 6 | ENSG00000124541.6 | RRP36 | 6: 43021645-43034156 |
| 7 | ENSG00000179526.12 | SHARPIN | 8: 144098633-144108124 |
| 8 | ENSG00000167157.9 | PRRX2 | 9: 129665641-129722674 |
| 9 | ENSG00000204172.7 | AGAP10 | 10: 47501854-47549750 |
| 10 | ENSG00000254929.2 | RP11-144G6.12 | 10: 47517816-47553514 |
| 11 | ENSG00000198035.9 | AGAP9 | 10: 48189612-48237508 |
| 12 | ENSG00000204164.6 | BMS1P5 | 10: 48901102-48950972 |
| 13 | ENSG00000255032.1 | RP11-45A12.2 | 11: 44719392-44736692 |
| 14 | ENSG00000248265.1 | FLJ12825 | 12: 54058254-54122234 |
| 15 | ENSG00000249388.1 | RP11-834C11.6 | 12: 54082118-54102693 |
| 16 | ENSG00000140265.8 | ZSCAN29 | 15: 43358172-43371025 |
| 17 | ENST00000561661.1 | ZSCAN29-006 | 15: 43369851-43371025 |
| 18 | ENSG00000007545.11 | CRAMP1L | 16: 1612325-1677908 |
| 19 | ENSG00000099822.2 | HCN2 | 19: 589893-617159 |
| 20 | ENSG00000175221.10 | MED16 | 19: 867630-893218 |

Example 4

C9ORF72 Induces Guanine Exchange on RAB5 and ARF3

The finding that C9ORF72 is haploinsufficient in ALS suggests that increasing C9ORF72 levels may mitigate disease progression. Additionally, determining the function of C9ORF72 may enable design of function-directed therapies.

Figure 11A:
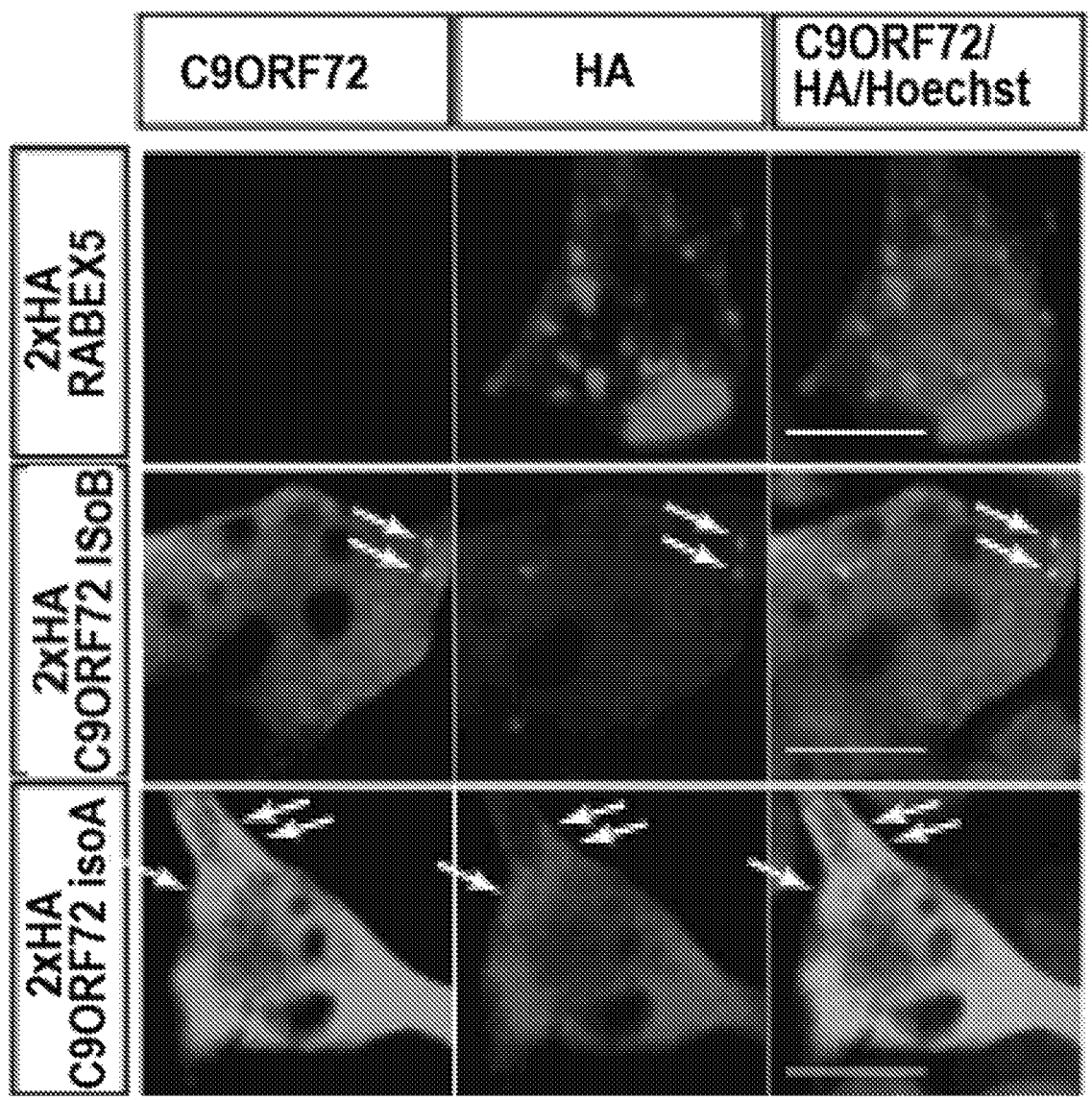
FIG. 11 shows data from confocal microscopy experiments to determine C9ORF72 localization. a, The confocal images show HEK293T-overexpressing HA-tagged RABEX5 or C9ORF72 (isoform A or B), showing the expression of the exogenous protein; HA (red) and C9ORF72 (green). Nuclei (blue) are labeled with Hoechst. b-c, The confocal images show control iMNs which express Hb9::ChR-YFP and show colocalization (arrows) of C9ORF72 (green) with RAB5 (b, red) but not with the lysosomal marker LAMP1 (c, red). d-e, The images show the confocal Z-axis scanning to determine C9ORF72 localization. C9ORF72 (green) colocalizes with RAB5 (d, red) and EEA1 (e, red) in 3-dimensional space. Nuclei are labeled with DAPI (blue). Scale bars: 10 μm (a); 5 (b-e).
Figure 11B:
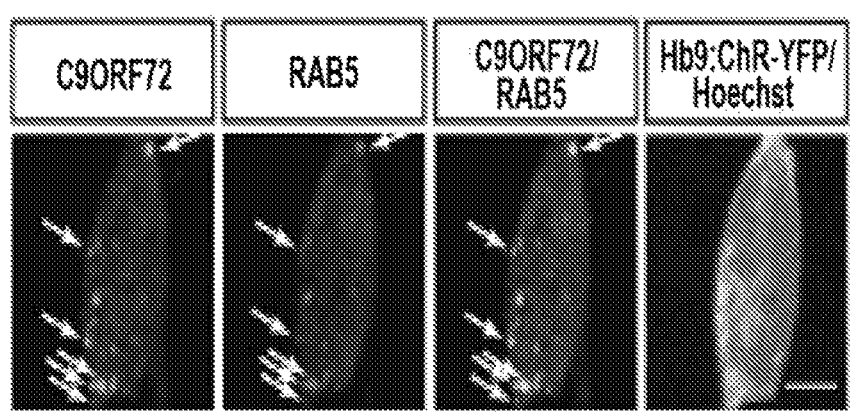
Figure 11C:
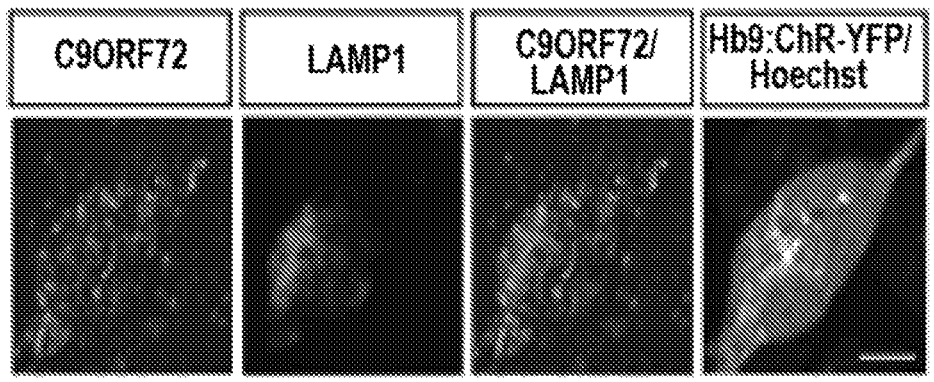
Figure 11D:
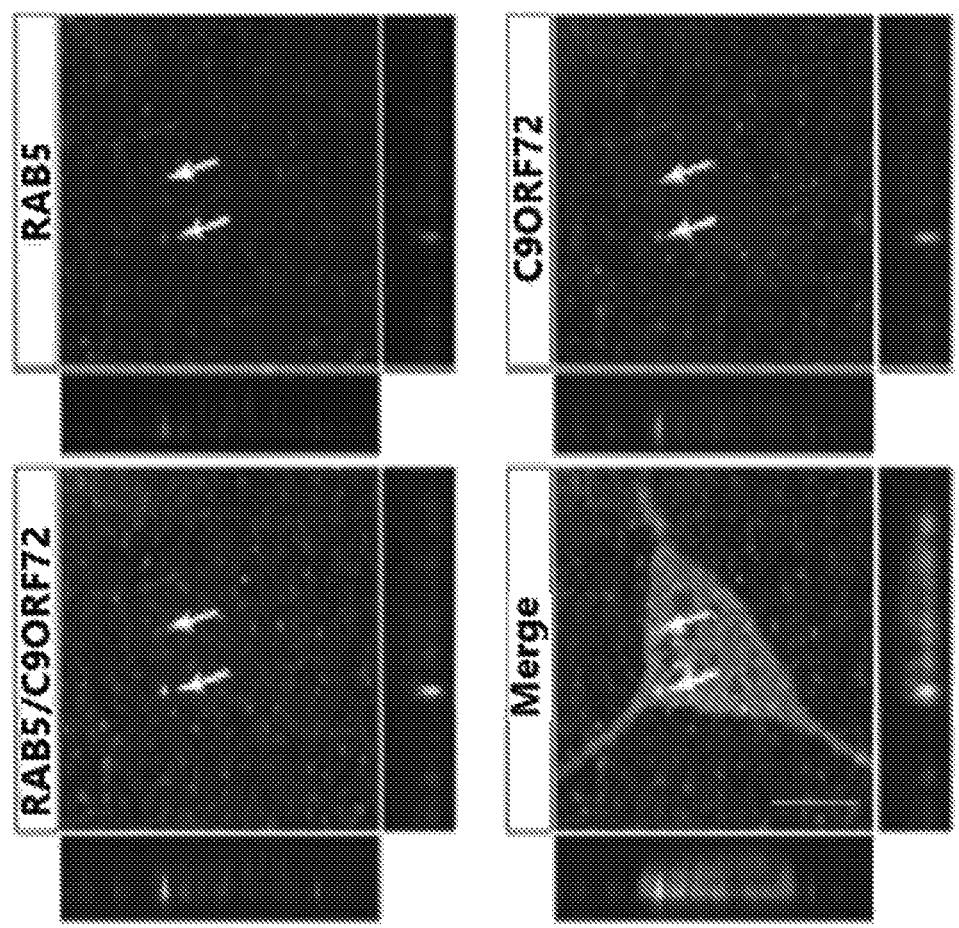
Figure 11E:
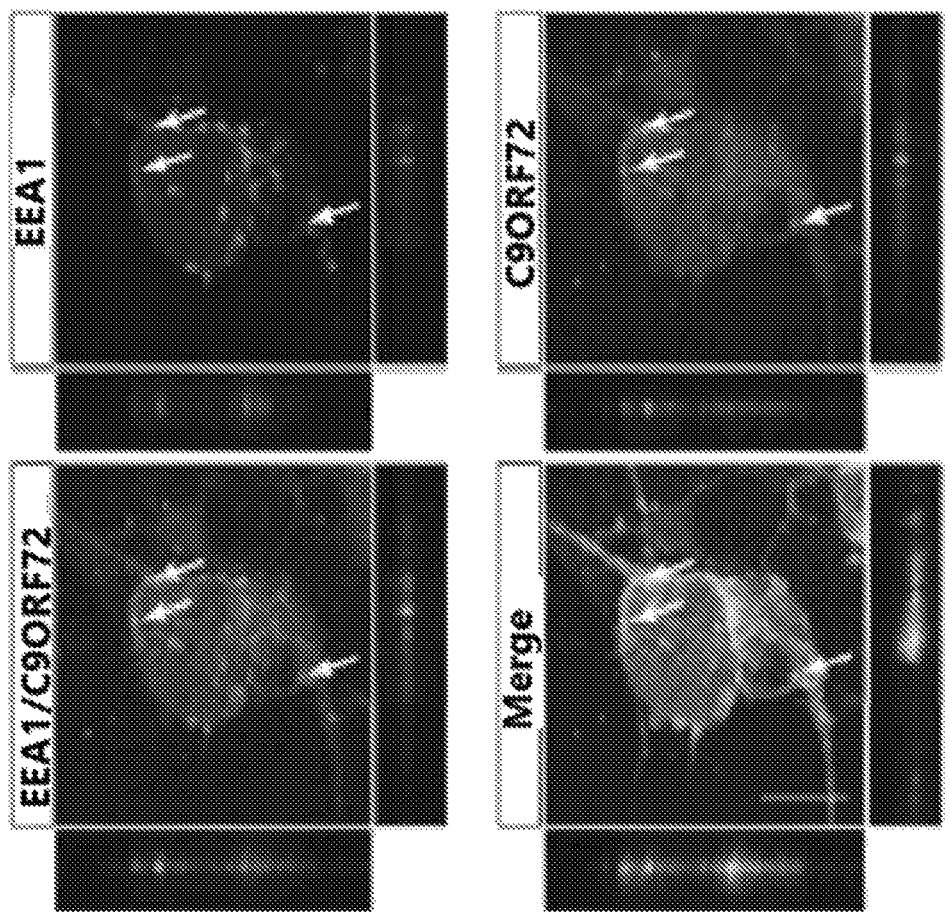

To examine the function of C9ORF72, C9ORF72 localization was determined in iMNs. A FLAG-tagged C9ORF72 construct was used to verify that the C9ORF72 antibody specifically recognizes C9ORF72 in cells (FIG. 11a). In iMNs, C9ORF72 co-localized to cytoplasmic puncta with early and late endosomal proteins: RAB5 (early endosome, ~80%), EEA1 (early endosome, ~80%), and RAB7 (late endosome, ~60%)(FIG. 3a, b and FIG. 11b-e). Only in rare vesicles did C9ORF72 co-localize with the lysosomal marker LAMP1 (20%)(FIG. 11c). Control and patient iMNs showed similar C9ORF72 localization (FIG. 3b). These data are consistent with C9ORF72 functioning in early or late endosomes in iMNs.

C9ORF72 displays limited structural homology to proteins related to Differentially Expressed in Normal and Neoplasia (DENN) (Levine, et al., *Bioinformatics*, 29: 499-503 (2013)). Several DENN domain proteins are guanine exchange factors that activate RAB GTPases by catalyzing the removal of GDP, allowing GTP binding (Marat, et al., *J Biol Chem*, 286: 13791-13800 (2011)). Different RAB GTPases, of which there are ~70 in humans (Marat, et al., *J Biol Chem*, 286: 13791-13800 (2011)), act together with ARF GTPases to mediate various aspects of endosomal trafficking, including endocytosis, lysosomal biogenesis, recycling, exocytosis, and autophagy (Marat, et al., J Biol Chem, 286: 13791-13800 (2011)). Each guanine exchange factor is typically selective for one or two GTPases. However, the catalytic cores of some RAB-activating guanine exchange factors are similar to those of ARF guanine exchange factors (Delprato, et al., *Cell*, 118: 607-617 (2004)) and the same protein can activate both a RAB and an ARF GTPase (Rosa, et al. *EMBO J*, 15: 4262-4273 (1996)). In addition, the ALS-linked guanine exchange factor ALSIN (encoded by ALS2) stimulates guanine exchange on both RAB5 and RAC1, a Rho GTPase (Tudor, et al., *J Biol Chem*, 280: 34735-34740, (2005) and Topp, et al., *J Biol Chem*, 279: 24612-24623 (2004)). Thus, guanine exchange factors can stimulate guanine exchange on GTPases from multiple families.

Although siRNA-mediated suppression of C9ORF72 levels can broadly affect endosomal trafficking (Farg, et al., *Hum Mol Genet*, 10: 1093 (2014)), there is little evidence that C9ORF72 has a direct role in endosomal trafficking. A recent study by Sellier and colleagues reported that C9ORF72 isoform A, but not isoform B, can form a complex with SMCR8 and WDR41 that can induce guanine nucleotide exchange on RAB8 and RAB39B GTPases (Sellier, et al., *EMBO J*, (2016)). However, the role of C9ORF72 isoform A was not directly tested, and SMCR8 binds to these GTPases independently of C9ORF72 (Sellier, et al., EMBO J, (2016)), suggesting that it alone may activate RAB8 and RAB39B. Moreover, since either exogenous C9ORF72 isoform B or isoform A rescues C9-ALS iMN degeneration in the assay performed in this study, it is unlikely that the mechanism described by Sellier and colleagues, which is isoform A-specific, could explain the rescue of patient iMNs.

To directly evaluate C9ORF72 for guanine exchange factor activity, an in vitro biochemical assay (Xiong, et al., *PLoS Biol*, 10: (2012)) was performed that measures the fluorescence of BODIPY-conjugated GDP that self-quenches when removed from GTPase proteins (FIG. 3c). All GTPases that were highly expressed in iMNs and could be purified efficiently from *E. coli*, as judged by their expression level and ability to bind BODIPY GDP in vitro (FIG. 12a-c). This included a panel of RAB, ARF, Rho, and RAN GTPases representing diverse aspects of endosomal trafficking (Yoshimura, et al., *J Cell Biol*, 191, 367-381 (2010)) and other cellular functions (FIG. 12b). It was then determined if C9ORF72 isoform A or B derived from cell extracts could induce removal of BODIPY-GDP from individual GTPases. Cell extracts overexpressing RABEX-5 (FIG. 12d), a guanine exchange factor specific for the early endosome GTPase RAB5 (Yoshimura, et al., J Cell Biol, 191, 367-381 (2010)), sharply decreased fluorescence when incubated with BODIPY-GDP-bound RAB5, indicating that it removed the GDP from RAB5 (FIG. 3d, e). In contrast to RABEX-5, DENND2D (guanine exchange factor specific for RAB9A and RAB9B) (Marat, et al., *J Biol Chem*, 286, 13791-13800 (2011)) or DsRed extracts did not display guanine exchange activity on RAB5A (FIG. 3*d, e*) and neither RABEX-5, DENN2D, or DsRed displayed activity on RAB11A (FIG. 3*e* and FIG. 12*e*), verifying the specificity of this assay. Similarly to RABEX-5, C9ORF72 isoforms A and B induced removal of BODIPY-GDP from RAB5 (FIG. 3*d, e* and FIG. 12*e*). In addition, C9ORF72 isoforms A and B stimulated guanine exchange on ARF3, another early endosome-associated GTPase (Kondo, et al., *Cell Structure and Function*, 37: 141-154 (2012)) (FIG. 3*e* and FIG. 12*e*). Significant activity was not observed using both C9ORF72 isoforms on the other GTPases tested (FIG. 3*e* and FIG. 12*e*). Thus, C9ORF72 stimulates guanine exchange on RAB5 and ARF3, and the 25-kDa isoform B fragment is sufficient for this activity.

To determine if neurodegeneration results from reduced activation of RAB5 by C9ORF72, it was assessed whether expression of a constitutively active RAB5 mutant (Bohdanowicz, et al., *Mol Biol Cell*, 23: 176-187 (2012)) could rescue C9ORF72 patient iMN survival in the glutamate treatment assay. The forced expression of constitutively active RAB5 significantly reduced the survival of control iMNs (FIG. 3*f*). In contrast, constitutively active RAB5 significantly increased the survival of iMNs from two different C9ORF72 patients (FIG. 3*g* and FIG. 12*g*). Neither wild-type RAB5 (FIG. 3*h*) nor constitutively active RAB7 (FIG. 3*i*) rescued C9ORF72 patient iMN survival, verifying that RAB5 activity was required for rescue. Thus, impaired C9ORF72-dependent RAB5 activation due to repeat expansion induces human motor neuron degeneration.

The effects of reduced C9ORF72 protein levels on endosomal trafficking was examined in iMNs. RAB GTPases tether to their target membrane compartments most efficiently when bound to GTP (Zerial, et al., *Nat Rev Mol Cell Biol*, 2: 107-117 (2001)). For example, in *C. elegans* GABAergic motor neurons, inactivation of the RAB5 guanine exchange factor RABX5 sharply reduces the intensity of RAB5-YFP fluorescence in early endosomes in the soma (Sann, et al., *PLoS One*, 7: e37930 (2012)). This assay provides an assessment of early endosome trafficking (Sann, et al., *PLoS One*, 7: e37930 (2012)) and it was verified that RAB5-RFP expression colocalizes with the early endosome marker EEA1 in iMNs (FIG. 13*a*). Consistent with the finding that C9ORF72 stimulates guanine exchange on RAB5, inactivating one copy of C9ORF72 in control iMNs (CTRL2 C9ORF72$^{+/-}$) significantly reduced the fluorescence intensity of individual RAB5-RFP+ vesicles and the overall RAB5-RFP fluorescence intensity within the soma of iMNs (FIG. 3*j, k* and FIG. 13*b*). Thus, suppression of C9ORF72 levels limits RAB5 activation in human motor neurons.

Figure 13C:
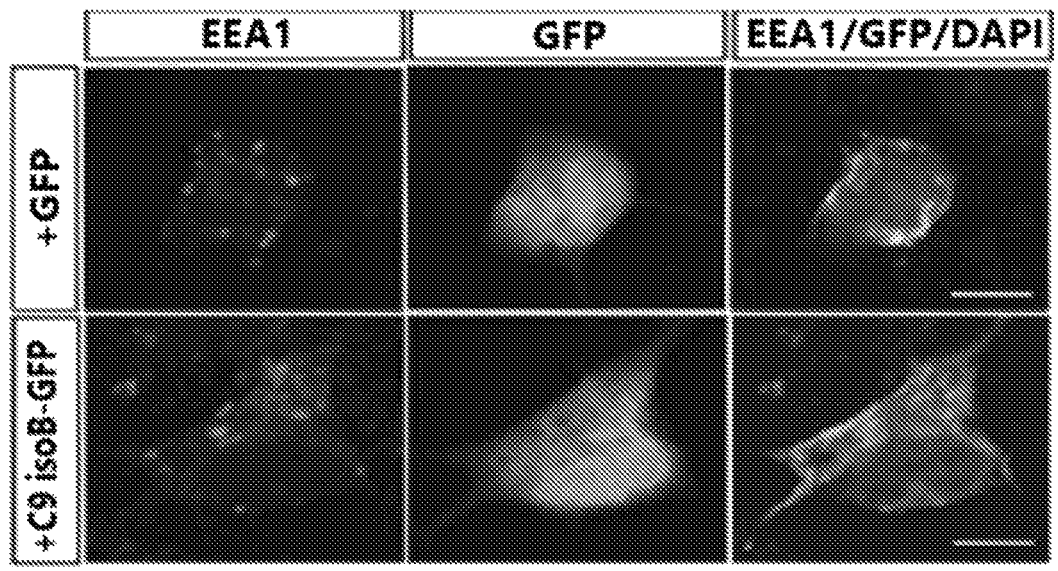

RAB5 activation enables recruitment of EEA1, which drives the fusion of early endosomes (Lemmon, et al., *Nat Rev Mol Cell Biol*, 9: 99-111 (2008)). Thus, if C9ORF72 activates RAB5, increased C9ORF72 levels should promote the fusion of early endosomes, leading to an increase in size (Roberts, et al., *J Cell Sci*, 112: 3667-3675 (1999)). Confocal and electron microscopy revealed that overexpression of C9ORF72 in iMNs and iPSC-derived fibroblasts significantly increased the size of EEA1+ early endosomes, providing additional evidence that it activates RAB5 in motor neurons and other cells (FIG. 3*l* and FIG. 13*c*).

Inactivation of RAB5 impairs lysosomal biogenesis (Zeigerer, et al., *Nature*, 485: 465-470 (2012) and Bucci, et al., *Mol Biol Cell*, 11: 467-480 (2000)). Using electron microscopy and immunocytochemistry analyses, it was found that loss of C9ORF72 activity sharply reduced the amount of lysosomes (identified by high electron density (Neiss, et al., *Histochemistry*, 77: 63-77 (1983))) in iPSC-derived fibroblasts and iMNs. (FIG. 3*n-p*). Forced expression of C9ORF72 isoform B expression in C9ORF72$^{+/-}$ iMNs restored the number of LAMP1+ lysosomes to control levels (FIG. 3*q*). In contrast to C9ORF72$^{+/-}$ iMNs, C9-ALS patient iMNs did not exhibit elevated levels of LAMP1+ lysosomes, which was inconsistent with their reduced C9ORF72 levels (FIG. 3*p*). However, since aggregate-prone proteins such as mutant Huntingtin activate lysosomal production in neurons (Kegel, et al., *Neurosci*, 20: 7268-7278 (2000)), it was hypothesized that disease processes such as the accumulation of dipeptide repeat protein aggregates (Wen, et al., *Neuron*, 84: 1213-1225 (2014)) were inducing activation of lysosomal biogenesis in patient iMNs, but that lysosomal biogenesis was still suboptimal because of reduced C9ORF72 activity. Consistent with this notion, forced expression of C9ORF72 isoform B further increased the number of lysosomes in patient iMNs, while it had no effect on control iMNs (FIG. 3*r*).

To determine if reduced C9ORF72 activity leads to impaired lysosomal biogenesis in motor neurons in vivo, the number of lysosomes in spinal motor neurons was measured in Nestin-Cre-Stop-Flox-C9orf72 mice (Koppers, et al., *Ann Neurol*, (2015)). Motor neurons containing a deletion of C9orf72 contained significantly fewer Lamp1+ lysosomes (FIG. 3*s, t*). Together, these results indicate that C9ORF72 regulates early endosomal trafficking and lysosomal biogenesis in human and mouse motor neurons by activating RAB5.

Example 5

Low C9ORF72 Activity Sensitizes iMNs to Glutamate

The observation that glutamate triggers the selective degeneration of C9ORF72 patient iMNs (FIG. 1*c-e*) suggests that the repeat expansion increases iMN glutamate sensing. In cortical neurons, RAB5 helps mediate homeostatic synaptic plasticity by enabling endocytosis and subsequent lysosomal degradation of glutamate receptors in response to chronic glutamate signaling (Wang, et al., *Neural plasticity*, (2012) and Chen, et al., *Mol Pharmacol*, 72: 40-51 (2007)). Defects in this process lead to the accumulation of glutamate receptors on the cell surface (Wang, et al., *Neural plasticity*, (2012) and Chen, et al., *Mol Pharmacol*, 72: 40-51 (2007)).

To determine if reduced C9ORF72 activity causes glutamate receptor accumulation on human motor neurons, levels of NMDA and AMPA receptor subunits (NR1 and GLUR1 respectively) were compared on C9ORF72$^{+/+}$ and C9ORF72$^{+/-}$ control iMNs under basal conditions. Immunostaining analysis revealed that C9ORF72$^{+/-}$ iMNs expressed elevated surface and total levels of NMDA and AMPA receptors compared to C9ORF72$^{+/+}$ iMNs (FIG. 4*a, b* and FIG. 14*a, e*). To determine if these phenotypes were due to off-target effects or specific to the method of generating motor neurons, a second C9ORF72$^{+/-}$ iPSC line was generated from a different control donor using a different guide RNA and produced motor neurons using a different method (retinoic acid/purmorphamine administration) (FIG. 14*b*). C9ORF72$^{+/-}$ motor neurons produced in this way also possessed increased NMDA and AMPA receptor levels compared to controls, suggesting this phenotype was not due to off-target effects nor was it specific to the method of generating motor neurons (FIG. 14c, f). Consistent with the reduced C9ORF72 levels observed in patient motor neurons (FIG. 2a-c), C9-ALS iMNs also showed elevated NR1 levels compared to controls (FIG. 4c, d and FIG. 14a). In contrast to NR1 levels, TRKB receptor levels were not elevated in patient iMNs compared to controls, indicating that the repeat expansion differentially affects specific receptors (FIG. 14g). qPCR analysis of flow-purified C9ORF72$^{+/-}$ iMNs showed that NR1 and GluR1 mRNA levels were not elevated, indicating that increased transcription could not explain the increased glutamate receptor levels in C9ORF72-deficient iMNs (FIG. 14h, i). Vesicular RAB11 levels were similar in patient and control iMNs, suggesting that the recycling endosome pathway remained active in patient iMNs and could return internalized but non-degraded glutamate receptors to the cell surface (FIG. 14j). These results indicate that reduction of C9ORF72 activity causes the accumulation of glutamate receptors on human motor neurons.

Figure 14K:
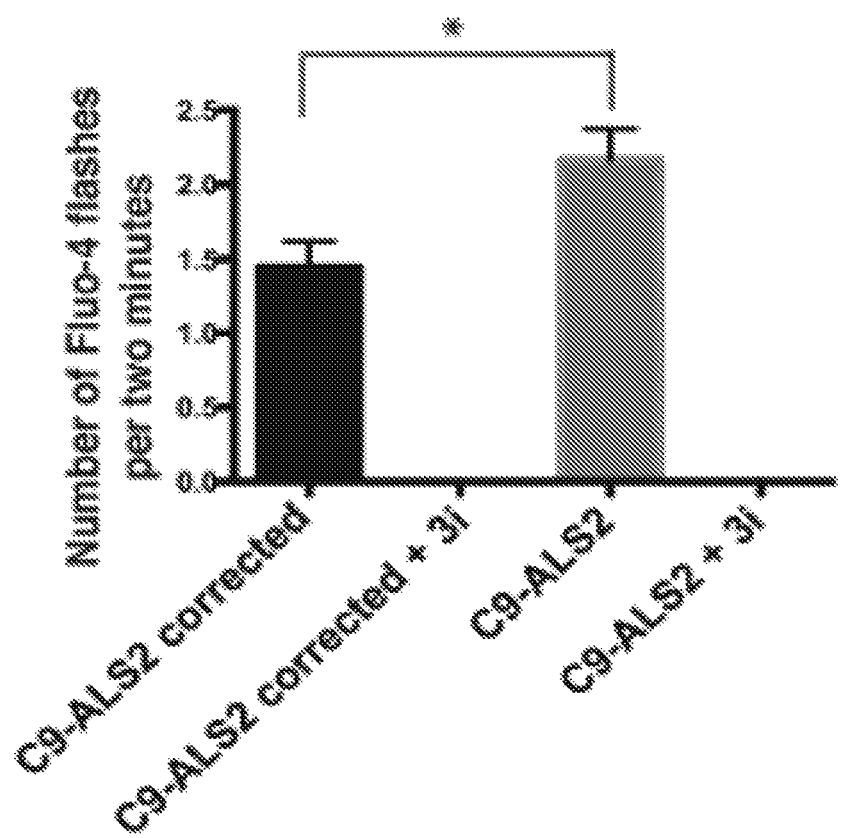

To determine if the extra glutamate receptors were functional, Gcamp6, a GFP-calmodulin fusion protein that fluoresces in the presence of calcium (Chen, et al., *Nature*, 499: 295-300 (2013)), was used to measure calcium influx into iMNs in response to glutamate. Glutamate triggered more frequent calcium influxes in C9ORF72 patient iMNs than controls (FIG. 4e). Moreover, C9ORF72$^{+/-}$ iMNs displayed an increased calcium influx frequency that was indistinguishable from that of C9ORF72 patient iMNs (FIG. 4e). Calcium imaging using Fluo-4 confirmed these results and depletion of intracellular calcium stores using 20 µM cyclopiazonic acid for 30 minutes before glutamate treatment verified that the observed calcium transients were due to influx (FIG. 14k). In addition, treatment with glutamate receptor antagonists eliminated calcium transients, verifying that the calcium transients are dependent on glutamate receptor activation (FIG. 14k). Thus, a 50% reduction of C9ORF72 activity induced a hyperexcitability phenotype similar to C9ORF72 patient motor neurons.

Figure 14L:
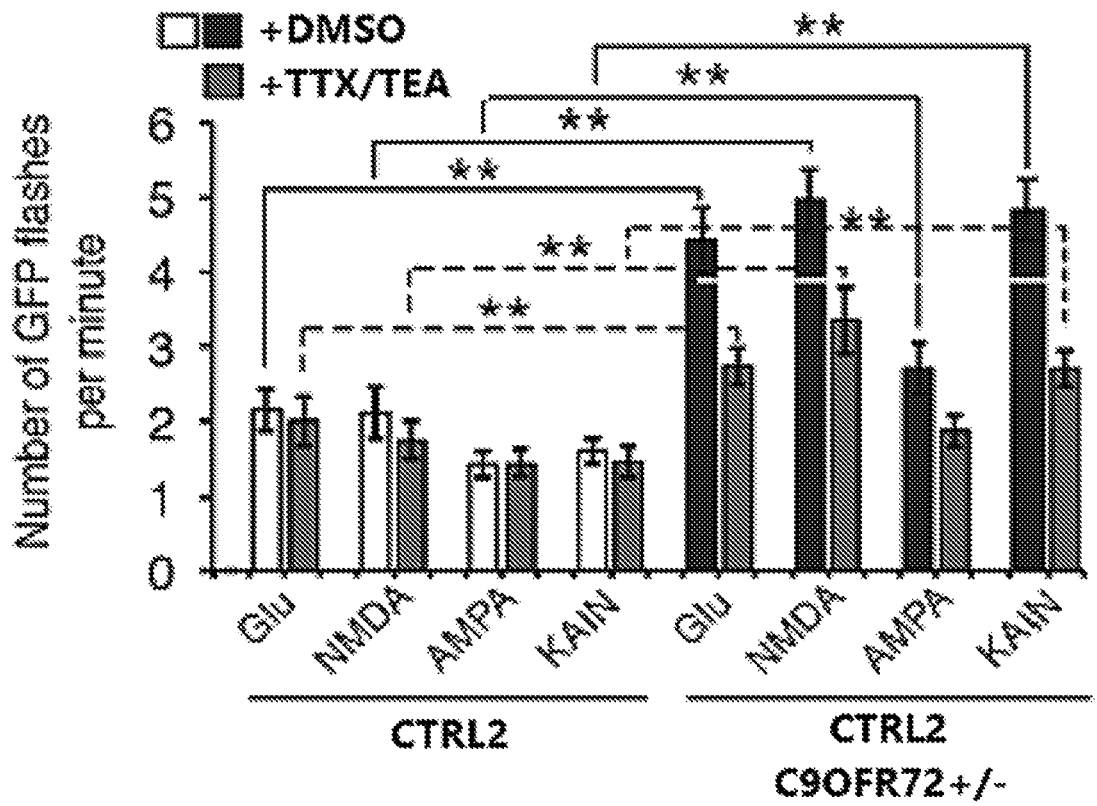

Since glutamate receptor activation and neuronal firing both induce calcium influx, their relative contributions to the increased Gcamp6 activation was determined. When TTX and TEA was used to block neuronal firing, C9ORF72$^{+/-}$ iMNs still displayed more frequent Gcamp6 activation than C9ORF72$^{+/+}$ iMNs (FIG. 14l), indicating that part of the hyperexcitability caused by reduced C9ORF72 activity is due to increased glutamate receptor activation. To determine which receptors were responsible for the increased glutamate response, small molecule agonists of specific glutamate receptor subtypes were tested. Activation of NMDA, AMPA, and kainate receptors was higher in C9ORF72$^{+/-}$ iMNs than controls (FIG. 14l). Therefore, a 50% reduction of C9ORF72 activity in human motor neurons leads to the aberrant accumulation of functional glutamate receptors of all three subtypes.

Figure 14M:
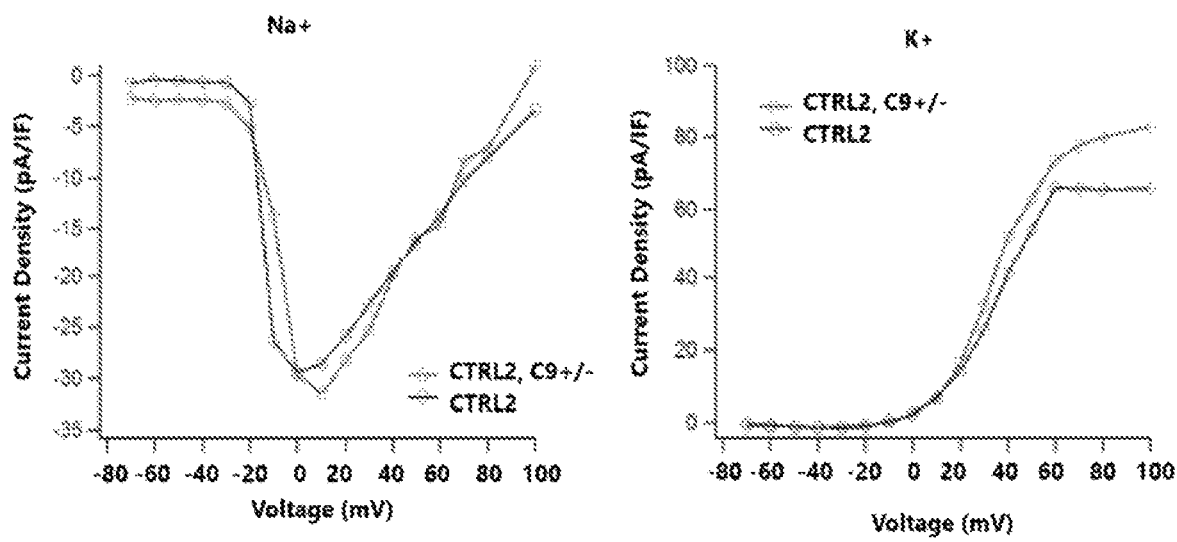

Removal of the ion channel inhibitors TTX and TEA during glutamate receptor agonist treatment revealed additional increases in Gcamp6 activation in C9ORF72$^{+/-}$ iMNs compared to controls, suggesting that C9ORF72$^{+/-}$ iMNs also fire action potentials more frequently than controls (FIG. 14l), although large changes in sodium or potassium currents in C9ORF72$^{+/-}$ iMNs were not detected (FIG. 14m). To determine if increased neuronal activity due in part to elevated glutamate receptor levels contributed to the neurodegeneration observed in C9ORF72 patient and C9ORF72$^{+/-}$ iMNs, iMN survival was measured in the presence or absence of retigabine. Retigabine is approved by the U.S. Food and Drug Administration for the treatment of epilepsy and reduces neuronal excitability by activating Kv7 potassium channels (Wainger, et al., *Cell Rep*, 7: 1-11 (2014)). In the glutamate treatment assay, retigabine administration significantly increased the survival of C9ORF72 patient, C9ORF72$^{+/-}$, and C9ORF72$^{-/-}$ iMNs, but not control iMNs (FIG. 4f and FIG. 15a-c). Thus, suppressing iMN firing blocks glutamate-induced neurodegeneration caused by reduced C9ORF72 activity.

To determine if reduced C9orf72 levels leads to glutamate receptor accumulation in vivo, glutamate receptor levels in spinal motor neurons deleted of C9orf72 was measured in Nestin-Cre-Stop-Flox-C9orf72 mice (Koppers, et al., *Ann Neurol*, (2015)). NR1 (NMDA), GluR1 (AMPA), and GluR6/7 (kainate) levels were elevated in C9orf72-null motor neurons (FIG. 4g, h and FIG. 16a-d). Thus, loss of C9orf72 causes glutamate receptor accumulation in vivo.

Figure 16E:
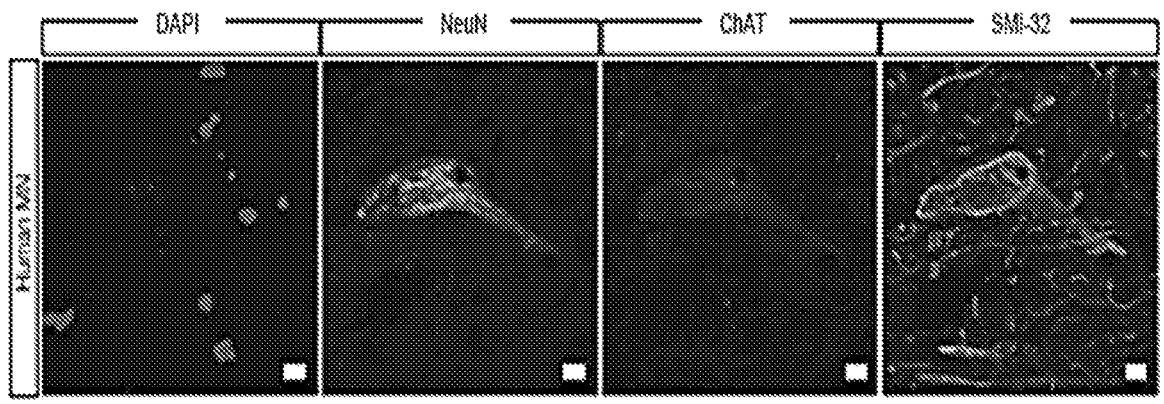
Figure 16F:
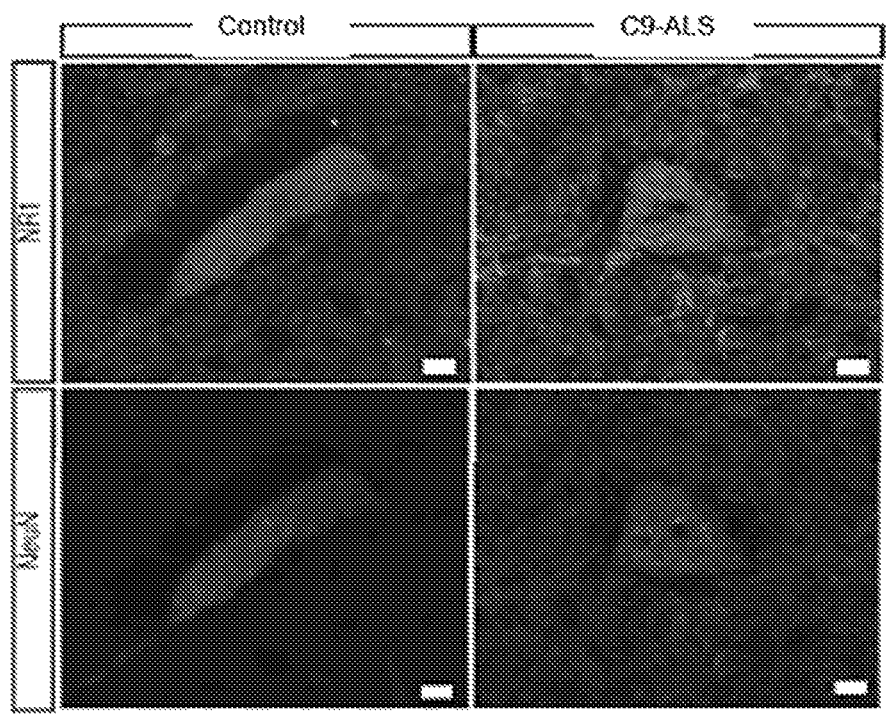
Figure 17A:
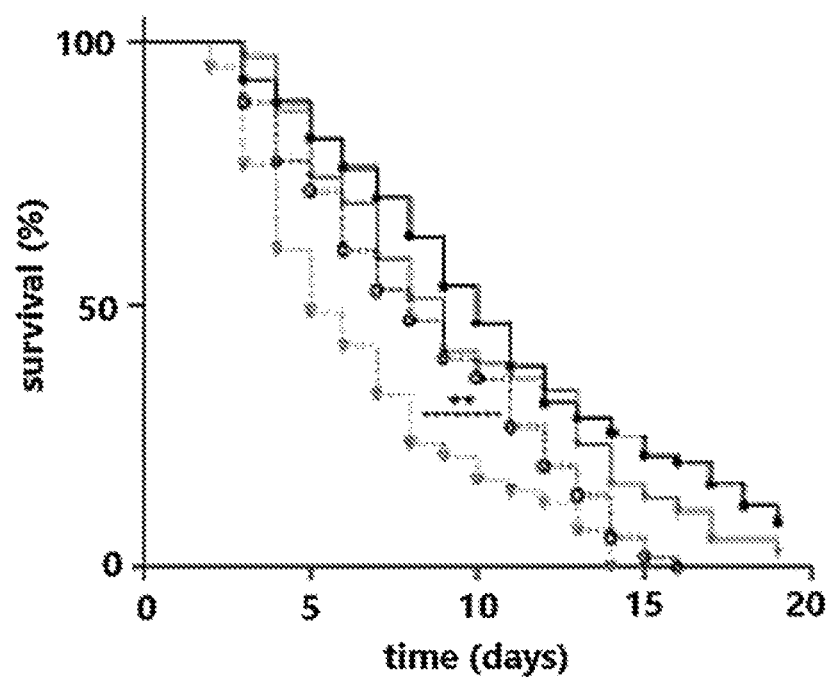
FIG. 17 shows the survival of control and CRISPR-mutant C9ORF72$^{-/-}$ iMNs in excess glutamate with overexpression of eGFP or PR(50)-eGFP (a) or GR(50)-eGFP (b).
Figure 17B:
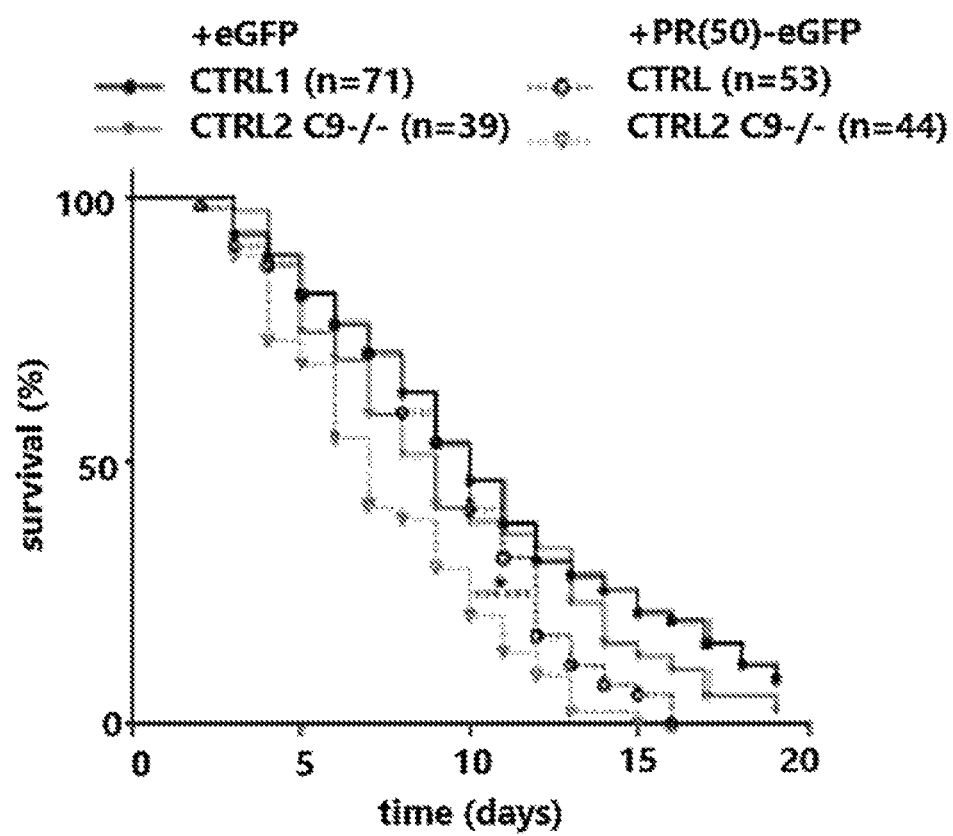

To determine if glutamate receptor accumulation occurs on C9ORF72 patient motor neurons in vivo, glutamate receptor expression was measured in lumbar spinal cord samples from 3 C9ORF72 ALS patients and 3 unaffected controls. Motor neurons were identified by size based on several CHAT+ neurons used as references (FIG. 16e). Similar to iMNs, spinal motor neurons from the C9ORF72 ALS patients expressed higher levels of NR1 and GLUR6/7 glutamate receptor subunits than control neurons (FIG. 4i, j and FIG. 16f). Therefore, reduced C9ORF72 activity leads to the accumulation of glutamate receptors and glutamate-induced excitotoxicity in vitro and in vivo.

Example 6

Low C9ORF72 Activity Sensitizes iMNs to Dipeptide Repeat Protein Toxicity

Because RAB5 activity is required for normal lysosomal biogenesis (Zeigerer, et al., *Nature*, 485: 465-470 (2012)) (FIG. 3m-q), it was analyzed if reduced C9ORF72 activity renders motor neurons vulnerable to insults that might be exacerbated by impaired lysosomal biogenesis, such as dipeptide repeat protein toxicity. Without excess glutamate treatment, C9ORF72$^{+/-}$, C9ORF72$^{-/-}$, and C9-ALS patient iMN survival was similar to control iMNs (FIG. 5a-d). Consistent with a previous study (Wen, et al., *Neuron*, 84: 1213-1225 (2014)), exogenous expression of PR$_{50}$ or GR$_{50}$ dipeptide repeat proteins using cassettes that do not contain the GGGGCC repeat expansion induced control iMN degeneration (FIG. 5a, b). Interestingly, C9ORF72$^{+/-}$, C9ORF72$^{-/-}$, and C9-ALS patient iMNs degenerated significantly faster than controls in response to PR$_{50}$ or GR$_{50}$ expression (FIG. 5a-d and FIG. 17). Thus, reduced C9ORF72 activity sensitizes iMNs to dipeptide repeat protein toxicity, revealing cooperativity between gain- and loss-of-function mechanisms from repeat expanded C9ORF72.

Because C9ORF72 activity drives lysosomal biogenesis, the effect of C9ORF72 activity on PR$_{50}$ clearance was measured. In C9ORF72$^{-/-}$ iPSC-derived fibroblasts that do not have endogenous C9ORF72, the clearance of PR$_{50}$-Dendra2 fusion proteins was measured with or without exogenous C9ORF72. Dendra2 is a green fluorescent protein that irreversibly converts to red fluorescence when exposed to blue light, enabling quantification of its degradation (Gurskaya, et al., *Nat Biotechnol*, 24: 461-465 (2006)). As observed in a previous study for PR$_{50}$ (Wen, et al., Neuron, 84: 1213-1225 (2014)), PR$_{50}$-Dendra2 formed discrete punctae within cells, indicating that Dendra2 did not prevent intracellular aggregation of $PR_{50}$ (FIG. 5e). Expression of C9ORF72-T2A-GFP in C9ORF72$^{-/-}$ iPSC-derived fibroblasts significantly enhanced the decay of $PR_{50}$-Dendra2 fluorescence over GFP alone, indicating that C9ORF72 activity promotes the clearance of dipeptide repeat proteins (FIG. 5f). To determine if C9ORF72 activity modulates dipeptide repeat protein clearance in human motor neurons, the decay of $PR_{50}$-Dendra2 in C9ORF72$^{+/+}$ and C9ORF72$^{+/-}$ iMNs was measured (FIG. 5g, h). $PR_{50}$-Dendra2 decayed significantly slower in C9ORF72$^{+/-}$ iMNs (FIG. 5h). Therefore, the reduction of C9ORF72 activity triggers neurotoxicity in a glutamate-independent manner by blocking the degradation of dipeptide repeat proteins.

Example 7

Small Molecule Regulators of Endosomal Trafficking Rescue Patient iMN Survival

Current therapeutic strategies in development for C9ORF72 ALS/FTD target gain-of-function mechanisms. These include antisense oligonucleotides (Sareen, D. et al., Sci Transl Med, 5: (2013), Donnelly, et al., Neuron, 80: 415-428 (2013), and Lagier-Tourenne, C. et al., Proc Natl Acad Sci, 110: E4530-4539 (2013)) and small molecules (Su, et al., Neuron, ePub (2014)) that disrupt RNA foci formation. However, these approaches have not achieved full rescue of neurodegeneration in human patient-derived neurons (Sareen, D. et al., Sci Transl Med, 5: (2013), Donnelly, et al., Neuron, 80: 415-428 (2013), Lagier-Tourenne, C. et al., Proc Natl Acad Sci, 110: E4530-4539 (2013) and (Su, et al., Neuron, ePub (2014)), indicating that replacing C9ORF72 function may be required and highlighting the need for new therapeutic targets.

To this end, a phenotypic screen was performed to identify small molecules that could rescue C9ORF72 patient iMN survival (FIG. 6a). To enrich for chemicals that might replace C9ORF72 function or compensate for its loss, 800 bioannotated compounds were screened targeting a diverse set of cellular processes including membrane trafficking.

An inhibitor of PIKFYVE kinase (YM201636) was identified that significantly increased the survival of C9ORF72 patient iMNs, but not control iMNs (FIG. 6b-e). PIKFYVE is a lipid kinase that converts phosphatidylinositol 3-phosphate (PI3P) into phosphatidylinositol (3,5)-bisphosphate $(PI(3,5)P_2)$ (Cai, et al., Chemistry & Biology, 20: 912-921 (2013)) (FIG. 6g). PI3P is generated by kinases recruited to early endosomes by RAB5, and PI3P forms a platform with RAB5 that enables anchoring of EEA1 to early endosomes (Lemmon, et al., Nat Rev Mol Cell Biol, 9: 99-111 (2008)) (FIG. 6g). EEA1, in turn, drives fusion with endocytic and other endosomal vesicles (Lemmon, et al., Nat Rev Mol Cell Biol, 9: 99-111 (2008)) (FIG. 6g). PIKFYVE-mediated conversion of PI3P to $PI(3,5)P_2$ blocks recruitment of EEA1 (Lemmon, et al., Nat Rev Mol Cell Biol, 9: 99-111 (2008)). Therefore, in C9ORF72 patient neurons, PIKFYVE inhibition could compensate for reduced RAB5 activity by increasing PI3P levels to enable early endosome maturation (FIG. 6g). Interestingly, FIG. 4 is a phosphatase that opposes PIKFYVE kinase by converting $PI(3,5)P_2$ to PI3P and mutations in FIG. 4 cause ALS, substantiating the relevance of this pathway to the disease (Chow, et al., Am J Hum Genet, 84: 85-88 (2009)).

To confirm that the PIKFYVE inhibitor YM201636 rescues C9ORF72 iMN survival, YM201636 was tested on iMNs from another C9ORF72 ALS/FTD patient. Again, it rescued patient iMN survival, indicating that YM201636 is efficacious on multiple C9ORF72 patient lines (FIG. 6f C9-ALS2).

Figure 18A:
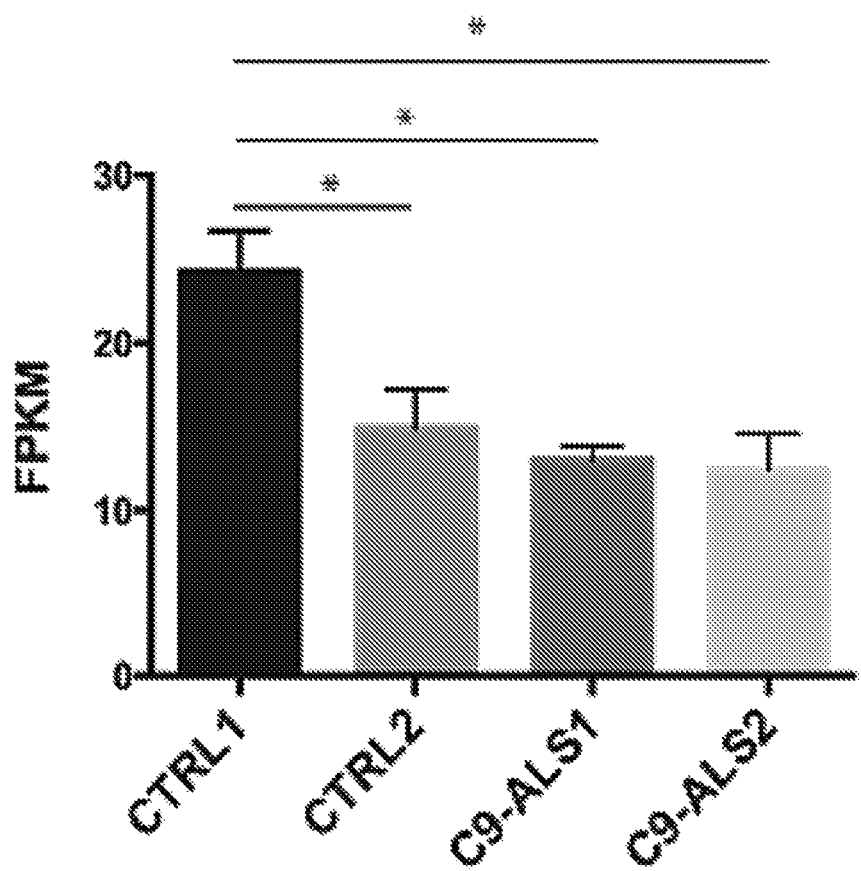
FIG. 18 shows PIKFYVE mRNA expression in control and C9-ALS iMNs, or wild-type and SOD1 A4V/+ iPSC-MNs (from Kiskinis et al.). Statistical analysis was performed using a two-tailed Student's t-test for pairwise comparisons, or one-way ANOVA for multiple comparisons. *-$p<0.05$, -$p<0.01$, *-$p<0.001$.
Figure 18B:
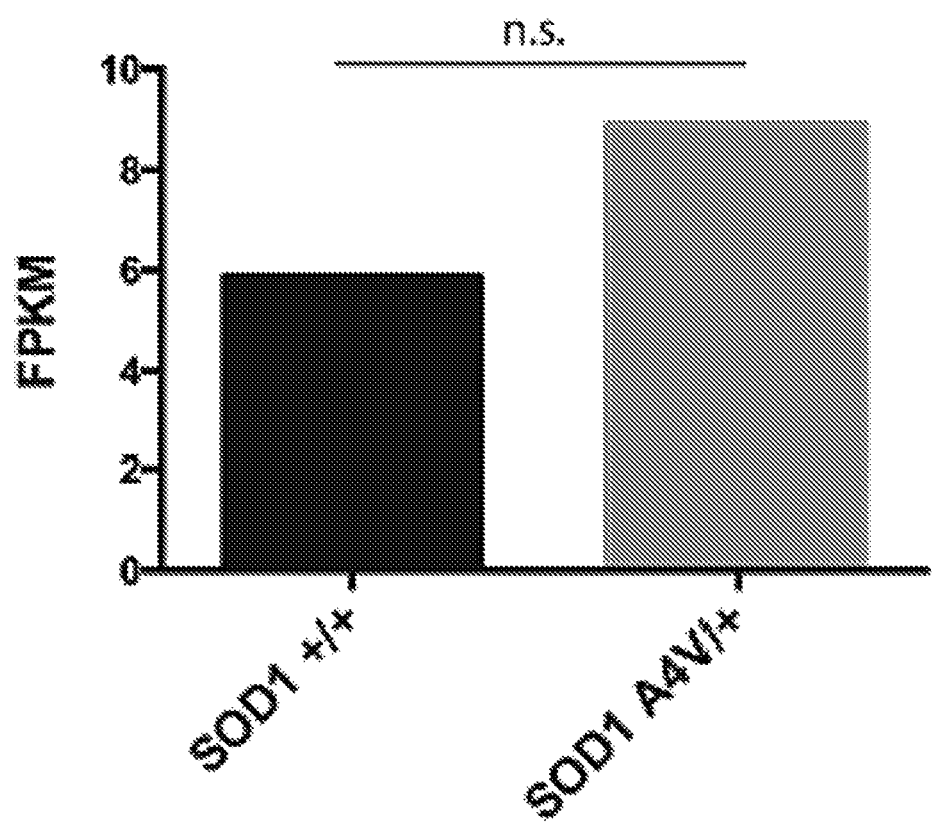

To verify that PIKFYVE is the functional target of the inhibitor, PIKFYVE expression was confirmed by qPCR in control and patient iMNs (FIG. 18). It was then assessed whether apilimod, a structurally distinct molecule that also inhibits PIKFYVE, could rescue patient iMN survival (Cai, et al., Chemistry & Biology, 20: 912-921 (2013)) (FIG. 6b). Indeed, apilimod increased the survival of iMNs from both C9ORF72 patient lines, but not control iMNs (FIG. 6d-f). Therefore, small molecule inhibition of PIKFYVE kinase can compensate for reduced C9ORF72 activity and rescue patient motor neuron survival.

Figure 6I:
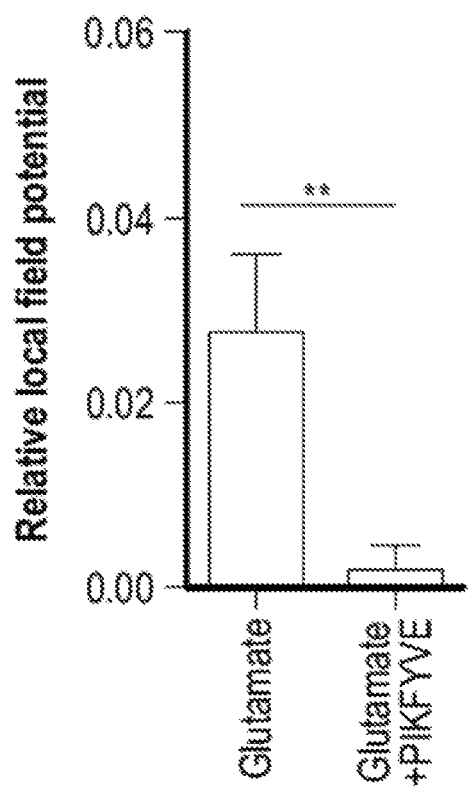
Figure 6J:
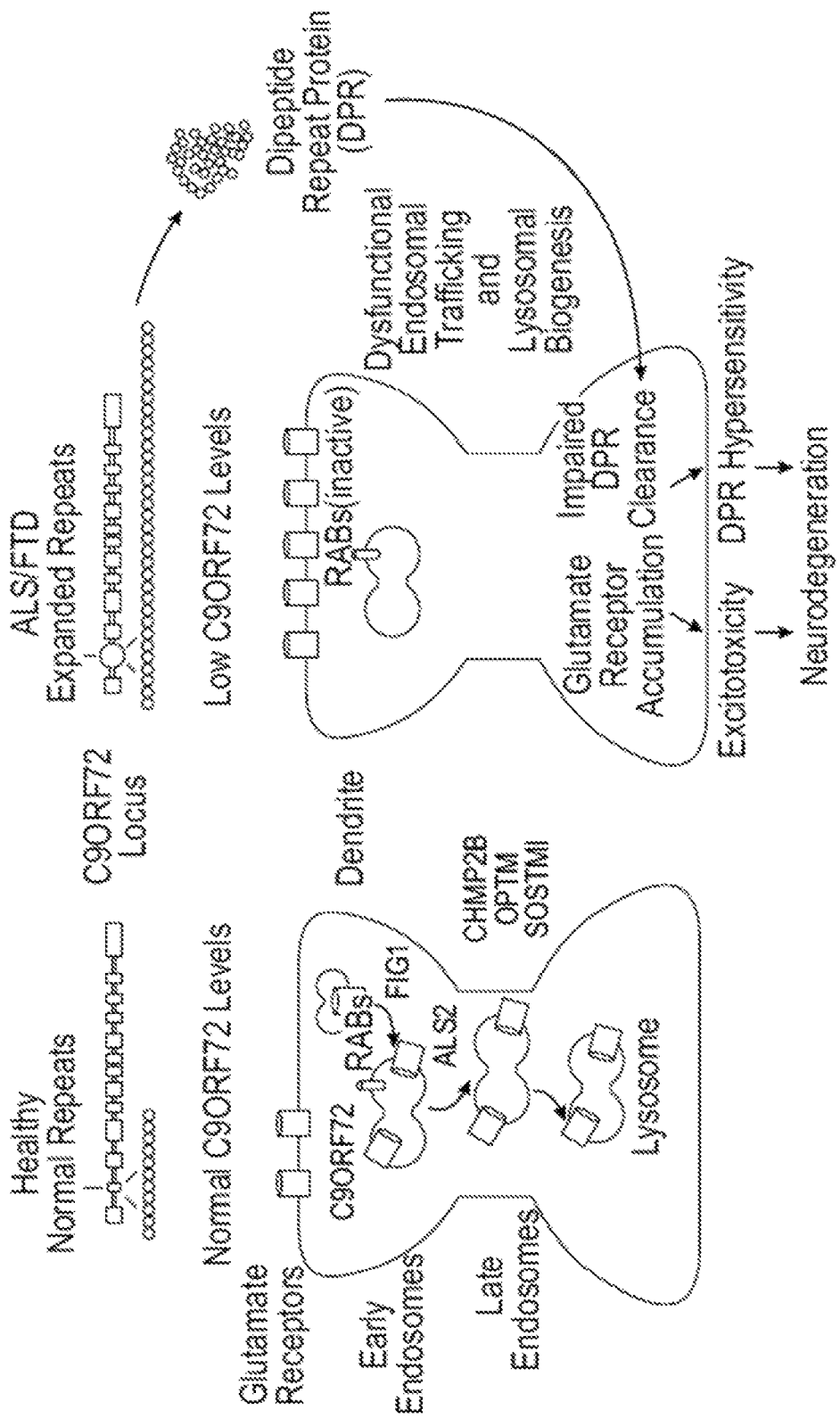

To determine if PIKFYVE inhibition rescued patient iMN survival by reversing endosomal trafficking defects, glutamate receptor levels were measured with and without PIKFYVE inhibitor treatment. PIKFYVE inhibition significantly lowered both NR1 (NMDA) and GluR1 (AMPA) levels in patient iMNs (FIG. 6h). In addition, PIKFYVE inhibition reduced electrophysiological activity in patient motor neurons in response to glutamate treatment (FIG. 6i). Thus PIKFYVE inhibition rescues patient iMN survival at least in part by reversing the glutamate receptor accumulation caused by defective endosomal trafficking.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method of treating a subject having a neurological disease, the method including the step of administering to the subject an effective dose of a PIKFYVE kinase inhibitor.

Clause 2. The method of clause 1, wherein the PIKFYVE kinase inhibitor is selected from the group consisting of apilimod and YM201636.

Clause 3. The method of clause 1, wherein the neurological disease is amyotrophic lateral sclerosis.

Clause 4. The method of clause 1, wherein the neurological disease is frontotemporal dementia.

Clause 5. The method of clause 1, wherein the neurological disease is associated with aberrant endosomal trafficking.

Clause 6. The method of clause 1, wherein the neurological disease is associated with aberrant lysosomal trafficking.

Clause 7. The method of clause 1, wherein the C9ORF72 gene comprises a $(GGGGCC)_n$ repeat.

Clause 8. The method of clause 7, wherein the subject is haploinsufficient for the C9ORF72 gene.

Clause 9. The method of clause 8, wherein the haploinsufficiency results in a 50% or greater reduction in C9ORF72 protein activity.

Clause 10. The method of clause 7, wherein the C9ORF72 gene product comprises a dipeptide repeat resulting from the $(GGGGCC)_n$ expansion.

Clause 11. The method of clause 10, wherein the dipeptide repeat is cytotoxic.

Clause 12. The method of clause 7, wherein the expansion is a gain-of-function or loss-of function mutation.

Clause 13. The method of clause 1, wherein the neurological disease is associated with neuronal hyperexcitability.

Clause 14. A method of treating a subject having a neurological disease characterized by neuronal hyperexcitability, the method including the step of administering to the patient an effective dose of a potassium channel activator.

Clause 15. The method of clause 14, wherein the potassium channel activator is retigabine.

Clause 16. The method of clause 14, wherein the neurological disease is amyotrophic lateral sclerosis.

Clause 17. The method of clause 14, wherein the neurological disease is frontotemporal dementia.

Clause 18. The method of clause 14, wherein the neurological disease is associated with aberrant endosomal trafficking.

Clause 19. The method of clause 14, wherein the neurological disease is associated with aberrant lysosomal trafficking.

Clause 20. The method of clause 14, wherein the C9ORF72 gene comprises a $(GGGGCC)_n$ repeat.

Clause 21. The method of clause 20, wherein the subject is haploinsufficient for the C9ORF72 gene.

Clause 22. The method of clause 21, wherein the haploinsufficiency results in a 50% or greater reduction in C9ORF72 protein activity.

Clause 23. The method of clause 20, wherein the C9ORF72 gene product comprises a dipeptide repeat resulting from the $(GGGGCC)_n$ expansion.

Clause 24. The method of clause 23, wherein the dipeptide repeat is cytotoxic.

Clause 25. The method of clause 20, wherein the expansion is a gain-of-function or loss-of function mutation.

Clause 26. A method of treating a subject having a neurological disease characterized by neuronal hyperexcitability, the method including the step of administering to the patient an effective dose of an inhibitor of glutamate receptors.

Clause 27. The method of clause 26, wherein the glutamate receptors are selected from the group consisting of NMDA, AMPA, and kainate receptors.

Clause 28. The method of clause 26, wherein the inhibitor of glutamate receptors is selected from the group consisting of AP5, CNQX, and NBQX.

Clause 29. The method of clause 26, wherein the neurological disease is amyotrophic lateral sclerosis.

Clause 30. The method of clause 26, wherein the neurological disease is frontotemporal dementia.

Clause 31. The method of clause 26, wherein the neurological disease is associated with aberrant endosomal trafficking.

Clause 32. The method of clause 26, wherein the neurological disease is associated with aberrant lysosomal trafficking.

Clause 33. The method of clause 26, wherein the C9ORF72 gene comprises a $(GGGGCC)_n$ repeat.

Clause 34. The method of clause 33, wherein the subject is haploinsufficient for the C9ORF72 gene.

Clause 35. The method of clause 34, wherein the haploinsufficiency results in a 50% or greater reduction in C9ORF72 protein activity.

Clause 36. The method of clause 33, wherein the C9ORF72 gene product comprises a dipeptide repeat resulting from the $(GGGGCC)_n$ expansion.

Clause 37. The method of clause 36, wherein the dipeptide repeat is cytotoxic.

Clause 38. The method of clause 33, wherein the expansion is a gain-of-function or loss-of function mutation.

Clause 39. A method of identifying a compound for inhibiting motor neuron degeneration, the method comprising:
 a. contacting the motor neuron cell with a candidate compound;
 b. determining whether the motor neuron cell degenerates;
 wherein if the motor neuron cell does not degenerate, the candidate compound is an inhibitor of motor neuron degeneration.

Clause 40. The method of clause 39, wherein the neurological disease is selected from the group consisting of amyloid lateral sclerosis, frontal temporal dementia, Alzheimer's, Parkinson's disease, multiple sclerosis, peripheral myopathy, Rasmussen's encephalitis, attention deficit hyperactivity disorder, autism, central pain syndromes, anxiety, and/or depression.

Clause 41. The method of clause 39, wherein the cell form the subject having the neurological disease comprises a (GGGGCC)n hexanucleotide expansion in C9ORF72.

Clause 42. The method of clause 42, wherein n is at least 30.

Clause 43. The method of clause 39, wherein step (b) is performed via imaging analysis.

Clause 44. The method of clause 39, wherein the motor neuron cell is converted from a pluripotent stem cell.

Clause 45. The method of clause 44, wherein the pluripotent stem cell is derived from a reprogrammed somatic cell.

Clause 46. The method of clause 45, wherein the somatic cell is a lymphocyte.

Clause 47. A method of treating a subject having a neurological disease, the method including the step of administering to the subject an effective dose of an endosomal and lysosomal trafficking modulator.

The invention claimed is:

1. A method of treating a subject having amyotrophic lateral sclerosis or frontotemporal dementia, comprising:
   administering to the subject an effective dose of a PIKFYVE kinase inhibitor selected from the croup consisting of apilimod and YM201636,
   wherein the treatment results in an alleviation, reduction, amelioration or improvement in the subject's condition, and wherein the subject has reduced C9ORF72 gene activity.

2. The method of claim 1, wherein the subject's C9ORF72 gene comprises a (GGGGCC)$_n$ repeat expansion located between exons 1a and 1b of the C9ORF72 gene, wherein n is an integer greater than 25.

3. The method of claim 2, wherein the subject is haploinsufficient for the C9ORF72 gene.

4. The method of claim 3, wherein the haploinsufficiency results in a 50% or greater reduction in C9ORF72 protein activity.

5. The method of claim 2, wherein the C9ORF72 gene product comprises a dipeptide repeat resulting from the (GGGGCC)$_n$ expansion.

6. The method of claim 5, wherein the dipeptide repeat is cytotoxic.

7. The method of claim 2, wherein the expansion is a gain-of-function or loss-of function mutation.

8. The method of claim 1, wherein the amyotrophic lateral sclerosis or frontotemporal dementia are associated with neuronal hyperexcitability.

* * * * *

UNITED STATES PATENT AND TRADEMARK OFFICE
CERTIFICATE OF CORRECTION

Page 1 of 1

PATENT NO. : 10,758,545 B2
APPLICATION NO. : 15/579546
DATED : September 1, 2020
INVENTOR(S) : Justin Ichida et al.

It is certified that error appears in the above-identified patent and that said Letters Patent is hereby corrected as shown below:

In the Specification

Column 1, Line 14, please replace the paragraph as follows:
--STATEMENT OF GOVERNMENT INTEREST
This invention was made with government support under W81XWH-15-1-0187 awarded by the Defense Health Agency, Medical Research and Development Branch, and R00 NS077435 awarded by the National Institutes of Health. The government has certain rights in the invention.--

Signed and Sealed this
Eighth Day of April, 2025

Coke Morgan Stewart
*Acting Director of the United States Patent and Trademark Office*